US012673108B2

(12) United States Patent
Wood et al.

(10) Patent No.: US 12,673,108 B2
(45) **Date of Patent: *Jul. 7, 2026**

(54) CELL-PENETRATING PEPTIDE CONJUGATES AND METHODS OF THEIR USE

(71) Applicants: Oxford University Innovation Limited, Oxford (GB); United Kingdom Research and Innovation, Swindon (GB)

(72) Inventors: Matthew Wood, Oxford (GB); Raquel Manzano, Saragossa (ES); Caroline Godfrey, Oxford (GB); Graham McClorey, Oxford (GB); Richard Raz, Copenhagen (DK); Michael Gait, Cambridge (GB); Andrey Arzumanov, Cambridge (GB); Liz O'Donovan, Cork (IE); Gareth Hazell, Didcot (GB); Ashling Holland, Dublin (IE); Miguel Varela, Oxford (GB); Subhashis Banerjee, Kolkata (IN)

(73) Assignees: Oxford University Innovation Limited, Oxford (GB); United Kingdom Research and Innovation, Swindon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/054,315

(22) Filed: Feb. 14, 2025

(65) Prior Publication Data

US 2025/0177543 A1 Jun. 5, 2025

Related U.S. Application Data

(63) Continuation of application No. 18/277,013, filed as application No. PCT/GB2022/050371 on Feb. 11, 2022.

(30) Foreign Application Priority Data

Feb. 12, 2021 (WO) ................ PCT/GB2021/050357

(51) Int. Cl.

*A61K 47/64* (2017.01)
*C07K 19/00* (2006.01)
*C12N 15/113* (2010.01)

(52) U.S. Cl.

CPC .............. *A61K 47/64* (2017.08); *C07K 19/00* (2013.01); *C12N 15/113* (2013.01); *C12N 2310/11* (2013.01); *C12N 2310/3233* (2013.01); *C12N 2310/3513* (2013.01)

(58) Field of Classification Search

CPC .... A61K 47/64; A61K 47/6455; C07K 19/00; C12N 15/113; C12N 2310/11; C12N 2310/3233; C12N 2310/3513

See application file for complete search history.

(56) References Cited

U.S. PATENT DOCUMENTS

| | | | | |
|---|---|---|---|---|
| 7,807,816 | B2 * | 10/2010 | Wilton | C12N 15/113 536/24.31 |
| 7,838,657 | B2 | 11/2010 | Singh et al. | |
| 8,324,371 | B2 | 12/2012 | Popplewell et al. | |
| 8,361,979 | B2 | 1/2013 | Aartsma-Rus et al. | |
| 8,575,305 | B2 | 11/2013 | Gait et al. | |
| 8,637,483 | B2 | 1/2014 | Wilton et al. | |
| 8,741,863 | B2 | 6/2014 | Moulton et al. | |
| 8,835,402 | B2 | 9/2014 | Kole et al. | |
| 9,018,368 | B2 | 4/2015 | Wilton et al. | |
| 9,079,934 | B2 | 7/2015 | Watanabe et al. | |
| 9,161,948 | B2 | 10/2015 | Hanson | |
| 9,238,052 | B2 | 1/2016 | Kameyama et al. | |
| 9,302,014 | B2 * | 4/2016 | Gait | C12N 15/00 |
| 9,447,417 | B2 | 9/2016 | Sazani et al. | |
| 9,528,109 | B2 | 12/2016 | De Kimpe et al. | |
| 9,582,637 | B1 | 2/2017 | Fernandez et al. | |
| 9,926,557 | B2 | 3/2018 | De Kimpe et al. | |
| 10,160,969 | B2 | 12/2018 | Meena et al. | |
| 10,385,092 | B2 | 8/2019 | Watanabe et al. | |
| 10,781,450 | B2 | 9/2020 | Wilton et al. | |
| 10,876,114 | B2 | 12/2020 | Van Deutekom | |

(Continued)

FOREIGN PATENT DOCUMENTS

| | | |
|---|---|---|
| CN | 103619356 A | 3/2014 |
| CN | 103998458 A | 8/2014 |

(Continued)

OTHER PUBLICATIONS

Evers et al. ("Targeting several CAG expansion diseases by a single antisense oligonucleotide." PloS one 6.9 (2011)).*

Mulders, Susan AM, et al. "Triplet-repeat oligonucleotide-mediated reversal of RNA toxicity in myotonic dystrophy." Proceedings of the National Academy of Sciences 106.33 (2009): 13915-13920.*

"Peptide Design," ThermoFisher Scientific, <https://www.thermofisher.com/US/en/home/life-science/protein-biology/protein-biology-learning-center/protein-biology-resource-library/pierce-protein-methods/peptide-design.html>, retrieved on Oct. 18, 2022 (9 pages).

Ablan et al., "Charge Distribution Fine-Tunes the Translocation of [alpha]-Helical Amphipathic Peptides across Membranes," Biophys J. 111(8):1738-49 (2016).

(Continued)

*Primary Examiner* — Kimberly Chong
(74) *Attorney, Agent, or Firm* — Clark & Elbing LLP

(57) ABSTRACT

Disclosed are conjugates of an oligonucleotide and a peptide covalently bonded or linked via a linker to the oligonucleotide, the peptide including at least one cationic domain comprising at least 4 amino acid residues and at least one hydrophobic domain comprising at least 3 amino acid residues, provided that the peptide includes a total of 7 to 40 amino acid residues and does not include any artificial amino acid residues; and the oligonucleotide including a total of 12 to 40 contiguous nucleobases, where at least 12 contiguous nucleobases are complementary to a target sequence in a human dystrophin gene.

4 Claims, 38 Drawing Sheets

Specification includes a Sequence Listing.

(56) References Cited

U.S. PATENT DOCUMENTS

| | | | |
|---|---|---|---|
| 12,268,749 B2 | 4/2025 | Wood et al. | |
| 12,465,646 B2 | 11/2025 | Raz et al. | |
| 12,472,264 B2 | 11/2025 | Wood et al. | |
| 2008/0306001 A1 | 12/2008 | Liik et al. | |
| 2009/0099066 A1 | 4/2009 | Moulton et al. | |
| 2010/0016215 A1 | 1/2010 | Moulton et al. | |
| 2010/0184833 A1 | 7/2010 | De Kimpe et al. | |
| 2011/0105403 A1 | 5/2011 | Gait et al. | |
| 2011/0269665 A1 | 11/2011 | Kole | |
| 2012/0289457 A1 | 11/2012 | Hanson | |
| 2014/0051646 A1 | 2/2014 | Gait et al. | |
| 2014/0315977 A1 | 10/2014 | Bestwick et al. | |
| 2014/0342992 A1 | 11/2014 | Gait et al. | |
| 2015/0183827 A1 | 7/2015 | Milletti | |
| 2015/0238627 A1 | 8/2015 | Leger et al. | |
| 2015/0246958 A1 | 9/2015 | Han | |
| 2016/0237426 A1 | 8/2016 | Hanson | |
| 2019/0177723 A1 | 6/2019 | Dickson | |
| 2019/0241892 A1 | 8/2019 | Van Deutekom | |
| 2020/0131231 A1 | 4/2020 | Wood et al. | |
| 2021/0024922 A1 | 1/2021 | Zain-Lugman et al. | |
| 2021/0299263 A1 | 9/2021 | Wood et al. | |
| 2021/0299264 A1 | 9/2021 | Wood et al. | |
| 2021/0388353 A1 | 12/2021 | Popplewell et al. | |
| 2022/0041662 A1 | 2/2022 | Wood et al. | |
| 2022/0090066 A1 | 3/2022 | Wood et al. | |
| 2022/0125934 A1* | 4/2022 | Raz | A61K 47/542 |
| 2022/0275372 A1 | 9/2022 | Wood et al. | |
| 2022/0288218 A1 | 9/2022 | Yokota et al. | |
| 2023/0193282 A1 | 6/2023 | Sun et al. | |
| 2024/0189434 A1 | 6/2024 | Godfrey et al. | |
| 2024/0200062 A1 | 6/2024 | Godfrey et al. | |
| 2024/0299563 A1 | 9/2024 | Wood et al. | |

FOREIGN PATENT DOCUMENTS

| | | | |
|---|---|---|---|
| CN | 104837997 | A | 8/2015 |
| EP | 2394665 | A1 | 12/2011 |
| EP | 3034074 | A1 | 6/2016 |
| EP | 2344637 | B2 | 2/2018 |
| EP | 3443976 | A1 | 2/2019 |
| EP | 3031920 | B1 | 8/2019 |
| GB | 2563964 | A | 1/2019 |
| JP | 2006-514602 | A | 5/2006 |
| JP | 2007-509978 | A | 4/2007 |
| JP | 2009-544749 | A | 12/2009 |
| JP | 2010-532168 | A | 10/2010 |
| JP | 2011-523557 | A | 8/2011 |
| JP | 2013-531988 | A | 8/2013 |
| JP | 2014-515762 | A | 7/2014 |
| JP | 2014-526238 | A | 10/2014 |
| JP | 2015-522264 | A | 8/2015 |
| JP | 2015-532264 | A | 11/2015 |
| JP | 2018-532695 | A | 11/2018 |
| KR | 10-2015-0032265 | A | 3/2015 |
| RU | 2556800 | C2 | 7/2015 |
| RU | 2674600 | C2 | 12/2018 |
| WO | WO-1999/67284 | A2 | 12/1999 |
| WO | WO-2000/39139 | A1 | 7/2000 |
| WO | WO-2003/106491 | A2 | 12/2003 |
| WO | WO-2004/097017 | A2 | 11/2004 |
| WO | WO-2005/042539 | A1 | 5/2005 |
| WO | WO-2006/000057 | A1 | 1/2006 |
| WO | WO-2008/012365 | A2 | 1/2008 |
| WO | WO-2008/109105 | A2 | 9/2008 |
| WO | WO-2009/005793 | A2 | 1/2009 |
| WO | WO-2009/144481 | A2 | 12/2009 |
| WO | WO-2009/147368 | A1 | 12/2009 |
| WO | WO-2011/157713 | A2 | 12/2011 |
| WO | WO-2012/012443 | A2 | 1/2012 |
| WO | WO-2012/072088 | A1 | 6/2012 |
| WO | WO-2012/090150 | A2 | 7/2012 |
| WO | WO-2012/150960 | A1 | 11/2012 |
| WO | WO-2013/030569 | A2 | 3/2013 |
| WO | WO-2013/040429 | A1 | 3/2013 |
| WO | WO-2014/001229 | A2 | 1/2014 |
| WO | WO-2014/041505 | A1 | 3/2014 |
| WO | WO-2014/043544 | A1 | 3/2014 |
| WO | WO-2014/052276 | A1 | 4/2014 |
| WO | WO-2015/022504 | A2 | 2/2015 |
| WO | WO-2015113922 | A1 | 8/2015 |
| WO | WO-2015/155753 | A2 | 10/2015 |
| WO | WO-2015/161255 | A1 | 10/2015 |
| WO | WO-2016/028187 | A1 | 2/2016 |
| WO | WO-2016/154328 | A2 | 9/2016 |
| WO | WO-2017/027848 | A1 | 2/2017 |
| WO | WO-2018/017190 | A2 | 1/2018 |
| WO | WO-2018/053316 | A1 | 3/2018 |
| WO | WO-2019/067975 | A1 | 4/2019 |
| WO | WO-2019/067979 | A1 | 4/2019 |
| WO | WO-2019/067981 | A1 | 4/2019 |
| WO | WO-2020/030927 | A1 | 2/2020 |
| WO | WO-2020/030928 | A1 | 2/2020 |
| WO | WO-2020/115494 | A1 | 6/2020 |
| WO | WO-2020/214763 | A1 | 10/2020 |
| WO | WO-2020/257489 | A1 | 12/2020 |
| WO | WO-2021/003573 | A1 | 1/2021 |
| WO | WO-2021/028666 | A1 | 2/2021 |
| WO | WO-2022/172019 | A1 | 8/2022 |
| WO | WO-2022/192749 | A2 | 9/2022 |
| WO | WO-2022/192754 | A2 | 9/2022 |

OTHER PUBLICATIONS

Alaybeyoglu et al., "Insights into membrane translocation of the cell-penetrating peptide pVEC from molecular dynamics calculations." Journal of Biomolecular Structure and Dynamics. 34(11): 2387-2398 (2016) (14 pages).

Amantana et al., "Pharmacokinetics, biodistribution, stability and toxicity of a cell-penetrating peptide-morpholino oligomer conjugate," Bioconjug Chem.18(4): 1325-31 (Jun. 2007).

Bahal et al., "In vivo correction of anaemia in beta-thalassemic mice by gammaPNA-mediated gene editing with nanoparticle delivery," Nature Communications, 7:13304 (2016) (14 pages).

Berezov T. T. et al., Biologiĭeskaâ himiâ [Biological Chemistry], Moscow, "Medicine", 1998, p. 34 third para., p. 59 last para (3 pages).

Betts et al., "Pip6-PMO, A New Generation of Peptide-oligonucleotide Conjugates With Improved Cardiac Exon Skipping Activity for DMD Treatment," Mol Ther nucleic Acids. 1(8):e38. doi: 10.1038/mtna.2012.30 (2012) (13 pages).

Borrelli et al., "Cell Penetrating Peptides as Molecular Carriers for Anti-Cancer Agents," Molecules. 23(2):295 (Jan. 2018) (28 pages).

Chan et al., "The complexity of antisense transcription revealed by the study of developing male germ cells," Genomics. 87(6):681-92 (2006).

Copolovici et al., "Cell-penetrating peptides: design, synthesis, and applications," ACS Nano. 8(3):1972-94 (Epub Feb. 2014) (Mar. 2014).

Deuss et al., "Parallel synthesis and splicing redirection activity of cell-penetrating peptide conjugate libraries of a PNA cargo." Organic & Biomolecular Chemistry. 11:7621-7630 (2013) (10 pages).

Dimachkie et al., "Distal myopathies," available in PMC Aug. 1, 2015, published in final edited form as: Neurol Clin. 32(3):817-42 (Aug. 2014) (Epub May 2014) (32 pages).

Dutot et al., "Glycosylated cell penetrating peptides and their conjugates to a proapoptotic peptide: Preparation by click chemistry and cell viability studies," Journal of Chemical Biology, 3(2):51-65 (2010).

Dyson et al. "Himiâ sinteticeskih lekarstvennyh vesestv," Chemistry of Synthetic Drugs. (1964) (9 pages).

Egleton et al., "Improved bioavailability to the brain of glycosylated Met-enkephalin analogs," Brain Research, 881 (1 ):37-46 (2000).

Futaki et al., "Translocation of branched chain arginine peptides through cell membranes: Flexibility in the spatial disposition of positive charges in membrane-permeable peptides," Biochemistry, 41(25):7925-7930 (2002).

(56) References Cited

OTHER PUBLICATIONS

Godfrey et al., "How much dystrophin is enough: the physiological consequences of different levels of dystrophin in the mdx mouse." Human Molecular Genetics. 24(15):4225-4237 (May 1, 2015) (13 pages).
González-Barriga et al., "Design and analysis of effects of triplet repeat oligonucleotides in cell models for myotonic dystrophy," Mol Ther Nucleic Acids. 2(3): 1-12 (Mar. 2013).
Hammond et al., "Systemic peptide-mediated oligonucleotide therapy improves long-term survival in spinal muscular atrophy," PNAS, 113(39):10962-10967 (2016).
Haurum et al., "Presentation of Cytosolic Glycosylated Peptides by Human Class I Major Histocompatibility Complex Molecules In Vivo". Journal of Experimental Medicine. 190(1): 145-150 (Jul. 5, 1999) (6 pages).
Ibraheem et al., "Gene therapy and DNA delivery systems," Int J Pharm. 459(1-2): 70-83 (Jan. 2014).
Jahn et al., "How to systematically evaluate immunogenicity of therapeutic proteins—regulatory considerations," N Biotechnol. 25(5):280-6 (2009).
Kalafatovic et al., "Cell-Penetrating Peptides: Design Strategies beyond Primary Structure and Amphipathicity," Molecules. 22(11):1929 (2017) (38 pages).
Kontermann et al., "Bispecific antibodies," Drug Discov Today. 20(7):838-47 (Jul. 2015) (12 pages).
Kuznetsova, "Brackets in text of a legal document as a linguistic and cognitive phenomenon," Vestnik MGOU. N3:37-43 (2015).
Lapidot et al., "Genome-wide natural antisense transcription: coupling its regulation to its different regulatory mechanisms," EMBO Rep. 7(12):1216-22 (2006).
Lécorché et al., "Cellular uptake and biophysical properties of galactose and/or tryptophan containing cell-penetrating peptides," Biochimica et Biophysica Acta, 1818(3):448-457 (2012).
Lehto et al., "Cellular trafficking determines the exon skipping activity of Pip6a-PMO in mdx skeletal and cardiac muscle cells." Nucleic Acids Res. 42(5):3207-3217 (Dec. 23, 2013) (11 pages).
Lehto et al., "Peptides for nucleic acid delivery," Adv Drug Deliv Rev. 106(Pt A):172-182 (2016).
Marks et al., "Spontaneous Membrane-Translocating Peptides by Orthogonal High-Throughput Screening." Journal of the American Chemical Society. 133: 8995-9004 (May 5, 2011) (10 pages).
McClorey et al., "Cell-Penetrating Peptides to Enhance Delivery of Oligonucleotide-Based Therapeutics," Biomedicines. 6(2):51. doi: 10.3390/biomedicines6020051 (May 2018) (15 pages).
Milletti, "Cell-penetrating peptides: classes, origin, and current landscape," Drug Discov Today. 17(15-16):850-860 (2012).
Nan et al., "Antisense Phosphorodiamidate Morpholino Oligomers as Novel Antiviral Compounds," Front Microbiol. 9: 1-15 (Apr. 2018).
Nikolenko et al., "Rehabilitation of children with progressive muscular dystrophy Duchenne," Russian Bulletin of Perinatology and Pediatrics. 4:28-31 (2014).
Osman et al., "Morpholino antisense oligonucleotides targeting intronic repressor Element1 improve phenotype in SMA mouse models," Human Molecular Genetics, 23(18):4832-4845 (2014).
Pinto et al., "Impeding Transcription of Expanded Microsatellite Repeats by Deactivated Cas9," Mol Cell. 68(3): 479-490 (Nov. 2017).
Pokrovskij V. I. "Populârnaâ medicinskaâ enciklopedia [Popular Medical Encyclopedia]," Ul'ânovsk "KNIGOCEJ", 4th ed., 1997, p. 317 (drugs) (2 pages).
Rihácek et al. [New Indings in Methotrexate Pharmacology—Diagnostic Possibilities and Impact on Clinical Care] Klin Onkol. 2015;28(3):163-70. doi: 10.14735/amko2015163. (abstract only) (1 page).
Rothbard et al., "Arginine-rich molecular transporters for drug delivery: Role of backbone spacina in cellular uptake," Journal of Medicinal Chemistry, 45(17):3612-8 (2002).
Rydberg et al. "Effects of Tryptophan Content and Backbone Spacing on the Uptake Efficiency of Cell-Penetrating Peptides," BIOCHEMISTRY. 51(27):5531-5539 (Jun. 28, 2021) (9 pages).
Rydberg et al., "Effects of tryptophan content and backbone spacing on the uptake efficiency of cell-penetrating peptides," Biophysical Journal, Board B253. 102(3):487a (2012).
Shabanpoor et al., "Bi-specific splice-switching PMO oligonucleotides conjugated via a single peptide active in a mouse model of Duchenne muscular dystrophy," Nucleic Acids Res. 43(1):29-39 (2015).
Shabanpoor et al., "Development of a general methodology for labelling peptide-morpholino oligonucleotide conjugates using alkyne-azide click chemistry," Chem Commun (Camb). 49(87):10260-2 (2013) (9 pages).
Shabanpoor et al., "Identification of a peptide for systemic brain delivery of a morpholino oligonucleotide in mouse models of spinal muscular atrophy," Nucleic Acid Therapeutics. 27(3):130-143 (2017) (15 pages).
Shen et al., "Single variable domain-IgG fusion. A novel recombinant approach to Fc domain-containing bispecific antibodies," J Biol Chem. 281(16):10706-14 (2006).
Swenson et al., "Chemical modifications of antisense morpholino oligomers enhance their efficacy against Ebola virus infection," Antimicrob Agents Chemother. 53(5): 2089-99 (May 2015).
Torres et al., "The immunoglobulin constant region contributes to affinity and specificity," Trends Immunol. 29(2):91-7 (2008).
Wermuth et al., "Glossary of terms used in medicinal chemistry," Pure & Appl. Chem. 70(5):1129-43 (1998).
Witt et al., "Peptide drug modifications to enhance bioavailability and blood-brain barrier permeability," Peptides. 22(12):2329-2343 (2001).
Wu et al., "Cell-penetrating peptides as transporters for morpholino oligomers: effects of amino acid composition on intracellular delivery and cytotoxicity," Nucleic Acids Res. 35(15):5182-91 (2007).
Wu et al., "Long-term rescue of dystrophin expression and improvement in muscle pathology and function in dystrophic mdx mice by peptide-conjugated morpholino," Am J Pathol. 181(2): 392-400. (Aug. 2012).
Yin et al., "Pip5 Transduction Peptides Direct High Efficiency Oligonucleotide-mediated Dystrophin Exon Skipping in Heart and Phenotypic Correction in mdx Mice," Molecular Therapy, 19(7):1295-1303 (2011).
Zhou et al., "A Novel Morpholino Oligomer Targeting ISS-N1 Improves Rescue of Severe Spinal Muscular Atrophy Transgenic Mice," Human Gene Therapy. 24(3):331-342 (2013).
Zorko et al., "Cell-penetrating peptides: mechanism and kinetics of cargo delivery," Adv Drug Deliv Rev. 57(4):529-45 (2005).
U.S. Appl. No. 19/131,778, Holland et al.
Lifetein, "Peptide Modifications: Linkers, Spacers and PEGylation," <https://www.lifetein.com/Peptide_Modifications_Pegylation_Linker.html?srsltid=AfmBOooYB4PzPAyhHF6IPK1QKG6LeqO0dw4Q_DMII6Nza-fRFSJnIx8G>Oct. 21, 2014>, retrieved on Apr. 5, 2025 (8 pages).
Bowie et al. Deciphering the Message in Protein Sequences: Tolerance to Amino Acid Substitutions, Science, 1990, 247:1306-1310 (Mar. 1990) (6 pages).
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. Cell Biol. 111: 2129-2138 (Nov. 1990) (10 pages).
Chen et al. Fusion Protein Linkers: Property, Design and Functionality, Adv. Drug Deliv. Rev. 65:1357-1369 (Oct. 2013) (32 pages).
He et al, Peptide Conjugates with Small Molecules Designed to Enhance Efficacy and Safety, Molecules, 2019, 24, 1855, 1-34 (May 2019) (34 pages).
Lazar et al., Transforming Growth Factor Alpha: Mutation of Aspartic Acid 47 and Leucine 48 Results in Different Biological Activities, Mol. Cell. Biol., 8:1247-1252, (Mar. 1988) (6 pages).
Lu et al, Linkers Having a Crucial Role in Antibody-Drug Conjugates, International Journal of Molecular Sciences, 2016, 17, 561, 1-22 (Apr. 2016) (22 pages).

(56) References Cited

OTHER PUBLICATIONS

Verdine et al., Stapled Peptides for Intracellular Drug Targets, Methods in Enzymology, 2012, vol. 503, 3-33 (Year: 2012).
Hilyard et al., "When Size Really Matters: The Eccentricities of Dystrophin Transcription and the Hazards of Quantifying mRNA from Very Long Genes," Biomedicines. 11(7) (2023) (65 pages).
Leiden Muscular Dystrophy pages, DMD (dystrophin) (2004) (5 pages).
Udd et al., "The myotonic dystrophies: molecular, clinical, and therapeutic challenges," Lancet Neurol. 11(10):891-905 (Oct. 2012).

* cited by examiner

Urinary NGAL (1x30mg/kg)

Blood Urea Nitrogen

Serum Creatinine

Diaphragm

Heart

Tibialis Anterior

Diaphragm

Heart

Myoblast Cell Viability

Kidney Injury Marker-1

CELL-PENETRATING PEPTIDE CONJUGATES AND METHODS OF THEIR USE

CROSS-REFERENCE TO RELATED APPLICATIONS

This Application is a Continuation of application Ser. No. 18/277,013 filed on Aug. 11, 2023, which is the U.S. National Stage of PCT/GB2022/050371 filed on Feb. 11, 2022, which claims priority from Application PCT/GB2021/050357 filed on Feb. 12, 2021.

SEQUENCE LISTING

The instant application contains a Sequence Listing which has been submitted electronically in XML format and is hereby incorporated by reference in its entirety. Said XML copy, created on Feb. 14, 2025, is named "51558-016003_Sequence_Listing_2_14_25" and is 383,708 bytes in size.

FIELD OF THE INVENTION

The invention relates to peptide conjugates of antisense oligonucleotides, compositions containing them, and methods of their use.

BACKGROUND

Nucleic acid drugs are genomic medicines with the potential to transform human healthcare. Research has indicated that such therapeutics could have applications across a broad range of disease areas including neuromuscular disease. The application of antisense oligonucleotide-based methods to modulate pre-mRNA splicing in the neuromuscular disease Duchenne muscular dystrophy (DMD) has placed this monogenic disorder at the forefront of advances in precision medicine.

However, therapeutic development of these promising antisense therapeutics has been hampered by insufficient cell-penetrance and poor distribution characteristics—a challenge that is further emphasized by the large volume and dispersed nature of the muscle tissue substrate in DMD.

DMD affects one in 3500 newborn boys. This severe, X-linked recessive disease results from mutations in the DMD gene that encodes dystrophin protein. The disorder is characterized by progressive muscle degeneration and wasting, along with the emergence of respiratory failure and cardiac complications, ultimately leading to premature death. The majority of mutations underlying DMD are genomic out-of-frame deletions that induce a premature truncation in the open reading frame that results in the absence of the dystrophin protein.

Exon skipping therapy utilizes splice switching antisense oligonucleotides (SSOs) to target specific regions of the DMD transcript, inducing the exclusion of individual exons, leading to the restoration of aberrant reading frames and resulting in the production of an internally deleted, yet partially functional, dystrophin protein. Despite the undoubted potential of antisense oligonucleotide exon skipping therapy for DMD, the successful application of this approach is currently limited by the relatively inefficient targeting of skeletal muscle, as well as the inadequate targeting of single stranded oligonucleotides to other affected tissues such as the heart. In September 2016 the Food and Drug Administration (FDA) granted accelerated approval for eteplirsen, a modulator of exon 51 splicing. Although this heralded the first US FDA-approved oligonucleotide that modulates splicing, the levels of dystrophin restoration were disappointing with approximately 1% of normal dystrophin levels. Comparisons with the allelic disorder Becker muscular dystrophy and experiments in the mdx mouse have indicated that homogenous sarcolemmal dystrophin expression of at least −15% of wild-type is needed to protect muscle against exercise induced damage.

Therefore, there is a need for new antisense oligonucleotide-based therapeutics for devastating genetic diseases such as DMD.

SUMMARY OF THE INVENTION PATENT

In general, the invention provides a conjugate, or a pharmaceutically acceptable salt thereof, of an oligonucleotide and a peptide covalently bonded or covalently linked via a linker to the oligonucleotide. The oligonucleotide is complementary to a target sequence within or proximal to exon 45, exon 51, or exon 53 of a human dystrophin gene.

In one aspect, the invention provides a conjugate, or a pharmaceutically acceptable salt thereof, of an oligonucleotide and a peptide covalently bonded or linked via a linker to the oligonucleotide, the peptide including at least one cationic domain including at least 4 amino acid residues and at least one hydrophobic domain including at least 3 amino acid residues, provided that the peptide includes a total of 7 to 40 amino acid residues and does not include any artificial amino acid residues; and the oligonucleotide including a total of 12 to 40 contiguous nucleobases, where at least 12 contiguous nucleobases are complementary to a target sequence in a human dystrophin gene.

In some embodiments, the target sequence includes a splice site for exon 45 or is disposed within 50 nucleobases of a splice site for exon 45. In some embodiments, the oligonucleotide includes at least 12 contiguous nucleobases from any one sequence in Table 1 and thymine-substituted versions thereof. In some embodiments, the oligonucleotide includes any one sequence in Table 1 or a thymine-substituted version thereof.

In some embodiments, the sequence in Table 1 is:

```
                                    (SEQ ID NO: 193)
5'-GCTGCCCAATGCCATCCTGGAGTTCCTGTAA-3'.
```

In some embodiments, the sequence in Table 1 is:

```
                                    (SEQ ID NO: 194)
5'-CAATGCCATCCTGGAGTTCCTG-3'.
```

In some embodiments, the target sequence includes a splice site for exon 51 or is disposed within 50 nucleobases of a splice site for exon 51. In some embodiments, the oligonucleotide includes at least 12 contiguous nucleobases from any one sequence in Table 2 and thymine-substituted versions thereof. In some embodiments, the oligonucleotide includes any one sequence in Table 3 or a thymine-substituted version thereof.

In some embodiments, the sequence in Table 2 is:

```
                                    (SEQ ID NO: 130)
5'-CUCCAACAUCAAGGAAGAUGGCAUUUCUAG-3'.
```

In some embodiments, the sequence in Table 2 is:

```
                                    (SEQ ID NO: 195)
5'-CTCCAACATCAAGGAAGATGGCATTTCTAG-3'.
```

In some embodiments, the target sequence includes a splice site for exon 53 or is disposed within 50 nucleobases of a splice site for exon 53. In some embodiments, the oligonucleotide includes at least 12 contiguous nucleobases from any one sequence in Table 3. In some embodiments, the oligonucleotide includes any one sequence in Table 3.

In some embodiments, the sequence in Table 3 is:

```
                                    (SEQ ID NO: 162)
5'-CCTCCGGTTCTGAAGGTGTTCT-3'.
```

In some embodiments, the sequence in Table 3 is:

```
                                    (SEQ ID NO: 171)
5'-GTTGCCTCCGGTTCTGAAGGTGTTC-3'.
```

In some embodiments, the splice site is an acceptor splice site. In some embodiments, the splice site is a donor splice site.

In some embodiments, the sequence is GGCCAAACCTCGGCTTACCTGAAAT (SEQ ID NO: 90).

In some embodiments, the peptide does not contain aminohexanoic acid (X) residues. In some embodiments, the peptide does not contain 6-aminohexanoic acid residue. In some embodiments, the peptide consists of natural amino acid residues. In some embodiments, each cationic domain has length of between 4 and 12 amino acid residues, preferably between 4 and 7 amino acid residues. In some embodiments, each cationic domain includes at least 40%, at least 45%, or at least 50% cationic amino acids. In some embodiments, each cationic domain includes a majority of cationic amino acids, preferably at least at least 55%, at least 60%, at least 65% at least 70%, at least 75%, at least 80%, at least 85%, at least 90%, at least 95% cationic amino acids. In some embodiments, each cationic domain includes arginine, histidine, beta-alanine, hydroxyproline and/or serine residues, preferably where each cationic domain consists of arginine, histidine, beta-alanine, hydroxyproline and/or serine residues. In some embodiments, each cationic domain is arginine rich and/or histidine rich, preferably each cationic domain includes at least 40%, at least 45%, at least 50%, at least 55%, at least 60%, at least 60%, at least 65%, least 70% arginine and/or histidine residues. In some embodiments, the peptide includes two cationic domains.

In some embodiments, each cationic domain includes one of the following sequences: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B (SEQ ID NO: 17), R[Hyp]H[Hyp]HB (SEQ ID NO: 18), R[Hyp]RR[Hyp]R (SEQ ID NO: 19) or any combination thereof; preferably where each cationic domain consists of one the following sequences: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B (SEQ ID NO: 17), R[Hyp]H[Hyp]HB (SEQ ID NO: 18), R[Hyp]RR[Hyp]R (SEQ ID NO: 19) or any combination thereof.

In some embodiments, each hydrophobic domain has a length of between 3-6 amino acids, preferably each hydrophobic domain has a length of 5 amino acids. In some embodiments, each hydrophobic domain includes a majority of hydrophobic amino acid residues, preferably each hydrophobic domain includes at least 70%, at least 75%, at least 80%, at least 85%, at least 90%, at least 95%, 100% hydrophobic amino acids. In some embodiments, each hydrophobic domain includes phenylalanine, leucine, Isoleucine, tyrosine, tryptophan, proline, and glutamine residues; preferably where each hydrophobic domain consists of phenylalanine, leucine, isoleucine, tyrosine, tryptophan, proline, and/or glutamine residues. In some embodiments, the peptide includes one hydrophobic domain. In some embodiments, each hydrophobic domain includes one of the following sequences: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), WWPW (SEQ ID NO: 26) or any combination thereof; preferably where the or each hydrophobic domain consists of one of the following sequences: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), WWPW (SEQ ID NO: 26) or any combination thereof.

In some embodiments, the peptide consists of two cationic domains and one hydrophobic domain, preferably where the peptide consists of one hydrophobic core domain flanked by two cationic arm domains.

In some embodiments, the peptide consists of one hydrophobic core domain including a sequence selected from: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), and WWPW (SEQ ID NO: 26), flanked by two cationic arm domains each including a sequence selected from: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B (SEQ ID NO: 17), R[Hyp]H[Hyp]HB (SEQ ID NO: 18), and R[Hyp]RR[Hyp]R (SEQ ID NO: 19).

In some embodiments, the peptide consists of one of the following sequences: RBRRBRRFQILYRBRBR (SEQ ID NO: 27), RBRRBRRYQFLIRBRBR (SEQ ID NO: 31), RBRRBRRILFQYRBRBR (SEQ ID NO: 32), RBRRBRFQILYBRBR (SEQ ID NO: 35), RBRRBRRFQILYRBHBH (SEQ ID NO: 37), RBRRBRRFQILYHBHBR (SEQ ID NO: 38), RBRRBRFQILYRBHBH (SEQ ID NO: 44).

In some embodiments, the peptide has the following amino acid sequence RBRRBRFQILYBRBR (SEQ ID NO: 35). In some embodiments, the peptide has the following amino acid sequence RBRRBRRFQILYRBHBH (SEQ ID NO: 37). In some embodiments, the peptide has the following amino acid sequence RBRRBRFQILYRBHBH (SEQ ID NO: 44). In some embodiments, the peptide is bonded to the rest of the conjugate through its N-terminus. In some embodiments, the C-terminus of the peptide is —$NH_2$.

In some embodiments, the peptide is bonded to the rest of the conjugate through its C-terminus. In some embodiments, the peptide is acylated at its N-terminus (e.g., with an acetyl group or an amino acid residue having $NH_2$— or AcNH— at its N-terminus). Preferably, in instances where the amino acid residue is present at the N-terminus of the peptide, it includes —$CONH_2$ in place of any —COOH that would otherwise be present.

In some embodiments, the conjugate is of the following structure:

[peptide]-[linker]-[oligonucleotide].

In some embodiments, the conjugate is of the following structure:

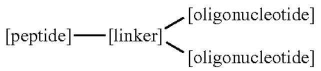

or

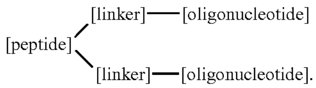

In some embodiments, the conjugate is of the following structure:

[peptide]-[linker]—[peptide]-[linker]-[oligonucleotide].

In some embodiments, each linker is independently of formula (I):

$$T_1\text{-}(CR^1R^2)_n\text{-}T_2. \quad \text{(I)}$$

where $T_1$ is a divalent group for attachment to the peptide and is selected from the group consisting of —NH— and carbonyl;

$T_2$ is a divalent group for attachment to an oligonucleotide and is selected from the group consisting of —NH— and carbonyl;

n is 1, 2 or 3;

each $R^1$ is independently —$Y^1$—$X^1$—$Z^1$, where $Y^1$ is absent or —$(CR^{A1}R^{A2})_m$—, where m is 1, 2, 3 or 4, and $R^{A1}$ and $R^{A2}$ are each independently hydrogen, OH, or (1-2C)alkyl;

$X^1$ is absent, —O—, —C(O)—, —C(O)O—, —OC(O)—, —CH($OR^{A3}$)—, —N($R^{A3}$)—, —N($R^{A3}$)—C(O)—, —N($R^{A3}$)—C(O)O—, —C(O)—N($R^{A3}$)—, —N($R^{A3}$)C(O)N($R^{A3}$)—, —N($R^{A3}$)C(N $R^{A3}$)N($R^{A3}$)—, —SO—, —S—, —SO2-, —$S(O)_2$N($R^{A3}$)—, or —N($R^{A3}$)$SO_2$—, where each $R^{A3}$ is independently selected from hydrogen and methyl; and $Z^1$ is a further oligonucleotide or is hydrogen, (1-6C)alkyl, (2-6C)alkenyl, (2-6C)alkynyl, aryl, (3-6C)cycloalkyl, (3-6C)cycloalkenyl, or heteroaryl, where each (1-6C)alkyl, (2-6C)alkenyl, (2-6C)alkynyl, aryl, (3-6C)cycloalkyl, (3-6C)cycloalkenyl, and heteroaryl is optionally substituted with one or more (e.g., 1, 2, 3, 4, or 5) substituent groups selected from the group consisting of (1-4C)alkyl, oxo, halo, cyano, nitro, hydroxy, carboxy, $NR^{A4}R^{A5}$, and (1-4C)alkoxy, where $R^{A4}$ and $R^{A5}$ are each independently selected from the group consisting of hydrogen and (1-4C)alkyl; and each $R^2$ is independently —$Y^2$—$X^2$—$Z^2$, where $Y^2$ is absent or a group of the formula —$[CR^{B1}R^{B2}]_m$— in which m is an integer selected from 1, 2, 3 or 4, and $R^{B1}$ and $R^{B2}$ are each independently selected from hydrogen, OH or (1-2C)alkyl;

$X^2$ is absent, —O—, —C(O)—, —C(O)O—, —OC(O)—, —CH($OR^{B3}$)—, —N($R^{B3}$)—, —N($R^{B3}$)—C(O)—, —N($R^{B3}$)—C(O)O—, —C(O)—N($R^{B3}$)—, —N($R^{B3}$)C(O)N($R^{B3}$)—, —N($R^{B3}$)C($NR^{B3}$)N($R^{B3}$)—, —SO—, —S— —$SO_2$—, —$S(O)_2$N($R^{B3}$)—, or —N($R^{B3}$)$SO_2$—, where each $R^{B3}$ is independently selected from hydrogen or methyl; and $Z^2$ is selected from hydrogen, (1-6C)alkyl, (2-6C)alkenyl, (2-6C)alkynyl, aryl, (3-6C)cycloalkyl, (3-6C)cycloalkenyl or heteroaryl, where each (1-6C)alkyl, (2-6C)alkenyl, (2-6C)alkynyl, aryl, (3-6C)cycloalkyl, (3-6C)cycloalkenyl or heteroaryl is optionally substituted by one or more (e.g., 1, 2, 3, 4, or 5) substituent groups selected from the group consisting of (1-4C) alkyl, oxo, halo, cyano, nitro, hydroxy, carboxy, $NR^{B4}R^{B5}$, and (1-4C)alkoxy, where $R^{B4}$ and $R^{B5}$ are each independently hydrogen or (1-2C) alkyl; with the proviso that; when n=1 and $T_1$ and $T_2$ are different to one another, then $R^1$ and $R^2$ are not both H; when n=1, $T_1$ and $T_2$ are different to one another and one of $R^1$ and $R^2$ is H then the other of $R^1$ and $R^2$ is not methyl; or when n=2 and each occurrence of $R^1$ and $R^2$ is H, then $T_1$ and $T_2$ are both —C(O)— or are both —NH—.

In some embodiments, $T_2$ is —C(O)—.

In some embodiments, each $R^1$ is independently —$Y^1$—$X^1$—$Z^1$, where:

$Y^1$ is absent or —$(CR^{A1}R^{A2})_m$—, where m is 1, 2, 3 or 4, and $R^{A1}$ and $R^{A2}$ are each hydrogen or (1-2C)alkyl;

$X^1$ is absent, —O—, —C(O)—, —C(O)O—, —N($R^{A3}$)—, —N($R^{A3}$)—C(O)—, —C(O)—N($R^{A3}$)—, —N($R^{A3}$)C(O)N($R^{A3}$)—, —N($R^{A3}$)C(N $R^{A3}$)N($R^{A3}$)— or —S—, where each $R^{A3}$ is independently hydrogen or methyl; and $Z^1$ is a further oligonucleotide or is hydrogen, (1-6C)alkyl, (2-6C)alkenyl, (2-6C)alkynyl, aryl, (3-6C)cycloalkyl, (3-6C)cycloalkenyl, or heteroaryl, where each (1-6C)alkyl, (2-6C) alkenyl, (2-6C)alkynyl, aryl, (3-6C)cycloalkyl, (3-6C)cycloalkenyl, and heteroaryl is optionally substituted by one or more (e.g., 1, 2, 3, 4, or 5) substituent groups selected from the group consisting of (1-4C)alkyl, oxo, halo, cyano, nitro, hydroxy, carboxy, NRA4RA5, and (1-4C)alkoxy, where $R^{M}$ and RA5 are each independently hydrogen or (1-2C)alkyl.

In some embodiments, each $R^1$ is independently —$Y^1$—$X^1$—$Z^1$, where:

$Y^1$ is absent or —$(CR^{A1}R^{A2})_m$—, where m is 1, 2, 3, or 4, and $R^{A1}$ and R" are each independently hydrogen or (1-2C)alkyl;

$X^1$ is absent, —O—, —C(O)—, —C(O)O—, —N($R^{A3}$)—, —N($R^{A3}$)—C(O)—, —C(O)—N($R^{A3}$)—, —N($R^{A3}$)C(O)N($R^{A3}$)—, —N($R^{A3}$)C($NR^{A3}$)N($R^{A3}$)—, or —S—, where each $R^{A3}$ is independently hydrogen or methyl; and $Z^1$ is a further oligonucleotide or is hydrogen, (1-6C)alkyl, aryl, (3-6C)cycloalkyl, or heteroaryl, where each (1-6C)alkyl, aryl, (3-6C)cycloalkyl, and heteroaryl is optionally substituted by one or more (e.g., 1, 2, 3, 4, or 5) substituent groups selected from the group consisting of (1-4C)alkyl, halo, and hydroxy.

In some embodiments, each $R^1$ is independently $—Y^1—X^1—Z^1$, where:

$Y^1$ is absent or a group of the formula $—(CR^{A1}R^{A2})_m—$, where m is 1, 2, 3 or 4, and $R^{A1}$ and $R^{A2}$ are each independently hydrogen or (1-2C)alkyl;

$X^1$ is absent, —C(O)—, —C(O)O—, $—N(R^{A3})—C(O)—$, $—C(O)—N(R^{A3})—$, where each $R^{A3}$ is hydrogen or methyl; and $Z^1$ is a further oligonucleotide or is hydrogen, (1-6C)alkyl, aryl, (3-6C)cycloalkyl, or heteroaryl, where each (1-6C)alkyl, aryl, (3-6C)cycloalkyl, and heteroaryl is optionally substituted by one or more (e.g., 1, 2, 3, 4, or 5) substituent groups selected from the group consisting of (1-4C)alkyl, halo, and hydroxy.

In some embodiments, each $R^1$ is independently a group of the formula $—Y^1—X^1—Z^1$, where:

$Y^1$ is absent, $—(CH_2)—$, or $—(CH_2CH_2)—$;

$X^1$ is absent, $—N(R^{A3})—C(O)—$, $—C(O)—N(R^{A3})—$, where each $R^{A3}$ is independently hydrogen or methyl; and $Z^1$ is hydrogen or (1-2C)alkyl.

In some embodiments, each $R^2$ is independently $—Y^2—Z^2$, where $Y^2$ is absent or $—(CR^{B1}R^{B2})_m—$, where m is 1, 2, 3 or 4, and $R^{B1}$ and $R^{B2}$ are each independently hydrogen or (1-2C)alkyl; and $Z^2$ is hydrogen or (1-6C)alkyl.

In some embodiments, each $R^2$ is hydrogen.

In some embodiments, n is 2 or 3. In some embodiments, n is 1.

In some embodiments, the linker is an acid residue selected from the group consisting of glutamic acid, succinic acid, and gamma-aminobutyric acid residues. In some embodiments, the linker is of the following structure:

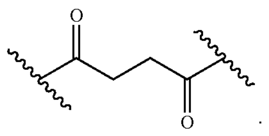 [SMILES: *C(=O)CCC(*)=O]

In some embodiments, the linker is of the following structure:

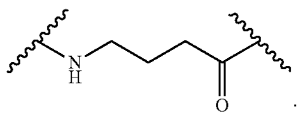 [SMILES: *NCCCC(*)=O]

In some embodiments, the linker is of the following structure:

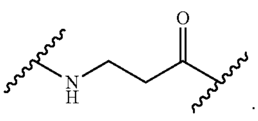 [SMILES: *NCCC(*)=O]

In some embodiments, the linker is of the following structure:

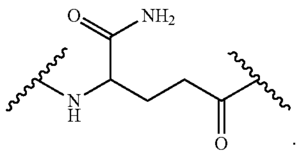 [SMILES: *NC(CCC(*)=O)C(N)=O]

In some embodiments, the linker is of the following structure:

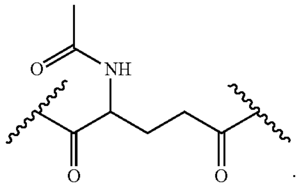 [SMILES: *C(=O)CCC(NC(C)=O)C(*)=O]

In some embodiments, the conjugate is of the following structure:

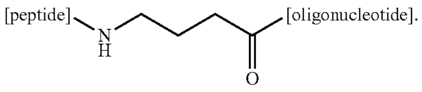

In some embodiments, the conjugate is of the following structure:

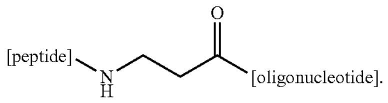

In some embodiments, the conjugate is of the following structure:

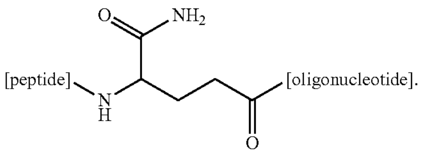

In some embodiments, the conjugate is of the following structure:

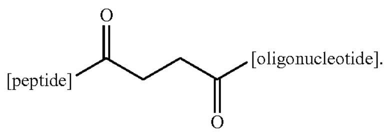

In some embodiments, the conjugate is of the following structure:

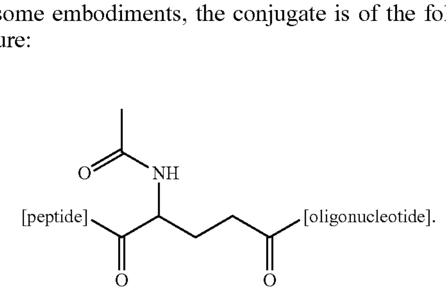

In some embodiments, the oligonucleotide is bonded to the linker or the peptide at its 3' terminus.

In some embodiments, the oligonucleotide includes the following group as its 5' terminus:

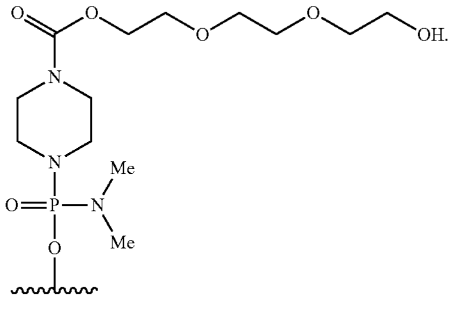 [SMILES: *OP(=O)(N(C)C)N1CCN(C(=O)OCCOCCOCCO)CC1]

In some embodiments, the oligonucleotide includes the following group as its 5' terminus:

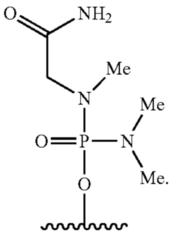

In some embodiments, the oligonucleotide includes hydroxyl as its 5' terminus.

In some embodiments, the conjugate is a conjugate, or a pharmaceutically acceptable salt thereof, of oligonucleotide 5'-CAATGCCATCCTGGAGTTCCTG-3' (SEQ ID NO: 194) having a 3'-terminus covalently linked via a glutamic acid residue to C-terminus of peptide Ac-RBRRBRFQILY-BRBR (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CAATGCCATCCTGGAGTTCCTG-3' (SEQ ID NO: 194) having a 3'-terminus covalently linked via a glutamic acid residue to N-terminus of peptide RBRRBRFQILY-BRBR—$NH_2$ (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CAATGCCATCCTGGAGTTCCTG-3' (SEQ ID NO: 194) having a 3'-terminus covalently linked via a beta-alanine residue to C-terminus of peptide Ac-RBRRBRFQI-LYBRBR (SEQ ID NO: 35).

In some embodiments, the conjugate is a conjugate, or a pharmaceutically acceptable salt thereof, of oligonucleotide 5'-CAATGCCATCCTGGAGTTCCTG-3' (SEQ ID NO: 194) having a 3'-terminus covalently linked via a glutamic acid residue to C-terminus of peptide Ac-RBRRBRFQI-LYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CAATGCCATCCTGGAGTTCCTG-3' (SEQ ID NO: 194) having a 3'-terminus covalently linked via a beta-alanine residue to C-terminus of peptide Ac-RBRRBRFQI-LYRBHBH (SEQ ID NO: 44).

In some embodiments, the conjugate is a conjugate of oligonucleotide 5'-GCTGCCCAATGCCATCCTG-GAGTTCCTGTAA-3' (SEQ ID NO: 193) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-GCTGCCCAATGCCATCCTGGAGTTCCTGTAA-3' (SEQ ID NO: 193) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-GCTGCCCAATGCCATCCTGGAGTTCCTGTAA-3' (SEQ ID NO: 193) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-ACATCAAGGAAGATGGCATTTCTAGTTTGG-3' (SEQ ID NO: 196) having a 3'-terminus covalently linked via a glutamic acid residue to N-terminus of peptide RBRR-BRFQILYBRBR—$NH_2$ (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-ACATCAAGGAAGATGGCATTTCTAGTTTGG-3' (SEQ ID NO: 196) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-ACATCAAGGAAGATGGCATTTCTAGTTTGG-3' (SEQ ID NO: 196) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-ACATCAAGGAAGATGGCATTTCTAGTTTGG-3' (SEQ ID NO: 196) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CTCCAACATCAAGGAAGATGGCATTTCTAG-3' (SEQ ID NO: 195) having a 3'-terminus covalently linked via a glutamic acid residue to C-terminus of peptide Ac-RBRRBRFQILYBRBR (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CTCCAACATCAAGGAAGATGGCATTTCTAG-3' (SEQ ID NO: 195) having a 3'-terminus covalently linked via a glutamic acid residue to N-terminus of peptide RBRRBRFQILYBRBR—$NH_2$ (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CTCCAACATCAAGGAAGATGGCATTTCTAG-3' (SEQ ID NO: 195) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-CTCCAACATCAAGGAAGATGGCATTTCTAG-3' (SEQ ID NO: 195) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CTCCAACATCAAGGAAGATGGCATTTCTAG-3' (SEQ ID NO: 195) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-GTTGCCTCCGGTTCTGAAGGTGTTC-3' (SEQ ID NO: 171) having a 3'-terminus covalently linked via a glutamic acid residue to C-terminus of peptide Ac-RBRRBRFQILYBRBR (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-GTTGCCTCCGGTTCTGAAGGTGTTC-3' (SEQ ID NO: 171) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-GTTGCCTCCGGTTCTGAAGGTGTTC-3' (SEQ ID NO: 171) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-GTTGCCTCCGGTTCTGAAGGTGTTC-3' (SEQ ID NO: 171) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-GTTGCCTCCGGTTCTGAAGGTGTTC-3' (SEQ ID NO: 171) having a 3'-terminus covalently linked via glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via glutamic acid residue to N-terminus of peptide RBRRBRFQILYBRBR—$NH_2$ (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via a glutamic acid residue to C-terminus of peptide Ac-RBRRBRFQILYBRBR (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CCTCCGGTTCTGAAGGTGTTCT-3' (SEQ ID NO: 162) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-CATTCAACTGTTGCCTCCGGTTCTGAAGGTG-3' (SEQ ID NO: 198) having a 3'-terminus covalently linked via a beta-alanine residue to C-terminus of peptide Ac-RBRRBRFQILYBRBR (SEQ ID NO: 35).

In some embodiments, the conjugate is a conjugate, or a pharmaceutically acceptable salt thereof, of oligonucleotide 5'-CATTCAACTGTTGCCTCCGGTTCTGAAGGTG-3' (SEQ ID NO: 198) having a 3'-terminus covalently linked via a glutamic acid residue to N-terminus of peptide RBRRBRFQILYBRBR—$NH_2$ (SEQ ID NO: 35), wherein free —COOH, if any, in the glutamic acid residue is replaced with —$CONH_2$.

In some embodiments, the conjugate is a conjugate, or a pharmaceutically acceptable salt thereof, of oligonucleotide 5'-CATTCAACTGTTGCCTCCGGTTCTGAAGGTG-3' (SEQ ID NO: 198) having a 3'-terminus covalently linked via a glutamic acid residue to C-terminus of peptide Ac-RBRRBRFQILYRBHBH (SEQ ID NO: 44), wherein free —COOH, if any, in the glutamic acid residue is replaced with —$CONH_2$.

In some embodiments, the conjugate is a conjugate, or a pharmaceutically acceptable salt thereof, of oligonucleotide 5'-CATTCAACTGTTGCCTCCGGTTCTGAAGGTG-3' (SEQ ID NO: 198) having a 3'-terminus covalently linked via a beta-alanine residue to C-terminus of peptide Ac-RBRRBRFQILYRBHBH (SEQ ID NO: 44).

In some embodiments, the conjugate is a conjugate, or a pharmaceutically acceptable salt thereof, of oligonucleotide 5'-CATTCAACTGTTGCCTCCGGTTCTGAAGGTG-3'

(SEQ ID NO: 198) having a 3'-terminus covalently linked via a glutamic acid residue to C-terminus of peptide Ac-RBRRBRFQILYBRBR (SEQ ID NO: 35), wherein free —COOH, if any, in the glutamic acid residue is replaced with —$CONH_2$.

For each conjugate, or pharmaceutically acceptable salt thereof, noted above or elsewhere herein in which the 3'-terminus of the oligonucleotide is covalently linked via a glutamic acid residue to C-terminus or N-terminus of the peptide, the conjugate or pharmaceutically acceptable salt thereof can therefore comprise the structure of:

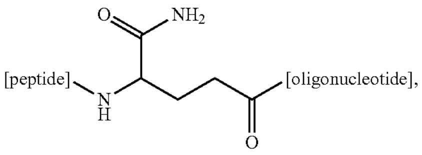

or a pharmaceutically acceptable salt thereof.

In some embodiments, the oligonucleotide comprises the following group as its 5' terminus:

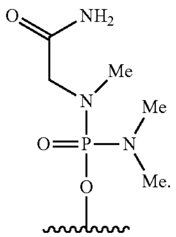

In another aspect, the invention provides a pharmaceutical composition including a conjugate described herein and a pharmaceutically acceptable excipient.

In yet another aspect, the invention provides a method of treating a subject having DMD or BMD, the method including administering to the subject a therapeutically effective amount of the conjugate described herein or the pharmaceutical composition described herein. The invention further includes the compositions described herein for use in treating a subject having DMD or BMD.

In some embodiments, the subject has DMD.

Preferably, the oligonucleotide is a morpholino (more preferably, a morpholino with all morpholino internucleoside linkages being —$P(O)(NMe_2)O$—).

Definitions

References to "X" throughout denote any form of the amino acid aminohexanoic acid, such as 6-aminohexanoic acid.

References to "B" throughout denote the amino acid beta-alanine.

References to "[Hyp]" throughout denote the amino acid hydroxyproline.

References to "Ac" throughout denote an acetyl group ($CH_3$—C(O)—).

References to other capital letters throughout denote the relevant genetically encoded amino acid residue in accordance with the accepted alphabetic amino acid code.

The term "alkyl," as used herein, refers to a straight or branched chain hydrocarbon group containing a total of one to twenty carbon atoms, unless otherwise specified (e.g., (1-6C)alkyl, (1-4C) alkyl, (1-3C)alkyl, or (1-2C)alkyl). Non-limiting examples of alkyls include methyl, ethyl, 1-methylethyl, propyl, 1-methylbutyl, 1-ethylbutyl, etc. References to individual alkyl groups such as "propyl" are specific for the straight chain version only, and references to individual branched chain alkyl groups such as "isopropyl" are specific for the branched chain version only.

The term "alkenyl", as used herein, refers to an aliphatic group containing having one, two, or three carbon-carbon double bonds and containing a total of two to twenty carbon atoms, unless otherwise specified (e.g., (2-6C)alkenyl, (2-4C)alkenyl, or (2-3C)alkenyl). Non-limiting examples of alkenyl include vinyl, allyl, homoallyl, isoprenyl, etc. Unless otherwise specified, alkenyl may be optionally substituted by one, two, three, four, or five groups selected from the group consisting of carbocyclyl, aryl, heterocyclyl, heteroaryl, oxo, halogen, and hydroxyl.

The term "alkynyl", as used herein, refers to an aliphatic group containing one, two, or three carbon-carbon triple bonds and containing a total of two to twenty carbon atoms, unless otherwise specified (e.g., (2-6C)alkynyl, (2-4C)alkynyl, or (2-3C)alkynyl). Non-limiting examples of alkynyl include ethynyl, propargyl, homopropargyl, but-2-yn-1-yl, 2-methyl-prop-2-yn-1-yl, etc. Unless otherwise specified, alkynyl may be optionally substituted by one, two, three, four, or five groups selected from the group consisting of carbocyclyl, aryl, heterocyclyl, heteroaryl, oxo, halogen, and hydroxyl.

The term amino acid "residue" refers to a divalent group that is an amino acid, in which one N—H bond is replaced with a valency and one carboxylic C—O bond is replaced with a valency. The N—H bond or the carboxylic C—O bond may be, e.g., on the side chain.

By "arginine rich," it is meant that at least 40% of the cationic domain is formed of arginine residues.

The term "artificial amino acid," as used herein, refers to an abiogenic amino acid (e.g., non-proteinogenic). For example, artificial amino acids may include synthetic amino acids, modified amino acids (e.g., those modified with sugars), non-natural amino acids, man-made amino acids, spacers, and non-peptide bonded spacers. Synthetic amino acids may be those that are chemically synthesized by man. For the avoidance of doubt, aminohexanoic acid (X) is an artificial amino acid in the context of the present invention. For the avoidance of doubt, beta-alanine (B) and hydroxyproline (Hyp) occur in nature and therefore are not artificial amino acids in the context of the present invention but are natural amino acids. Artificial amino acids may include, for example, 6-aminohexanoic acid (X), tetrahydroisoquinoline-3-carboxylic acid (TIC), 1-(amino)cyclohexanecarboxylic acid (Cy), 3-azetidine-carboxylic acid (Az), and 11-aminoundecanoic acid.

The term "aryl," as used herein, refers to a carbocyclic ring system containing one, two, or three rings, at least one of which is aromatic. An unsubstituted aryl contains a total of 6 to 14 carbon atoms. The term aryl includes both monovalent species and divalent species. Examples of aryl groups include, but are not limited to, phenyl, naphthyl, indanyl, and the like. In particular embodiments, an optionally substituted aryl is optionally substituted phenyl.

By "bridged ring systems," as used herein, are meant ring systems in which two rings share more than two atoms, see for example Advanced Organic Chemistry, by Jerry March, 4$^{th}$ Edition, Wiley Interscience, pages 131-133, 1992. Examples of bridged heterocyclyl ring systems include, aza-bicydo [2.2.1]heptane, 2-oxa-5-azabicyclo[2.2.1]heptane, aza-bicyclo[2.2.2]octane, aza-bicyclo [3.2.1]octane, quinuclidine, etc.

The term "carbonyl," as used herein, refers to a group of the following structure —C(O)—. Non-limiting examples of carbonyl groups include those found, e.g., in acetone, ethyl acetate, proteinogenic amino acids, acetamide, etc.

References made herein to "cationic" denote an amino acid or domain of amino acids having an overall positive charge at physiological pH.

The term "(m-nC)" or "(m-nC) group" used alone or as a prefix, refers to a group having a total of m to n carbon atoms, when unsubstituted.

The term "complementary," as used herein in reference to a nucleobase sequence, refers to the nucleobase sequence having a pattern of contiguous nucleobases that permits an oligonucleotide having the nucleobase sequence to hybridize to another oligonucleotide or nucleic acid to form a duplex structure under physiological conditions. Complementary sequences include Watson-Crick base pairs formed from natural and/or modified nucleobases. Complementary sequences can also include non-Watson-Crick base pairs, such as wobble base pairs (guanosine-uracil, hypoxanthine-uracil, hypoxanthine-adenine, and hypoxanthine-cytosine) and Hoogsteen base pairs.

The term "cycloalkyl," as used herein, refers to a saturated carbocyclic ring system containing one or two rings, and containing a total of 3 to 10 carbon atoms, unless otherwise specified. The two-ring cycloalkyls may be arranged as fused ring systems (two bridgehead carbon atoms are directly bonded to one another), bridged ring systems (two bridgehead carbon atoms are linked to one another via a covalent linker containing at least one carbon atom), and spiro-ring (two rings are fused at the same cabron atom) systems. Non-limiting examples of cycloalkyl include cyclopropyl, cyclobutyl, cyclopentyl, cyclohexyl, cycloheptyl, bicyclo[2.2.1]heptyl, etc.

The term "cycloalkenyl," as used herein, refers to a non-aromatic, unsaturated, carbocyclic ring system containing one or two rings; containing one, two, or three endocyclic double bonds; and containing a total of 3 to 10 carbon atoms, unless otherwise specified. The two-ring cycloalkenyls may be arranged as fused ring systems (two bridgehead carbon atoms are directly bonded to one another), bridged ring systems (two bridgehead carbon atoms are linked to one another via a covalent linker containing at least one carbon atom), and spiro-ring (two rings are fused at the same cabron atom) systems. Non-limiting examples of cycloalkenyl include cyclobutenyl, cyclopentenyl, cyclohexenyl, cycloheptenyl, 3-cyclohexen-1-yl, cyclooctenyl, etc.

"Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2 and 3. Alpha-helices 1 and 3 are each formed by 7 helix turns, probably interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between amino acids 47 and 48 in the first part of alpha-helix 2. The other intron is found at different positions in the repeat, usually scattered over helix-3. Dystrophin also contains a cysteine-rich domain at about amino acids 3080-3360), including a cysteine-rich segment (i.e., 15 Cysteines in 280 amino acids) showing homology to the C-terminal domain of the slime mold (*Dictyostelium discoideum*) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence that lead to incorrect splicing. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

An "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA. The human dystrophin gene has about 75 exons.

"Exon skipping" refers generally to the process by which an entire exon, or a portion thereof, is removed from a given pre-processed RNA, and is thereby excluded from being present in the mature RNA, such as the mature mRNA that is translated into a protein. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence that otherwise causes aberrant splicing. In certain embodiments, the exon being skipped is exon 45, 51, and/or 53 of the human dystrophin gene.

The term "halo" or "halogeno," as used herein, refer to fluoro, chloro, bromo, and iodo.

By "histidine rich," it is meant that at least 40% of the cationic domain is formed of histidine residues.

The terms "heteroaryl" or "heteroaromatic," as used interchangeably herein, refer to a ring system containing one, two, or three rings, at least one of which is aromatic and containing one to four (e.g., one, two, or three) heteroatoms selected from the group consisting of nitrogen, oxygen, and sulfur. An unsubstituted heteroaryl group contains a total of one to nine carbon atoms. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example, a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example, a single heteroatom. In some embodiments, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1.2.3.4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4, 5,6,7-tetrahydrobenzofuranyl, indolinyl, 1,2,3,4-tetrahydro-1,8-naphthyridinyl, 1.2.3.4-tetrahydropyrido[2,3-b]pyrazinyl and 3,4-dihydro-2W-pyrido[3,2-b][1,4]oxazinyl. Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups. Examples of six membered heteroaryl groups include but are not limited to pyridyl, pyrazinyl, pyridazinyl, pyrimidinyl and triazinyl. A bicyclic heteroaryl group may be, for example, a group selected from: a benzene ring fused to a 5- or 6-membered ring containing 1, 2 or 3 ring heteroatoms; a pyridine ring fused to a 5- or 6-membered ring containing 1, 2 or 3 ring heteroatoms; a pyrimidine ring fused to a 5- or 6-membered ring containing 1 or 2 ring heteroatoms; a pyrrole ring fused to a 5- or 6-membered ring containing 1, 2 or 3 ring heteroatoms; a pyrazole ring fused to a 5- or 6-membered ring containing 1 or 2 ring heteroatoms; a pyrazine ring fused to a 5- or 6-membered ring containing 1 or 2 ring heteroatoms; an imidazole ring fused to a 5- or 6-membered ring containing 1 or 2 ring heteroatoms; an oxazole ring fused to a 5- or 6-membered ring containing 1 or 2 ring heteroatoms; an isoxazole ring fused to a 5- or 6-membered ring containing 1 or 2 ring heteroatoms; a thiazole ring fused to a 5- or 6-membered ring containing 1 or 2 ring heteroatoms; an isothiazole ring fused to a 5- or 6-membered ring containing 1 or 2 ring heteroatoms; a thiophene ring fused to a 5- or 6-membered ring containing 1, 2 or 3 ring heteroatoms; a furan ring fused to a 5- or 6-membered ring containing 1, 2 or 3 ring heteroatoms; a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms. Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups. Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The terms "heterocyclyl," as used herein, refer to a ring system containing one, two, or three rings, at least one of which containing one to four (e.g., one, two, or three) heteroatoms selected from the group consisting of nitrogen, oxygen, and sulfur, provided that the ring system does not contain aromatic rings that also include an endocyclic heteroatom. An unsubstituted heterocyclyl group contains a total of two to nine carbon atoms. The term heterocyclyl includes both monovalent species and divalent species. Examples of heterocyclyl groups are monocyclic and bicyclic groups containing from five to twelve ring members, and more usually from five to ten ring members. The heterocyclyl group can be, for example, a 5- or 6-membered monocyclic ring or a 9- or 10-membered bicyclic ring, for example, a bicyclic structure formed from fused five and six membered rings or two fused six membered rings. Each ring may contain up to about four heteroatoms typically selected from nitrogen, sulfur and oxygen. Non-limiting examples of heterocyclyl groups include, e.g., pyrrolidine, piperazine, piperidine, azepane, 1,4-diazepane, tetrahydrofuran, tetrahydropyran, oxepane, 1,4-dioxepane, tetrahydrothiophene, tetrahydrothiopyran, indoline, benzopyrrolidine, 2,3-dihydrobenzofuran, phthalan, isochroman, and 2,3-dihydrobenzothiophene.

The term "internucleoside linkage," as used herein, represents a group or bond that forms a covalent linkage between adjacent nucleosides in an oligonucleotide. An internucleoside linkage is an unmodified internucleoside linkage or a modified internucleoside linkage. An "unmodified internucleoside linkage" is a phosphate (—O—P(O)(OH)—O—) internucleoside linkage ("phosphate phosphodiester"). A "modified internucleoside linkage" is an internucleoside linkage other than a phosphate phosphodiester. The two main classes of modified internucleoside linkages are defined by the presence or absence of a phosphorus atom. Non-limiting examples of phosphorus-containing internucleoside linkages include phosphodiester linkages, phosphotriester linkages, phosphorothioate diester linkages, phosphorothioate triester linkages, morpholino internucleoside linkages, methylphosphonates, and phosphoramidate. Non-limiting examples of non-phosphorus internucleoside linkages include methylenemethylimino (—$CH_2$—$N(CH_3)$—O—$CH_2$—), thiodiester (—O—C(O)—S—), thionocarbamate (—O—C(O)(NH)—S—), siloxane (—O—$Si(H)_2$—O—), and N,N'-dimethylhydrazine (—$CH_2$—$N(CH_3)$—$N(CH_3)$—). Phosphorothioate linkages are phosphodiester linkages and phosphotriester linkages in which one of the non-bridging oxygen atoms is replaced with a sulfur atom. In some embodiments, an internucleoside linkage is a group of the following structure:

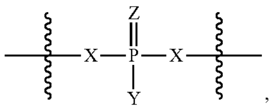

where

Z is O, S, or Se;

Y is —X-L-$R^1$;

each X is independently —O—, —S—, —N(-L-$R^1$)—, or L;

each L is independently a covalent bond or a linker (e.g., optionally substituted $C_{1-60}$ aliphatic linker or optionally substituted $C_{2-60}$ heteroaliphatic linker);

each $R^1$ is independently hydrogen, —S—S—$R^2$, —O—CO—$R^2$, —S—CO—$R^2$, optionally substituted $C_{1-9}$ heterocyclyl, or a hydrophobic moiety; and each $R^2$ is independently optionally substituted $C_{1-10}$ alkyl, optionally substituted $C_{2-10}$ heteroalkyl, optionally substituted $C_{6-10}$ aryl, optionally substituted $C_{6-10}$ aryl $C_{1-6}$ alkyl, optionally substituted $C_{1-9}$ heterocyclyl, or optionally substituted $C_{1-9}$ heterocyclyl $C_{1-6}$ alkyl.

When L is a covalent bond, $R^1$ is hydrogen, Z is oxygen, and all X groups are —O—, the internucleoside group is known as a phosphate phosphodiester. When L is a covalent bond, $R^1$ is hydrogen, Z is sulfur, and all X groups are —O—, the internucleoside group is known as a phosphorothioate diester. When Z is oxygen, all X groups are —O—, and either (1) L is a linker or (2) $R^1$ is not a hydrogen, the internucleoside group is known as a phosphotriester. When Z is sulfur, all X groups are —O—, and either (1) L is a linker or (2) $R^1$ is not a hydrogen, the internucleoside group is known as a phosphorothioate triester. Non-limiting examples of phosphorothioate triester linkages and phosphotriester linkages are described in US 2017/0037399, the disclosure of which is incorporated herein by reference.

An "intron" refers to a nucleic acid region (within a gene) that is not translated into a protein. An intron is a non-coding section that is transcribed into a precursor mRNA (pre-mRNA), and subsequently removed by splicing during formation of the mature RNA.

The term "morpholino," as used herein in reference to a class of oligonucleotides, represents an oligomer of at least 10 morpholino monomer units interconnected by morpholino internucleoside linkages. A morpholino includes a 5' group and a 3' group. For example, a morpholino may be of the following structure:

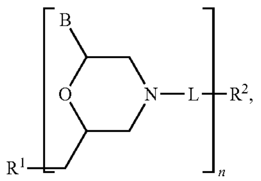

where n is an integer of at least 10 (e.g., 12 to 30) indicating the number of morpholino subunits and associated groups L;

each B is independently a nucleobase;

$R^1$ is a 5' group ($R^1$ may be referred to herein as a 5' terminus);

$R^2$ is a 3' group ($R^2$ may be referred to herein as a 3' terminus); and

L is (i) a morpholino internucleoside linkage or, (ii) if L is attached to $R^2$, a covalent bond.

A 5' group in morpholino may be, e.g., hydroxyl, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a bond to a peptide, a bond to a peptide/linker combination, an endosomal escape moiety, a neutral organic polymer, or a group of the following structure:

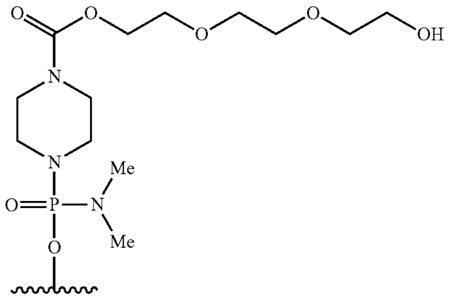

or

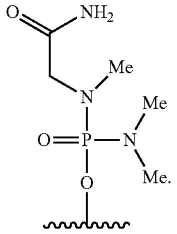

Preferred 5' group are hydroxyl and groups of the following structure:

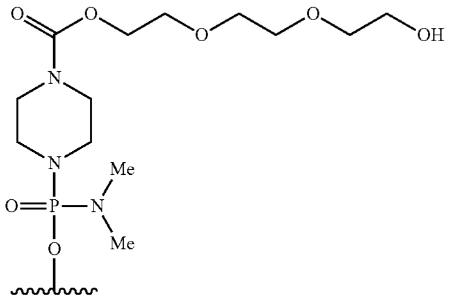

or

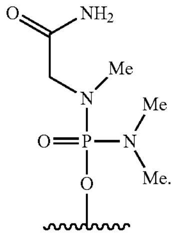

A more preferred 5' group is of the following structure:

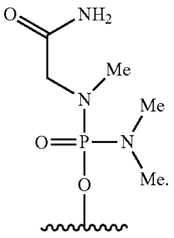

A 3' group in morpholino may be, e.g., hydrogen, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a bond to a peptide, a bond to a peptide/linker combination, an endosomal escape moiety, a neutral organic polymer, or a group of the following structure:

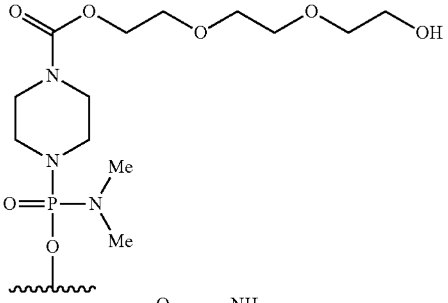

or

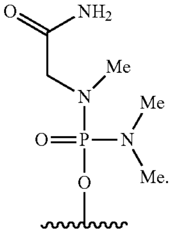

In a conjugate of an oligonucleotide that is a morpholino and a peptide that is covalently bonded or linked to the oligonucleotide, the preferred 3' group is a bond to a peptide or a bond to a peptide/linker combination.

The term "morpholino internucleoside linkage," as used herein, represents a divalent group of the following structure:

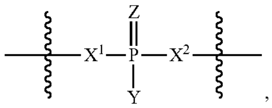

, where

Z is O or S;

$X^1$ is a bond, —$CH_2$—, or —O—;

$X^2$ is a bond, —$CH_2$—O—, or —O—; and

Y is —$NR_2$, where each R is independently H or $C_{1-6}$ alkyl (e.g., methyl), or both R combine together with the nitrogen atom to which they are attached to form a $C_{2-9}$ heterocyclyl (e.g., N-piperazinyl); provided that both $X^1$ and $X^2$ are not simultaneously a bond.

The term "morpholino subunit," as used herein, refers to the following structure:

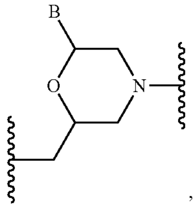

, where B is a nucleobase.

The term "nucleobase," as used herein, represents a nitrogen-containing heterocyclic ring found at the 1' position of the ribofuranose/2'-deoxyribofuranose of a nucleoside. Nucleobases are unmodified or modified. As used herein, "unmodified" or "natural" nucleobases include the purine bases adenine (A) and guanine (G), and the pyrimidine bases thymine (T), cytosine (C), and uracil (U). Modified nucleobases include 5-substituted pyrimidines, 6-azapyrimidines, alkyl or alkynyl substituted pyrimidines, alkyl substituted purines, and N-2, N-6 and O-6 substituted purines, as well as synthetic and natural nucleobases, e.g., 5-methylcytosine, 5-hydroxymethyl cytosine, xanthine, hypoxanthine, 2-aminoadenine, 6-alkyl (e.g., 6-methyl) adenine and guanine, 2-alkyl (e.g., 2-propyl) adenine and guanine, 2-thiouracil, 2-thiothymine, 2-thiocytosine, 5-halouracil, 5-halocytosine, 5-propynyl uracil, 5-propynyl cytosine, 5-trifluoromethyl uracil, 5-trifluoromethyl cytosine, 7-methyl guanine, 7-methyl adenine, 8-azaguanine, 8-azaadenine, 7-deazaguanine, 7-deazaadenine, 3-deazaguanine, 3-deazaadenine. Certain nucleobases are particularly useful for increasing the binding affinity of nucleic acids, e g., 5-substituted pyrimidines; 6-azapyrimidines; N2-, N6-, and/or O6-substituted purines. Nucleic acid duplex stability can be enhanced using, e.g., 5-methylcytosine. Non-limiting examples of nucleobases include: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example, 7-deazaadenine, 7-deazaguanine, 2-aminopyridine, or 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613;

Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

The term "nucleoside," as used herein, represents sugar-nucleobase compounds and groups known in the art, as well as modified or unmodified 2'-deoxyribofuranrpose-nucleobase compounds and groups known in the art. The sugar may be ribofuranose. The sugar may be modified or unmodified. An unmodified ribofuranose-nucleobase is ribofuranose having an anomeric carbon bond to an unmodified nucleobase. Unmodified ribofuranose-nucleobases are adenosine, cytidine, guanosine, and uridine. Unmodified 2'-deoxyribofuranose-nucleobase compounds are 2'-deoxyadenosine, 2'-deoxycytidine, 2'-deoxyguanosine, and thymidine. The modified compounds and groups include one or more modifications selected from the group consisting of nucleobase modifications and sugar modifications described herein. A nucleobase modification is a replacement of an unmodified nucleobase with a modified nucleobase. A sugar modification may be, e.g., a 2'-substitution, locking, carbocyclization, or unlocking. A 2'-substitution is a replacement of 2'-hydroxyl in ribofuranose with 2'-fluoro, 2'-methoxy, or 2'-(2-methoxy) ethoxy. Alternatively, a 2'-substitution may be a 2'-(ara) substitution, which corresponds to the following structure:

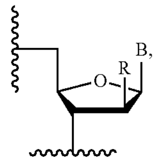

where B is a nucleobase, and R is a 2'-(ara) substituent (e.g., fluoro). 2'-(ara) substituents are known in the art and can be same as other 2'-substituents described herein. In some embodiments, 2'-(ara) substituent is a 2'-(ara)-F substituent (R is fluoro). A locking modification is an incorporation of a bridge between 4'-carbon atom and 2'-carbon atom of ribofuranose. Nucleosides having a locking modification are known in the art as bridged nucleic acids, e.g., locked nucleic acids (LNA), ethylene-bridged nucleic acids (ENA), and cEt nucleic acids. The bridged nucleic acids are typically used as affinity enhancing nucleosides. A "nucleoside" may also refer to a morpholino subunit.

The term "nucleotide," as used herein, represents a nucleoside bonded to an internucleoside linkage or a monovalent group of the following structure $—X_1—P(X^2)(R^1)_2$, where $X^1$ is O, S, or NH, and $X^2$ is absent, =O, or =S, and each $R^1$ is independently —OH, $—N(R^2)_2$, or $—O—CH_2CH_2CN$, where each $R^2$ is independently an optionally substituted alkyl, or both $R^2$ groups, together with the nitrogen atom to which they are attached, combine to form an optionally substituted heterocyclyl.

The term "oligonucleotide," as used herein, represents a structure containing 10 or more contiguous nucleosides covalently bound together by internucleoside linkages; a morpholino containing 10 or more morpholino subunits; or a peptide nucleic acid containing 10 or more morpholino subunits. Preferably, an oligonucleotide is a morpholino.

The term "optionally substituted" refers to groups, structures, or molecules that may be substituted or unsubstituted as described for each respective group. The term "wherein a/any CH, $CH_2$, $CH_3$ group or heteroatom (i.e., NH) within a $R^1$ group is optionally substituted" means that (any) one of the hydrogen radicals of the $R^1$ group is substituted by a relevant stipulated group.

In this specification the term "operably linked" may include the situation where a selected nucleotide sequence and regulatory nucleotide sequence are covalently linked in such a way as to place the expression of a nucleotide coding sequence under the control of the regulatory sequence, as such, the regulatory sequence is capable of effecting transcription of a nucleotide coding sequence which forms part or all of the selected nucleotide sequence. Where appropriate, the resulting transcript may then be translated into a desired peptide.

The term "pharmaceutically acceptable," as used herein, refers to those compounds, materials, compositions, and/or dosage forms, which are suitable for contact with the tissues of an individual (e.g., a human), without excessive toxicity, irritation, allergic response and other problem complications commensurate with a reasonable benefit/risk ratio.

The term "pharmaceutically acceptable salt," as used herein, means any pharmaceutically acceptable salt of a conjugate, oligonucleotide, or peptide disclosed herein. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutical composition," as used herein, represents a composition containing an oligonucleotide described herein, formulated with a pharmaceutically acceptable excipient, and manufactured or sold with the approval of a governmental regulatory agency as part of a therapeutic regimen for the treatment of disease in a subject.

The term "reduce" or "inhibit" may relate generally to the ability of one or more compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy, or reductions in the expression of defective forms of dystrophin, such as the altered forms of dystrophin that are expressed in individuals with DMD or BMD. A "decrease" in a response may be statistically significant as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "subject," as used herein, represents a human or non-human animal (e.g., a mammal) that is suffering from, or is at risk of, disease, disorder, or condition, as determined by a qualified professional (e.g., a doctor or a nurse practitioner) with or without known in the art laboratory test(s) of sample(s) from the subject. Non-limiting examples of diseases, disorders, and conditions include Duchenne muscular dystrophy (DMD) and Becker muscular dystrophy (BMD).

A "sugar" or "sugar moiety," includes naturally occurring sugars having a furanose ring or a structure that is capable of replacing the furanose ring of a nucleoside. Sugars included in the nucleosides of the invention may be non-furanose (or 4'-substituted furanose) rings or ring systems or open systems. Such structures include simple changes relative to the natural furanose ring (e.g., a six-membered ring). Alternative sugars may also include sugar surrogates wherein the furanose ring has been replaced with another ring system such as, e.g., a morpholino or hexitol ring system. Non-limiting examples of sugar moieties useful that may be included in the oligonucleotides of the invention include β-D-ribose, β-D-2'-deoxyribose, substituted sugars (e.g., 2', 5', and bis substituted sugars), 4'-S-sugars (e.g., 4'-S-ribose, 4'-S-2'-deoxyribose, and 4'-S-2'-substituted ribose), bicyclic sugar moieties (e.g., the 2'-O—$CH_2$-4' or 2'-O—$(CH_2)_2$-4' bridged ribose derived bicyclic sugars) and sugar surrogates (when the ribose ring has been replaced with a morpholino or a hexitol ring system).

"Treatment" and "treating," as used herein, refer to the medical management of a subject with the intent to improve, ameliorate, or stabilize a disease, disorder, or condition (e.g., DMD or BMD). This term includes active treatment (treatment directed to improve DMD or BMD); palliative treatment (treatment designed for the relief of symptoms of DMD or BMD); and supportive treatment (treatment employed to supplement another therapy).

Throughout the description and claims of this specification, the words "comprise" and "contain" and variations of them mean "including but not limited to," and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references to "conjugates" also refer to solvates thereof.

All references to "oligonucleotides" also refer to salts and solvates thereof. Unless otherwise specified, all peptides are shown herein in N-terminus to C-terminus direction (left to right). Unless otherwise specified, all oligonucleotides are shown herein in 5' to 3' direction (left to right).

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive.

DETAILED DESCRIPTION PATENT

Figure 1:
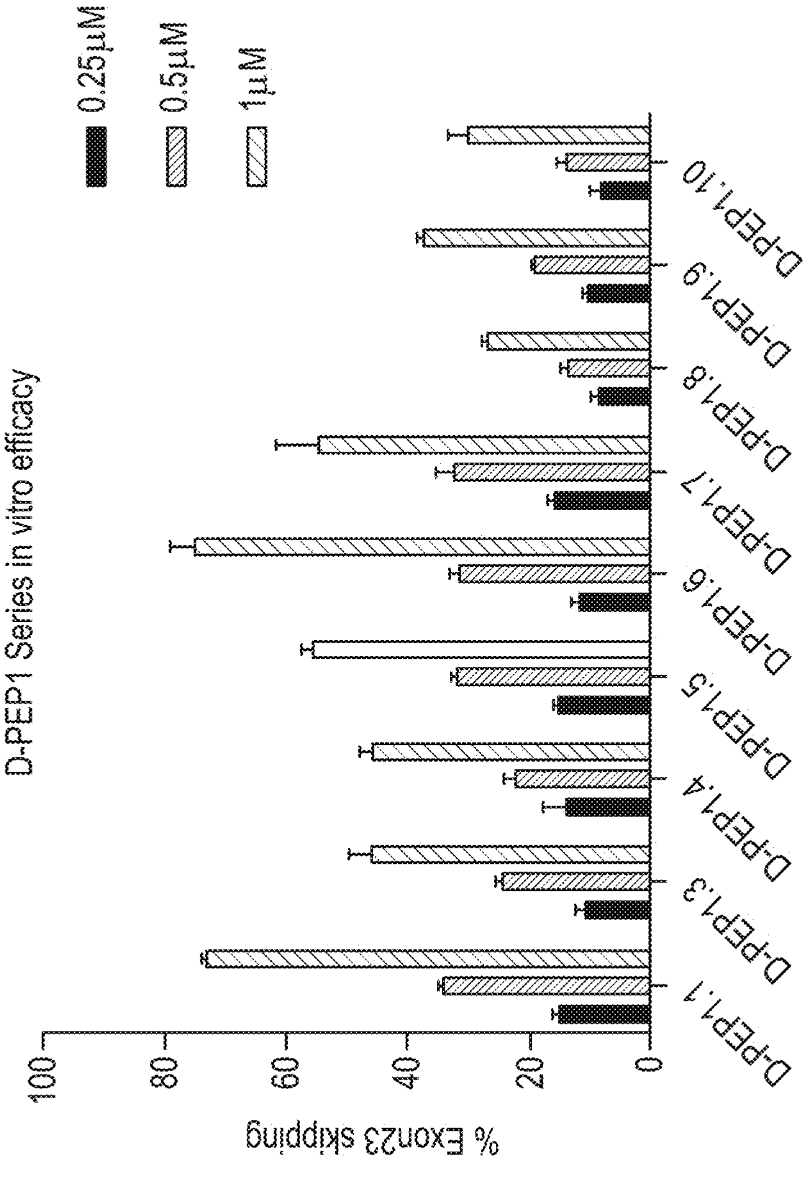
FIG. 1: shows the in vitro exon 23 skipping efficacy of some of the DPEP1 series of peptides conjugated to an antisense therapeutic PMO at 0.25 μM, 0.5 μM and 1 μM in H2K-mdx cells as measured by densitometry analysis of nested RT-PCR (Error bars: standard deviation, n$^{3}$3)
Figure 2:
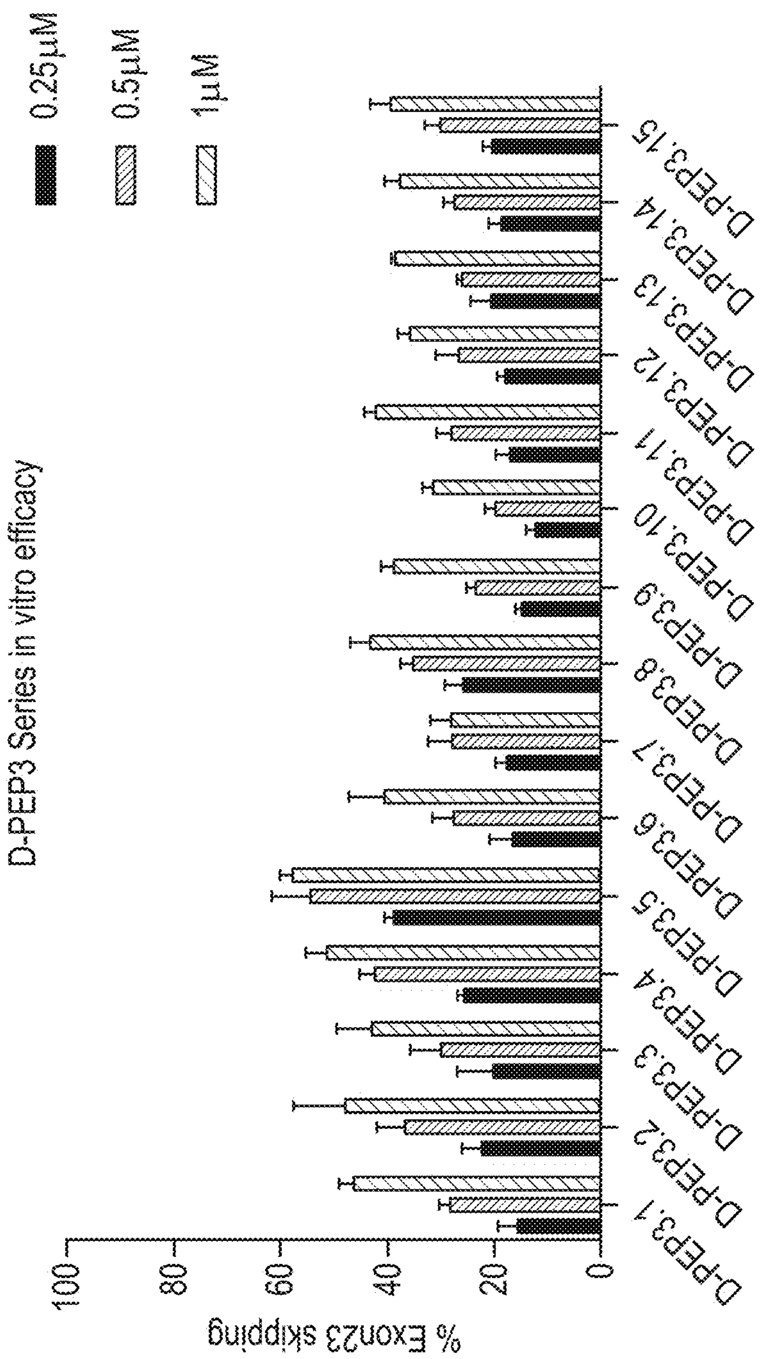
FIG. 2: shows the in vitro exon 23 skipping efficacy of some of the DPEP3 series of peptides conjugated to an antisense therapeutic PMO at 0.25 μM, 0.5 μM and 1 μM in H2K-mdx cells as measured by densitometry analysis of nested RT-PCR (Error bars: standard deviation, n$^{3}$3)
Figure 3A:
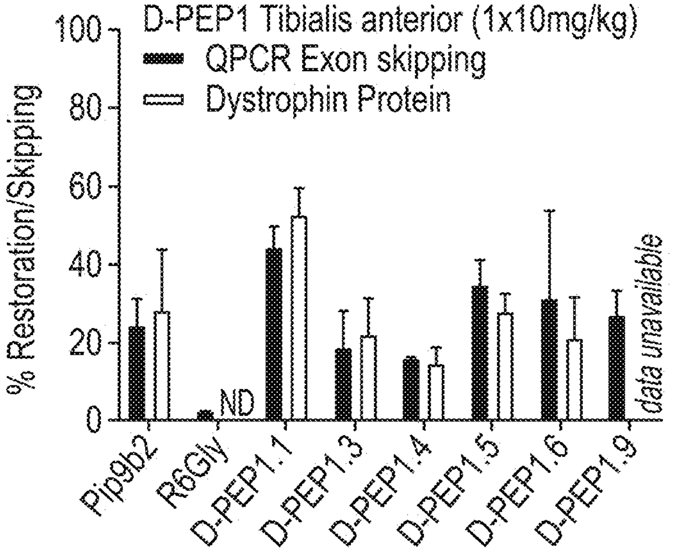
FIGS. 3A-3C: show the in vivo efficacy of some of the DPEP1 series of peptides conjugated to an antisense therapeutic PMO in (3A) Tibalis anterior muscle, (3B) diaphragm, and (3C) heart muscle following a single 10 mg/kg intravenous dose into mdx mice measured by western blot and qRT-PCR (Error bars: standard deviation, n=3)
Figure 3B:
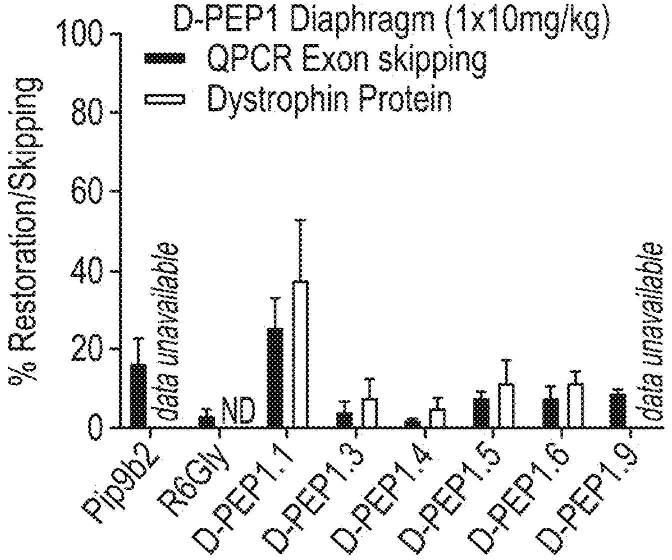
Figure 3C:
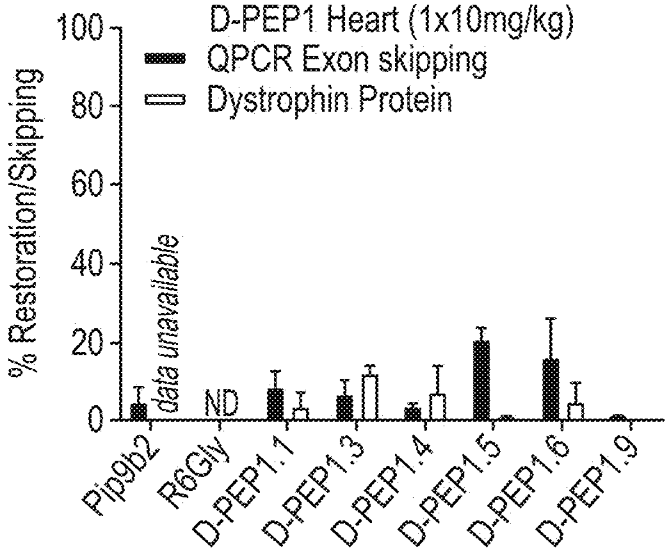
Figure 4A:
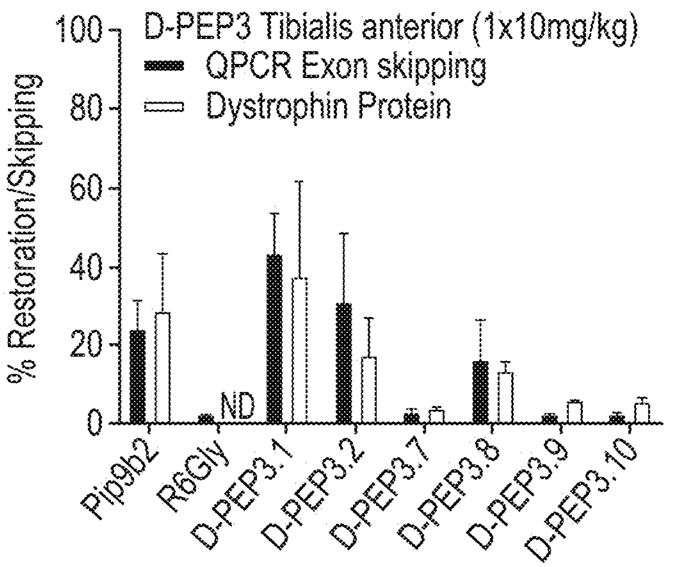
FIGS. 4A-4C: show the in vivo efficacy of some of the DPEP3 series of peptides conjugated to an antisense therapeutic PMO in (4A) Tibalis anterior muscle, (4B) diaphragm, and (4C) heart muscle following a single 10 mg/kg intravenous dose into mdx mice measured by western blot and qRT-PCR (Error bars: standard deviation, n=3)
Figure 4B:
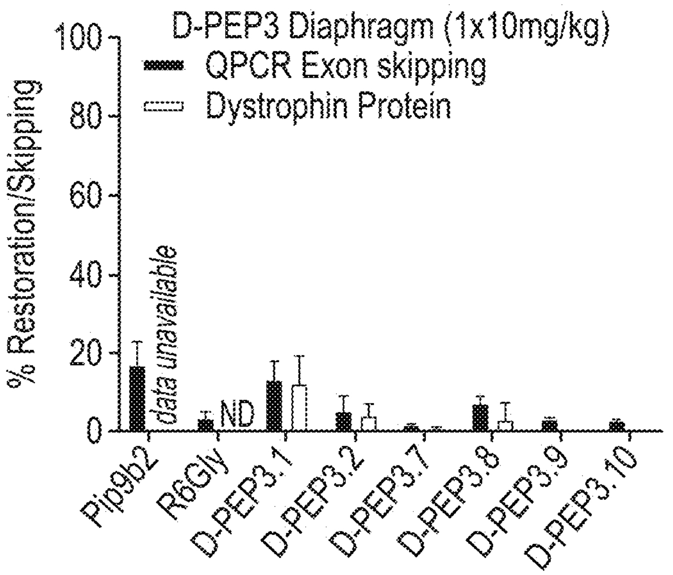
Figure 4C:
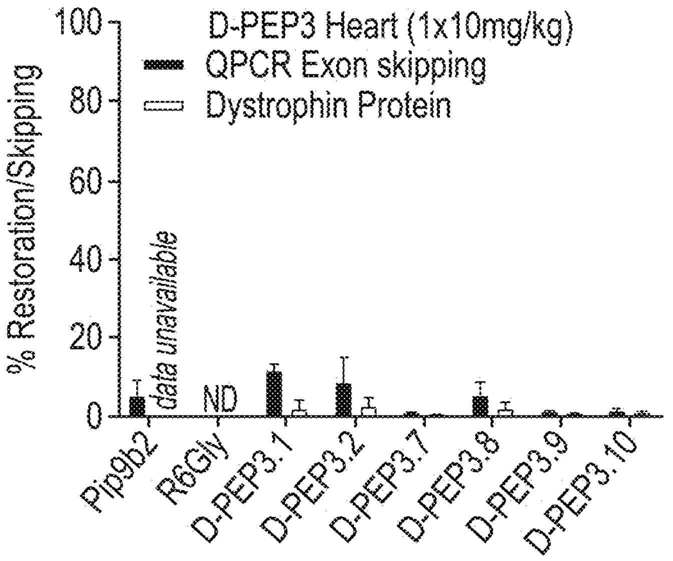
Figure 5:
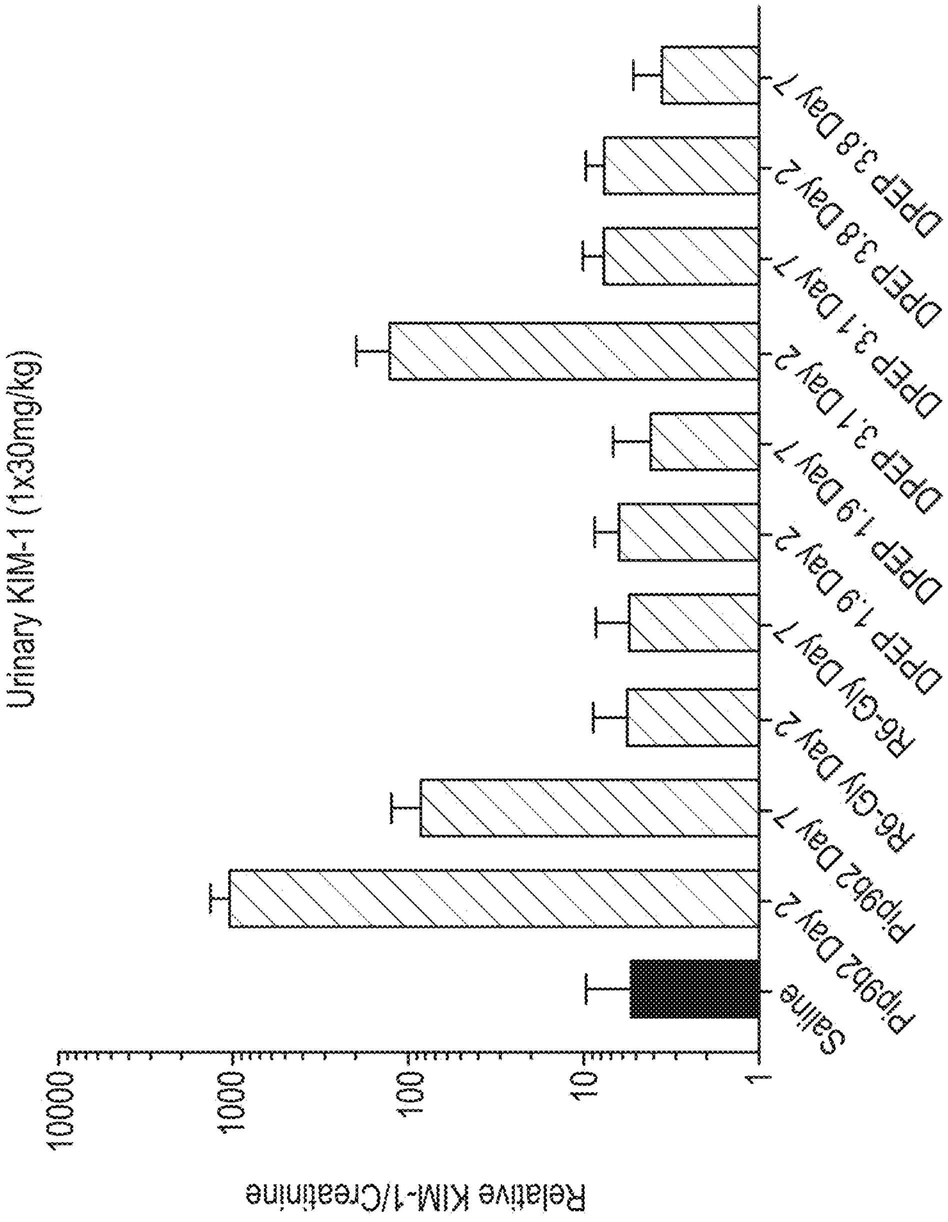
FIG. 5: shows the relative KIM-1 levels measured in the urine of C67BL/6 mice 2 days and 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 6:
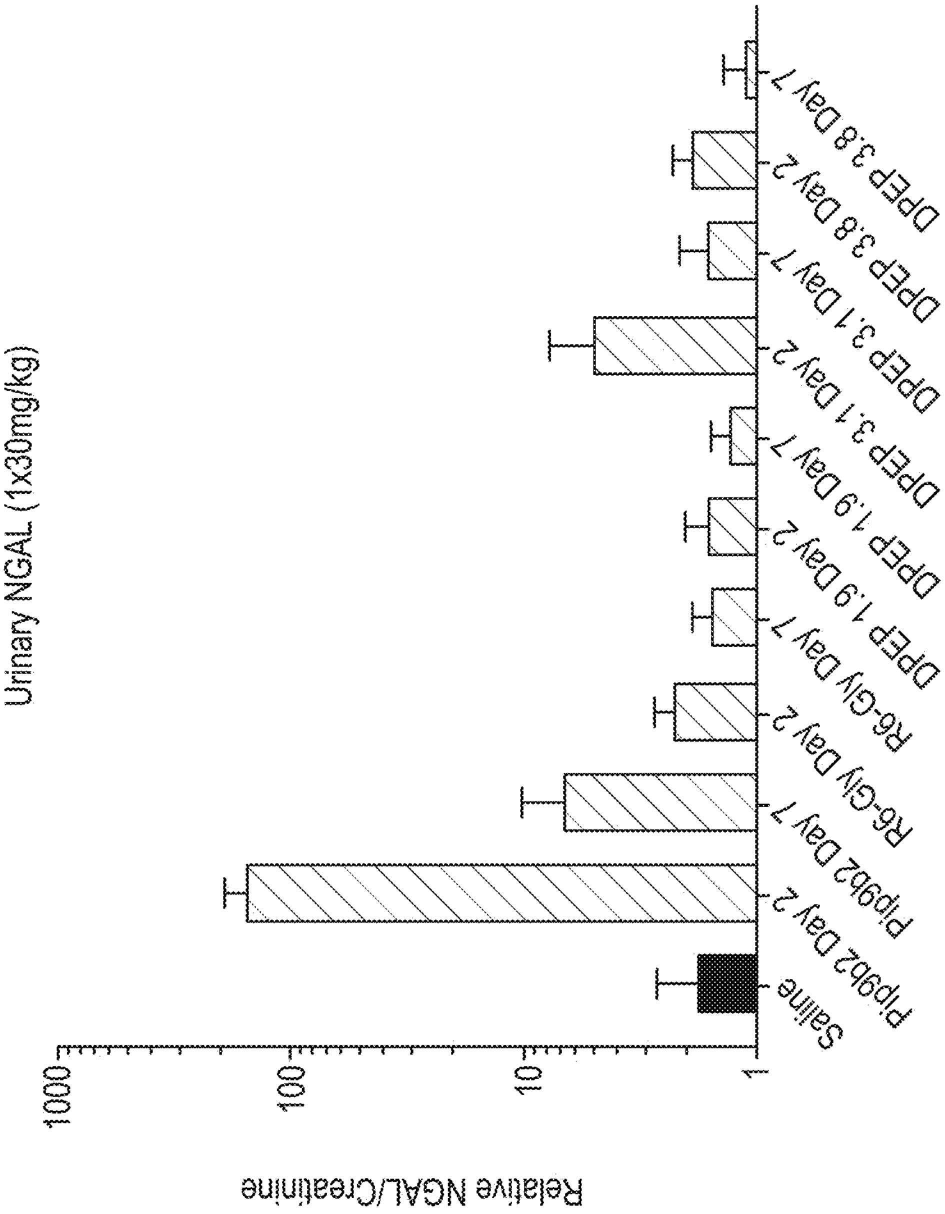
FIG. 6: shows the relative NGAL levels measured in the urine of C67BL/6 mice 2 days and 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)

In general, the invention provides a conjugate, or a pharmaceutically acceptable salt thereof, of an oligonucleotide and a peptide covalently bonded or covalently linked via a linker to the oligonucleotide. The oligonucleotide is complementary to a target sequence within or proximal to exon 45, exon 51, or exon 53 of a human dystrophin gene. The peptide includes at least one positively charged domain and at least one hydrophobic domain. Without wishing to be bound by theory, the peptide may act as a cell-penetrating peptide to enhance the activity of the conjugated oligonucleotide, e.g., by improving intracellular delivery of the conjugated oligonucleotide. Advantageously, as described in the Examples below, the conjugates disclosed herein exhibit reduced toxicity relative to certain alternative peptide structures.

In some embodiments, the antisense oligonucleotide sequence is for inducing exon skipping of a single exon of the dystrophin gene for use in the treatment of DMD. In some embodiments, the single exon is selected from any exon implicated in DMD, which may be any exon in the dystrophin gene, such as for example, exon 45, 51 or 53. PMO oligonucleotides of any sequence may be purchased (for example from Gene Tools Inc, USA).

In some embodiments, the oligonucleotide of the conjugate is an oligonucleotide complementary to the pre-mRNA of a gene target.

In some embodiments, the oligonucleotide complementary to the pre-mRNA of a gene target gives rise to a steric blocking event that alters the pre-mRNA leading to an altered mRNA and hence a protein of altered sequence. In some embodiments, the gene target is the dystrophin gene. In some embodiments, the steric blocking event may be exon inclusion or exon skipping. In some embodiments, the steric blocking event is exon skipping, e.g., exon skipping of a single exon of the dystrophin gene. Optionally, lysine residues may be added to one or both ends of an oligonucleotide (such as a PMO or PNA) before attachment to the peptide to improve water solubility.

In some embodiments, the oligonucleotide has a molecular weight of less than 5,000 Da, e.g., less than 3,000 Da or less than 1,000 Da.

In some embodiments, the peptide is covalently linked to the oligonucleotide at the C-terminus.

In some embodiments, the peptide is covalently linked to the oligonucleotide through a linker if required. The linker may act as a spacer to separate the peptide sequence from the oligonucleotide. The linker may be selected from any suitable sequence.

In some embodiments, the linker is present between the peptide and the oligonucleotide. In some embodiments, the linker is a separate group to the peptide and the oligonucleotide. Accordingly, the linker may comprise artificial amino acids.

In some embodiments, the conjugate comprises the peptide covalently linked via a linker to a oligonucleotide. In some embodiments, the conjugate comprises the following structure:

[peptide]-[linker]-[oligonucleotide]

In some embodiments, the conjugate consists of the following structure:

[peptide]-[linker]-[oligonucleotide]

In some embodiments, any of the peptides listed herein may be used in the conjugate according to the invention.

Preferably, the oligonucleotide is a morpholino (more preferably, a morpholino with all morpholino internucleoside linkages being —$P(O)(NMe_2)O$—). Typically, the phosphorus atom of the morpholinio internucleoside linkage is bonded to the nitrogen atom of the morpholino subunit.

Oligonucleotides

Oligonucleotides used in the conjugates disclosed herein may be those complementary to a target site within dystrophin gene. Without wishing to be bound by theory, it is believed that an oligonucleotide hybridizing to certain target areas within a human dystrophin gene may induce the skipping of exon 45, exon 51, or exon 53 during the dystrophin pre-mRNA splicing, thereby ameliorating Duchenne's muscular dystrophy. Non-limiting examples of nucleobase sequences that may be used in the oligonucleotides of the invention can be found in U.S. Pat. Nos. 9,018,368; 9,079,934; 9,447,417; 10,385,092; 10,781,450. Alternatively, the sequence is GGCCAAACCTCGGCTTACCTGAAAT (SEQ ID NO: 90), which targets exon 23 in the murine dystrophin gene.

An oligonucleotide includes a nucleobase sequence complementary to a human dystrophin gene and, e.g., capable of inducing exon 45 skipping. Non-limiting examples of such sequences are listed in Table 1. For example, an oligonucleotide may include, e.g., at least 12 (e.g., at least 15, at least 16, at least 17, at least 18, at least 19, or at least 20) contiguous nucleobases from any one of sequences listed in Table 1. In certain preferred embodiments, an oligonucleotide includes at least 12 (e.g., at least 15, at least 16, at least 17, at least 18, at least 19, or at least 20) contiguous nucleobases from 5'-CAAUGCCAUCCUGGAGUUCCUG-3' (SEQ ID NO: 122) or its thymine-substitution analogue, 5'-CAATGCCATCCTGGAGTTCCTG-3' (SEQ ID NO: 194). In certain preferred embodiments, an oligonucleotide includes a nucleobase sequence selected from the group consisting of 5'-CAAUGCCAUCCUGGAGUUCCUG-3' (SEQ ID NO: 122) or its thymine-substitution analogue, 5'-CAATGCCATCCTGGAGTTCCTG-3' (SEQ ID NO: 194).

TABLE 1

| # | SEQ ID NO: | Sequence |
|---|---|---|
| 1 | 106 | 5'-CCAAUGCCAUCCUGGAGUUCCUGUAAGAUA-3' |
| 2 | 107 | 5'-GCUGCCCAAUGCCAUCCUGGAGUUCCUGUA-3' |
| 3 | 108 | 5'-CAAUGCCAUCCUGGAGUUCCUGUAAGA-3' |
| 4 | 109 | 5'-GCUGCCCAAUGCCAUCCUGGAGUUCCUGUA-3' |
| 5 | 110 | 5'-GCUGCCCAAUGCCAUCCUGGAGUUCCUGUAAGAUACC AA-3' |
| 6 | 111 | 5'-GCCCAAUGCCAUCCUGGAGUUCCUGUAAGA-3' |
| 7 | 112 | 5'-UGCCAUCCUGGAGUUCCUGUAAGAUACC-3' |
| 8 | 115 | 5'-UGCCAUCCUGGAGUUCCUGUAAGAU-3' |
| 9 | 116 | 5'-CAAUGCCAUCCUGGAGUUCCUGUAAGAU-3' |
| 10 | 117 | 5'-GCCCAAUGCCAUCCUGGAGUUCCUGUAAGAU-3' |
| 11 | 118 | 5'-UUGCCGCUGCCCAAUGCCAUCCUGGAGUUC-3' |
| 12 | 119 | 5'-GCUGCCCAAUGCCAUCCUGGAGUUCCUGUA-3' |
| 13 | 120 | 5'-GCCCAAUGCCAUCCUGGAGUUCCUGUAA-3' |
| 14 | 121 | 5'-GCCGCUGCCCAAUGCCAUCCUGGAGUUCCU-3' |
| 15 | 122 | 5'-CAAUGCCAUCCUGGAGUUCCUG-3' |
| 16 | 113 | 5'-GCCCAAUGCCAUCCUGGAGUUCCUG-3' |
| 17 | 114 | 5'-GCUGCCCAAUGCCAUCCUGGAGUUCCUG-3' |
| 18 | 123 | 5'-GCUGCCCAAUGCCAUCCUGGAGUUCCUGUAA-3' |
| 19 | 124 | 5'-CAAUGCCAUCCUGGAGUUCCUGUAAGAUACC-3' |

In some embodiments, one or more uracils (e.g., all uracils) in an oligonucleotide sequence shown in Table 1 are replaced with thymines. For example, an oligonucleotide sequence may be, e.g., 5'-CAAUGCCAUCCUGGAGUUCCUG-3' (SEQ ID NO: 122). Alternatively, the oligonucleotide sequence may be, e.g., 5'-CAATGCCATCCTGGAGTTCCTG-3' (SEQ ID NO: 194).

An oligonucleotide includes a nucleobase sequence complementary to a human dystrophin gene and, e.g., capable of inducing exon 51 skipping. Non-limiting examples of such sequences are listed in Table 2. For example, an oligonucleotide may include, e.g., at least 12 (e.g., at least 15, at least 16, at least 17, at least 18, at least 19, or at least 20) contiguous nucleobases from any one of sequences listed in Table 2. In certain preferred embodiments, an oligonucleotide includes at least 12 (e.g., at least 15, at least 16, at least 17, at least 18, at least 19, or at least 20) contiguous nucleobases from 5'-CUCCAACAUCAAGGAAGAUGGCAUUUCUAG-3' (SEQ ID NO: 130) or its thymine-substitution analogue, 5'-CTCCAACATCAAGGAAGATGGCATTTCTAG-3' (SEQ ID NO: 195). In certain preferred embodiments, an oligonucleotide includes a nucleobase sequence selected from the group consisting of 5'-CUCCAACAUCAAGGAAGAUGGCAUUUCUAG-3' (SEQ ID NO: 130) or its thymine-substitution analogue, 5'-CTCCAACATCAAGGAAGATGGCATTTCTAG-3' (SEQ ID NO: 195).

TABLE 2

| # | SEQ ID NO: | Sequence |
|---|---|---|
| 1 | 125 | 5'-ACCAGAGUAACAGUCUGAGUAGGAGC-3' |
| 2 | 126 | 5'-CUCAUACCUUCUGCUUGAUGAUC-3' |
| 3 | 127 | 5'-UUCUGUCCAAGCCCGGUUGAAAUC-3' |
| 4 | 128 | 5'-ACAUCAAGGAAGAUGGCAUUUCUAGUUUGG-3' |
| 5 | 129 | 5'-ACAUCAAGGAAGAUGGCAUUUCUAG-3' |
| 6 | 130 | 5'-CUCCAACAUCAAGGAAGAUGGCAUUUCUAG-3' |
| 7 | 131 | 5'-AUCAUUUUUUCUCAUACCUUCUGCUAG-3' |
| 8 | 132 | 5'-AUCAUUUUUUCUCAUACCUUCUGCUAGGAGCUAAA AAG-3' |
| 9 | 133 | 5'-CACCCACCAUCACCCUCUGUG-3' |
| 10 | 134 | 5'-AUCAUCUCGUUGAUAUCCUCAA-3' |

In some embodiments, one or more uracils (e.g., all uracils) in an oligonucleotide sequence shown in Table 2 are replaced with thymines. For example, an oligonucleotide sequence may be, e.g., 5'-CUCCAACAUCAAGGAAGAUGGCAUUUCUAG-3' (SEQ ID NO: 130). Alternatively, the oligonucleotide sequence may be, e.g., 5'-CTCCAACATCAAGGAAGATGGCATTTCTAG-3' (SEQ ID NO: 195).

An oligonucleotide includes a nucleobase sequence complementary to a human dystrophin gene and, e.g., capable of inducing exon 53 skipping. Non-limiting examples of such sequences are listed in Table 3. For example, an oligonucleotide may include, e.g., at least 12 (e.g., at least 15, at least 16, at least 17, at least 18, at least 19, or at least 20) contiguous nucleobases from any one of sequences listed in Table 3. In certain preferred embodiments, an oligonucleotide includes at least 12 (e.g., at least 15, at least 16, at least 17, at least 18, at least 19, or at least 20) contiguous nucleobases from 5'-CCTCCGGTTCTGAAGGTGTTCT-3' (SEQ ID NO: 162) or 5'-GTTGCCTCCGGTTCTGAAGGTGTTC-3' (SEQ ID NO: 171). In certain preferred embodiments, an oligonucleotide includes a nucleobase sequence selected from the group consisting of 5'-CCTCCGGTTCTGAAGGTGTTCT-3' (SEQ ID NO: 162) and 5'-GTTGCCTCCGGTTCTGAAGGTGTTC-3' (SEQ ID NO: 171).

TABLE 3

| # | SEQ ID NO: | Sequence |
|---|---|---|
| 1 | 135 | 5'-CCGGTTCTGAAGGTGTTCTTGTA-3' |
| 2 | 136 | 5'-TCCGGTTCTGAAGGTGTTCTTGTA-3' |
| 3 | 137 | 5'-CTCCGGTTCTGAAGGTGTTCTTGTA-3' |
| 4 | 138 | 5'-CCTCCGGTTCTGAAGGTGTTCTTGTA-3' |
| 5 | 139 | 5'-GCCTCCGGTTCTGAAGGTGTTCTTGTA-3' |
| 6 | 140 | 5'-TGCCTCCGGTTCTGAAGGTGTTCTTGTA-3' |
| 7 | 141 | 5'-CCGGTTCTGAAGGTGTTCTTGT-3' |
| 8 | 142 | 5'-TCCGGTTCTGAAGGTGTTCTTGT-3' |
| 9 | 143 | 5'-CTCCGGTTCTGAAGGTGTTCTTGT-3' |
| 10 | 144 | 5'-CCTCCGGTTCTGAAGGTGTTCTTGT-3' |
| 11 | 145 | 5'-GCCTCCGGTTCTGAAGGTGTTCTTGT-3' |
| 12 | 146 | 5'-TGCCTCCGGTTCTGAAGGTGTTCTTGT-3' |
| 13 | 147 | 5'-CCGGTTCTGAAGGTGTTCTTG-3' |
| 14 | 148 | 5'-TCCGGTTCTGAAGGTGTTCTTG-3' |
| 15 | 149 | 5'-CTCCGGTTCTGAAGGTGTTCTTG-3' |
| 16 | 150 | 5'-CCTCCGGTTCTGAAGGTGTTCTTG-3' |
| 17 | 151 | 5'-GCCTCCGGTTCTGAAGGTGTTCTTG-3' |
| 18 | 152 | 5'-TGCCTCCGGTTCTGAAGGTGTTCTTG-3' |
| 19 | 153 | 5'-CCGGTTCTGAAGGTGTTCTT-3' |
| 20 | 154 | 5'-TCCGGTTCTGAAGGTGTTCTT-3' |
| 21 | 155 | 5'-CTCCGGTTCTGAAGGTGTTCTT-3' |
| 22 | 156 | 5'-CCTCCGGTTCTGAAGGTGTTCTT-3' |
| 23 | 157 | 5'-GCCTCCGGTTCTGAAGGTGTTCTT-3' |
| 24 | 158 | 5'-TGCCTCCGGTTCTGAAGGTGTTCTT-3' |
| 25 | 159 | 5'-CCGGTTCTGAAGGTGTTCT-3' |
| 26 | 160 | 5'-TCCGGTTCTGAAGGTGTTCT-3' |
| 27 | 161 | 5'-CTCCGGTTCTGAAGGTGTTCT-3' |
| 28 | 162 | 5'-CCTCCGGTTCTGAAGGTGTTCT-3' |
| 29 | 163 | 5'-GCCTCCGGTTCTGAAGGTGTTCT-3' |
| 30 | 164 | 5'-TGCCTCCGGTTCTGAAGGTGTTCT-3' |
| 31 | 165 | 5'-CCGGTTCTGAAGGTGTTC-3' |
| 32 | 166 | 5'-TCCGGTTCTGAAGGTGTTC-3' |
| 33 | 167 | 5'-CTCCGGTTCTGAAGGTGTTC-3' |
| 34 | 168 | 5'-CCTCCGGTTCTGAAGGTGTTC-3' |
| 35 | 169 | 5'-GCCTCCGGTTCTGAAGGTGTTC-3' |
| 36 | 170 | 5'-TGCCTCCGGTTCTGAAGGTGTTC-3' |
| 37 | 171 | 5'-GTTGCCTCCGGTTCTGAAGGTGTTC-3' |
| 38 | 172 | 5'-CAUUCAACUGUUGCCUCCGGUUCUGAAGGUG-3' |

In some embodiments, one or more thymines (e.g., all thymines) in an oligonucleotide sequence shown in Table 3 are replaced with uracils. In some embodiments, one or more uracils (e.g., all uracils) in an oligonucleotide sequence shown in Table 3 are replaced with thymines.

Peptides

Peptides that may be used in the conjugates described herein include those disclosed in WO 2020030927 and WO 2020115494. Preferably, peptides included in the conjugates described herein include no artificial amino acid residues.

In some embodiments, the peptide does not contain aminohexanoic acid residues. In some embodiments, the peptide does not contain any form of aminohexanoic acid residues. In some embodiments, the peptide does not contain 6-aminohexanoic acid residues.

In some embodiments, the peptide contains only natural amino acid residues, and therefore consists of natural amino acid residues.

In some embodiments, artificial amino acids such as 6-aminohexanoic acid that are typically used in cell-penetrating peptides are replaced by natural amino acids. In some embodiments, the artificial amino acids such as 6-aminohexanoic acid that are typically used in cell-penetrating peptides are replaced by amino acids selected from beta-alanine, serine, proline, arginine and histidine or hydroxyproline.

In some embodiments, aminohexanoic acid is replaced by beta-alanine. In some embodiments, 6-aminohexanoic acid is replaced by beta-alanine In some embodiments, aminohexanoic acid is replaced by histidine. In some embodiments, 6-aminohexanoic acid is replaced by histidine.

In some embodiments, aminohexanoic acid is replaced by hydroxyproline. In some embodiments, 6-aminohexanoic acid is replaced by hydroxyproline.

In some embodiments, the artificial amino acids such as 6-aminohexanoic acid that are typically used in cell-penetrating peptides may be replaced by a combination of any of beta-alanine, serine, proline, arginine and histidine or hydroxyproline, e.g., a combination of any of beta-alanine, histidine, and hydroxyproline.

In some embodiments, there is provided a peptide having a total length of 40 amino acid residues or less, the peptide comprising: two or more cationic domains each comprising at least 4 amino acid residues; and one or more hydrophobic domains each comprising at least 3 amino acid residues; wherein at least one cationic domain comprises histidine residues. In some embodiments, wherein at least one cationic domain is histidine rich.

In some embodiments, what is meant by histidine rich is defined herein in relation to the cationic domains. Cationic Domain The present invention relates to short cell-penetrating peptides having a particular structure in which there are at least two cationic domains having a certain length.

In some embodiments, the peptide comprises up to 4 cationic domains, up to 3 cationic domains.

In some embodiments, the peptide comprises 2 cationic domains.

As defined above, the peptide comprises two or more cationic domains each having a length of at least 4 amino acid residues.

In some embodiments, each cationic domain has a length of between 4 to 12 amino acid residues, e.g., a length of between 4 to 7 amino acid residues.

In some embodiments, each cationic domain has a length of 4, 5, 6, or 7 amino acid residues. In some embodiments, each cationic domain is of similar length, e.g., each cationic domain is the same length.

In some embodiments, each cationic domain comprises cationic amino acids and may also contain polar and or nonpolar amino acids.

Non-polar amino acids may be selected from: alanine, beta-alanine, proline, glycine, cysteine, valine, leucine, isoleucine, methionine, tryptophan, phenylalanine. In some embodiments, non-polar amino acids do not have a charge.

Polar amino acids may be selected from: serine, asparagine, hydroxyproline, histidine, arginine, threonine, tyrosine, glutamine. In some embodiments, the selected polar amino acids do not have a negative charge.

Cationic amino acids may be selected from: arginine, histidine, lysine. In some embodiments, cationic amino acids have a positive charge at physiological pH.

In some embodiments, each cationic domain does not comprise anionic or negatively charged amino acid residues. In some embodiments, each cationic domain comprises arginine, histidine, beta-alanine, hydroxyproline and/or serine residues.

In some embodiments, each cationic domain consists of arginine, histidine, beta-alanine, hydroxyproline and/or serine residues.

In some embodiments, each cationic domain comprises at least 40%, at least 45%, at least 50% cationic amino acids.

In some embodiments, each cationic domain comprises a majority of cationic amino acids. In some embodiments, each cationic domain comprises at least 55%, at least 60%, at least 65% at least 70%, at least 75%, at least 80%, at least 85%, at least 90%, at least 95% cationic amino acids.

In some embodiments, each cationic domain comprises an isoelectric point (pi) of at least 7.5, at least 8.0, at least 8.5, at least 9.0, at least 9.5, at least 10.0, at least 10.5, at least 11.0, at least 11.5, at least 12.0.

In some embodiments, each cationic domain comprises an isoelectric point (pi) of at least 10.0.

In some embodiments, each cationic domain comprises an isoelectric point (pi) of between 10.0 and 13.0

In some embodiments, each cationic domain comprises an isoelectric point (pi) of between 10.4 and 12.5.

In some embodiments, the isoelectric point of a cationic domain is calculated at physiological pH by any suitable means available in the art. In some embodiments, by using the I PC (www.isoelectric.org) a web-based algorithm developed by Lukasz Kozlowski, Biol Direct. 2016; 11:55. DOI: 10.1186/s 13062-016-0159-9.

In some embodiments, each cationic domain comprises at least 1 cationic amino acid, e.g., 1-5 cationic amino acids. In some embodiments, each cationic domain comprises at least 2 cationic amino acids, e.g., 2-5 cationic amino acids.

In some embodiments, each cationic domain is arginine rich and/or histidine rich. In some embodiments, a cationic domain may contain both histidine and arginine.

In some embodiments, each cationic domain comprises a majority of arginine and/or histidine residues.

In some embodiments, each cationic domain comprises at least 40%, at least 45%, at least 50%, at least 55%, at least 60%, at least 60%, at least 65%, least 70% arginine and/or histidine residues. In some embodiments, a cationic domain may comprise at least 40%, at least 45%, at least 50%, at least 55%, at least 60%, at least 60%, at least 65%, least 70% arginine residues.

In some embodiments, a cationic domain may comprise at least 40%, at least 45%, at least 50%, at least 55%, at least 60%, at least 60%, at least 65%, least 70% histidine residues.

In some embodiments, a cationic domain may comprise a total of between 1-5 histidine and 1-5 arginine residues. In some embodiments, a cationic domain may comprise between 1-5 arginine residues. In some embodiments, a cationic domain may comprise between 1-5 histidine residues. In some embodiments, a cationic domain may comprise a total of between 2-5 histidine and 3-5 arginine residues. In some embodiments, a cationic domain may comprise between 3-5 arginine residues. In some embodiments, a cationic domain may comprise between 2-5 histidine residues.

In some embodiments, each cationic domain comprises one or more beta-alanine residues. In some embodiments, each cationic domain may comprise a total of between 2-5 beta-alanine residues, e.g., a total of 2 or 3 beta-alanine residues.

In some embodiments, a cationic domain may comprise one or more hydroxyproline residues or serine residues.

In some embodiments, a cationic domain may comprise between 1-2 hydroxyproline residues. In some embodiments, a cationic domain may comprise between 1-2 serine residues.

In some embodiments, all of the cationic amino acids in a given cationic domain may be histidine, alternatively, e.g., all of the cationic amino acids in a given cationic domain may be arginine.

In some embodiments, the peptide may comprise at least one histidine rich cationic domain. In some embodiments, the peptide may comprise at least one arginine rich cationic domain.

In some embodiments, the peptide may comprise at least one arginine rich cationic domain and at least one histidine rich cationic domain.

In some embodiments, the peptide comprises two arginine rich cationic domains.

In some embodiments, the peptide comprises two histidine rich cationic domains.

In some embodiments, the peptide comprises two arginine and histidine rich cationic domains.

In some embodiments, the peptide comprises one arginine rich cationic domain and one histidine rich cationic domain. In some embodiments, each cationic domain comprises no more than 3 contiguous arginine residues, e.g., no more than 2 contiguous arginine residues.

In some embodiments, each cationic domain comprises no contiguous histidine residues.

In some embodiments, each cationic domain comprises arginine, histidine and/or beta-alanine residues. In some embodiments, each cationic domain comprises a majority of arginine, histidine and/or beta-alanine residues. In some embodiments, at least 70%, at least 75%, at least 80%, at least 85%, at least 90%, at least 95%, 100% of the amino acid residues in each cationic domain are arginine, histidine and/or beta-alanine residues. In some embodiments, each cationic domain consists of arginine, histidine and/or beta-alanine residues.

In some embodiments, the peptide comprises a first cationic domain comprising arginine and beta-alanine residues and a second cationic domain comprising arginine and beta-alanine residues.

In some embodiments, the peptide comprises a first cationic domain comprising arginine and beta-alanine resides, and a second cationic domain comprising histidine, beta-alanine, and optionally arginine residues.

In some embodiments, the peptide comprises a first cationic domain comprising arginine and beta-alanine resides, and a second cationic domain comprising histidine and beta-alanine residues.

In some embodiments, the peptide comprises a first cationic domain consisting of arginine and beta-alanine residues and a second cationic domain consisting of arginine and beta-alanine residues.

In some embodiments, the peptide comprises a first cationic domain consisting of arginine and beta-alanine residues and a second cationic domain consisting of arginine, histidine and beta-alanine residues.

In some embodiments, the peptide comprises at least two cationic domains, e.g., these cationic domains form the arms of the peptide. In some embodiments, the cationic domains are located at the N and C terminus of the peptide. In some embodiments, therefore, the cationic domains may be known as the cationic arm domains.

In some embodiments, the peptide comprises two cationic domains, wherein one is located at the N-terminus of the peptide and one is located at the C-terminus of the peptide. In some embodiments, at either end of the peptide. In some embodiments, no further amino acids or domains are present at the N-terminus and C-terminus of the peptide, with the exception of other groups such as a terminal modification, linker and/or oligonucleotide. For the avoidance of doubt, such other groups may be present in addition to 'the peptide' described and claimed herein. In some embodiments, therefore each cationic domain forms the terminus of the peptide. In some embodiments, this does not preclude the presence of a further linker group as described herein.

In some embodiments, the peptide may comprise up to 4 cationic domains. In some embodiments, the peptide comprises two cationic domains.

In some embodiments, the peptide comprises two cationic domains that are both arginine rich.

In some embodiments, the peptide comprises one cationic domain that is arginine rich.

In some embodiments, the peptide comprises two cationic domains that are both arginine and histidine rich.

In some embodiments, the peptide comprises one cationic domain that is arginine rich and one cationic domain that is histidine rich.

In some embodiments, the cationic domains comprise amino acid units selected from the following: R, H, B, RR, HH, BB, RH, HR, RB, BR, HB, BH, RBR, RBB, BRR, BBR, BRB, RBH, RHB, HRB, BRH, HRR, RRH, HRH, HBB, BBH, RHR, BHB, HBH, or any combination thereof.

In some embodiments, a cationic domain may also include serine, proline and/or hydroxyproline residues. In some embodiments, the cationic domains may further comprise amino acid units selected from the following: RP, PR, RPR, RRP, PRR, PRP, Hyp; R[Hyp]R, RR[Hyp], [Hyp]RR, [Hyp]R[Hyp], [Hyp][Hyp]R, R[Hyp][Hyp], SB, BS, or any combination thereof, or any combination with the above listed amino acid units.

In some embodiments, each cationic domain comprises any of the following sequences: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B (SEQ ID NO: 17), R[Hyp]H[Hyp]HB (SEQ ID NO: 18), R[Hyp]RR[Hyp]R (SEQ ID NO: 19) or any combination thereof.

In some embodiments, each cationic domain consists of any of the following sequences: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B, R[Hyp]H[Hyp]HB, R[Hyp]RR[Hyp]R (SEQ ID NO: 19) or any combination thereof.

In some embodiments, each cationic domain consists of one of the following sequences: RBRRBRR (SEQ ID NO: 1), RBRBR (SEQ ID NO: 2), RBRRBR (SEQ ID NO: 4), BRBR (SEQ ID NO: 7), RBHBH (SEQ ID NO: 8), HBHBR (SEQ ID NO: 9).

In some embodiments, each cationic domain in the peptide may be identical or different. In some embodiments, each cationic domain in the peptide is different.

Hydrophobic Domain

The present invention relates to short cell-penetrating peptides having a particular structure in which there is at least one hydrophobic domain having a certain length.

References to 'hydrophobic' herein denote an amino acid or domain of amino acids having the ability to repel water or which do not mix with water.

In some embodiments, the peptide comprises up to 3 hydrophobic domains, up to 2 hydrophobic domains. In some embodiments, the peptide comprises 1 hydrophobic domain.

As defined above, the peptide comprises one or more hydrophobic domains each having a length of at least 3 amino acid residues.

In some embodiments, each hydrophobic domain has a length of between 3-6 amino acids. In some embodiments, each hydrophobic domain has a length of 5 amino acids.

In some embodiments, each hydrophobic domain may comprise nonpolar, polar, and hydrophobic amino acid residues.

Hydrophobic amino acid residues may be selected from: alanine, valine, leucine, isoleucine, phenylalanine, tyrosine, methionine, and tryptophan.

Non-polar amino acid residues may be selected from: proline, glycine, cysteine, alanine, valine, leucine, isoleucine, tryptophan, phenylalanine, methionine.

Polar amino acid residues may be selected from: Serine, Asparagine, hydroxyproline, histidine, arginine, threonine, tyrosine, glutamine.

In some embodiments, the hydrophobic domains do not comprise hydrophilic amino acid residues.

In some embodiments, each hydrophobic domain comprises a majority of hydrophobic amino acid residues. In some embodiments, each hydrophobic domain comprises at least 70%, at least 75%, at least 80%, at least 85%, at least 90%, at least 95%, 100% hydrophobic amino acids. In some embodiments, each hydrophobic domain consists of hydrophobic amino acid residues.

In some embodiments, each hydrophobic domain comprises a hydrophobicity of at least 0.3, at least 0.4, at least 0.5, at least 0.6, at least 0.7, at least 0.8, at least 0.8, at least 1.0, at least 1.1, at least 1.2, at least 1.3.

In some embodiments, each hydrophobic domain comprises a hydrophobicity of at least 0.3, at least 0.35, at least 0.4, at least 0.45.

In some embodiments, each hydrophobic domain comprises a hydrophobicity of at least 1.2, at least 1.25, at least 1.3, at least 1.35.

In some embodiments, each hydrophobic domain comprises a hydrophobicity of between 0.4 and 1.4

In some embodiments, each hydrophobic domain comprises of a hydrophobicity of between 0.45 and 0.48.

In some embodiments, each hydrophobic domain comprises a hydrophobicity of between 1.27 and 1.39

In some embodiments, hydrophobicity is as measured by White and Wimley: W. C. Wimley and S. H. White, "Experimentally determined hydrophobicity scale for proteins at membrane interfaces" Nature Struct Biol 3:842 (1996).

In some embodiments, each hydrophobic domain comprises at least 3, at least 4 hydrophobic amino acid residues.

In some embodiments, each hydrophobic domain comprises phenylalanine, leucine, Isoleucine, tyrosine, tryptophan, proline, and glutamine residues. In some embodiments, each hydrophobic domain consists of phenylalanine, leucine, isoleucine, tyrosine, tryptophan, proline, and/or glutamine residues.

In some embodiments, each hydrophobic domain consists of phenylalanine, leucine, isoleucine, tyrosine and/or glutamine residues.

In some embodiments, each hydrophobic domain consists of tryptophan and/or proline residues.

In some embodiments, the peptide comprises one hydrophobic domain. In some embodiments, the or each hydrophobic domain is located in the center of the peptide. In some embodiments, therefore, the hydrophobic domain may be known as a core hydrophobic domain. In some embodiments, the or each hydrophobic core domain is flanked on either side by an arm domain. In some embodiments, the arm domains may comprise one or more cationic domains and one or more further hydrophobic domains. In some embodiments, each arm domain comprises a cationic domain.

In some embodiments, the peptide comprises two arm domains flanking a hydrophobic core domain, wherein each arm domain comprises a cationic domain.

In some embodiments, the peptide consists of two cationic arm domains flanking a hydrophobic core domain.

In some embodiments, the or each hydrophobic domain comprises one of the following sequences: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), WWPW (SEQ ID NO: 26) or any combination thereof.

In some embodiments, the or each hydrophobic domain consists of one of the following sequences: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), WWPW (SEQ ID NO: 26) or any combination thereof.

In some embodiments, the or each hydrophobic domain consists of one of the following sequences FQILY (SEQ ID NO: 21), YQFLI (SEQ ID NO: 20), ILFQY (SEQ ID NO: 22).

In some embodiments, the or each hydrophobic domain consists of FQILY (SEQ ID NO: 21). In some embodiments, each hydrophobic domain in the peptide may have the same sequence or a different sequence.

The present invention relates to short cell-penetrating peptides for use in transporting therapeutic cargo molecules in the treatment of medical conditions.

The peptide has a sequence that is a contiguous single molecule, therefore the domains of the peptide are contiguous. In some embodiments, the peptide comprises several domains in a linear arrangement between the N-terminus and the C-terminus. In some embodiments, the domains are selected from cationic domains and hydrophobic domains described above. In some embodiments, the peptide consists of cationic domains and hydrophobic domains wherein the domains are as defined above.

Each domain has common sequence characteristics as described in the relevant sections above, but the exact sequence of each domain is capable of variation and modification. Thus a range of sequences is possible for each domain. The combination of each possible domain sequence yields a range of peptide structures, each of which form part of the present invention. Features of the peptide structures are described below.

In some embodiments, a hydrophobic domain separates any two cationic domains. In some embodiments, each hydrophobic domain is flanked by cationic domains on either side thereof. In some embodiments, no cationic domain is contiguous with another cationic domain. In some embodiments, the peptide comprises one hydrophobic domain flanked by two cationic domains in the following arrangement:

[cationic domain]-[hydrophobic domain]-[cationic domain]

In some embodiments, the hydrophobic domain may be known as the core domain and each of the cationic domains may be known as an arm domain. In some embodiments, the hydrophobic arm domains flank the cationic core domain on either side thereof.

In some embodiments, the peptide consists of two cationic domains and one hydrophobic domain.

In some embodiments, the peptide consists of one hydrophobic core domain flanked by two cationic arm domains.

In some embodiments, the peptide consists of one hydrophobic core domain comprising a sequence selected from: YQFLI (SEQ ID NO: 20), FQILY (SEQ ID NO: 21), ILFQY (SEQ ID NO: 22), FQIY (SEQ ID NO: 23), WWW, WWPWW (SEQ ID NO: 24), WPWW (SEQ ID NO: 25), and WWPW (SEQ ID NO: 26), flanked by two cationic arm domains each comprising a sequence selected from: RBRRBRR (SEQ ID NO: 1), RBRBR (SEQ ID NO: 2), RBRR (SEQ ID NO: 3), RBRRBR (SEQ ID NO: 4), RRBRBR (SEQ ID NO: 5), RBRRB (SEQ ID NO: 6), BRBR (SEQ ID NO: 7), RBHBH (SEQ ID NO: 8), HBHBR (SEQ ID NO: 9), RBRHBHR (SEQ ID NO: 10), RBRBBHR (SEQ ID NO: 11), RBRRBH (SEQ ID NO: 12), HBRRBR (SEQ ID NO: 13), HBHBH (SEQ ID NO: 14), BHBH (SEQ ID NO: 15), BRBSB (SEQ ID NO: 16), BRB[Hyp]B (SEQ ID NO: 17), R[Hyp]H[Hyp]HB (SEQ ID NO: 18), and R[Hyp]RR[Hyp]R (SEQ ID NO: 19).

In some embodiments, the peptide consists of one hydrophobic core domain comprising a sequence selected from: FQILY (SEQ ID NO: 21), YQFLI (SEQ ID NO: 20), and ILFQY (SEQ ID NO: 22), flanked by two cationic arm domains comprising a sequence selected from: RBRRBRR (SEQ ID NO: 1), RBRBR (SEQ ID NO: 2), RBRRBR (SEQ ID NO: 4), BRBR (SEQ ID NO: 7), RBHBH (SEQ ID NO: 8), HBHBR (SEQ ID NO: 9). In some embodiments, the peptide consists of one hydrophobic core domain comprising the sequence: FQILY (SEQ ID NO: 21), flanked by two cationic arm domains comprising a sequence selected from: RBRRBRR (SEQ ID NO: 1), RBRBR (SEQ ID NO: 2), RBRRBR (SEQ ID NO: 4), BRBR (SEQ ID NO: 7), RBHBH (SEQ ID NO: 8).

In any such embodiment, further groups may be present such as a linker, terminal modification and/or oligonucleotide.

In some embodiments, the peptide is N-terminally modified.

In some embodiments, the peptide is N-acetylated, N-methylated, N-trifluoroacetylated, N-trifluoromethylsulfonylated, or N-methylsulfonylated. In some embodiments, the peptide is N-acetylated.

Optionally, the N-terminus of the peptide may be unmodified.

In some embodiments, the peptide is N-acetylated.

In some embodiments, the peptide is C-terminal modified.

In some embodiments, the peptide comprises a C-terminal modification selected from: Carboxy-, Thioacid-, Aminooxy-, Hydrazino-, thioester-, azide, strained alkyne, strained alkene, aldehyde-, thiol or haloacetyl-group.

Advantageously, the C-terminal modification provides a means for linkage of the peptide to the oligonucleotide.

Accordingly, the C-terminal modification may comprise the linker and vice versa. In some embodiments, the C-terminal modification may consist of the linker or vice versa. Suitable linkers are described herein elsewhere.

In some embodiments, the peptide comprises a C-terminal carboxyl group.

In some embodiments, the C-terminal carboxyl group is provided by a glycine or beta-alanine residue.

In some embodiments, the C terminal carboxyl group is provided by a beta-alanine residue. In some embodiments, the C terminal beta-alanine residue is a linker.

In some embodiments, therefore each cationic domain may further comprise an N or C terminal modification. In some embodiments, the cationic domain at the C terminus comprises a C-terminal modification. In some embodiments, the cationic domain at the N terminus comprises a N-terminal modification. In some embodiments, the cationic domain at the C terminus comprises a linker group, In some embodiments, the cationic domain at the C terminus comprises a C-terminal beta-alanine. In some embodiments, the cationic domain at the N terminus is N-acetylated.

The peptide of the present invention is defined as having a total length of 40 amino acid residues or less. The peptide may therefore be regarded as an oligopeptide.

In some embodiments, the peptide has a total length of 3-30 amino acid residues, e.g., of 5-25 amino acid residues, of 10-25 amino acid residues, of 13-23 amino acid residues, of 15-20 amino acid residues.

In some embodiments, the peptide has a total length of at least 12, at least 13, at least 14, at least 15, at least 16, at least 17 amino acid residues.

In some embodiments, the peptide is capable of penetrating cells. The peptide may therefore be regarded as a cell-penetrating peptide.

In some embodiments, the peptide is for attachment to an oligonucleotide. In some embodiments, the peptide is for transporting an oligonucleotide into a target cell. In some embodiments, the peptide is for delivering an oligonucleotide into a target cell. The peptide may therefore be regarded as a carrier peptide.

In some embodiments, the peptide is capable of penetrating into cells and tissues, e.g., into the nucleus of cells. In some embodiments, into muscle tissues.

In some embodiments, the peptide may be selected from any of the following sequences:

(SEQ ID NO: 27)
RBRRBRRFQILYRBRBR (SEQ ID NO: 28)
RBRRBRRFQILYRBRR (SEQ ID NO: 29)
RBRRBRFQILYRRBRBR (SEQ ID NO: 30)
RBRBRFQILYRBRRBRR (SEQ ID NO: 31)
RBRRBRRYQFLIRBRBR (SEQ ID NO: 32)
RBRRBRRILFQYRBRBR (SEQ ID NO: 33)
RBRRBRFQILYRBRBR (SEQ ID NO: 34)
RBRRBFQILYRBRRBR (SEQ ID NO: 35)
RBRRBRFQILYBRBR (SEQ ID NO: 36)
RBRRBFQILYRBRBR (SEQ ID NO: 37)
RBRRBRRFQILYRBHBH (SEQ ID NO: 38)
RBRRBRRFQILYHBHBR (SEQ ID NO: 39)
RBRRBRRFQILYHBRBH (SEQ ID NO: 40)
RBRRBRRYQFLIRBHBH (SEQ ID NO: 41)
RBRRBRRILFQYRBHBH (SEQ ID NO: 42)
RBRHBHRFQILYRBRBR (SEQ ID NO: 43)
RBRBBHRFQILYRBHBH (SEQ ID NO: 44)
RBRRBRFQILYRBHBH (SEQ ID NO: 45)
RBRRBRFQILYHBHBH (SEQ ID NO: 46)
RBRRBHFQILYRBHBH (SEQ ID NO: 47)
HBRRBRFQILYRBHBH (SEQ ID NO: 48)
RBRRBFQILYRBHBH (SEQ ID NO: 49)
RBRRBRFQILYBHBH (SEQ ID NO: 50)
RBRRBRYQFLIHBHBH (SEQ ID NO: 51)
RBRRBRILFQYHBHBH (SEQ ID NO: 52)
RBRRBRRFQILYHBHBH

In some embodiments, the peptide may be selected from any of the following additional sequences:

(SEQ ID NO: 53)
RBRRBRFQILYBRBS (SEQ ID NO: 54)
RBRRBRFQILYBRB[Hyp]

(SEQ ID NO: 55)
RBRRBRFQILYBR[Hyp]R (SEQ ID NO: 56)
RRBRRBRFQILYBRBR (SEQ ID NO: 57)
BRRBRRFQILYBRBR (SEQ ID NO: 58)
RBRRBRWWWBRBR (SEQ ID NO: 59)
RBRRBRWWPWWBRBR (SEQ ID NQ: 60)
RBRRBRWPWWBRBR (SEQ ID NO: 61)
RBRRBRWWPWBRBR (SEQ ID NO: 62)
RBRRBRRWWWRBRBR (SEQ ID NO: 63)
RBRRBRRWWPWWRBRBR (SEQ ID NO: 64)
RBRRBRRWPWWRBRBR (SEQ ID NO: 65)
RBRRBRRWWPWRBRBR (SEQ ID NO: 66)
RBRRBRRFQILYBRBR (SEQ ID NO: 67)
RBRRBRRFQILYRBR (SEQ ID NO: 68)
BRBRBWWPWWRBRRBR (SEQ ID NO: 69)
RBRRBRRFQILYBHBH (SEQ ID NO: 70)
RBRRBRRFQIYRBHBH (SEQ ID NO: 71)
RBRRBRFQILYBRBH (SEQ ID NO: 72)
RBRRBRFQILYR[Hyp]H[Hyp]H (SEQ ID NO: 73)
R[Hyp]RR[Hyp]RFQILYRBHBH (SEQ ID NO: 74)
R[Hyp]RR[Hyp]RFQILYR[Hyp]H[Hyp]H (SEQ ID NO: 75)
RBRRBRWWWRBHBH (SEQ ID NO: 76)
RBRRBRWWPRBHBH (SEQ ID NO: 77)
RBRRBRPWWRBHBH (SEQ ID NO: 78)
RBRRBRWWPWWRBHBH

-continued (SEQ ID NO: 79)
RBRRBRWWPWRBHBH (SEQ ID NO: 80)
RBRRBRWPWWRBHBH (SEQ ID NO: 81)
RBRRBRRWWWRBHBH (SEQ ID NO: 82)
RBRRBRRWWPWWRBHBH (SEQ ID NO: 83)
RBRRBRRWPWWRBHBH (SEQ ID NO: 84)
RBRRBRRWWPWRBHBH (SEQ ID NO: 85)
RRBRRBRFQILYRBHBH (SEQ ID NO: 86)
BRRBRRFQILYRBHBH (SEQ ID NO: 87)
RRBRRBRFQILYBHBH (SEQ ID NO: 88)
BRRBRRFQILYBHBH (SEQ ID NO: 89)
RBRRBHRFQILYRBHBH (SEQ ID NO: 101)
RBRRBRFQILY[Hyp]R[Hyp]R (SEQ ID NO: 102)
R[Hyp]RR[Hyp]RFQILYBRBR (SEQ ID NO: 103)
R[Hyp]RR[Hyp]RFQILY[Hyp]R[Hyp]R (SEQ ID NO: 104)
RBRRBRWWWBRBR (SEQ ID NO: 105)
RBRRBRWWPWWBRBR In some embodiments, the peptide may be selected from one of the following sequences:

(SEQ ID NO: 27)
RBRRBRRFQILYRBRBR (SEQ ID NO: 31)
RBRRBRRYQFLIRBRBR (SEQ ID NO: 32)
RBRRBRRILFQYRBRBR (SEQ ID NO: 35)
RBRRBRFQILYBRBR (SEQ ID NO: 37)
RBRRBRRFQILYRBHBH (SEQ ID NO: 38)
RBRRBRRFQILYHBHBR (SEQ ID NO: 44)
RBRRBRFQILYRBHBH

In some embodiments, the peptide consists of the following sequence: RBRRBRFQILYBRBR (SEQ ID NO: 35).

In some embodiments, the peptide consists of the following sequence: RBRRBRRFQILYRBHBH (SEQ ID NO: 37).

In some embodiments, the peptide consists of the following sequence: RBRRBRFQILYRBHBH (SEQ ID NO: 44).

Conjugate

In some embodiments, the conjugate comprises a peptide selected from one of the following sequences: RBRRBRFQILYBRBR (SEQ ID NO: 35), RBRRBRRFQILYRBHBH (SEQ ID NO: 37) and RBRRBRFQILYRBHBH (SEQ ID NO: 44). In some embodiments, the conjugate comprises a peptide selected from any one of SEQ ID NOs: 27-52; SEQ ID NOs: 53-89; SEQ ID NOs, 101-105; and SEQ ID NOs: 27, 31, 32, 35, 37, 38, and 44. In some embodiments, the conjugate comprises an oligonucleotide sequence of Table 1, Table 2, or Table 3.

In some embodiments, in any case, the peptide may further comprise N-terminal modifications as described above.

Suitable linkers include, for example, a C-terminal cysteine residue that permits formation of a disulphide, thioether or thiol-maleimide linkage, a C-terminal aldehyde to form an oxime, a click reaction or formation of a morpholino linkage with a basic amino acid on the peptide or a carboxylic acid moiety on the peptide covalently conjugated to an amino group to form a carboxamide linkage.

In some embodiments, the linker is between 1-5 amino acids in length. In some embodiments, the linker may comprise any linker that is known in the art. In some embodiments, the linker is selected from any of the following sequences: G, BC, XC, C, GGC, BBC, BXC, XBC, X, XX, B, BB, BX and XB. In some embodiments, wherein X is 6-aminohexanoic acid.

In some embodiments, the linker may be a polymer, such as for example PEG.

In some embodiments, the linker is beta-alanine.

In some embodiments, the peptide is conjugated to the oligonucleotide through a carboxamide linkage.

The linker of the conjugate may form part of the oligonucleotide to which the peptide is attached. Alternatively, the attachment of the oligonucleotide may be directly linked to the C-terminus of the peptide. In some embodiments, in such embodiments, no linker is required.

Alternatively, the peptide may be chemically conjugated to the oligonucleotide. Chemical linkage may be via a disulphide, alkenyl, alkynyl, aryl, ether, thioether, triazole, amide, carboxamide, urea, thiourea, semicarbazide, carbazide, hydrazine, oxime, phosphate, phosphoramidate, thiophosphate, boranophosphate, iminophosphates, or thiol-maleimide linkage, for example.

Optionally, cysteine may be added at the N-terminus of an oligonucleotide to allow for disulphide bond formation to the peptide, or the N-terminus may undergo bromoacetylation for thioether conjugation to the peptide.

The peptide of the invention may equally be covalently linked to an imaging molecule in order to provide a conjugate.

In some embodiments, the imaging molecule may be any molecule that enables visualisation of the conjugate. In some embodiments, the imaging molecule may indicate the location of the conjugate. In some embodiments, the location of the conjugate in vitro or in vivo. In some embodiments, there is provided a method of monitoring the location of a conjugate comprising an imaging molecule comprising: administering the conjugate to a subject and imaging the subject to locate the conjugate.

Examples of imaging molecules include detection molecules, contrast molecules, or enhancing molecules. Suitable imaging molecules may be selected from radionuclides; fluorophores; nanoparticles (such as a nanoshell); nanocages; chromogenic agents (for example an enzyme), radioisotopes, dyes, radiopaque materials, fluorescent compounds, and combinations thereof.

In some embodiments, imaging molecules are visualised using imaging techniques, these may be cellular imaging techniques or medical imaging techniques. Suitable cellular imaging techniques include image cytometry, fluorescent microscopy, phase contrast microscopy, SEM, TEM, for example. Suitable medical imaging techniques include X-ray, fluoroscopy, MRI, scintigraphy, SPECT, PET, CT, CAT, FNRI, for example.

In some cases, the imaging molecule may be regarded as a diagnostic molecule. In some embodiments, a diagnostic molecule enables the diagnosis of a disease using the conjugate. In some embodiments, diagnosis of a disease may be achieved through determining the location of the conjugate using an imaging molecule. In some embodiments, there is provided a method of diagnosis of a disease comprising administering an effective amount of a conjugate comprising an imaging molecule to a subject and monitoring the location of the conjugate.

In some embodiments, further details such as the linkage of a conjugate comprising an imaging molecule are the same as those described above in relation to a conjugate comprising an oligonucleotide.

In some embodiments, the peptide of the invention may be covalently linked to an oligonucleotide and an imaging molecule in order to provide a conjugate.

In some embodiments, the conjugate is capable of penetrating into cells and tissues, e.g., into the nucleus of cells, e.g., into muscle tissues.

Linkers

Conjugates described herein may include a linker covalently linking a peptide described herein to an oligonucleotide described herein. Linkers useful in the present invention can be found in WO 2020/115494, the disclosure of which is incorporated herein by reference.

The linker may be of formula (I):

$$T_1\text{-}(CR^1R^2)_n\text{-}T^2. \qquad (I)$$

where $T_1$ is a divalent group for attachment to the peptide and is selected from the group consisting of —NH— and carbonyl;

$T_2$ is a divalent group for attachment to an oligonucleotide and is selected from the group consisting of —NH— and carbonyl;

n is 1, 2 or 3;

each $R^1$ is independently —$Y^1$—$X_1$—$Z^1$, where $Y^1$ is absent or —$(CR^{A1}R^{A2})_m$—, where m is 1, 2, 3 or 4, and $R^{A1}$ and $R^{A2}$ are each independently hydrogen, OH, or (1-2C)alkyl;

$X^1$ is absent, —O—, —C(O)—, —C(O)O—, —OC(O)—, —CH($OR^{A3}$)—, —N($R^{A3}$)—, —N($R^{A3}$)—C(O)—, —N($R^{A3}$)—C(O)O—, —C(O)—N($R^{A3}$)—, —N($R^{A3}$)C(O)N($R^{A3}$)—, —N($R^{A3}$)C(N $R^{A3}$)N($R^{A3}$)—, —SO—, —S—, —$SO_2$—, —$S(O)_2$N($R^{A3}$)—, or —N($R^{A3}$)$SO_2$—, where each $R^{A3}$ is independently selected from hydrogen and methyl; and $Z^1$ is a further oligonucleotide or is hydrogen, (1-6C)alkyl, (2-6C)alkenyl, (2-6C)alkynyl, aryl, (3-6C)cycloalkyl, (3-6C)cycloalkenyl, or heteroaryl, where each (1-6C)alkyl, (2-6C)alkenyl, (2-6C)alkynyl, aryl, (3-6C)cycloalkyl, (3-6C) cycloalkenyl, and heteroaryl is optionally substituted with one or more (e.g., 1, 2, 3, 4, or 5) substituent groups selected from the group consisting of (1-4C)alkyl, oxo, halo, cyano, nitro, hydroxy, carboxy, $NR^{A4}R^{A5}$, and (1-4C)alkoxy, where $R^{A4}$ and $R^{A5}$ are each independently selected from the group consisting of hydrogen and (1-4C)alkyl; and each $R^2$ is independently —$Y^2$—$X^2$—$Z^2$, where $Y^2$ is absent or a group of the formula —$[CR^{B1}R^{B2}]_m$— in which m is an integer selected from 1, 2, 3 or 4, and RB1 and RB2 are each independently selected from hydrogen, OH or (1-2C)alkyl;

$X^2$ is absent, —O—, —C(O)—, —C(O)O—, —OC(O)—, —CH($OR^{B3}$)—, —N($R^{B3}$)—, —N($R^{B3}$)—C(O)—, —N($R^{B3}$)—C(O)O—, —C(O)—N($R^{B3}$)—, —N($R^{B3}$)C(O)N($R^{B3}$)—, —N($R^{B3}$)C($NR^{B3}$)N($R^{B3}$)—, —SO—, —S— —$SO_2$—, —$S(O)_2N$($R^{B3}$)—, or —N($R^{B3}$)$SO_2$—, where each $R^{B3}$ is independently selected from hydrogen or methyl; and $Z^2$ is selected from hydrogen, (1-6C)alkyl, (2-6C)alkenyl, (2-6C)alkynyl, aryl, (3-6C)cycloalkyl, (3-6C)cycloalkenyl or heteroaryl, where each (1-6C)alkyl, (2-6C)alkenyl, (2-6C)alkynyl, aryl, (3-6C)cycloalkyl, (3-6C)cycloalkenyl or heteroaryl is optionally substituted by one or more (e.g., 1, 2, 3, 4, or 5) substituent groups selected from the group consisting of (1-4C) alkyl, oxo, halo, cyano, nitro, hydroxy, carboxy, $NR^{B4}R^{B5}$, and (1-4C)alkoxy, where $R^{B4}$ and $R^{B5}$ are each independently hydrogen or (1-2C) alkyl; with the proviso that; when n=1 and $T_1$ and $T_2$ are different to one another, then $R^1$ and $R^2$ are not both H; when n=1, $T_1$ and $T_2$ are different to one another and one of $R^1$ and $R^2$ is H then the other of $R^1$ and $R^2$ is not methyl; or when n=2 and each occurrence of $R^1$ and $R^2$ is H, then $T_1$ and $T_2$ are both —C(O)— or are both —NH—.

In some embodiments, the linker is of the following structure:

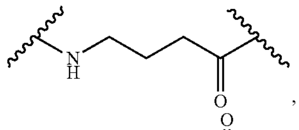
,
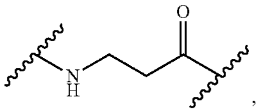
,
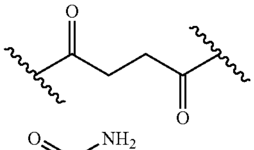
,
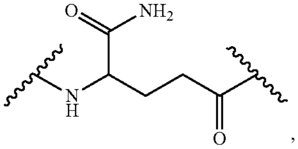
, or
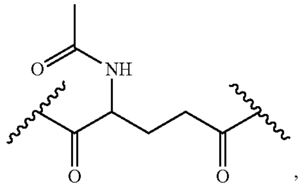
,

Pharmaceutical Compositions

The conjugate of the invention, or a pharmaceutically acceptable salt thereof, may formulated into a pharmaceutical composition.

In some embodiments, the pharmaceutical composition comprises a conjugate of the invention or a pharmaceutically acceptable salt thereof.

In some embodiments, the pharmaceutical composition may further comprise a pharmaceutically acceptable diluent, adjuvant or carrier.

Suitable pharmaceutically acceptable diluents, adjuvants and carriers are well known in the art.

It should be understood that the pharmaceutical compositions of the present disclosure can further include additional known therapeutic agents, drugs, modifications of compounds into prodrugs, and the like for alleviating, mediating, preventing, and treating the diseases, disorders, and conditions described herein under medical use.

In some embodiments, the pharmaceutical composition is for use as a medicament, e.g., for use as a medicament in the same manner as described herein for the conjugate. All features described herein in relation to medical treatment using the conjugate apply to the pharmaceutical composition.

Accordingly, in a further aspect of the invention there is provided a pharmaceutical composition according to the fourth aspect for use as a medicament. In a further aspect, there is provided a method of treating a subject for a disease condition comprising administering an effective amount of a pharmaceutical composition disclosed herein.

Medical Use

The conjugate comprising the peptide of the invention may be used as a medicament for the treatment of a disease.

The medicament may be in the form of a pharmaceutical composition as defined above.

A method of treatment of a patient or subject in need of treatment for a disease condition is also provided, the method comprising the step of administering a therapeutically effective amount of the conjugate to the patient or subject. In some embodiments, the medical treatment requires delivery of the oligonucleotide into a cell, e.g., into the nucleus of the cell.

Diseases to be treated may include any disease where improved penetration of the cell and/or nuclear membrane by an oligonucleotide may lead to an improved therapeutic effect.

In some embodiments, the conjugate is for use in the treatment of diseases of the neuromuscular system.

Conjugates comprising peptides of the invention are suitable for the treatment of Duchenne Muscular Dystrophy (DMD) or Becker Muscular Dystrophy (BMD).

In some embodiments, the conjugate is for use in the treatment of diseases caused by splicing deficiencies. In such embodiments, the oligonucleotide may comprise an oligonucleotide capable of preventing or correcting the splicing defect and/or increasing the production of correctly spliced mRNA molecules.

In some embodiments, the conjugate is for use in the treatment of DMD.

In some embodiments, there is provided a conjugate according to the second aspect for use in the treatment of DMD. In some embodiments, in such an embodiment, the oligonucleotide of the conjugate is operable to increase expression of the dystrophin protein. In some embodiments, in such an embodiment, the oligonucleotide of the conjugate is operable to increase the expression of functional dystrophin protein.

In some embodiments, the conjugate increases dystrophin expression by 10%, 15%, 20%, 25%, 30%, 35%, 40%, 45%, 50%, 55%, 60%, 65%, 70%. In some embodiments, the conjugate increases dystrophin expression by up to 50%. In some embodiments, the conjugate restores dystrophin protein expression by 10%, 15%, 20%, 25%, 30%, 35%, 40%, 45%, 50%, 55%, 60%, 65%, 70%. In some embodiments, the conjugate restores dystrophin protein expression by up to 50%.

In some embodiments, the conjugate restores dystrophin protein function by 10%, 15%, 20%, 25%, 30%, 35%, 40%, 45%, 50%, 55%, 60%, 65%, 70%. In some embodiments, the conjugate restores dystrophin protein function by up to 50%.

In some embodiments, the oligonucleotide of the conjugate is operable to do so by causing skipping of one or more exons during dystrophin transcription.

In some embodiments, the oligonucleotide of the conjugate causes 10%, 15%, 20%, 25%, 30%, 35%, 40%, 45%, 50%, 55%, 60%, 65%, 70%, 75%, 80%, 85% skipping of one or more exons of the dystrophin gene. In some embodiments, the oligonucleotide of the conjugate causes up to 50% skipping of one or more exons of the dystrophin gene.

In some embodiments, the patient or subject to be treated may be any animal or human. In some embodiments, the patient or subject may be a non-human mammal. In some embodiments, the patient or subject may be male or female. In some embodiments, the subject is male.

In some embodiments, the patient or subject to be treated may be any age. In some embodiments, the patient or subject to be treated is aged between 0-40 years, e.g., 0-30, e.g., 0-25, e.g., 0-20 years of age.

In some embodiments, the conjugate is for administration to a subject systemically for example by intramedullary, intrathecal, intraventricular, intravitreal, enteral, parenteral, intravenous, intra-arterial, intramuscular, intratumoral, subcutaneous oral or nasal routes.

In some embodiments, the conjugate is for administration to a subject intravenously.

In some embodiments, the conjugate is for administration to a subject intravenously by injection.

In some embodiments, the conjugate is for administration to a subject in a "therapeutically effective amount", by which it is meant that the amount is sufficient to show benefit to the individual. The actual amount administered, and rate and time-course of administration, will depend on the nature and severity of the disease being treated. Decisions on dosage are within the responsibility of general practitioners and other medical doctors. Examples of the techniques and protocols can be found in Remington's Pharmaceutical Sciences, 20th Edition, 2000, pub. Lippincott, Williams & WIkins. Exemplary doses may be between 0.01 mg/kg and 50 mg/kg, 0.05 mg/kg and 40 mg/kg, 0.1 mg/kg and 30 mg/kg, 0.5 mg/kg and 18 mg/kg, 1 mg/kg and 16 mg/kg, 2 mg/kg and 15 mg/kg, 5 mg/kg and 10 mg/kg, 10 mg/kg and 20 mg/kg, 12 mg/kg and 18 mg/kg, 13 mg/kg and 17 mg/kg.

Advantageously, the dosage of the conjugates of the present invention may be lower, e.g., an order or magnitude lower, than the dosage required to see any effect from the oligonucleotide alone.

In some embodiments, after administration of the conjugates of the present invention, one or more markers of toxicity are significantly reduced compared to prior conjugates using currently available peptide carriers Suitable markers of toxicity may be markers of nephrotoxicity.

Suitable markers of toxicity include KIM-1, NGAL, BUN, creatinine, alkaline phosphatase, alanine transferase, and aspartate aminotransferase.

In some embodiments, the level of at least one of KIM-1, NGAL, and BUN is reduced after administration of the conjugates of the present invention when compared to prior conjugates using currently available peptide carriers.

In some embodiments, the levels of each of KIM-1, NGAL, and BUN are reduced after administration of the conjugates of the present invention when compared to prior conjugates using currently available peptide carriers.

In some embodiments, the levels of the or each marker/s is significantly reduced when compared to prior conjugates using currently available peptide carriers.

In some embodiments, the levels of the or each marker/s is reduced by up to 5%, 10%, 15%, 20%, 25%, 30%, 35%, 40%, 45%, 50% after administration of the conjugates of the present invention when compared to prior conjugates using currently available peptide carriers.

Advantageously, the toxicity of the peptides and therefore the resulting conjugates is significantly reduced compared to prior cell-penetrating peptides and conjugates. In particular, KIM-1 and NGAL-1 are markers of toxicity and these are significantly reduced by up to 120 times compared to prior conjugates using currently available peptide carriers.

Peptide Preparation

Peptides of the invention may be produced by any standard protein synthesis method, for example chemical synthesis, semi-chemical synthesis or through the use of expression systems. Accordingly, the present invention also relates to the nucleotide sequences comprising or consisting of the DNA coding for the peptides, expression systems e.g. vectors comprising said sequences accompanied by the necessary sequences for expression and control of expression, and host cells and host organisms transformed by said expression systems.

Accordingly, a nucleic acid encoding a peptide according to the present invention is also provided.

In some embodiments, the nucleic acids may be provided in isolated or purified form.

An expression vector comprising a nucleic acid encoding a peptide according to the present invention is also provided.

In some embodiments, the vector is a plasmid.

In some embodiments, the vector comprises a regulatory sequence, e.g. promoter, operably linked to a nucleic acid encoding a peptide according to the present invention. In some embodiments, the expression vector is capable of expressing the peptide when transfected into a suitable cell, e.g. mammalian, bacterial or fungal cell.

A host cell comprising the expression vector of the invention is also provided.

Expression vectors may be selected depending on the host cell into which the nucleic acids of the invention may be inserted. Such transformation of the host cell involves conventional techniques such as those taught in Sambrook et al [Sambrook, J., Russell, D. (2001) Molecular Cloning: A Laboratory Manual, Cold Spring Harbor Laboratory Press, NY, USA] Selection of suitable vectors is within the skills of the person knowledgeable in the field. Suitable vectors include plasmids, bacteriophages, cosmids, and viruses.

The peptides produced may be isolated and purified from the host cell by any suitable method e.g. precipitation or chromatographic separation e.g. affinity chromatography.

Suitable vectors, hosts and recombinant techniques are well known in the art.

The following examples are meant to illustrate the invention. They are not meant to limit the invention in any way.

EXAMPLES

Example 1

1. Materials and Methods 1.1 P-PMO Synthesis and Preparation

9-Fluorenylmethoxycarbonyl (Fmoc) Protected L-Amino Acids, benzotriazole-1-yl-Oxy-tris-pyrrolidino-phosphonium (PyBOP), 2-(1H-benzotriazole-1-yl)-1,1,3,3-tetramethyluronium hexafluorophosphate (HBTU), and the Fmoc^-Ala-OH preloaded Wang resin (0.19 or 0.46 mmol $g-^{1}$) were obtained from Merck (Hohenbrunn, Germany). HPLC grade acetonitrile, methanol and synthesis grade N-methyl-2-pyrrolidone (NMP) were purchased from Fisher Scientific (Loughborough, UK). Peptide synthesis grade Al,N-dimethylformamide (DMF) and diethyl ether were obtained from VWR (Leicestershire, UK). Piperidine and trifluoroacetic acid (TFA) were obtained from Alfa Aesar (Heysham, England). PMO was purchased from Gene Tools Inc. (Philomath, USA). Chicken Embryo Extract and horse serum were obtained from Sera Laboratories International Ltd (West Sussex, UK). Interferon was obtained from Roche Applied Science (Penzberg, Germany). All other reagents were obtained from Sigma-Aldrich (St. Louis, MO, USA) unless otherwise stated. MALDI-TOF mass spectrometry was carried out using a Voyager DE Pro BioSpectrometry workstation. A stock solution of 10 mg $mL^{1}$ of a-cyano-4-hydroxycinnamic acid or sinapinic acid in 50% acetonitrile in water was used as matrix. Error bars are ±0.1%.

1.2 Synthesis of P-PMO Peptides for Screening in H2k Mdx Cells a) Preparation of a Library of Peptide Variants Peptides were either prepared on a 10 pmol scale using an Intavis Parallel Peptide Synthesizer or on a 100 pmol scale using a CEM Liberty Blue™ Peptide Synthesizer (Buckingham, UK) using Fmoc^-Ala-OH preloaded Wang resin (0.19 or 0.46 mmol $g^{-1}$, Merck Millipore) by applying standard Fmoc chemistry and following manufacturer's recommendations. In the case of synthesis using the Intavis Parallel Peptide Synthesizer, double coupling steps were used with a PyBOP/NMM coupling mixture followed by acetic anhydride capping after each step. For synthesis using the CEM Liberty Blue Peptide Synthesizer, single standard couplings were implemented for all amino acids except arginine, which was performed by double couplings. The coupling was carried out once at 75° C. for 5 min at 60-watt microwave power except for arginine residues, which were coupled twice each. Each deprotection reaction was carried out at 75° C. twice, once for 30 sec and then for 3 min at 35-watt microwave power. Once synthesis was complete, the resin was washed with DMF (3×50 mL) and the N-terminus of the solid phase bound peptide was acetylated with acetic anhydride in the presence of DI PEA. at room temperature. After acetylation of the N-terminus, the peptide resin was washed with DMF (3×20 mL) and DCM (3×20 mL). The peptides were cleaved from the solid support by treatment with a cleavage cocktail consisting of trifluoroacetic acid (TFA): H2O: triisopropylsilane (TIPS) (95%: 2.5%: 2.5%: 3-10 mL) for 3 h at room temperature. After peptide release, excess TFA was removed by sparging with nitrogen. The crude peptide was precipitated by the addition of cold diethyl ether (15-40 mL depending on scale of the synthesis) and centrifuged at 3200 rpm for 5 min. The crude peptide pellet was washed thrice with cold diethyl ether (3×15 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of $CH_3CN$ in 0.1% TFA/$H_2O$ with a flow rate of 15 mL $min^{1}$. Detection was performed at 220 nm and 260 nm. The fractions containing the desired peptide were combined and lyophilized to yield the peptide as a white solid.

TABLE 4 peptides as synthesised for testing in the examples with N-terminal acetylation and C-terminal beta-alanine linker. Pip9b2 and R6Gly (SEQ ID NO: 176) are comparative peptides. R6Gly (SEQ ID NO: 176) uses a C-terminal glycine as a linker. b) Synthesis of a library of PMO-peptide conjugates

| Peptide Number | Sequence ID NO. incorporated | Sequence Tested (with additional C and N terminal modifications) |
|---|---|---|
| D-PEP 1.1 | 27 | Ac-RBRRBRRFQILYRBRBR-B (SEQ ID NO: 199) |
| D-PEP 1.2 | 28 | Ac-RBRRBRRFQILYRBRR-B (SEQ ID NO: 200) |
| D-PEP 1.3 | 29 | Ac-RBRRBRFQILYRRBRBR-B (SEQ ID NO: 201) |
| D-PEP 1.4 | 30 | AC-RBRBRFQILYRBRRBRR-B (SEQ ID NO: 202) |
| D-PEP 1.5 | 31 | Ac-RBRRBRRYQFLIRBRBR-B (SEQ ID NO: 203) |
| D-PEP 1.6 | 32 | AC-RBRRBRRILFQYRBRBR-B (SEQ ID NO: 204) |
| D-PEP 1.7 | 33 | Ac-RBRRBRFQILYRBRBR-B (SEQ ID NO: 205) |
| D-PEP 1.8 | 34 | Ac-RBRRBFQILYRBRRBR-B (SEQ ID NO: 206) |
| D-PEP 1.9 | 35 | Ac-RBRRBRFQILYBRBR-B (SEQ ID NO: 207) |
| D-PEP 1.10 | 36 | Ac-RBRRBFQILYRBRBR-B (SEQ ID NO: 208) |
| D-PEP 3.1 | 37 | Ac-RBRRBRRFQILYRBHBH-B (SEQ ID NO: 209) |
| D-PEP 3.2 | 38 | Ac-RBRRBRRFQILYHBHBR-B (SEQ ID NO: 210) |
| D-PEP 3.3 | 39 | AC-RBRRBRRFQILYHBRBH-B (SEQ ID NO: 211) |
| D-PEP 3.4 | 40 | Ac-RBRRBRRYQFLIRBHBH-B (SEQ ID NO: 212) |
| D-PEP 3.5 | 41 | Ac-RBRRBRRILFQYRBHBH-B (SEQ ID NO: 213) |
| D-PEP 3.6 | 42 | Ac-RBRHBHRFQILYRBRBR-B (SEQ ID NO: 214) |
| D-PEP 3.7 | 43 | Ac-RBRBBHRFQILYRBHBH-B (SEQ ID NO: 215) |

TABLE 4-continued peptides as synthesised for testing in the examples with N-terminal acetylation and C-terminal beta-alanine linker. Pip9b2 and R6Gly (SEQ ID NO: 176) are comparative peptides. R6Gly (SEQ ID NO: 176) uses a C-terminal glycine as a linker. b) Synthesis of a library of PMO-peptide conjugates

| Peptide Number | Sequence ID NO. incor-porated | Sequence Tested (with additional C and N terminal modifications) |
|---|---|---|
| D-PEP 3.8 | 44 | Ac-RBRRBRFQILYRBHBH-B (SEQ ID NO: 216) |
| D-PEP 3.9 | 45 | Ac-RBRRBRFQILYHBHBH-B (SEQ ID NO: 217) |
| D-PEP 3.10 | 46 | Ac-RBRRBHFQILYRBHBH-B (SEQ ID NO: 218) |
| D-PEP 3.11 | 47 | AC-HBRRBRFQILYRBHBH-B (SEQ ID NO: 219) |
| D-PEP 3.12 | 48 | Ac-RBRRBFQILYRBHBH-B (SEQ ID NO: 220) |
| D-PEP 3.13 | 49 | Ac-RBRRBRFQILYBHBH-B (SEQ ID NO: 221) |
| D-PEP 3.14 | 50 | Ac-RBRRBRYQFLIHBHBH-B (SEQ ID NO: 222) |
| D-PEP 3.15 | 51 | Ac-RBRRBRILFQYHBHBH-B (SEQ ID NO: 223) |
| D-PEP 3.16 | 52 | Ac-RBRRBRRFQILYHBHBH-B (SEQ ID NO: 224) |
| Pip9b2 | 175 | Ac-RXRRBRR-FQILY-RBRXR-B |
| R6Gly | 176 | RRRRRR-G |

A 25-mer PMO antisense sequence for mouse dystrophin exon-23 (GGCCAAACCTCGGCTTACCTGAAAT (SEQ ID NO: 90)) was used. The peptide was conjugated to the 3'-end of the PMO through its C-terminal carboxyl group. This was achieved using 2.3 and 2 equivalents of PyBOP and HOAt in NMP respectively in the presence of 2.3 equivalents of DIPEA over peptide and 2.5 fold excess of peptide over PMO dissolved in DMSO. In a few examples, 2.3 equivalents of HBTU were used in place of PyBOP for activation of the C-terminal carboxyl group of the peptide. In general, to a solution of peptide (2500 nmol) in N-methylpyrrolidone (NMP, 80 mL) were added PyBOP (19.2 mL of 0.3 M in NMP), HOAt in (16.7 mL of 0.3 M NMP), DIPEA (1.0 pL) and PMO (100 mL of 10 mM in DMSO). The mixture was left for 2.5 h at 40° C. and the reaction was quenched by the addition of 0.1% TFA in $H_2O$ (300 mL). This solution was purified by lon exchange chromatography using a converted Gilson HPLC system. The PMO-peptide conjugates were purified on an ion exchange column (Resource S 4 mL, GE Healthcare) using a linear gradient of sodium chloride (0 to 1 M) in sodium phosphate buffer (25 mM, pH 7.0) containing 20% $CH_3CN$ at a flow rate of 4 mL min-1. The fractions containing the desired compound were combined and lyophilized to yield the peptide-PMO derivative as a white solid. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 pm cellulose acetate membrane before use. The concentration of peptide-PMO was determined by the molar absorption of the conjugates at 265 nm in 0.1 N HCl solution (see Table 5 for yields).

TABLE 5

Yields of P-PMO conjugates for cell culture analysis (The yields are based on dried weight of the lyophilised purified PPMO. The purity for the P-PMOs is greater than 95% as ascertained by normal phase HPLC at 220 nm and 260 nm.

| Peptide-PMO | Yield |
|---|---|
| D-Pep 1.1-PMO | 36% |
| D-Pep 1.2-PMO | — |
| D-Pep 1.3-PMO | 25%[a] |
| D-Pep 1.4-PMO | 24%[a] |
| D-Pep 1.5-PMO | 24%[a] |
| D-Pep 1.6-PMO | 25%[a] |
| D-Pep 1.7-PMO | 33% |
| D-pep 1.8-PMO | 41% |
| D-Pep 1.9-PMO | 35% |
| D-Pep 1.10-PMO | 33% |
| D-Pep 3.1-PMO | 28% |
| D-Pep 3.2-PMO | 33% |
| D-Pep 3.3-PMO | 33% |
| D-Pep 3.4-PMO | 35% |
| D-Pep 3.5-PMO | 37% |
| D-Pep 3.6-PMO | 34% |
| D-Pep 3.7-PMO | 26% |
| D-pep 3.8-PMO | 34% |
| D-Pep 3.9-PMO | 28% |
| D-Pep 3.10-PMO | 28% |
| D-Pep 3.11-PMO | 29% |
| D-Pep 3.12-PMO | 29% |
| D-Pep 3.13-PMO | 31% |
| D-Pep 3.14-PMO | 34% |
| D-Pep 3.15-PMO | 32% |
| D-Pep 3.16-PMO | — |

[a]The P-PMO was synthesised using HBTU activation instead of PyBOP).

1.3 Cell Culture

Murine H2k mdx myoblasts were cultured in gelatin (0.01%) coated flasks at 33° C., under 10% $CO_2$ in Dulbecco's modified Eagles medium (DM EM PAA laboratories) supplemented with 20% heat-inactivated fetal bovine serum (FBS Gold, PAA laboratories), 2% chicken embryo extract (Seralab), 1% penicillin-streptomycin-neomycin antibiotic mixture (PSN, Gibco) and 3 pg/pL g-interferon (Roche). Cells were seeded in gelatin (0.01%) coated 24-well plates at a density of $2\times10^5$ cell/mL and left for 2 days at 33° C., 10% $CO_2$. To differentiate into myotubes, cells were further grown in DM EM supplemented with 5% horse serum (Sigma) and 1% PSN at 37° C., under 5% $CO_2$ for 2 days.

1.4 Cell Transfection

Cells were incubated with peptide-PMO conjugates prepared as described above which were made up in serum-free Opti-MEM and 350 mL was added to each well as duplicates and incubated at 37° C. for 4 hr. The transfection medium was then replaced with DM EM supplemented with 5% horse serum and 1% PSN and the cells incubated for a further 20 hr at 37° C. Cells were washed with PBS and 0.5 mL of TRI RNA (Sigma) isolation reagent was added to each well. Cells were frozen at −80° C. for 1 hr.

1.5 RNA Extraction and Nested RT-PCR Analysis

Total cellular RNA was extracted using TRI reagent with an extra further precipitation with ethanol. The purified RNA was quantified using a Nanodrop® ND-1000 (Thermo Scientific). The RNA (400 ng) was used as a template for RT-PCR using a OneStep RT-PCR Kit (Roche, Indianapolis, USA). For primer sequences refer to Table 7. The cycle conditions for the initial reverse transcription were 50° C. for 30 min and 94° C. for 7 min for 1 cycle followed by 30 cycles of 94° C. for 20 sec, 55° C. for 40 sec and 68° C. for 80 sec. One microliter of the RT-PCR product was used as template for the second PCR step. The amplification was carried out using 0.5 U of SuperTAQ in 25 cycles at 94° C. for 30 sec, 55° C. for 1 min and 72° C. for 1 min. The products were separated by electrophoresis using 1.5% agarose gel. The images of agarose gels were taken on a Molecular Imager ChemiDoc™XRS+ imaging system (Bio-Rad, UK) and the images were analysed using Image Lab (V4.1). Microsoft Excel was used to analyse and plot the exon-skipping assay data, which were expressed as the percentage of exon-23 skipping from at least three independent experiments.

1.6 Synthesis of PMO-Peptide Conjugates for Testing in H2k Mdx Mice a) Synthesis of Peptide Variants Peptides were synthesized on a 100 pmol scale using a CEM Liberty Blue™ microwave Peptide Synthesizer (Buckingham, UK) and Fmoc chemistry following manufacturer's recommendations. The side chain protecting groups used were labile to trifluoroacetic acid treatment and the peptide was synthesized using a 5-fold excess of Fmoc-protected amino acids (0.25 mmol) that were activated using PyBOP (5-fold excess) in the presence of DIPEA. Piperidine (20% v/v in DMF) was used to remove N-Fmoc protecting groups. The coupling was carried out once at 75° C. for 5 min at 60-watt microwave power except for arginine residues, which were coupled twice each. Each deprotection reaction was carried out at 75° C. twice, once for 30 sec and then once for 3 min at 35-watt microwave power. Once synthesis was complete, the resin was washed with DMF (3×50 mL) and the N-terminus of the solid phase bound peptide was acetylated with acetic anhydride in the presence of DI PEA at room temperature. After acetylation of the N-terminus, the peptide resin was washed with DMF (3×20 mL) and DCM (3×20 mL). The peptide was cleaved from the solid support by treatment with a cleavage cocktail consisting of trifluoroacetic acid (TFA): $H_2O$: triisopropylsilane (TIPS) (95%: 2.5%: 2.5%, 10 mL) for 3 h at room temperature. Excess TFA was removed by sparging with nitrogen. The cleaved peptide was precipitated via the addition of ice-cold diethyl ether and centrifuged at 3000 rpm for 5 min. The crude peptide pellet was washed thrice with cold diethyl ether (3·40 mL) and purified by RP-HPLC using a Varian 940-LC HPLC System fitted with a 445-LC Scale-up module and 440-LC fraction collector. Peptides were purified by semi preparative HPLC on an RP-C18 column (10×250 mm, Phenomenex Jupiter) using a linear gradient of $CH_3CN$ in 0.1% TFA/$H_2O$ with a flow rate of 15 mL min 1. Detection was performed at 220 nm and 260 nm.

b) Synthesis of PMO-peptide conjugates A 25-mer PMO antisense sequence for mouse dystrophin exon-23 (GGCCAAACCTCGGCTTACCTGAAAT (SEQ ID NO: 90)) was used. The peptide was conjugated to the 3'-end of the PMO through its C-terminal carboxyl group. This was achieved using 2.3 and 2-fold equivalents of PyBOP and HOAt in NMP respectively in the presence of 2.3 eq of DIPEA over peptide and a 2.5-fold excess of peptide over PMO dissolved in DMSO. In a few examples, HBTU (2.3 equivalents) were used in place of PyBOP for activation of the C-terminal carboxyl group of the peptide. In general, to a solution of peptide (10 pmol) in N-methylpyrrolidone (NMP, 100 mL) were added PyBOP (76.6 mL of 0.3 M in NMP), HOAt in (66.7 mL of 0.3 M NMP), DIPEA (4.0 mL) and PMO (400 mL of 10 mM in DMSO). The mixture was left for 2 h at 40° C. and the reaction was quenched by the addition of 0.1% TFA (1 mL). The reaction was purified on a cation exchange chromatography column (Resource S 6 mL column, GE Healthcare) using a linear gradient of sodium chloride (0 to 1 M) in sodium phosphate buffer (25 mM, pH 7.0) containing 20% $CH_3CN$ at a flow rate of 6 mL min-1. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 pm cellulose acetate membrane before use. The concentration of peptide-PMO was determined by the molar absorption of the conjugates at 265 nm in 0.1 N HCl solution. Overall yields (Table 6) were 25-36% based on PMO.

TABLE 6

Yields of P-PMO conjugates synthesized on larger scale for in vivo analysis (The yields are based on dried weight of the lyophilised purified PPMO. The purity for the PPMOs is greater than 95% as ascertained by normal phase HPLC at 220 nm and 260 nm.

| Peptide-PMO | Yield |
|---|---|
| D-Pep 1.1-PMO | 36% |
| D-Pep 1.3-PMO | 25%[a] |
| D-Pep 1.4-PMO | 24%[a] |
| D-Pep 1.5-PMO | 25%[a] |
| D-Pep 1.6-PMO | 25%[a] |
| D-Pep 3.1-PMO | 28% |
| D-Pep 3.2-PMO | 33% |
| D-Pep 3.7-PMO | 26% |
| D-pep 3.8-PMO | 34% |
| D-Pep 3.9-PMO | 28% |
| D-Pep 3.10-PMO | 28% |

[a]The PPMO was synthesised using HBTU activation instead of PyBOP)

1.7 In Vivo Assessment of Dystrophin Restoration by P-PMO

Experiments were conducted in the Biomedical Sciences Unit, University of Oxford, under Home Office Project Licence authorisation following institutional ethical review. Mice were housed in a minimal disease facility; the environment was temperature controlled with a 12 hour light-dark cycle. All animals received commercial rodent chow and water ad libitum.

Experiments were performed in 10-12 week old female mdx mice. Mdx mice were restrained prior to a single tail vein injection of 10 mg/kg of P-PMO. One week post injection mice were sacrificed and TA, heart and diaphragm muscles removed and snap frozen in dry-ice cooled isopentane and stored at −80° C.

1.8 Western Blot Analysis

To assess the duration of dystrophin restoration following a single administration, one-third of the muscle (for TA and diaphragm) or ninety 7 pm thick transverse cryosections (for heart) were lysed in 300 ml buffer (50 mM Tris pH 8, 150 mM NaCl, 1% NP40, 0.5% sodium deoxycholate, 10% SDS and protease/phosphatase inhibitors) prior to centrifuging at 13000 rpm (Heraeus, #3325B) for 10 min. Supernatant was collected and heated at 100° C. for 3 min. Protein was quantified by BCA method and 40 pg protein/sample were resolved in a NuPage a 3-8% Tris-Acetate gel as previously described (19). Proteins were transferred to a 0.45 pm pore size PVDF membrane for 1 h at 30V followed by 1 h at 100V, and probed with monoclonal anti-dystrophin (1:200, NCL-DYS1, Novocastra) and anti-vinculin (loading control, 1:100 000, hVIN-1, Sigma) antibodies as previously described (37). Secondary antibody IRDye 800 CW goat anti-mouse was used at a dilution of 1:20000 (LiCOR).

The levels of dystrophin restoration in P-PMO treated mdx mice were expressed as relative to the levels of C57BL/10 wildtype control mice, considered as 100%. For this, a standard curve was generated by including 5 serial C57BL/10 protein dilutions in parallel to the P-PMO treated mdx samples. Dilution series were as follows: 75%, 40%, 15%, 5% or 0% respectively of the 40 pg total protein loaded per lane were from C57BL/10 protein lysates and the remaining from un-treated mdx protein lysates. These standards were aliquoted and used in each western blot in parallel to the treated mdx samples. For all standards and treated samples, Dystrophin intensity quantification was performed by Fluorescence Odyssey imaging system and normalized by calculating the ratio to the Vinculin fluorescence intensity in all samples. Standard normalized values were plotted against their known concentration of dystrophin to obtain the mathematical expression of best fit and this expression used to interpolate the normalized values of each sample of P-PMO treated mdx mice.

1.9 RT-qPCR Analysis of in Vivo Dmd Exon 23 Skipping

Quantification of exclusion of exon 23 from the mouse Dmd transcript was performed on skeletal muscle and heart tissue treated with peptide-PMO. Briefly, RNA was extracted from homogenised tissue using Trizol-based extraction method and cDNA synthesised using random primers. Primer/probes were synthesised by Integrated DNA Technologies and designed to amplify a region spanning exon 23-24 representing unskipped product (mDMD23-24, see Table 7), or to amplify specifically transcripts lacking exon 23 using a probe spanning the boundary of exon 22 and 24 (mDMD22-24). Levels of respective transcripts were determined by calibration to standard curves prepared using known transcript quantities, and skipping percentages derived by [skip]/[skip+unskip].

TABLE 7

Primer and probe sequences for quantification of exon 23 skipping by nested RT-PCR or quantitative RT-PCR methods.

| Assay ID | Primer Sequence (5'-3') | Sequence ID NO. |
|---|---|---|
| | Nested RT-PCR | |
| Exon20Fo | CAGAATTCTGCCAATTGCTGAG | 91 |
| Exon26Ro | TTCTTCAGCTTGTGTCATCC | 92 |
| Exon20Fi | CCCAGTCTACCACCCTATCAGAGC | 93 |
| Exon26Ri | CCTGCCTTTAAGGCTTCCTT | 94 |
| | qRT-PCR | |
| mDMD23-24 | Primer 1 CAGGCCATTCCTCTTTCAGG | 95 |
| | Primer 2 GAAACTTTCCTCCCAGTTGGT | 96 |
| | Probe /5FAM/TCAACTTCA/ZEN/ GCCATCCATTTCTGTAAGGT/3IABkFQ/ | 97 |
| mDMD22-24 | Primer 1 CTGAATATGAAATAATGGAGGAG AGACTCG | 98 |
| | Primer 2 CTTCAGCCATCCATTTCTGTAAG GT | 99 |
| | Probe/5FAM/ATGTGATTC/ZEN/ TGTAATTTCC/3IABkFQ/ | 100 |

1.10 Toxicological Assessment of Peptide-PMO

Female C57BL/6 mice aged 8-10 weeks were administered a single 30 mg/kg dose of peptide-PMO in 0.9% saline by bolus intravenous tail vein injection. Urine was non-invasively collected under chilled conditions at Day 2 and Day 7 post-administration following 20 hours housing in metabolic cages (Tecniplast, UK). Serum was collected from jugular vein at Day 7 at necropsy, as was tibialis anterior, diaphragm and heart tissue.

The same procedure was followed at different single dosage amounts ranging from 2.5 mg/kg up to 50 mg/kg of peptide-PMO in 0.9% saline by intravenous tail vein injection.

Urinary levels of KIM-1 (Kidney injury molecule-1) and NGAL (Neutrophil Gelatinase-Associated Lipocalin) were quantified by ELISA (KIM-1 R&D cat #MKM100, NGAL R&D cat #MLCN20) following appropriate dilution of urine to fit standard curves. Values were normalised to urinary creatinine levels that were quantified at MRC Harwell Institute, Mary Lyon Centre, Oxfordshire, UK. Serum blood urea nitrogen levels were quantified at MRC Harwell Institute, Mary Lyon Centre, Oxfordshire, UK.

All levels were quanitifed on an AU680 Clinical Chemistry Analyser, Beckman Coulter. Quantification of exon skipping efficacy was determined by quantitative RT-PCR of exon 23 skipped and unskipped transcripts and expressed as percentage of skipped versus total (skipped and unskipped) transcripts (see Table 7 for sequences).

2. Results

The results provided herein demonstrate a clear dose response effect of the peptide-PMO conjugates generated herein in exon skipping activity within cells (FIGS. 1, 2, and 12A-12C). These FIGS. also highlight that all of the DPEP1 and DPEP3 series, i.e. the peptides of the invention, have sufficient cell penetrating efficacy in cells to be considered for therapeutic use.

Figure 7:
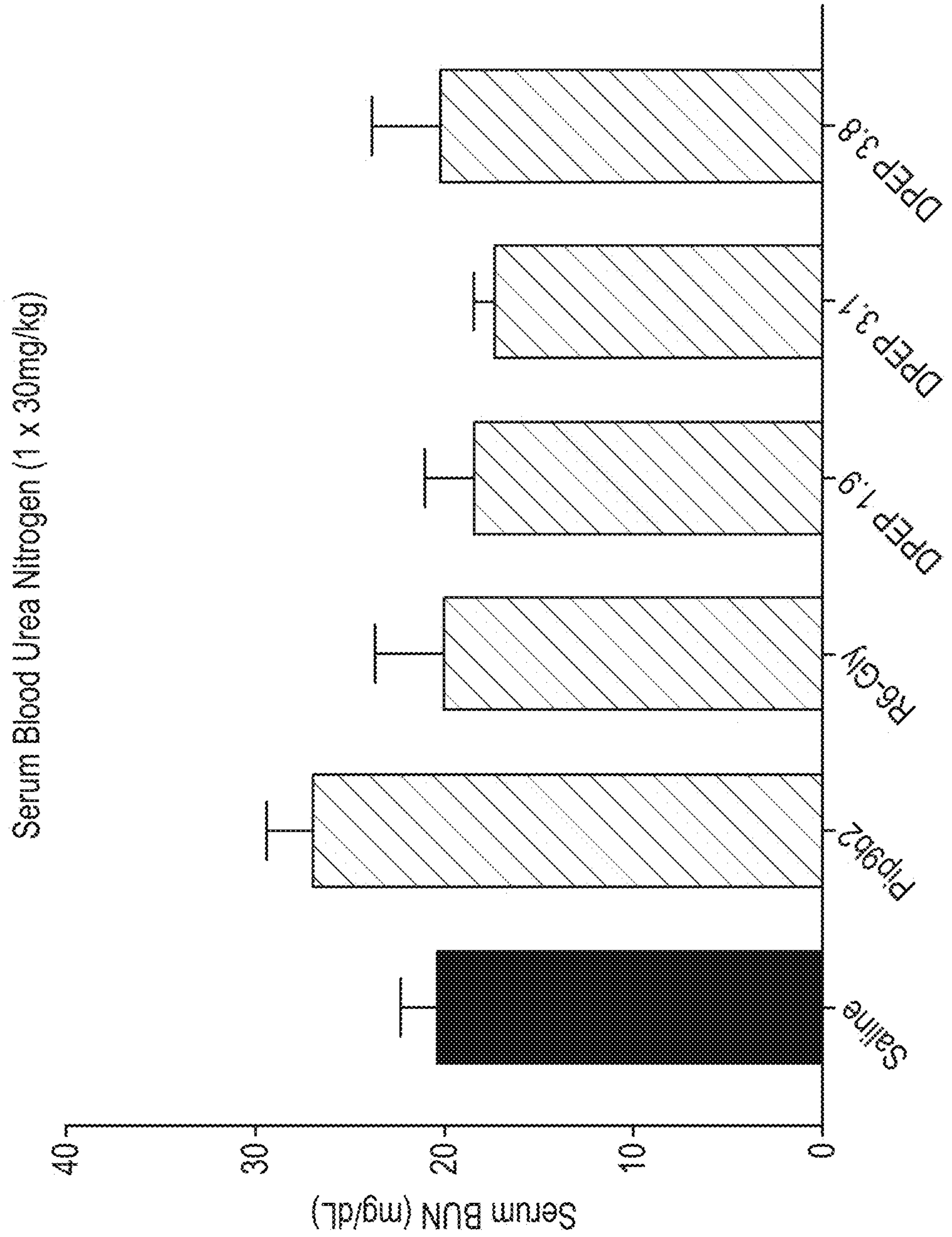
FIG. 7: shows the BUN serum levels measured in C67BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 8:
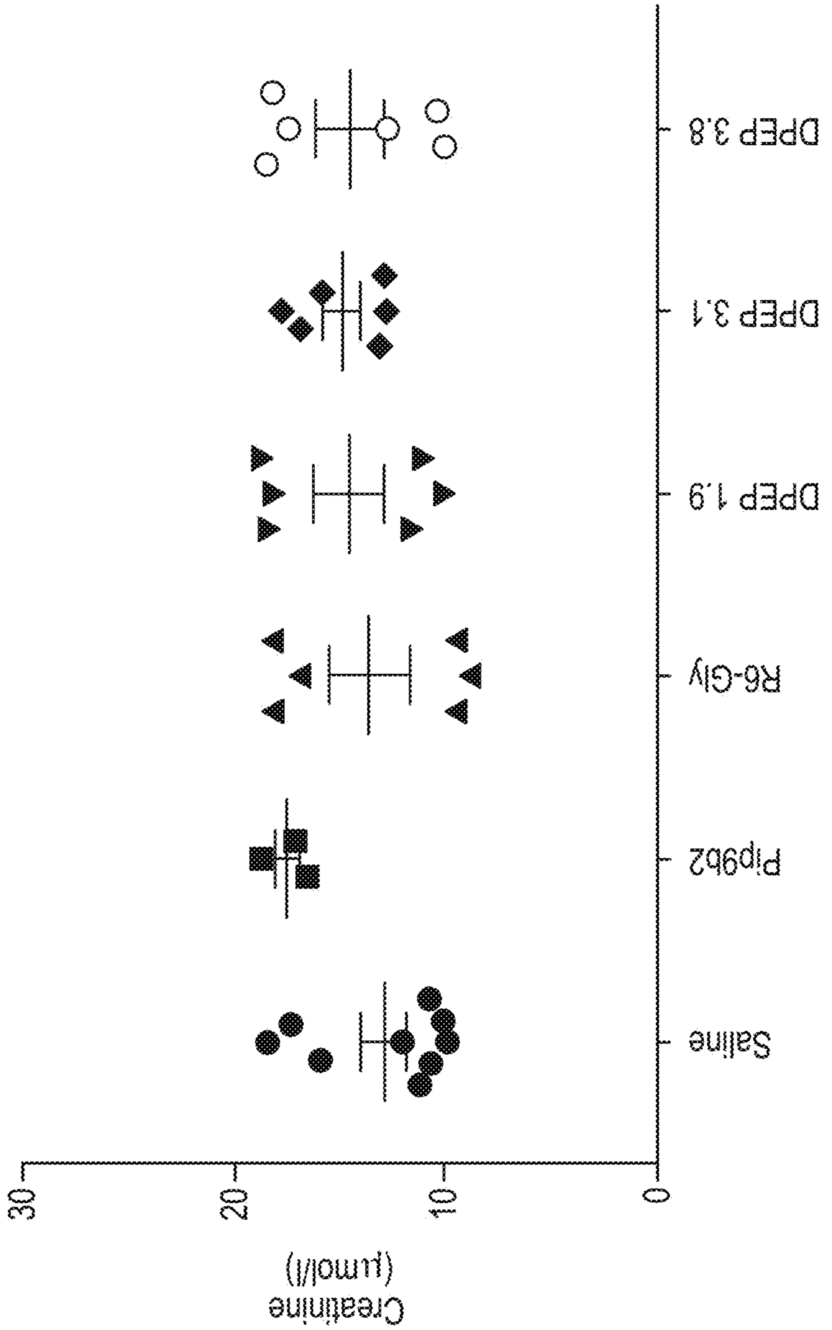
FIG. 8: shows the Creatinine serum levels measured in C67BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 9A:
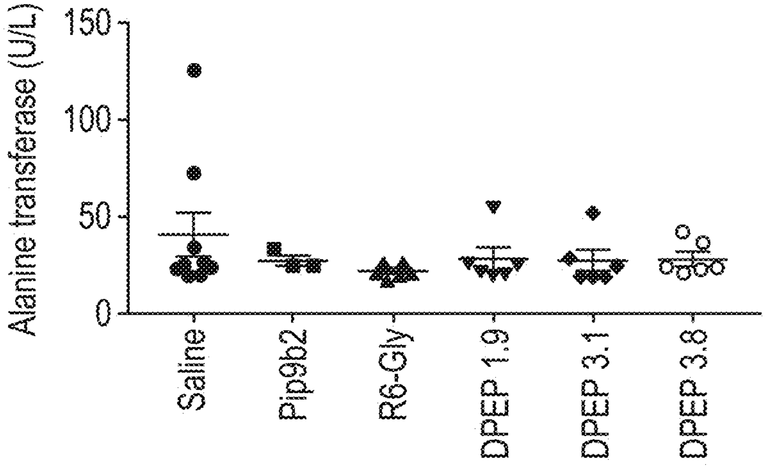
FIGS. 9A-9C: show the (9A) Alanine Transferase, (9B) Alkaline Phosphatase and (9C) aspartate aminotransferase serum levels measured in C57BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 9B:
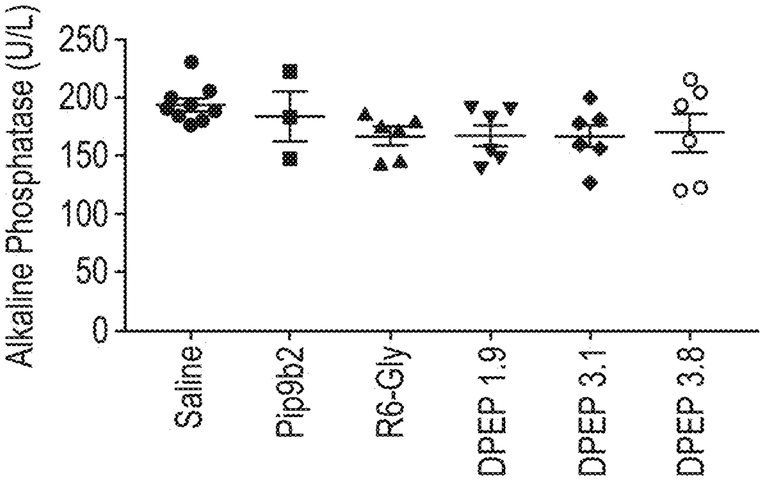
Figure 9C:
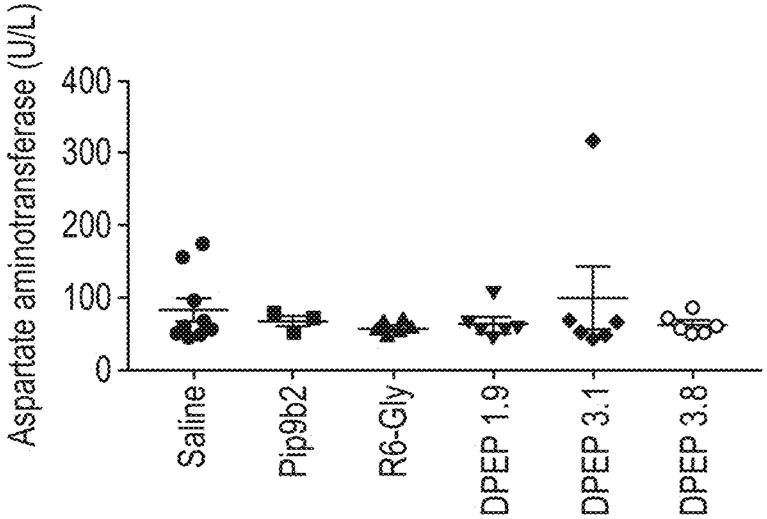
Figure 10A:
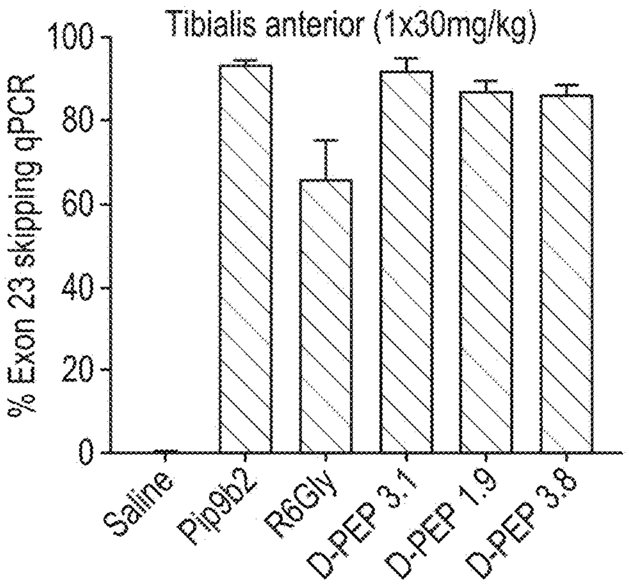
FIGS. 10A-10C: show the in vivo efficacy of exon 23 skipping assessed by qRT-PCR in (10A) tibalis anterior, (10B) diaphragm and (10C) heart of C57BL/6 mice following a single 30 mg/kg intravenous administration of various DPEP peptides conjugated to an antisense therapeutic PMO, in comparison with currently available peptide carriers conjugated to the same antisense therapeutic PMO and saline.
Figure 10B:
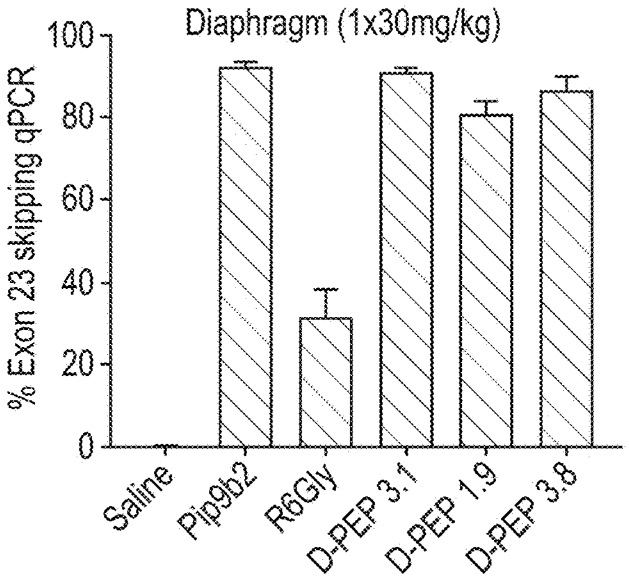
Figure 10C:
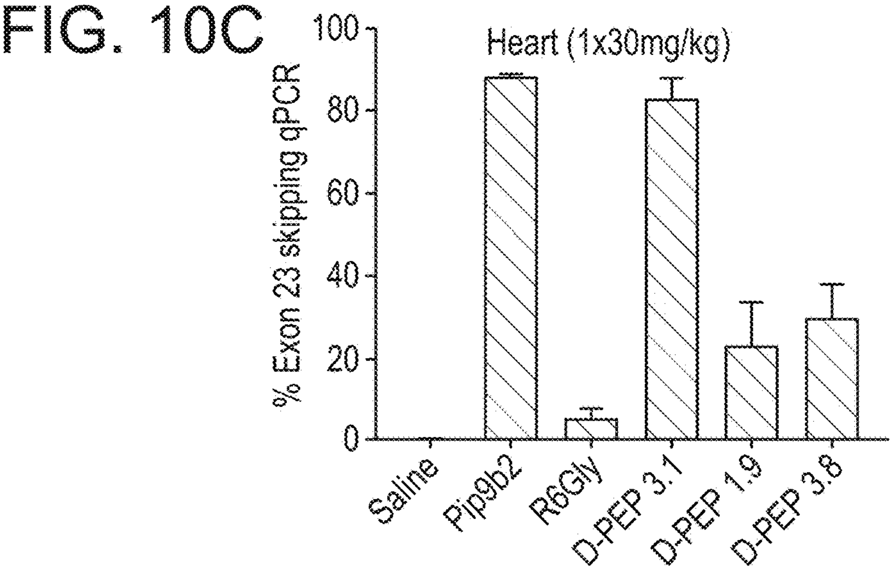
Figure 11A:
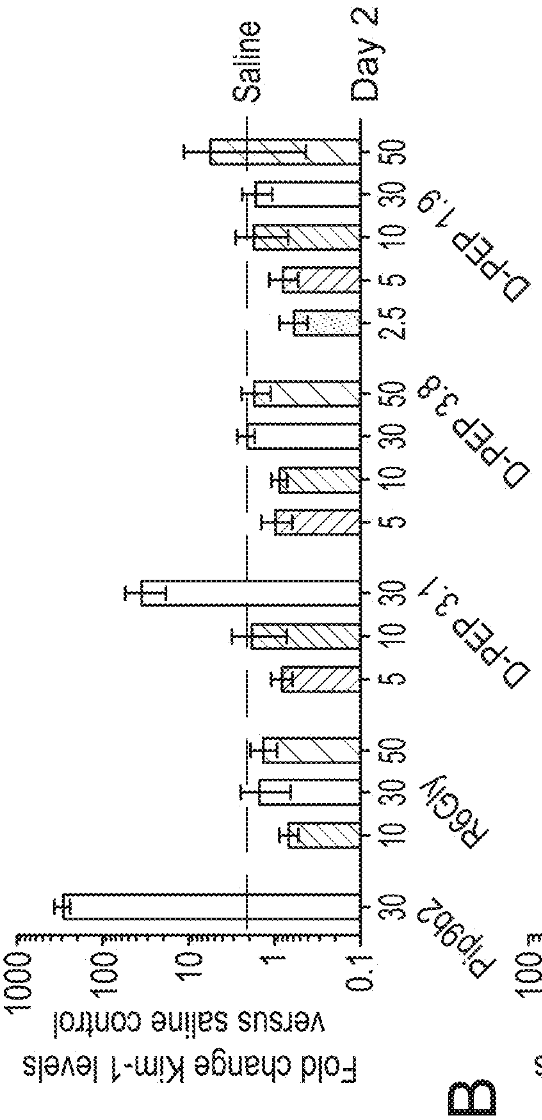
FIGS. 11A and 11B: Assessment of urinary KIM-1 levels at Day 2 or Day 7 following single dose administration of different amounts of peptide-PMOs between 2.5-50 mg/kg to 8-10 week old C57BL6 mice (n=4-6) in comparison with a currently available peptide carriers conjugated to the same antisense therapeutic PMO. KIM-1 levels were determined by ELISA and normalised to urinary creatinine levels. Data is presented as fold-change over saline injected mice control KIM-1 levels (n=10).
Figure 11B:
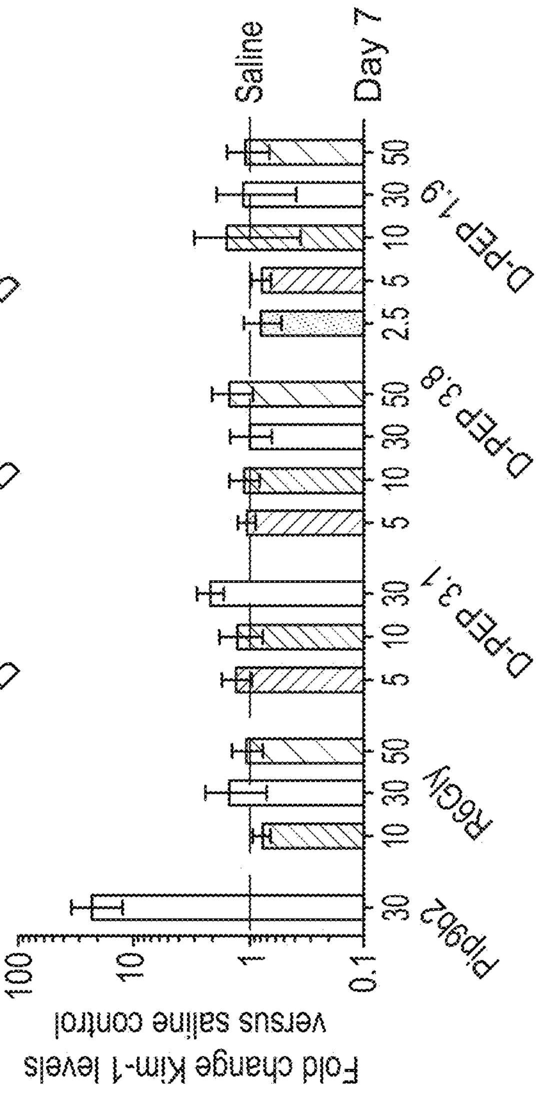
Figure 12A:
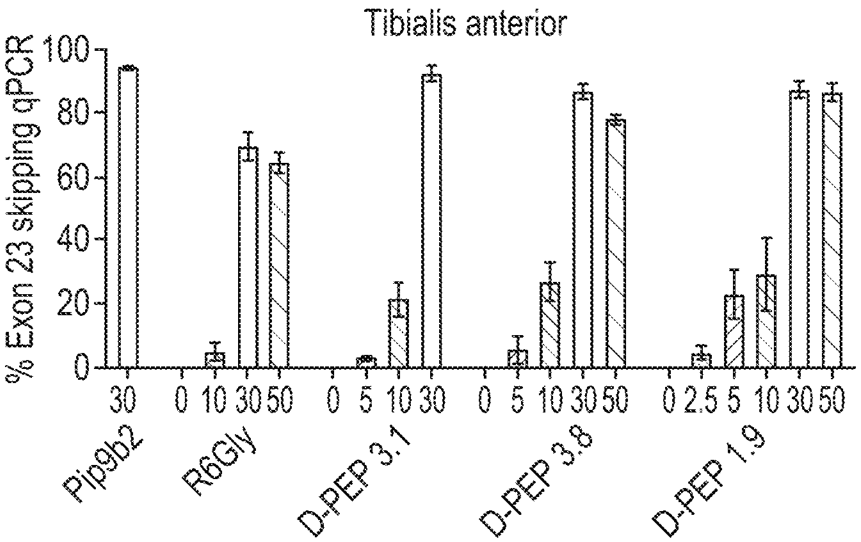
FIGS. 12A-12C: Dose-response comparative study of in vivo exon skipping efficacy of peptide-PMOs following single dose administration of increasing amounts from 2.5-50 mg/kg to 8-10 week old C57BL6 mice (n=3-6) in comparison with currently available peptide carriers conjugated to the same antisense therapeutic PMO. qPCR analysis of exon 23 exclusion was assessed in (12A) tibialis anterior, (12B) diaphragm and (12C) heart at 7 days post-administration.
Figure 12B:
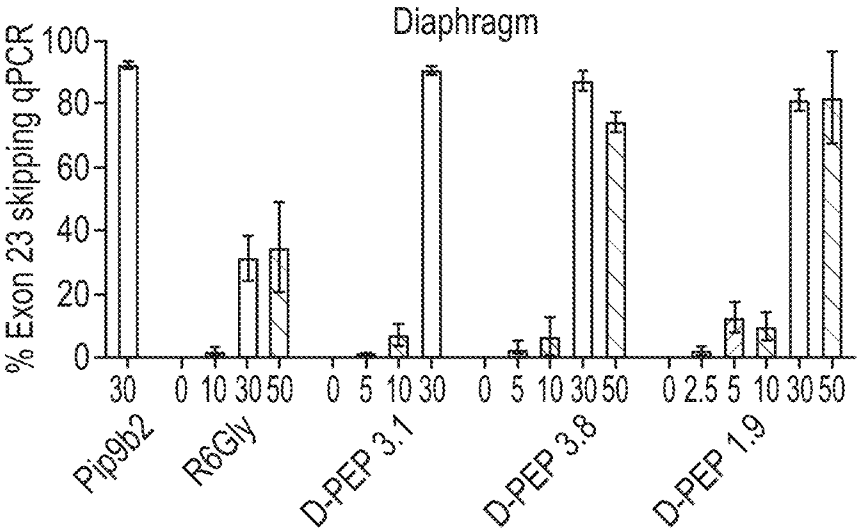
Figure 12C:
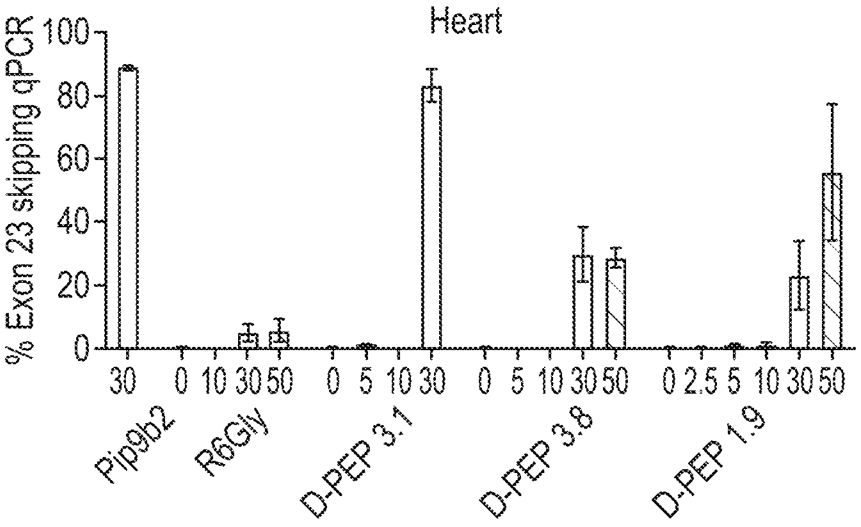

The results provided herein further highlight the activity of the peptide-PMO conjugates in vivo in a relevant mouse model of disease (FIGS. 3A-4C). Overall the results suggest that activity of such conjugates is greatest in tibialis anterior>diaphragm>heart. These figures demonstrate that the DPEP peptide conjugates of the invention have good exon skipping activity in vivo and provide an increase in dystrophin protein expression in vivo. Furthermore, the DPEP conjugates of the invention compare favourably in both respects with previous cell-penetrating peptides, such as 'PIP' peptides and R6Gly (SEQ ID NO: 176), when used in the same conjugate. Also demonstrated herein is that the levels of KIM-1 and NGAL (which are indicators of nephrotoxicity) after administration of the DPEP peptide conjugate compounds are all significantly lower than conjugates with previous cell-penetrating peptides. DPEP 1.9 and 3.8 conjugates demonstrated the lowest levels of such markers (FIGS. 5, 6 and 11A-11B). Serum blood urea nitrogen levels (another marker of kidney dysfunction) are also only elevated for conjugates with Pip9b2 and not for conjugates with the DPEP peptides of the invention (FIG. 7). The second main finding is that seven days following administration, KIM-1 and NGAL levels are reduced to near saline levels for all DPEP peptide conjugates which suggests that there is also some reversal and improvement of kidney-related toxicity. No such effect was seen with conjugates using previous cell-penetrating peptides. This effect of reversal of toxicity is still seen with the DPEP peptides of the invention when given at high doses of 50 mg/kg (FIGS. 11A-11B). Prior cell penetrating peptides showed no decrease in toxicity after 7 days, and remained much higher in toxic markers throughout.

Further demonstrated is that exon skipping activity remains high for all of the DPEP peptide conjugates in TA and diaphragm (FIGS. 10A-10C and 12A-12C) at higher doses of 30 and 50 mg/kg, which when corroborated with the reduced levels of kidney damage markers, suggests a wider therapeutic index for these compounds because toxicity markers are many-fold lower. It is also notable that all of the DPEP peptide conjugates have higher activity than the known R6Gly (SEQ ID NO: 176) comparator in a conjugate, whilst at least maintaining similar levels of toxicity markers, and similar activity to the known PIP peptide comparator in a conjugate whilst having much lower levels of toxicity markers. In some cases, the DPEP peptide conjugates of the invention display not only increased activity compared to the known R6Gly (SEQ ID NO: 176) conjugate but also reduced toxicity markers.

Therefore, the DPEP1 and 3 peptides of the invention provide promising cell-penetrating peptides for improving the efficacy and reducing the toxicity of therapeutic conjugates for the treatment of neuromuscular disorders in humans.

3. Further Examples

P-PMO Synthesis and Preparation 9-Fluorenylmethoxycarbonyl (Fmoc) protected L-amino acids, benzotriazole-1-yl-oxy-tris-pyrrolidino-phosphonium (PyBOP), 2-(1H-benzotriazole-1-yl)-1,1,3,3-tetramethyluronium hexafluorophosphate (HBTU), and the Fmoc^-Ala-OH preloaded Wang resin (0.19 or 0.46 mmol g−1) were obtained from Merck (Hohenbrunn, Germany). 1-Hydroxy-7-azabenzotriazole (HOAt) was obtained from Sigma-Aldrich. HPLC grade acetonitrile, methanol and synthesis grade N-methyl-2-pyrrolidone (NMP) were purchased from Fisher Scientific (Loughborough, UK). Peptide synthesis grade N,N-dimethylformamide (DMF) and diethyl ether were obtained from VWR (Leicestershire, UK). Piperidine and trifluoroacetic acid (TFA) were obtained from Alfa Aesar (Heysham, England). PMO was purchased from Gene Tools Inc. (Philomath, USA). All other reagents were obtained from Sigma-Aldrich (St. Louis, MO, USA) unless otherwise stated. MALDI-TOF mass spectrometry was carried out using a Voyager DE Pro BioSpectrometry workstation. A stock solution of 10 mg mL−1 of a-cyano-4-hydroxycinnamic acid or sinapinic acid in 50% acetonitrile in water was used as matrix. Error bars are ±0.1%.

Synthesis of P-PMO Peptides for Screening in Cells a) Preparation of a Library of Peptide Variants Peptides were either prepared on a 10 pmol scale using an Intavis Parallel Peptide Synthesizer or on a 100 pmol scale using a CEM Liberty Blue™ Peptide Synthesizer (Buckingham, UK) using Fmoc^-Ala-OH preloaded Wang resin (0.19 or 0.46 mmol g−1, Merck Millipore) by applying standard Fmoc chemistry and following manufacturer's recommendations. In the case of synthesis using the Intavis Parallel Peptide Synthesizer, double coupling steps were used with a PyBOP/NMM coupling mixture followed by acetic anhydride capping after each step. For synthesis using the CEM Liberty Blue Peptide Synthesizer, single standard couplings were implemented for all amino acids except arginine, which was performed by double couplings. The coupling was carried out once at 75° C. for 5 min at 60-watt microwave power except for arginine residues, which were coupled twice each. Each deprotection reaction was carried out at 75° C. twice, once for 30 sec and then for 3 min at 35-watt microwave power. Once synthesis was complete, the resin was washed with DMF (3×50 mL) and the N-terminus of the solid phase bound peptide was acetylated with acetic anhydride in the presence of DIPEA. at room temperature. After acetylation of the N-terminus, the peptide resin was washed with DMF (3×20 mL) and DCM (3×20 mL). The peptides were cleaved from the solid support by treatment with a cleavage cocktail consisting of trifluoroacetic acid (TFA):$H_2O$:triisopropylsilane (TIPS) (95%: 2.5%: 2.5%: 3-10 mL) for 3 h at room temperature. After peptide release, excess TFA was removed by sparging with nitrogen. The crude peptide was precipitated by the addition of cold diethyl ether (15-40 mL depending on scale of the synthesis) and centrifuged at 3200 rpm for 5 min. The crude peptide pellet was washed thrice with cold diethyl ether (3×15 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of $CH_3CN$ in 0.1% TFA/$H_2O$ with a flow rate of 15 mL min-1. Detection was performed at 220 nm and 260 nm. The fractions containing the desired peptide were combined and lyophilized to yield the peptide as a white solid (see Table 8 for yields).

TABLE 8 peptides as synthesized for testing in the examples with N-terminal acetylation (Ac), C-terminal b-alanine linker (B), S* is a glucosylated serine residue. DPEP5.7, Pip9b2, and Pip6a are comparative peptides. b) Synthesis of a library of Peptide-PMO conjugates

| Peptide Number | Sequence ID NO. incorporated | Sequence Tested (with additional C and N terminal modifications) |
|---|---|---|
| D-PEP 1.1 | 27 | Ac-RBRRBRRFQILYRBRBR-B |
| D-PEP 1.7 | 33 | Ac-RBRRBRFQILYRBRBR-B |
| D-PEP 1.8 | 34 | AC-RBRRBFQILYRBRRBR-B |
| D-PEP 1.9 | 35 | Ac-RBRRBRFQILYBRBR-B |
| D-PEP 1.9W3 | 104 | AC-RBRRBRWWWBRBR-B (SEQ ID NO: 225) |
| DPEP 1.9W4P | 105 | AC-RBRRBRWWPWBRBR-B (SEQ ID NO: 226) |
| D-PEP 3.1 | 37 | AC-RBRRBRRFQILYRBHBH-B |
| D-PEP 3.8 | 44 | AC-RBRRBRFQILYRBHBH-B |
| D-PEP 5.70 | 173 | Ac-RBRBRS*RBRBR-B |
| Pip6a | 174 | AC-RXRRBRRXR-YQFLI-RXRBRXR-B |
| Pip9b2 | 175 | Ac-RXRRBRR-FQILY-RBRXR-B |

A 21-mer PMO antisense sequence for triplet repeat sequences CAGCAGCAGCAGCAGCAGCAG (SEQ ID NO: 192) otherwise known as $[CAG]_7$ was used. The peptide was conjugated to the 3'-end of the PMO through its C-terminal carboxyl group. This was achieved using 2.5 and 2 equivalents of PyBOP and HOAt in NMP respectively in the presence of 2.5 equivalents of DIPEA and 2.5 fold excess of peptide over PMO dissolved in DMSO was used. In general, to a solution of peptide (2500 nmol) in N-methylpyrrolidone (NMP, 80 pL) were added PyBOP (19.2 mL of 0.3 M in NMP), HOAt in (16.7 mL of 0.3 M NMP), DIPEA (1.0 mL) and PMO (180 pL of 10 mM in DMSO). The mixture was left for 2.5 h at 40° C. and the reaction was quenched by the addition of 0.1% TFA in $H_2O$ (300 pL). This solution was purified by lon exchange chromatography using a converted Gilson HPLC system. The PMO-peptide conjugates were purified on an ion exchange column (Resource S 4 mL, GE Healthcare) using a linear gradient of sodium phosphate buffer (25 mM, pH 7.0) containing 20% $CH_3CN$. A sodium chloride solution (1 M) was used to elute the conjugate from the column at a flow rate of either 4 mL min−1 or 6 mL min-1. The fractions containing the desired compound were combined desalted immediately. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 pm cellulose acetate membrane before use. The concentration of peptide-PMO was determined by the molar absorption of the conjugates at 265 nm in 0.1 N HCl solution (see Table 9 for yields).

TABLE 9

Yields of P-PMO conjugates for cell culture analysis and in vivo experiments (The yields are based on dried weight of the lyophilised purified P-PMO. The purity for the P-PMOs is greater than 95% as ascertained by normal phase HPLC at 220 nm and 260 nm.

| Peptide | Yield |
|---|---|
| D-Pep 1.1 | 36% |
| D-Pep 1.7 | 41% |
| D-pep 1.8 | 38% |
| D-Pep 1.9 | 40% |
| D-Pep 1.9W3 | 43% |
| D-Pep 1.9W4P | 23% |
| D-Pep 3.1 | 31% |
| D-Pep 3.8 | 36% |
| D-Pep 5.70 | 31% |

Synthesis of Peptide-PMO Conjugates.

Peptides were synthesized and conjugated to PMO as described previously. The PMO sequence targeting CUG/CTG expanded repeats (5-CAGCAGCAGCAGCAGCAGCAG-3' (SEQ ID NO: 192)) was purchased from Gene Tools LLC. This is a $[CAG]_7$ PMO as referenced elsewhere herein.

Cell Culture and Peptide-PMO Treatment.

Immortalized myoblasts from healthy individual or DM1 patient with 2600 CTG repeats were cultivated in a growth medium consisting of a mix of M 199: DM EM (1:4 ratio; Life technologies) supplemented with 20% FBS (Life technologies), 50 pg/ml gentamycin (Life technologies), 25 pg/ml fetuin, 0.5 ng/ml bFGF, 5 ng/ml EGF and 0.2 pg/ml dexamethasone (Sigma-Aldrich). Myogenic differentiation was induced by switching confluent cell cultures to DMEM medium supplemented with 5 pg/ml insulin (Sigma-Aldrich) for myoblasts. For treatment, WT or DM1 cells are differentiated for 4 days. Then, medium was changed with fresh differentiation medium with peptide-PMO conjugates at a 1, 2, 5 10, 20 or 40 pM concentration. Cells were harvested for analysis 48 h after treatment. Cell viability was quantified in after 2 days of transfection of peptide-PMOs at 40 uM in human hepatocytes or at a 1, 2, 5 10, 20 or 40 pM concentration in human myoblasts using a fluorescent-based assay (Promega). RNA isolation, RT-PCR and qPCR analysis.

For mice tissues: prior to RNA extraction, muscles were disrupted in TriReagent (Sigma-Aldrich) using Fastprep system and Lysing Matrix D tubes (MP biomedicals). For human cells: prior to RNA extraction, cells were lysed in a proteinase K buffer (500 mM NaCl, 10 mM Tris-HCl, pH 7.2, 1.5 mM $MgCl_2$, 10 mM EDTA, 2% SDS and 0.5 mg/ml of proteinase K) for 45 min at 55° C. Total RNAs were isolated using TriReagent according to the manufacturer's protocol. One microgram of RNA was reverse transcribed using M-MLV first-strand synthesis system (Life Technologies) according to the manufacturer's instructions in a total of 20 pL. One microliter of cDNA preparation was subsequently used in a semi-quantitative PCR analysis according to standard protocol (ReddyMix, Thermo Scientific). PCR amplification was carried out for 25-35 cycles within the linear range of amplification for each gene. PCR products were resolved on 1.5-2% agarose gels, ethidium bromide-stained and quantified with ImageJ software. The ratios of exon inclusion were quantified as a percentage of inclusion relative to total intensity of isoform signals. Primers are shown in the following table 10:

TABLE 10 primers for PCR

| Primer Name | SEQ ID NO. | Species/Gene/ Exon | Sequence (5'-3') |
|---|---|---|---|
| Mbnl1.F | 177 | Mouse-Human/ mbnl1/exon5 | GCTGCCCAATACCAGGTCAAC |
| MbNl1.R | 178 | Mouse-Human/ mbnl1/exon5 | TGGTGGGAGAAATGCTGTATGC |
| DMD.F | 179 | Human/DMD/ exon78 | TTAGAGGAGGTGATGGAGCA |
| DMD.R | 180 | Human/DMD/ exon78 | GATACTAAGGACTCCATCGC |

Toxicology

Toxicology Assessments Were Performed as Described Above in Section 1.10.

Results

Figure 13:
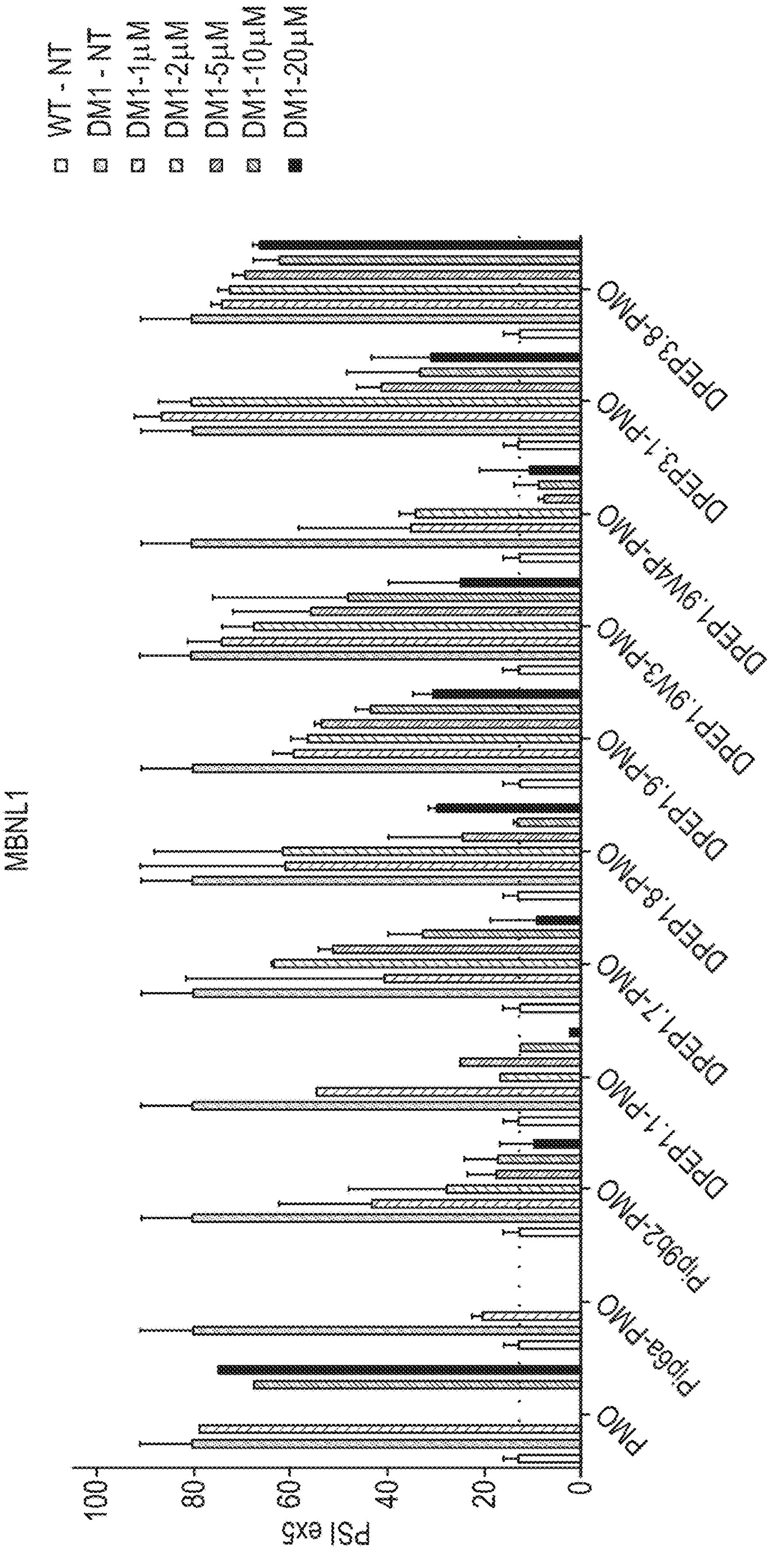
FIG. 13: shows different DPEP1/3-[CAG]$_7$ PMO (SEQ ID NO: 192) conjugates correct splicing defects of Mbnll transcripts in vitro in DM 1 patient myoblasts derived from DM 1 patients with 2600 repeats in the DMPK gene at various concentrations (n=1-3)
Figure 14:
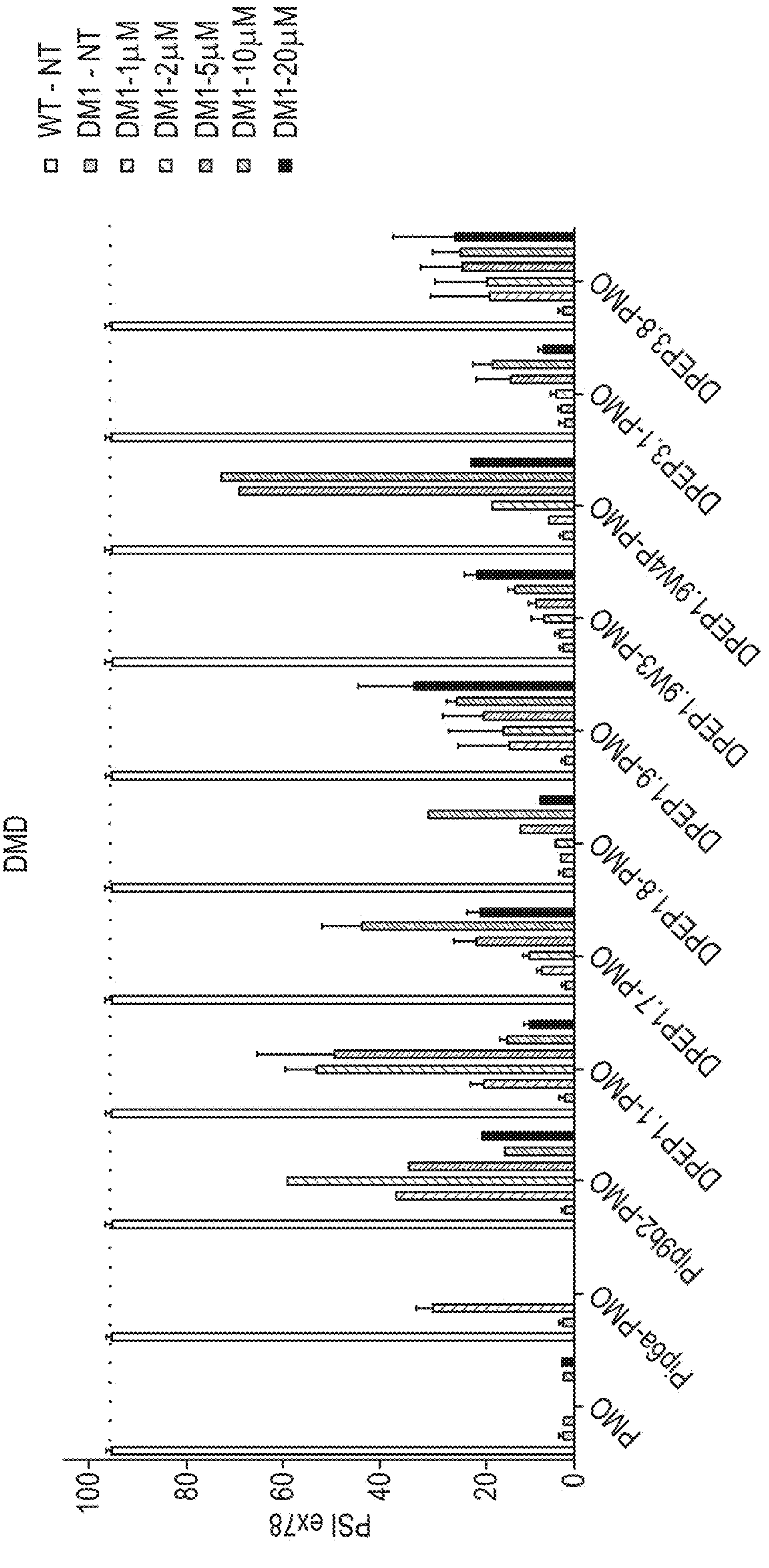
FIG. 14: shows different DPEP1/3-[CAG]$_7$ PMO (SEQ ID NO: 192) conjugates correct splicing defects of DMD transcripts in vitro in DM 1 patient myoblasts derived from DM 1 patients with 2600 repeats in the DMPK gene at various concentrations (Error bars: mean±SEM, n=1-3)
Figure 15:
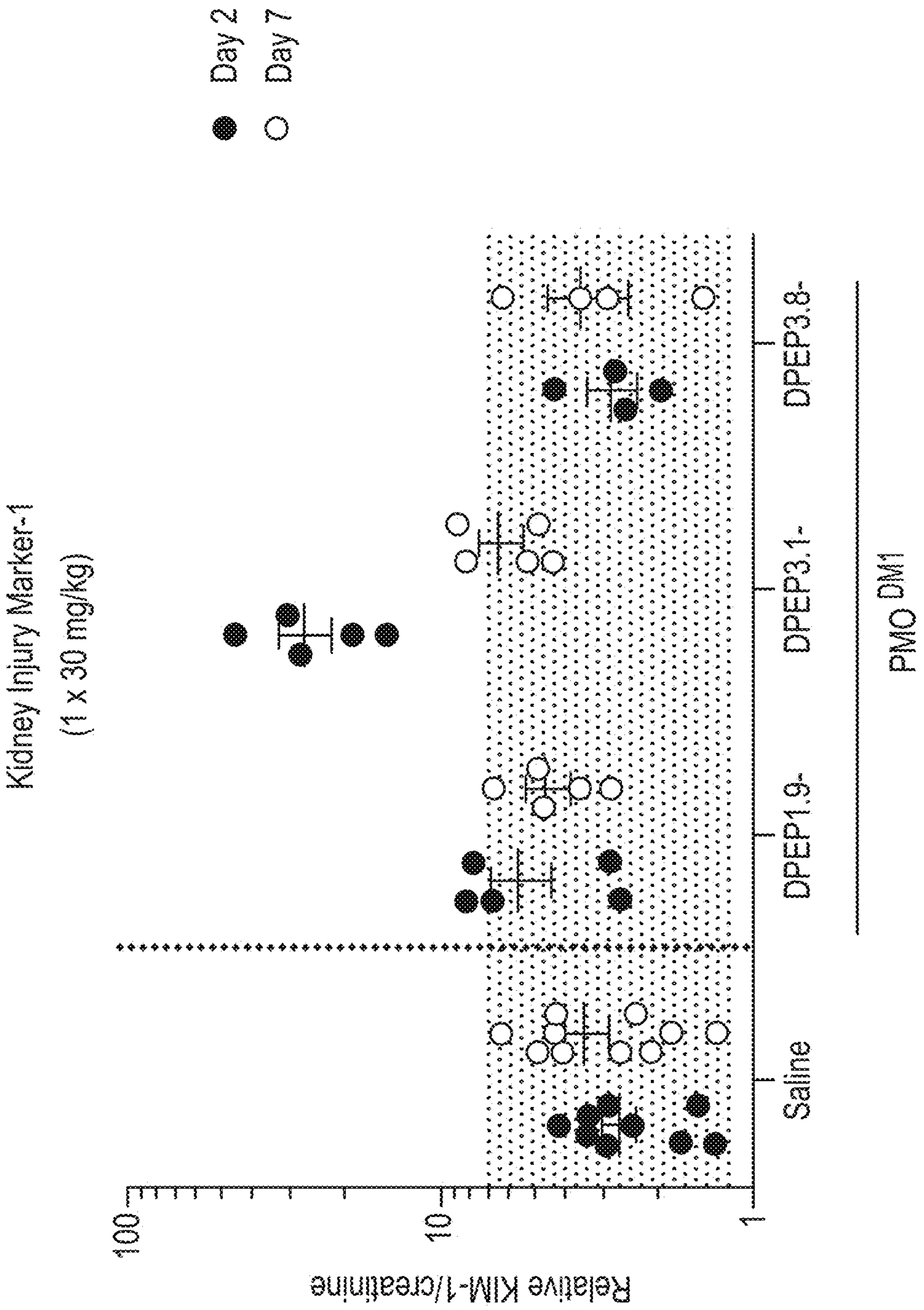
FIG. 15: shows the relative KIM-1 levels assessed in urine from Day 2 and Day 7 post injection of different DPEP1/3-[CAG]$_7$ PMO (SEQ ID NO: 192) conjugates in C57BL6 female mice measured by ELISA with samples diluted to fit within standard curve. Values were normalised to urinary creatinine levels to account for urine protein concentration. KIM-1 levels were similar to saline control injections in comparison to the fold increases induced by the prior Pip series of peptide carriers (Error bars: mean±SEM, n=4-10)
Figure 16:
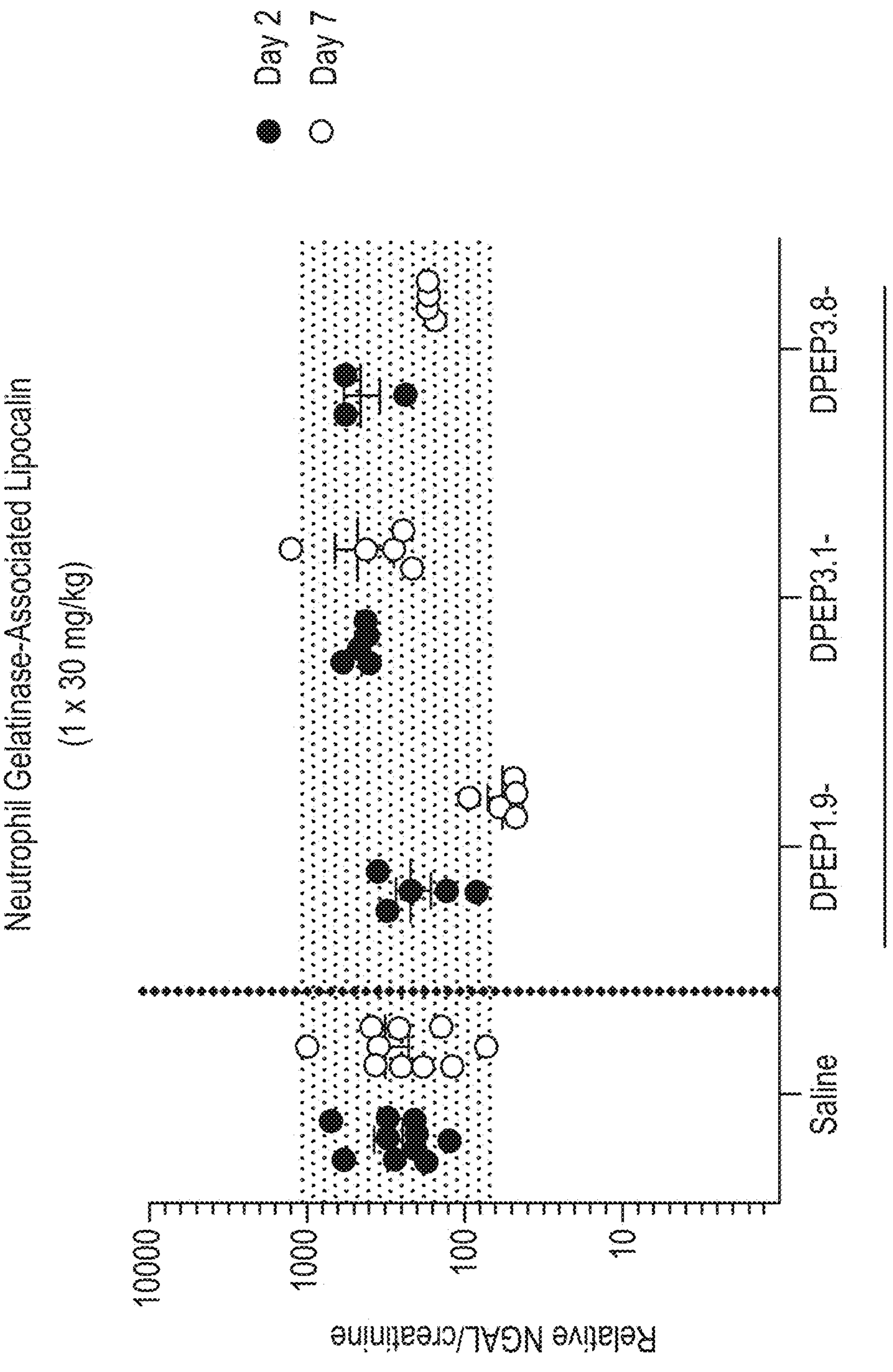
FIG. 16: shows the relative NGAL levels measured in the urine from Day 2 and Day 7 post injection of different DPEP1/3-[CAG]$_7$ PMO (SEQ ID NO: 192) conjugates in C57BL6 female mice measured by ELISA with samples diluted to fit within standard curve. Values were normalised to urinary creatinine levels to account for urine protein concentration. NGAL levels were similar to saline control injections in comparison to the fold increases induced by the prior Pip series of peptide carriers (Error bars: mean±SEM, n=4-10)
Figure 17:
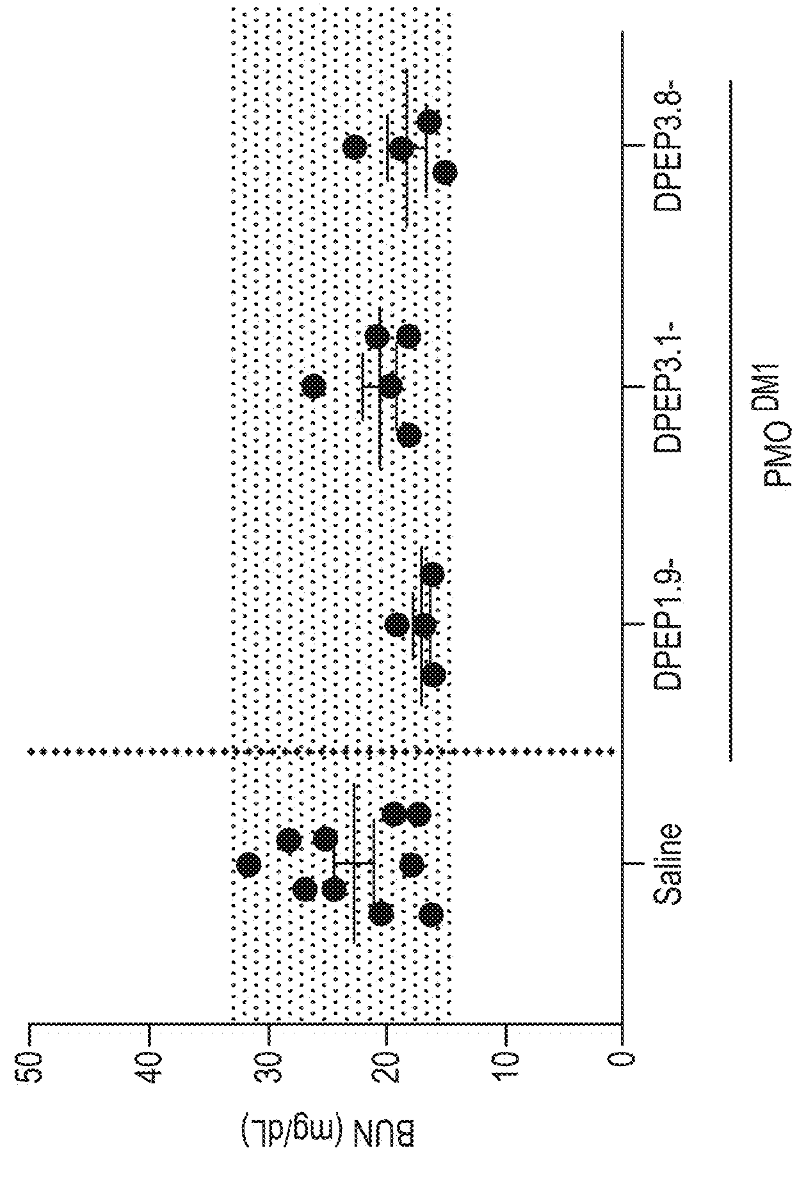
FIG. 17: shows the BUN levels assessed in serum from Day 7 post-injection of different DPEP1/3-[CAG]$_7$ PMO (SEQ ID NO: 192) conjugates in C57BL6 female mice compared to saline. BUN levels were similar to saline control injections in comparison to the fold increases induced by prior Pip series of peptide carriers (Error bars: mean±SEM, n=4-10)
Figure 18:
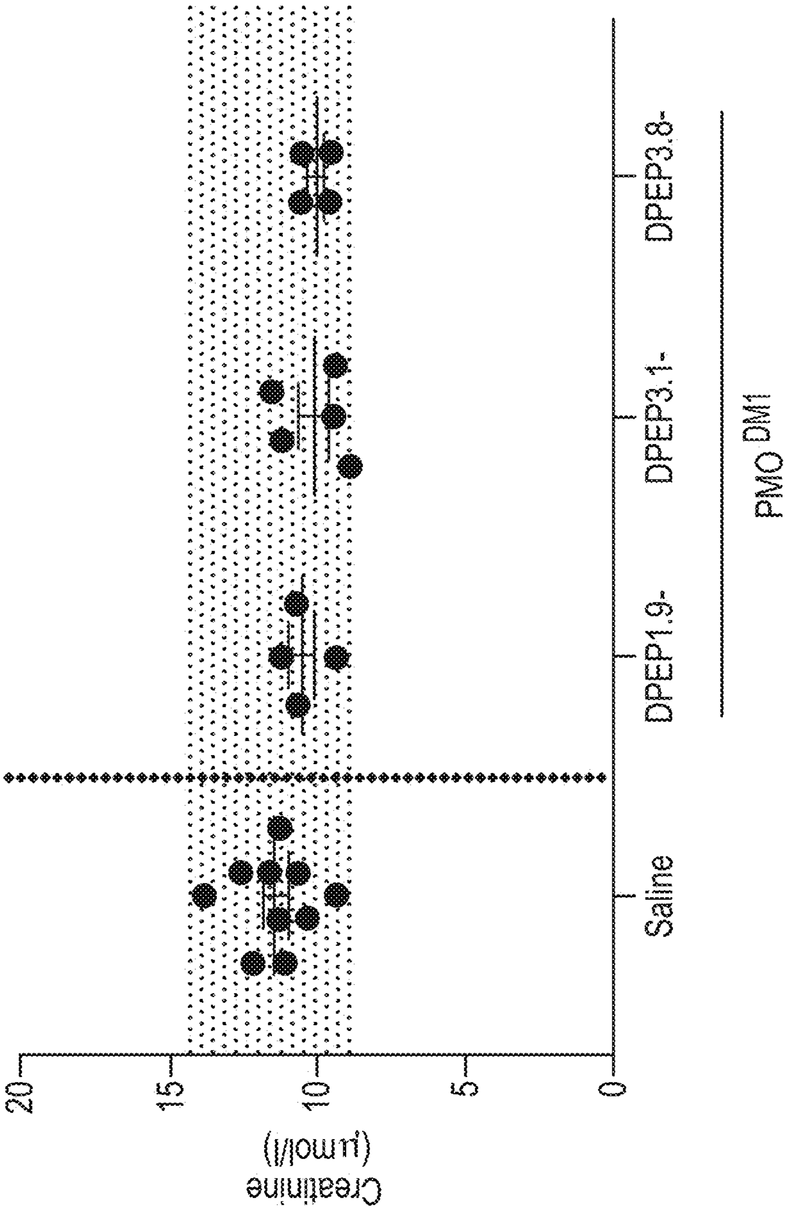
FIG. 18: shows the creatinine levels assessed in serum from Day 7 post-injection of different DPEP1/3-[CAG]$_7$ PMO (SEQ ID NO: 192) conjugates in C57BL6 female mice compared to saline. Creatinine levels were similar to saline control injections in comparison to the fold increases induced by prior Pip series of peptide carriers (Error bars: mean±SEM, n=4-10)
Figure 19A:
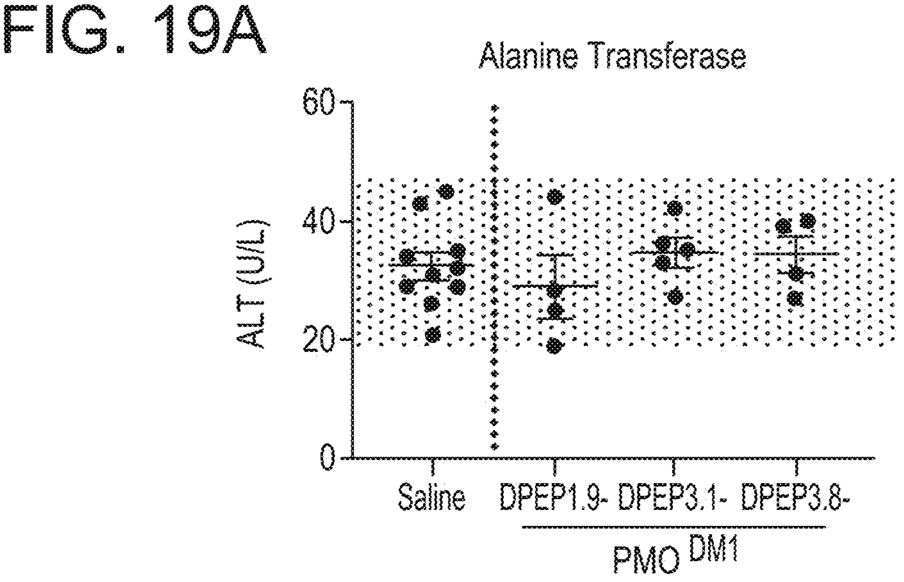
FIGS. 19A-19C: show the (19A) alanine transferase (ALT), (19B) alkaline phosphatase (ALP) and (19C) aspartate aminotransferase (AST) levels assessed in serum from C57BL6 female mice, who were administered by bolus IV (tail vein) injection of different DPEP1/3-[CAG]$_7$ PMO (SEQ ID NO: 192) conjugates, at day 7 post-injection collection compared to saline. ALP, ALT, AST levels were similar to saline control injections in comparison to the fold increases induced by the prior Pip series of peptide carriers.
Figure 19B:
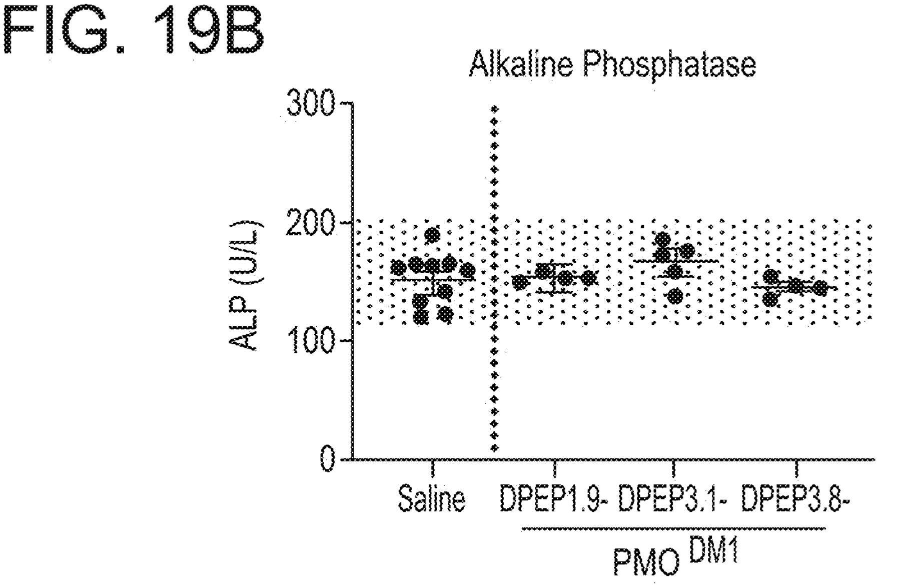
Figure 19C:
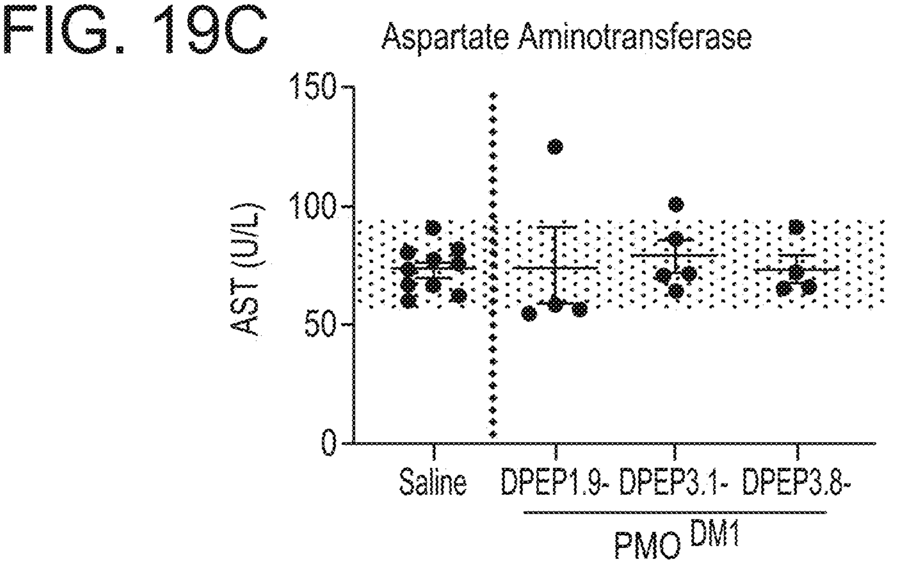
Figure 20:
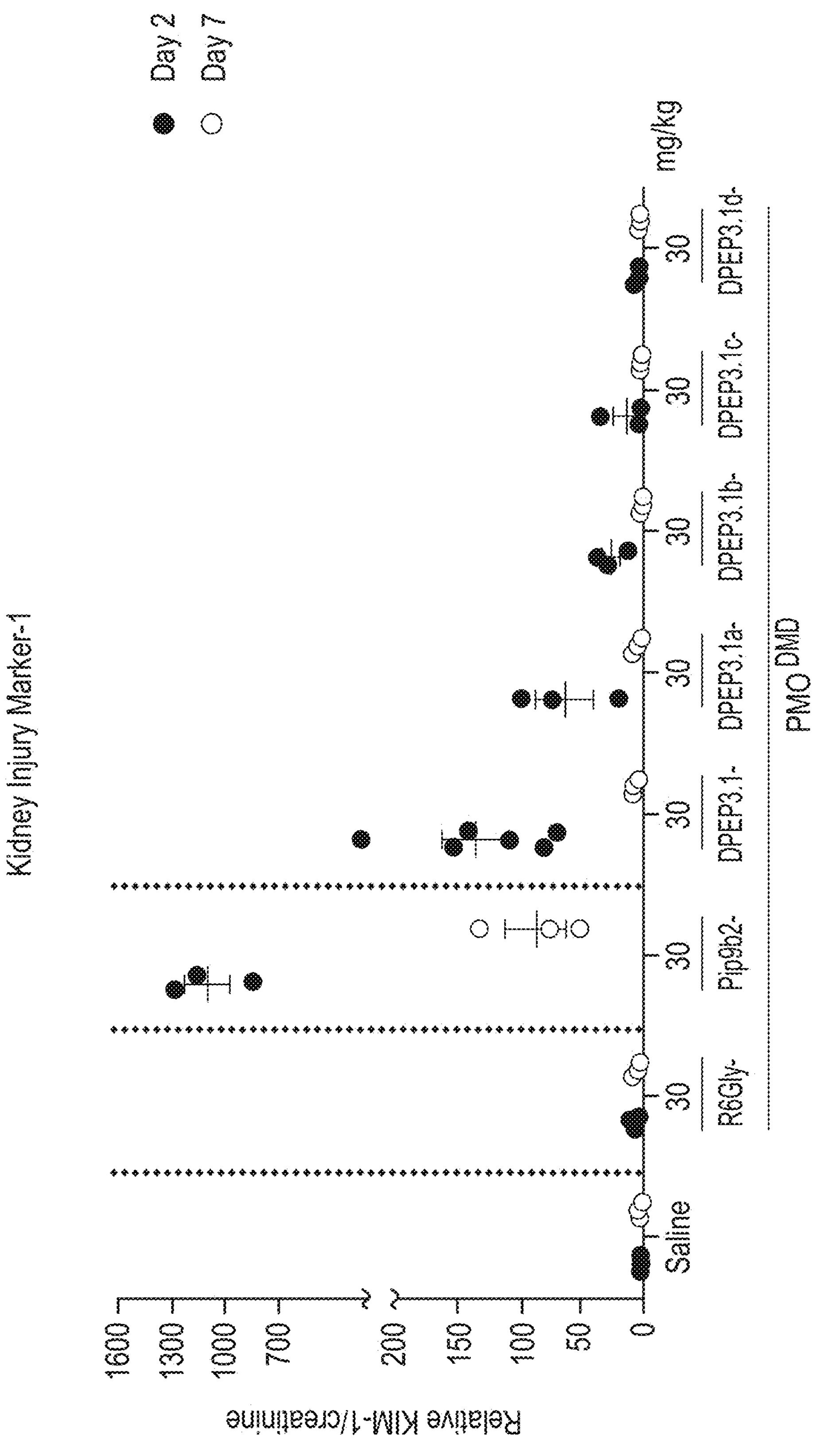
FIG. 20: shows the relative levels of urinary kidney-injury marker-1 (KIM-1) normalized to urinary creatinine measured in the urine of C57BL/6 mice on day 2 and day 7 post administration of a single dose of 30 mg/kg of DPEP3.1 peptide conjugated via different linkers to a therapeutic antisense PMO$^{DMD}$, in comparison with 0.9% saline control and currently available peptide carriers (R6Gly-(SEQ ID NO: 176) and Pip9b2-) conjugated to the same therapeutic antisense PMO$^{DMD}$ (error bars: mean with SEM, n=3-10).
Figure 21A:
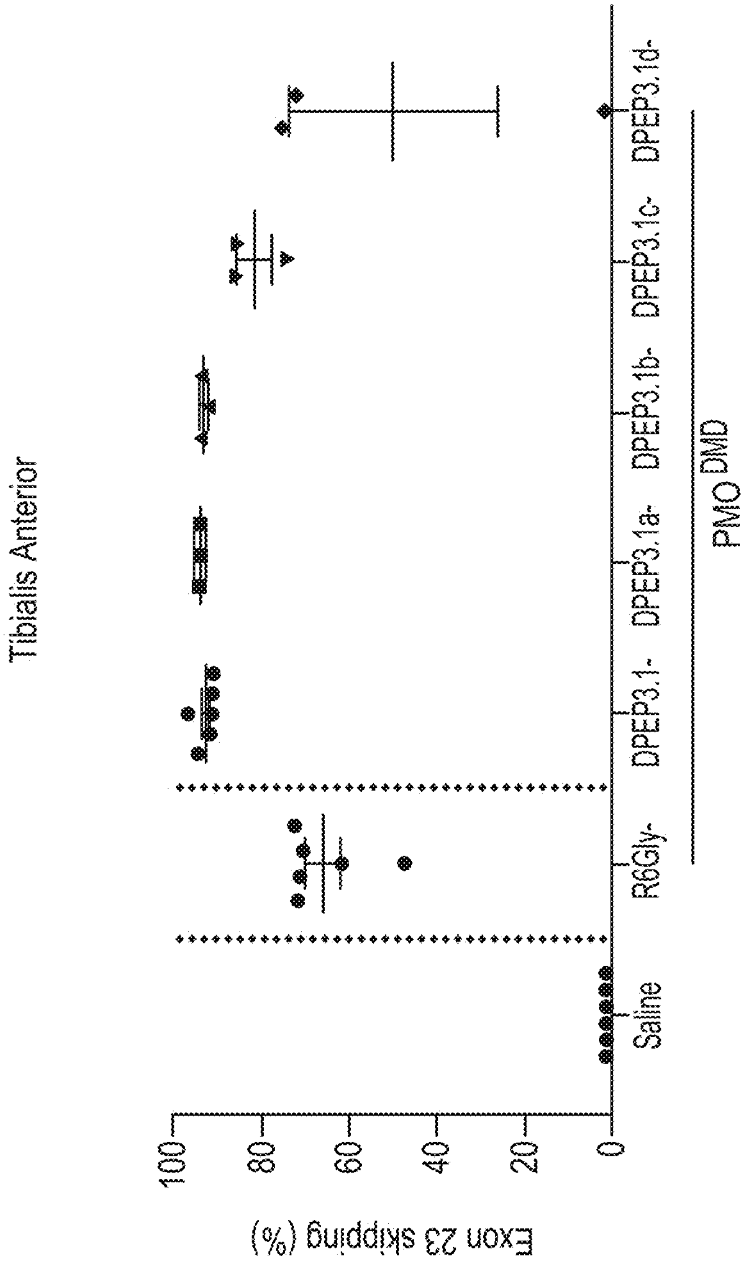
FIGS. 21A-21C: show the in vivo efficacy of DPEP3.1 peptide conjugated via different linkers to a therapeutic antisense PMO$^{DMD}$ in (FIG. 21A) tibialis anterior, (FIG. 21B) diaphragm, and (FIG. 21C) heart muscle following a single 30 mg/kg intravenous bolus administration in C57BL/6 mice. Efficacy was measured 7 days post administration by qPCR for exon skipping of dystrophin (exon 23). Exon skipping efficiency was used in comparison with 0.9% saline control and currently available peptide carriers (R6Gly-(SEQ ID NO: 176) and Pip9b2-) conjugated to the same therapeutic antisense PMO$^{DMD}$. Outlier for DPEP3.1 d-PMO$^{DMD}$ suggests a missed injection, (error bars: mean with SEM, n=3-10).
Figure 21B:
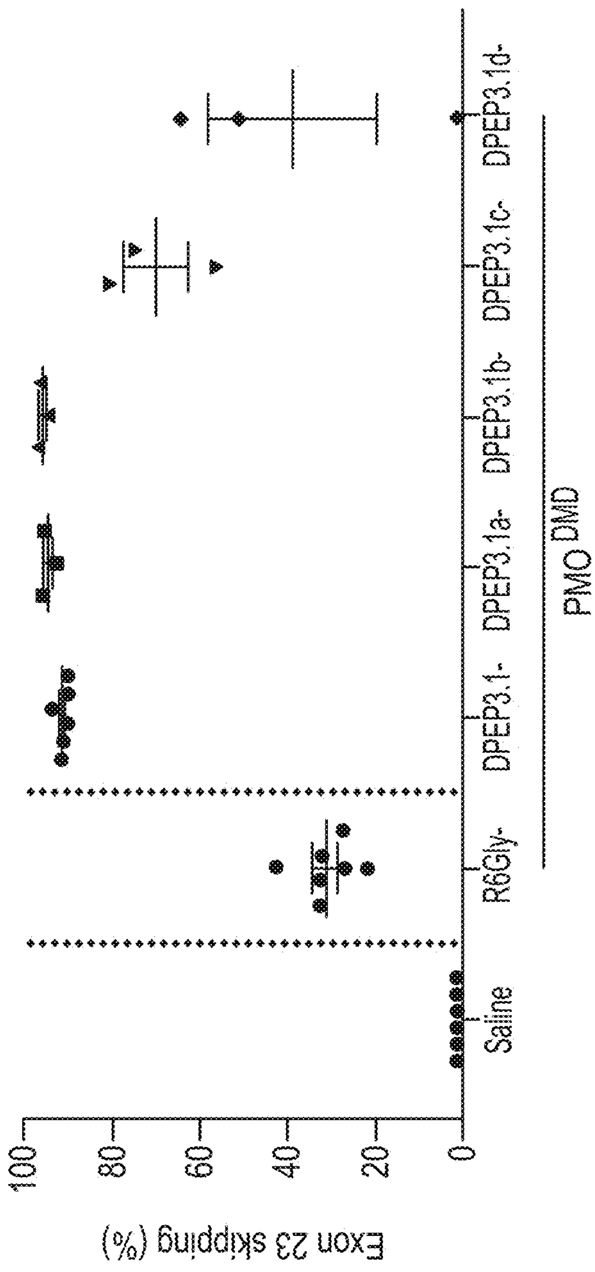
Figure 21C:
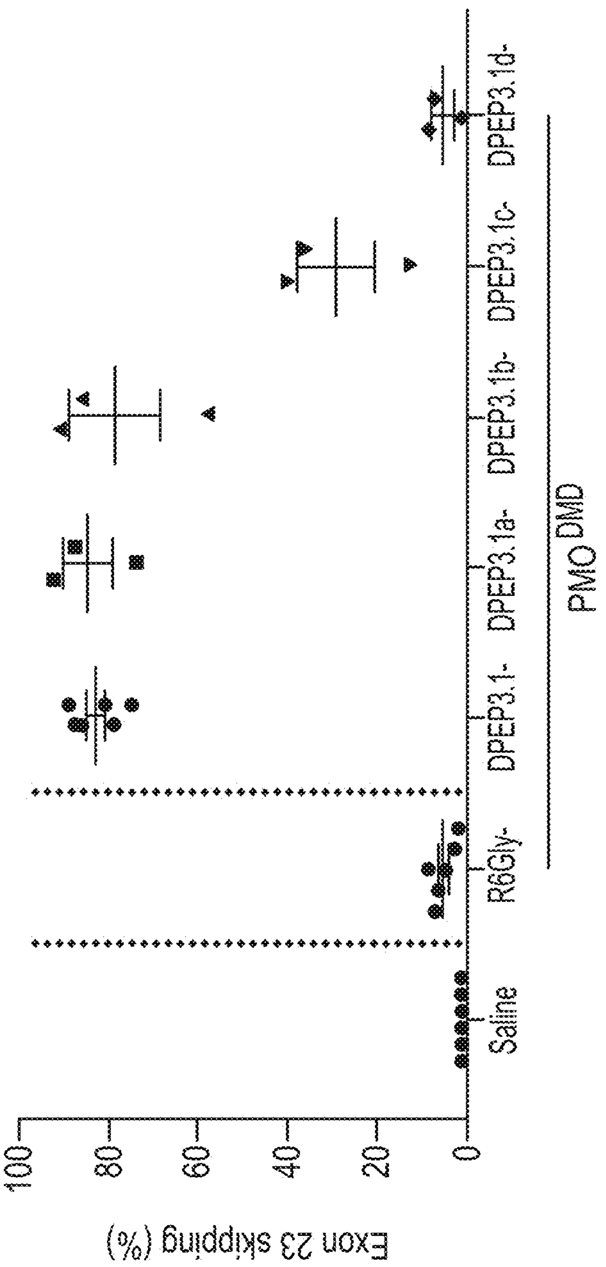
Figure 22:
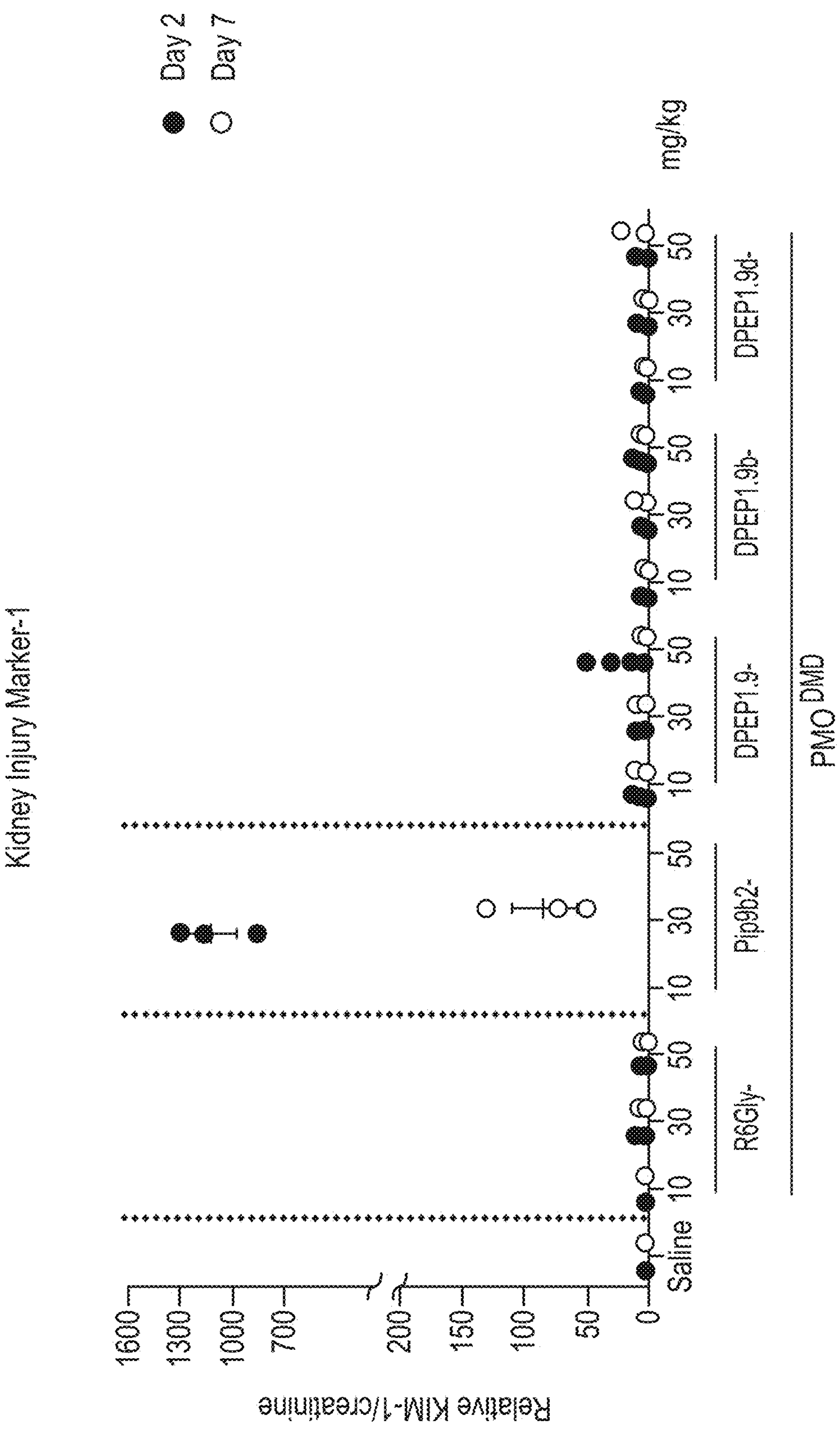
FIG. 22: shows the relative levels of urinary kidney-injury marker-1 (KIM-1) normalized to urinary creatinine measured in the urine of C57BL/6 mice on day 2 and day 7 post administration of a single dose of 10 mg/kg, 30 mg/kg or 50 mg/kg of DPEP1.9 peptide conjugated via different linkers to a therapeutic antisense PMO$^{DMD}$, in comparison with 0.9% saline control and currently available peptide carriers (R6Gly-(SEQ ID NO: 176) and Pip9b2-) conjugated to the same therapeutic antisense PMO$^{DMD}$ (error bars: mean with SEM, n=3-10).
Figure 23A:
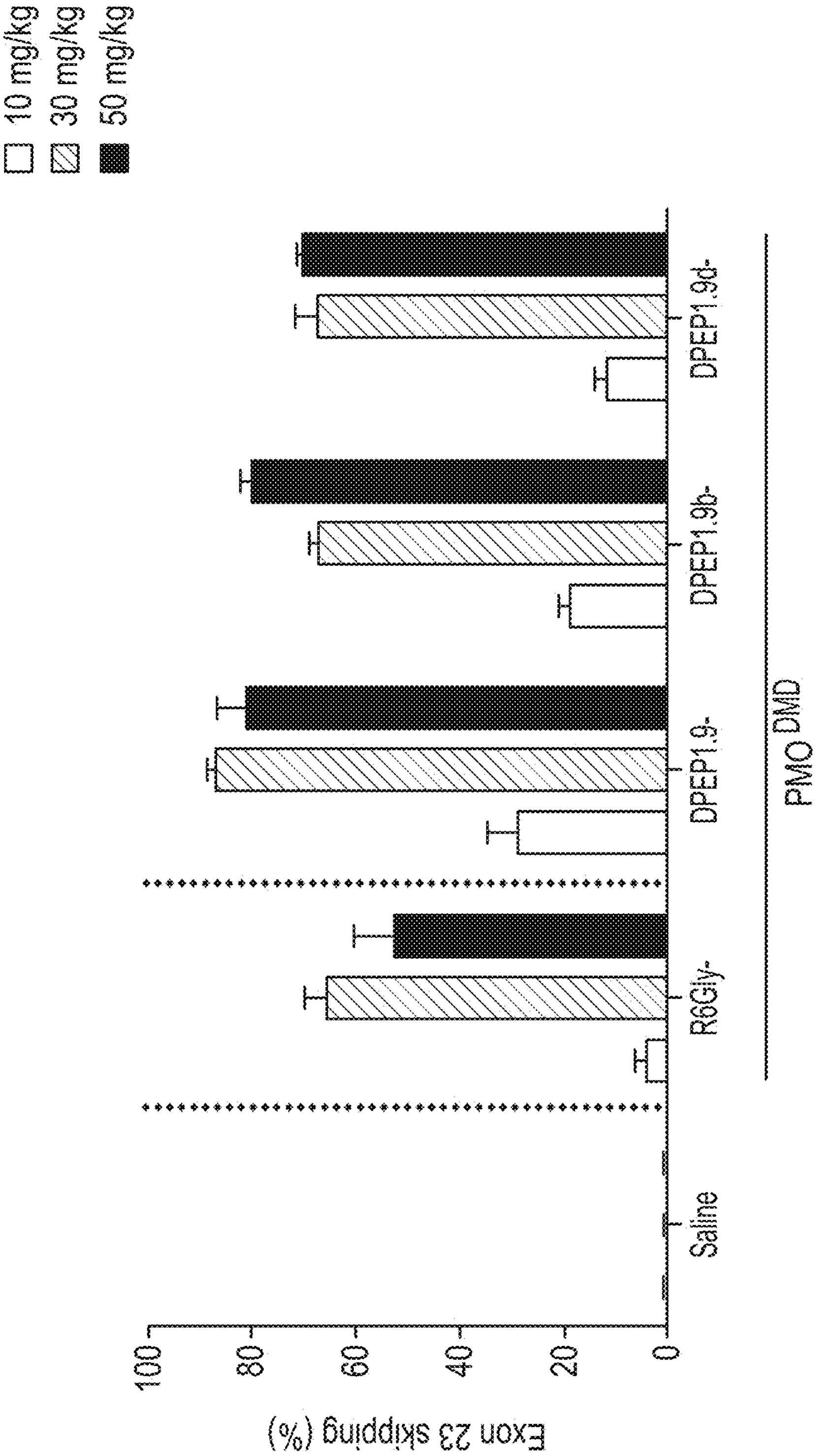
FIGS. 23A-23C: show the in vivo efficacy of DPEP1.9 peptide conjugated via different linkers to a therapeutic antisense PMO$^{DMD}$ in (FIG. 23A) tibialis anterior, (FIG. 23B) diaphragm, and (FIG. 23C) heart muscle following a single 10 mg/kg, 30 mg/kg or 50 mg/kg intravenous bolus administration in C57BL/6 mice. Efficacy was measured 7 days post administration by qPCR for exon skipping of dystrophin (exon 23). Exon skipping efficiency was used in comparison with 0.9% saline control and currently available peptide carriers (R6Gly-(SEQ ID NO: 176) and Pip9b2-) conjugated to the same therapeutic antisense PMO$^{DMD}$ (error bars: mean with SEM, n=3-10).
Figure 23B:
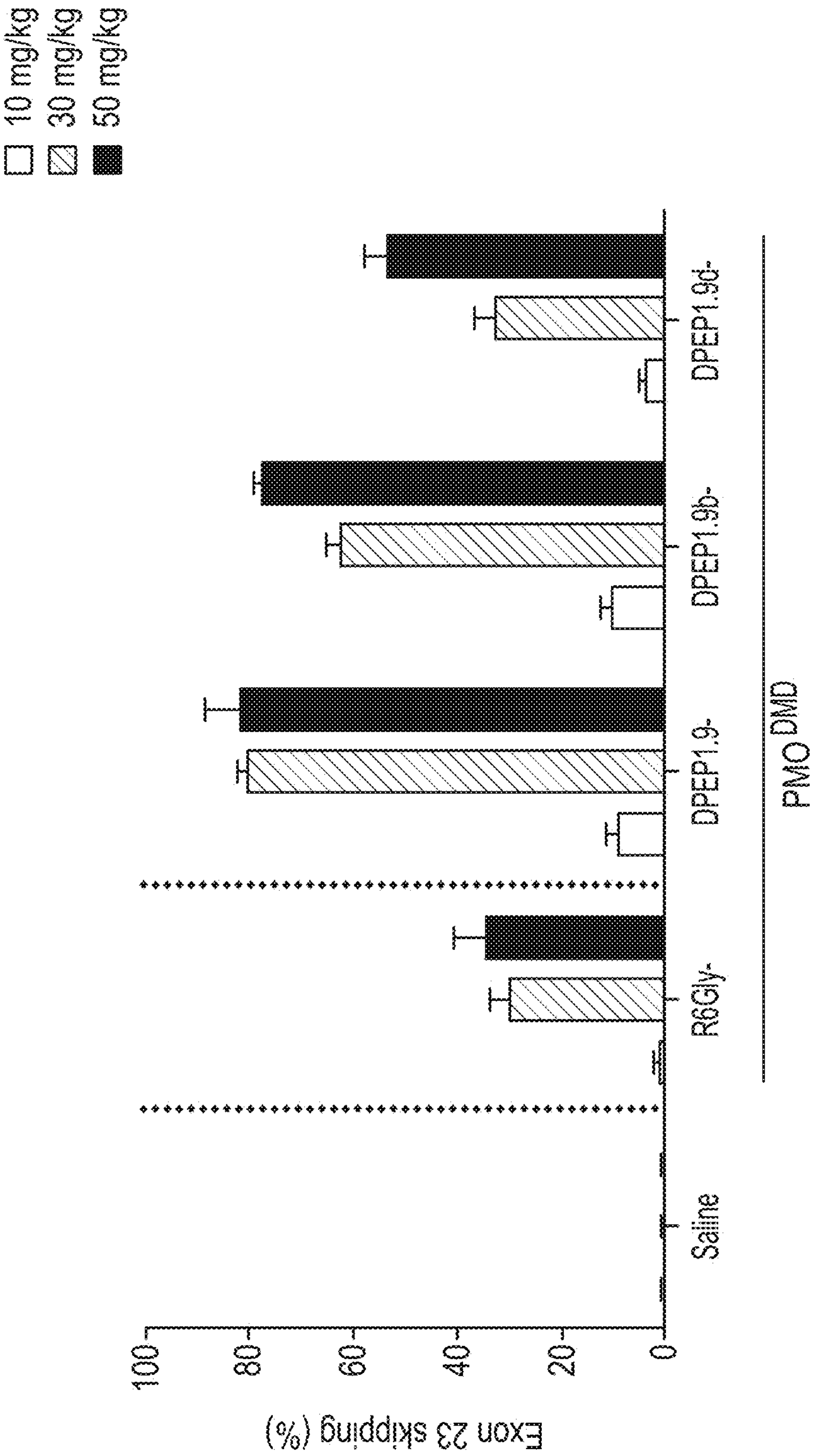
Figure 23C:
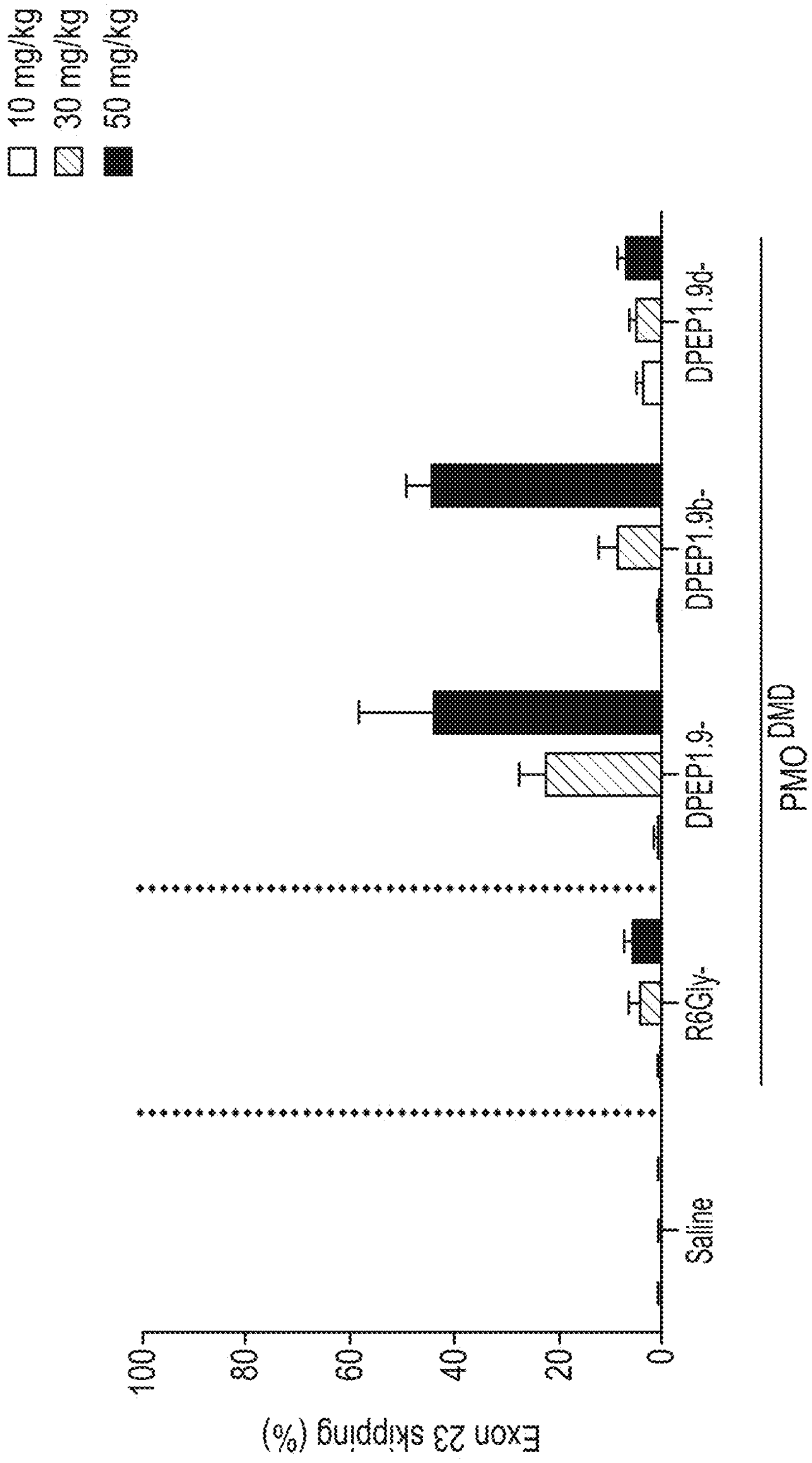
Figure 24:
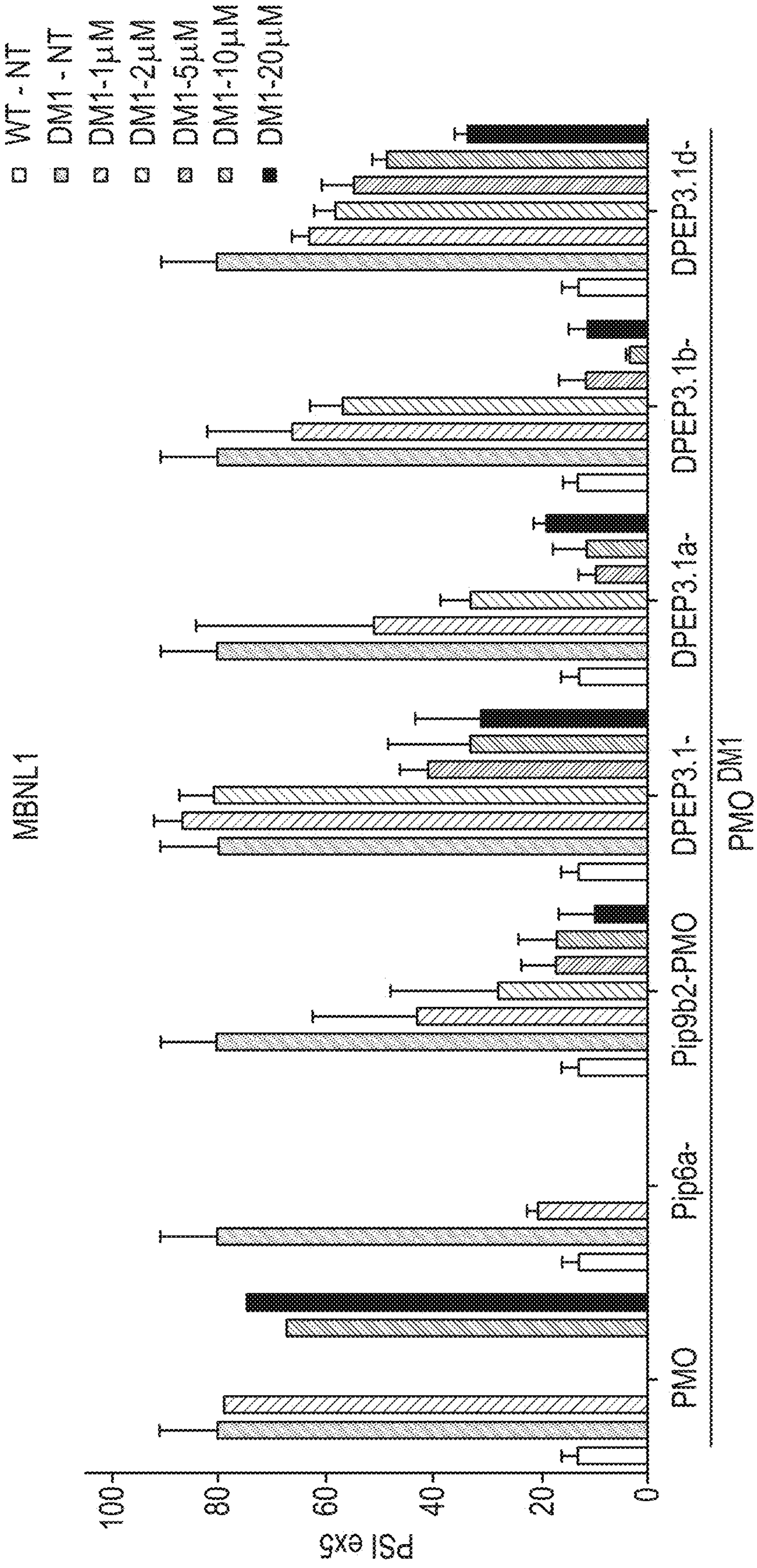
FIGS. 24 and 25; show that different DPEP1/3-[CAG]$_7$ (SEQ ID NO: 192) conjugates using linkers a, b and d at various concentrations corrected splicing defects of MbnH-dependent transcripts in DM1 patient myoblasts derived from DM1 patients with 2600 CTG repeats in the DMPK gene.
Figure 25:
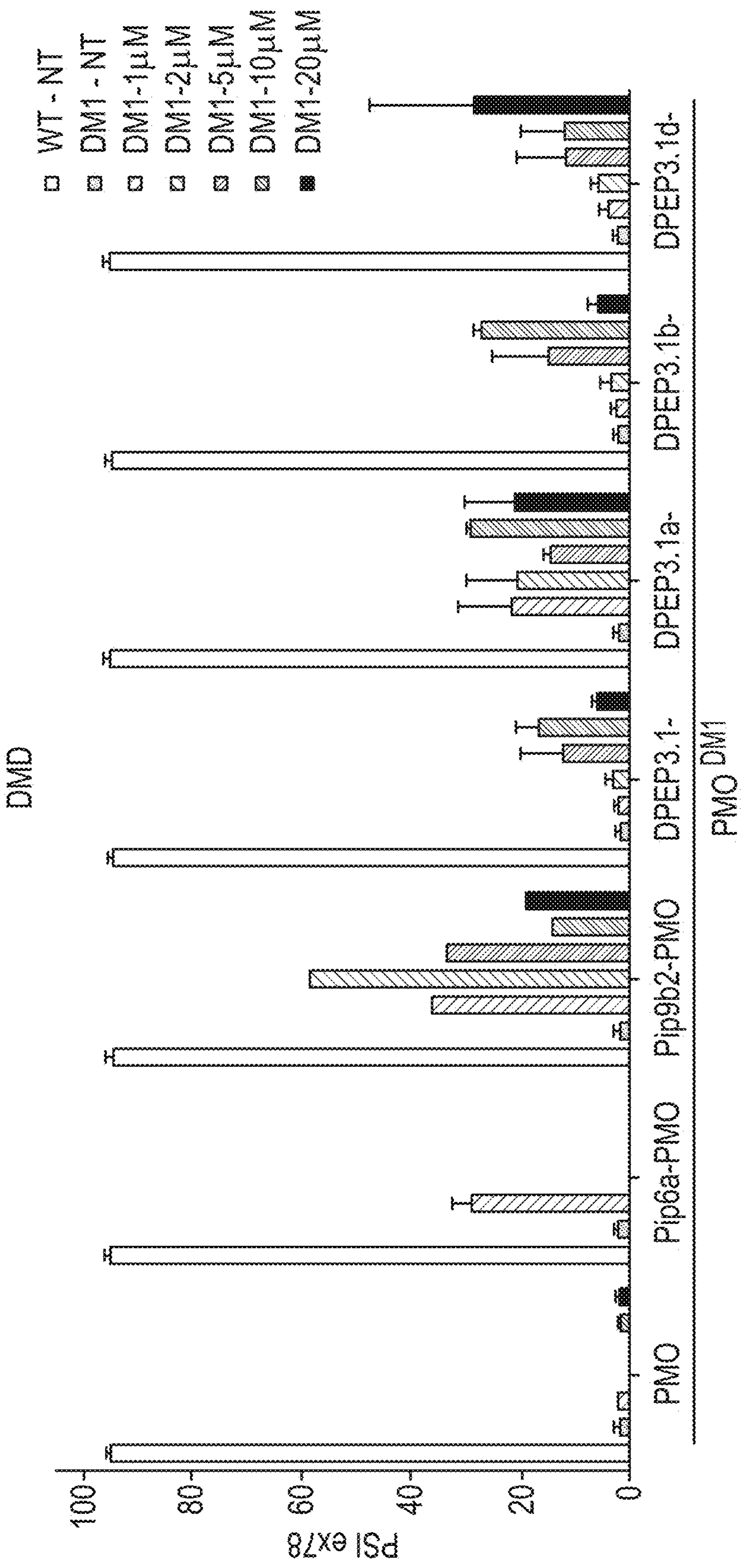
Figure 26:
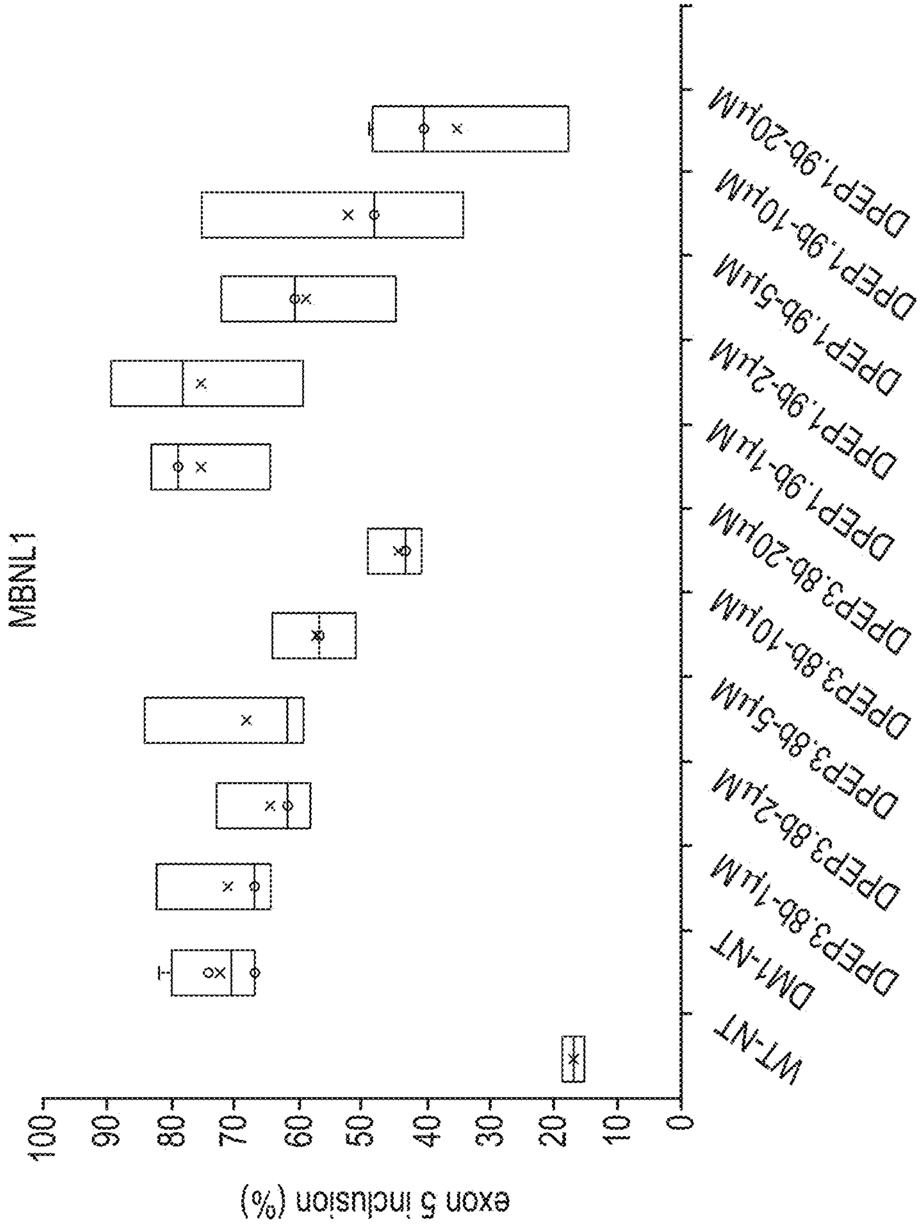
FIG. 26: shows different DPEP1/3-$[CAG]_7$ PMO (SEQ ID NO: 192) conjugates using linkers a, b and d at various concentrations correct splicing defects of DMD transcripts in vitro in DM1 patient myoblasts derived from DM1 patients with 2600 repeats in the DMPK gene at various concentrations.
Figure 27:
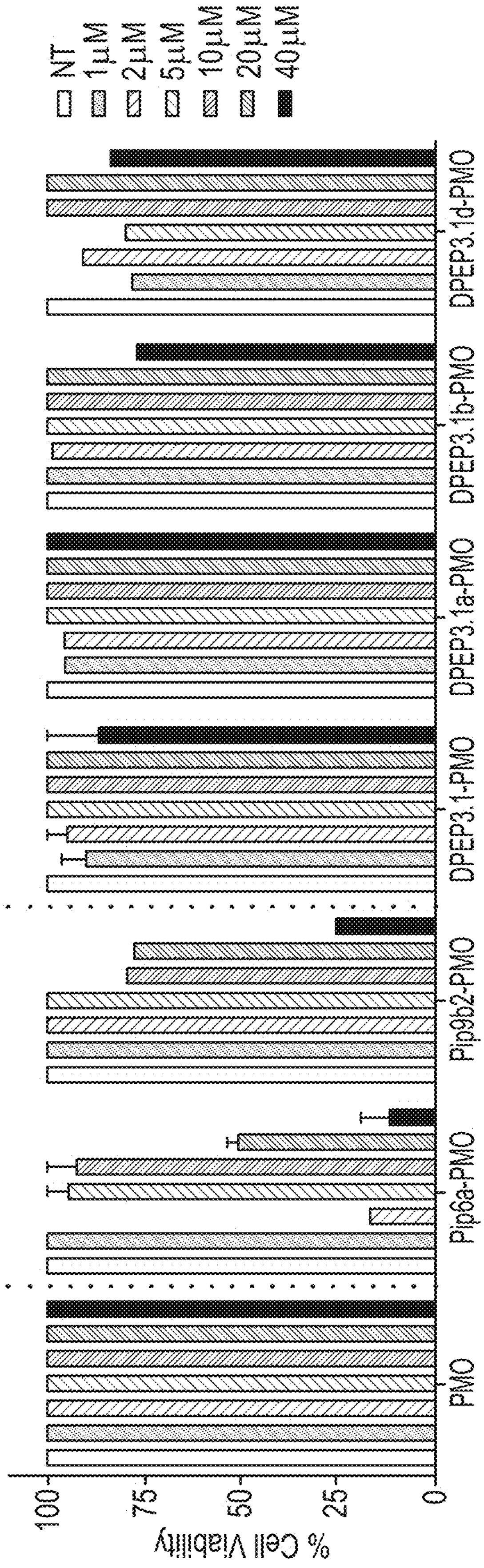
FIG. 27: shows the percentage myoblast cell viability of DM1 patient myoblasts with 2600 CTG repeats 48 hours transfected with various doses of different DPEP1/3-$[CAG]_7$ (SEQ ID NO: 192) conjugates using linkers a, b and d. The concentration of conjugate can be increased several fold from therapeutic levels without causing cell mortality.
Figure 28:
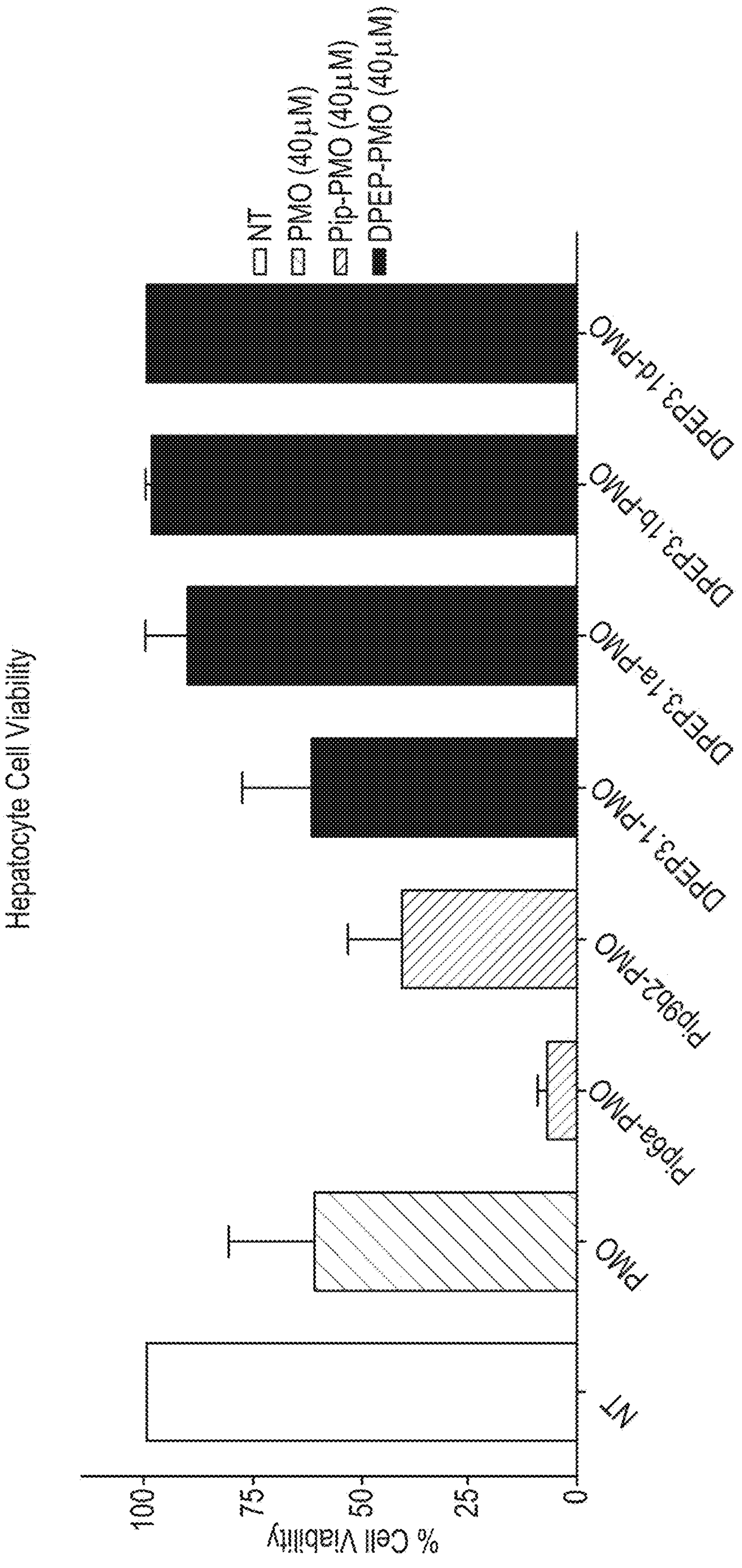
FIG. 28: shows the percentage hepatocyte cell viability transfected with 40 uM of different DPEP1/3-$[CAG]_7$ (SEQ ID NO: 192) conjugates using linkers a, b and d. The concentration of conjugate can be increased several fold from therapeutic levels without causing cell mortality contrary to Pip6a conjugates.
Figure 29:
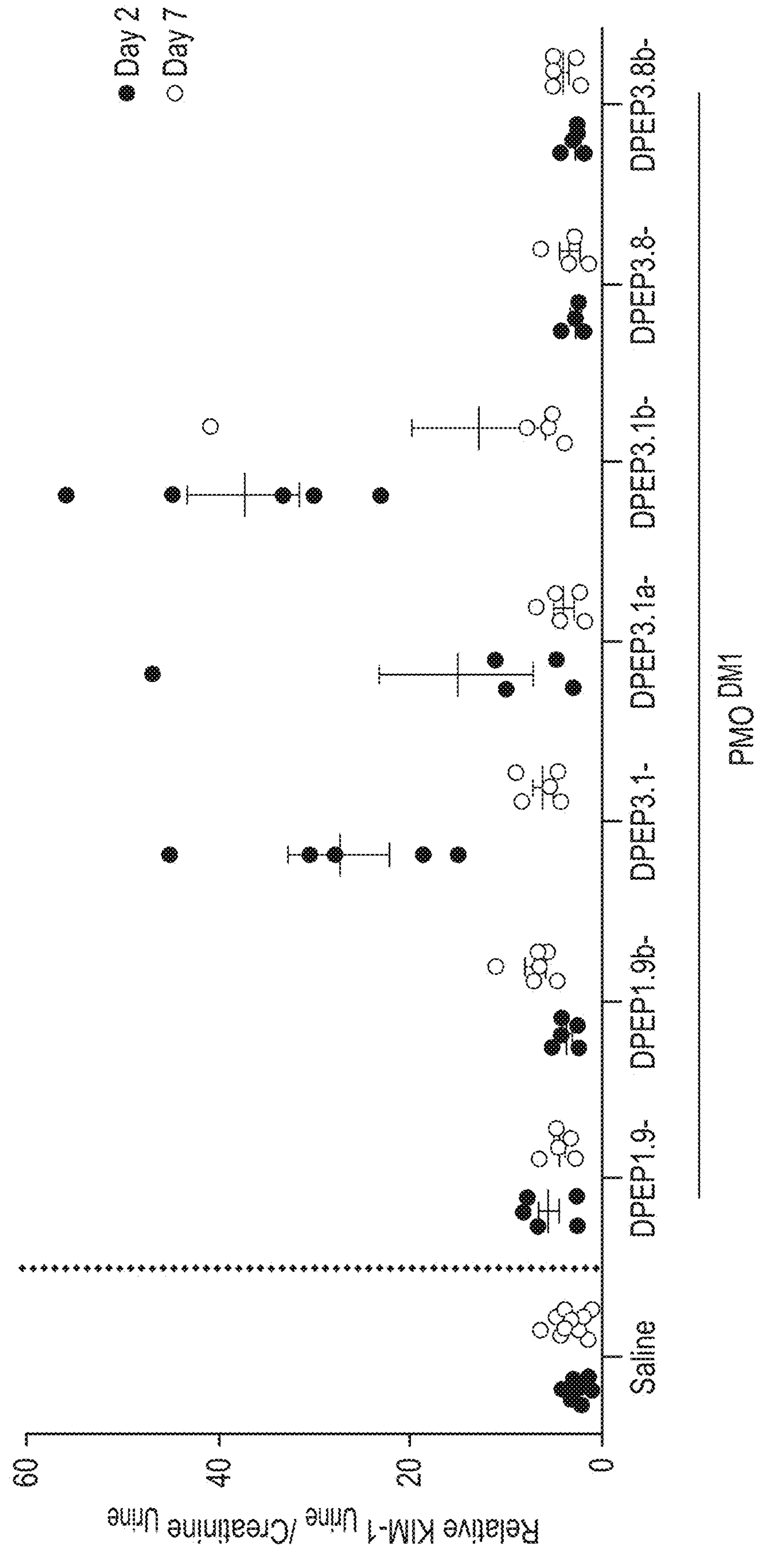
FIGS. 29 and 30: show urine toxicology markers from Day 2 and Day 7 post-injection of different DPEP1/3-$[CAG]_7$ PMO (SEQ ID NO: 192) conjugates to C57BL6 female mice measured by ELISA (R&D cat #MKM100) with samples diluted to fit within standard curve. Values were normalised to urinary creatinine levels (Harwell) to account for urine protein concentration. KIM-1 levels were similar to saline control injections in comparison to the fold increases induced by the prior Pip series of peptide carriers.
Figure 30:
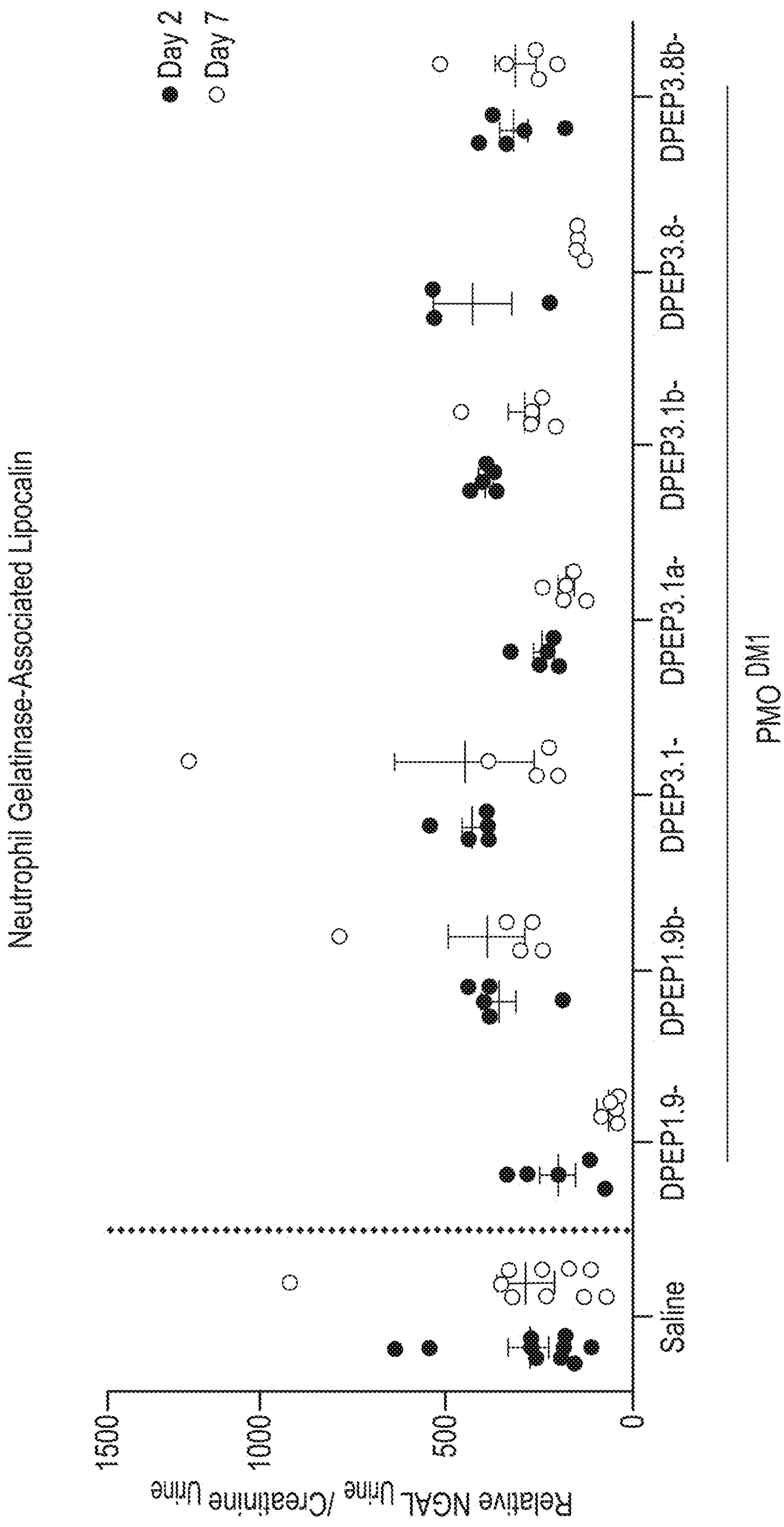
Figure 31A:
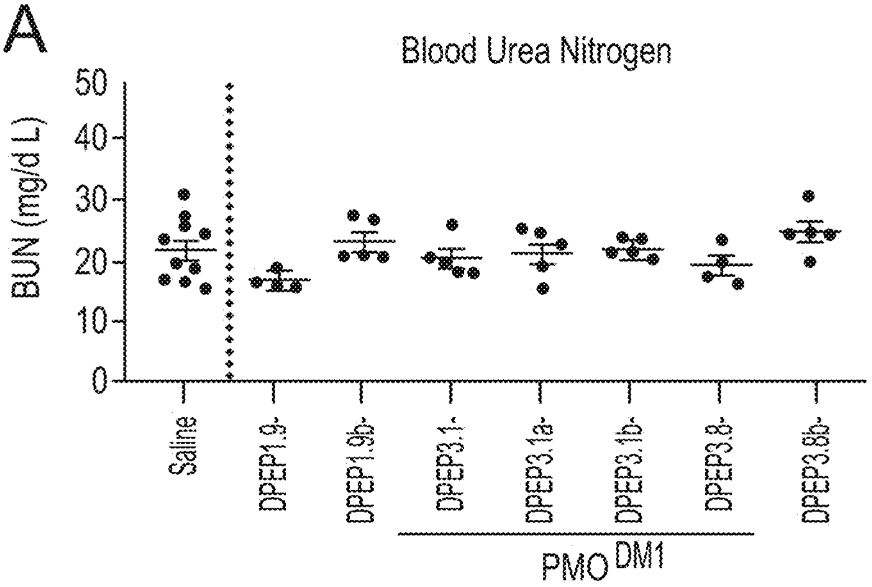
FIGS. 31A-31C and 32A-32B: show toxicology markers assessed in serum from C57BL6 female mice (8-10 weeks age, n=5 per group), who were administered bolus IV (tail vein) injection of different DPEP1/3-$[CAG]_7$ PMO (SEQ ID NO: 192) conjugates with different linkers. At day 7 post-injection collection in serum compared to saline. All levels were similar to saline control injections at day 7 post-injection.
Figure 31B:
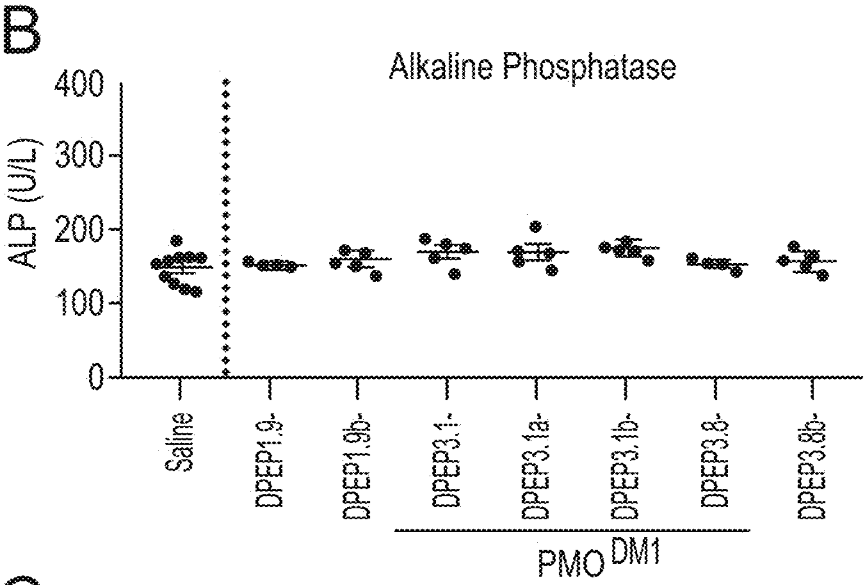
Figure 31C:
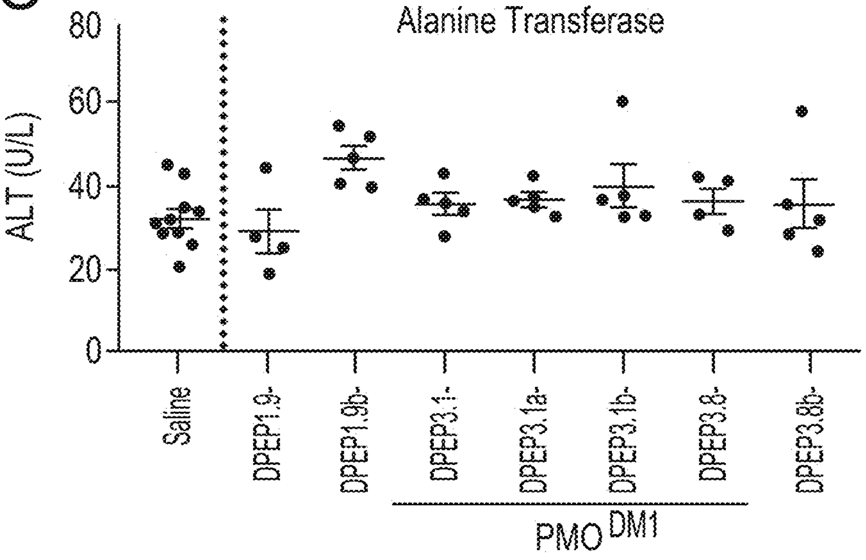
Figure 32A:
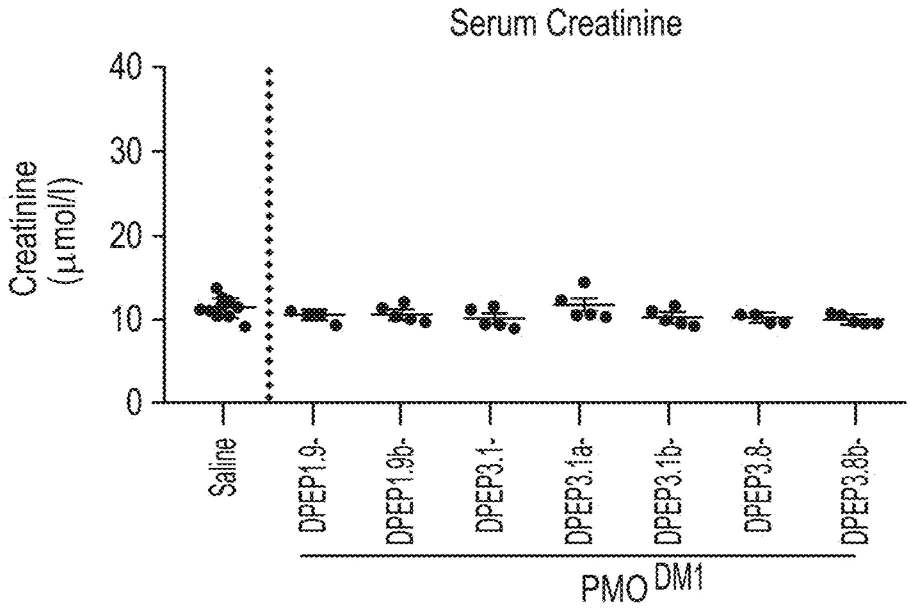
Figure 32B:
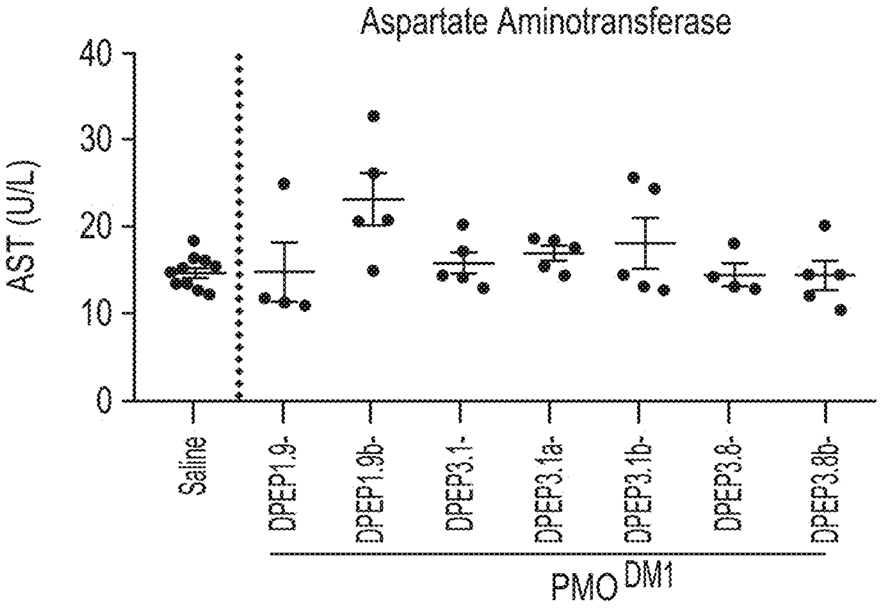

The treated DM1 patient derived muscle cells (myoblasts) showed that the DPEP 1 or 3 peptide-$[CAG]_7$ PMO (SEQ ID NO: 192) conjugates specifically target mutant CUGexp-DMPK transcripts to abrogate the detrimental sequestration of MBNL1 splicing factor by nuclear RNA foci and consequently MBNL1 functional loss, responsible for splicing defects and muscle dysfunction. The DPEP1/3 peptide-$[CAG]_7$ PMO (SEQ ID NO: 192) conjugates penetrate cells and induce splicing normalisation with high efficacy (FIG. 13). These new generation of so called DPEP1 and DPEP3' peptides have shown high efficacy in correcting splicing defects in vitro when conjugated to a $CAG_7$ (SEQ ID NO: 192) repeat antisense oligonucleotide PMO, indicating potential therapeutic use for treatment of DM 1.

Furthermore, the preliminary toxicology evaluation of conjugates formed with DPEP1/3 indicate that ALP, ALT, AST, KIM-1, BUN, NGAL, and creatinine levels were similar to saline control injections, in contrast to the fold increases typically induced by currently available peptide carriers from the Pip series. With this preliminary data we showed that conjugates formed from DPEP peptides with a $[CAG]_7$ PMO (SEQ ID NO: 192) are as active as conjugates formed with prior peptides such as Pip6a yet have wider therapeutic window because they are less toxic (FIGS. 15-19C).

Example 2

1. Material and Methods 1.1 Materials

9-Fluroenylmethoxycarbonyl (Fmoc) protected L-amino acids, benzotriazole-1-yl-oxy-tris-pyrrolidino-phosphonium (PyBOP), Rink amide resin (0.46 mmol-g[1]), and the Fmoc-P-Ala-OH preloaded Wang resin (0.19 or 0.46 mmol-g[1]) were obtained from Merck Millipore (Hohenbrunn, Germany). Tentagel Hydroxy-trityl resin was purchased from Rapp Polymere (Tuebingen, Germany). HPLC grade acetonitrile, methanol and synthesis grade N-methyl-2-pyrrolidone (NMP) were purchased from Fisher Scientific (Loughborough, UK). Peptide synthesis grade Al,Al-dimethylformamide (DMF) and diethyl ether were obtained from VWR (Leicestershire, UK). Piperidine and trifluoroacetic acid (TFA) were obtained from Alfa Aesar (Heysham, England). PMOs were purchased from Gene Tools Inc. (Philomath, USA). MALDI-TOF mass spectrometry was carried out using a Voyager DE Pro BioSpectrometry (Applied Biosystems, Cheshire UK) workstation. A stock solution of 10 mg-mL$^{-1}$ of a-cyano-4-hydroxycinnamic acid or sinapinic acid in 50% acetonitrile in water was used as matrix. Analytical and semi-preparative HPLC was performed on a Varian 940-LC HPLC System (Yarnton, UK). DMEM medium (31966047), fetal bovine serum (FBS) (10270106), antibiotic antimycotic solution (A5955), ethidium bromide (1558501 1), 2x ReddyMix PCR Master Mix (AB0575DCLDB), M-MLV first-strand synthesis system (28025013) and TRIzol reagent (15596026) were purchased from ThermoFisher Scientific. RealTime-Glo™ MT Cell Viability Assay (G9711), Maxwell® 16 Total RNA Purification Kit (AS1050) were purchased from Promega. Myoblast cells were cultured with PromoCell skeletal muscle cell growth media kit (C-23160). Insulin (91077C) and agarose (A9539) were from SigmaAldrich. DNA Marker-HyperLadder 50 bp (BIO-33039) was from BioLine Reagents. AH primers were ordered through IDT. For urine collection mice were singly house in metabolic cages from Tecniplast, UK and urinary biomarker ELISA for kidney injury marker-1 (KIM-1) (MKM100) was from R&D. AH other reagents were obtained from Sigma-Aldrich (United Kingdom) unless otherwise stated.

1.2 Synthesis of Peptide-PMO Conjugates 1.2.1 Synthesis of Peptide Variants via Microwave Synthesiser Peptides were synthesized on a 100 pmol scale using a CEM Liberty Blue™ microwave Peptide Synthesizer (Buckingham, UK) and Fmoc chemistry following manufacturer's recommendations. Peptides synthesised with glutamic acid, or succinic acid as linker were synthesised with a Rink amide resin to afford an amide on the carboxyl terminus of the peptide after TFA cleavage. Peptides with a b-alanine linker were synthesised using a preloaded Wang resin. A full list of the peptides synthesised with their methods and linkers are summarised in Table 11. The side chain protecting groups used were labile to TFA treatment and the peptide was synthesized using a 5-fold excess of Fmoc-protected amino acids (0.25 mmol) that were activated using PyBOP (5-fold excess) in the presence of DIPEA. Piperidine (20% v/v in DMF) was used to remove N-Fmoc protecting groups. The coupling was carried out once at 75° C. for 5 min at 60-watt microwave power except for arginine residues, which were coupled twice each. Each deprotection reaction was carried out at 75° C. twice, once for 30 sec and then once for 3 min at 35-watt microwave power. Once the synthesis was complete, the resin was washed with DMF (3×50 mL) and the N-terminus of the solid phase bound peptide was acetylated with acetic anhydride in the presence of DIPEA at room temperature for 15 min. After acetylation of the N-terminus, the peptide resin was washed with DMF (3×20 mL) and DCM (3×20 mL). For DPEP peptides with succinic acid on the N-terminus, acetylation of the N-terminus was not performed. Instead, the free N-terminus of the peptide was treated with succinic anhydride in the presence of DIPEA at room temperature for 30 min followed by washing with DMF (3×20 mL). For DPEP peptides carrying glutamic acid on the N-terminus as a linker, the N-terminus was acetylated as described, but attachment of the PMO was performed on the side chain carboxylic group.

1.2.2 Synthesis of peptide variants via Intavis Multipep Synthesiser Peptides synthesised with a y-aminobutyric acid linker were synthesised on a Tentagel Cl-trityl resin at room temperature using an Intavis Multipep Synthesiser and Fmoc chemistry following manufacturer's recommendations. The Tentagel® Cl-trityl resin was prepared from Tentagel® Hydroxy-trityl resin using acetyl chloride as per manufacturer's recommendations. Briefly, the resin (1 g) was washed with DMF (2×10 mL), dry DCM (3×10 mL) and dry toluene (3×10 mL) transferred to a round bottom tube fitted with a condenser. Enough toluene was added to cover the resin and then acetyl chloride was added dropwise (1 mL-g$^{-1}$ of resin, total volume 1 mL) and the mixture was heated for 3 h at 60-70° C. with gentle stirring. Upon completion, the resin was allowed to cool to room temperature and then washed thoroughly with toluene (5×15 mL), DMF (5×15 mL) and finally dry DCM (3×15 mL). The resin was then loaded with Fmoc-y-aminobutyric acid (3 equivalents) in DCM with DIEA (8 equivalents) for 15 min, after which additional DIEA (4 equivalents) was added and the reaction was allowed to mix for a total of 1 h. After 1 h, resin was then capped with MeOH (0.8 mL-g$^{-1}$) for 15 min and then washed with DMF (5×10 mL) and DCM (5×15 mL). The yield and loading of the resin was performed by Fmoc determination on a UV/visible spectrophotometer at 304 nm to be 0.41 mmol-g[1] and the resin was used immediately.

Typically, peptides were synthesised on a 100 pmol scale using standard Fmoc amino acids with side chain protecting groups labile to TFA and the peptide was synthesized using a 5-fold excess of Fmoc-protected amino acids (0.50 mmol) that were activated using PyBOP (5-fold excess) in the presence of 4-methylmorpholine. Double coupling steps were used followed by acetic anhydride capping after each step. Piperidine (20% v/v in DMF) was used to remove N-Fmoc protecting groups. Each deprotection cycle was carried out at room temperature twice, each for 10 min. Once synthesis was complete, the resin was washed with DMF (3×50 mL) and the N-terminus of the solid phase bound peptide was acetylated with acetic anhydride in the presence of DIPEA at room temperature for 15 min. After acetylation of the N-terminus, the peptide resin was washed with DMF (3×20 mL) and DCM (3×20 mL).

TABLE 11

Synthesis method and resins used of the peptides with different linkers and the resulting C-terminal modification.

| DPEP peptide | Linker | Location of linker with respect to peptide | Modification of C-term | Resin used | Synthesis method |
|---|---|---|---|---|---|
| DPEP1.9 | β-Ala | C-terminus | Carboxylic acid | Pre-loaded Wang resin | microwave synthesiser |
| DPEP1.9b | Glu | C-terminus | Amide | Rink amide resin | microwave synthesiser |
| DPEP1.9d | Glu | N-terminus | Amide | Rink amide resin | microwave synthesiser |
| DPEP3.1 | β-Ala | C-terminus | Carboxylic acid | Pre-loaded Wang resin | microwave synthesiser |
| DPEP3.1a | γ-Ab | C-terminus | Carboxylic acid | Cl-Trityl tentagel resin | Intavis Multipep |
| DPEP3.1b | Glu | C-terminus | Amide | Rink amide resin | microwave synthesiser |
| DPEP3.1c | Succ | N-terminus | Amide | Rink amide resin | microwave synthesiser |
| DPEP3.1d | Glu | N-terminus | Amide | Rink amide resin | microwave synthesiser |
| DPEP3.8b | Glu | C-terminus | Amide | Rink amide resin | microwave synthesiser |

1.2.3 Cleavage From the Solid Support and Purification of the Peptide via Semi-Prep HPLC The peptide was cleaved from the solid support by treatment with a cleavage cocktail consisting of TFA/$H_2O$/triisopropylsilane (TIPS) (95:2.5:2.5, 10 mL) for 3 h at room temperature. Excess TFA was removed by sparging with nitrogen. The cleaved peptide was precipitated via the addition of ice-cold diethyl ether and centrifuged at 3000 rpm for 5 min. The crude peptide pellet was washed thrice with cold diethyl ether (3·40 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of CH3CN in 0.1% TFA/$H_2O$ (0-99%, 0.1% TFA in $CH_3CN$) with a flow rate of 15 mL-mim[1] over 15 min. Detection was performed at 220 nm and 260 nm.

1.2.4 Synthesis of Peptide-PMO Conjugates

A 25-mer PMO antisense sequence for mouse dystrophin exon-23 (GGCC AAACCT CGGCTT ACCT G AAAT (SEQ ID NO: 90) was used. The peptide was conjugated to the 3'-end of the PMO through either its C-terminal carboxyl group or N-terminal amino group depending on the linker attachment site. This was achieved using 2.3 and 2-fold equivalents of PyBOP and HOAt in NMP respectively in the presence of 2.3 equivalents of DIPEA over peptide and a 2.5-fold excess of peptide over PMO dissolved in DMSO. In general, to a solution of peptide (10 mmol) in N-methylpyrrolidone (NMP, 100 mL) were added PyBOP (76.6 mL of 0.3 M in NMP), HOAt in (66.7 ml_ of 0.3 M NMP), DIPEA (4.0 mL) and PMO (4 pmol, 400 pL of 10 mM in DMSO). The mixture was left for 2 h at 40° C. and the reaction was quenched by the addition of $H_2O$ (1 mL). The reaction was purified on a cation exchange chromatography column (Re-

TABLE 12

Peptide sequences as synthesised for testing in the examples with varying linkers and attachment points.

| Peptide number | Sequence ID NO. incorporated | Sequence tested (with additional C and N terminal modifications)[a] | Linker/ attachment point[b] | Yield |
|---|---|---|---|---|
| DPEP1.9 | 35 | Ac-RBRRBRFQILYBRBR-B | B (C-term) | 38% |
| DPEP1.9b | 197 | Ac-RBRRBRFQILYBRBR-E | E (C-term) | 40% |
| DPEP1.9d | 181 | E-RBRRBRFQILYBRBR-$NH_2$ | E (N-term) | 36% |
| DPEP3.1 | 37 | Ac-RBRRBRRFQILYRBHBH-B | B (C-term) | 34% |
| DPEP3.1a | 182 | Ac-RBRRBRRFQILYRBHBH-Ab | Ab (C-term) | 37% |
| DPEP3.1b | 183 | Ac-RBRRBRRFQILYRBHBH-E | E (C-term) | 34% |
| DPEP3.1c | 37 | Succ-RBRRBRRFQILYRBHBH-$NH_2$ | Succ (N-term) | 26% |
| DPEP3.1d | 184 | E-RBRRBRRFQILYRBHBH-$NH_2$ | E (N-term) | 34% |
| DPEP3.8b | 185 | Ac-RBRRBRFQILYRBHBH-E | E(C-term) | 34% |

[a]Linkers are listed as their single amino acid abbreviations. [b]Linker attachment is with respect to the peptide, C-term = carboxyl terminus, N-term = amino terminus. The Sequence ID number refers to the sequence of the peptide without any additional N and C terminal modifications such as linkers.

source S 6H mL column, GE Healthcare) using a linear gradient of sodium chloride (0 to 1 M) in sodium phosphate buffer (25 mM, pH 7.0) containing 20% $CH_3CN$ at a flow rate of 6 mL-mim[1]. The removal of excess salts from the peptide-PMO (P-PMO) conjugate was afforded through the filtration of the fractions collected after ion exchange using an Amicon® ultra-15 3K centrifugal filter device. The conjugate was lyophilized and analysed by MALDI-TOF. The conjugates were dissolved in sterile water and filtered through a 0.22 pm cellulose acetate membrane before use. The concentration of P-PMO was determined by the molar absorption of the conjugates at 265 nm in 0.1 M HCl solution. Overall yields (Table 13) were 26-64% based on P-PMO.

1.3 Quantification and Reconstitution of P-PMO

The P-PMO was dissolved in RNase-free water. From this solution, an aliquot was diluted 100 fold in 0.1 M HCl and measured via UV-VIS at 265 nm. The concentration was determined using the Beer-Lambert law;

$$c = \frac{A_{265}}{\varepsilon_{265} l}$$

Prior to use, the P-PMO was thawed to room temperature (if frozen beforehand) and vortexed briefly, then incubated for 30 min at 37° C. The P-PMO aliquot was subsequently sonicated for 5 min in a sonicator bath. Finally, the P-PMO was briefly vortexed and pulse spun.

TABLE 13

Yields of P-PMO conjugates synthesized on larger scale for in vivo analysis (the yields are calculated via UV-Vis spectroscopy and are based on the extinction coefficient of the PMO). The purity for the P-PMO s is greater than 95% as ascertained by normal phase HPLC at 220 nm and 260 nm.

| P-PMO conjugates[a] | Conjugate Sequence[b] | Yield | SEQ ID NO: |
|---|---|---|---|
| DPEP1.9b | Ac-RBRRBRFQILYBRBR-(E)-**PMO** | 39% | 197 |
| DPEP1.9d | **PMO**-(E)-RBRRBRFQILYBRBR-$NH_2$ | 29% | 181 |
| DPEP3.1a | Ac-RBRRBRRFQILYRBHBH-(Ab)-**PMO** | 26% | 182 |
| DPEP3.1b | Ac-RBRRBRRFQILYRBHBH-(E)-**PMO** | 27% | 183 |
| DPEP3.1c | **PMO**-(Succ)-RBRRBRRFQILYRBHBH-$NH_2$ | 64% | 37 |
| DPEP3.1d | **PMO**-(E)-RBRRBRRFQILYRBHBH-$NH_2$ | 48% | 184 |
| DPEP3.8b | Ac-RBRRBRFQILYRBHBH-(E)-**PMO** | 49% | 185 |

[a]The PMO used to conjugate to the peptide has the following sequence, 5'-GGC-CAAACCTCGGCTTACCTGAAAT-3' (SEQ ID NO: 90). The attachment of the PMO is given here in bold italics, the linker in brackets.

The following comparison conjugates were also synthesised/obtained and the same PMO was conjugated to the peptide using comparative linkers.

TABLE 14 comparison peptides

| Peptide class | Peptide Name | Sequence (N->C terminal) with linker | SEQ ID NO. Incorporated | Linker | PMO attachment site |
|---|---|---|---|---|---|
| Comparison peptide | R6Gly | Ac-RRRRRR-(G) | 176 | Glycine | Terminal extremity of the peptide |
| | Pip9b2 | Ac-RXRRBRRFQILYRBRXR-(B) | 175 | β-Alanine | Terminal extremity of the peptide |
| | Pip6a | Ac-RXRRBRRXR-YQFLI-RXRBRXR-(B) | 174 | β-Alanine | Terminal extremity of the peptide |

The injection solution was prepared by combining the P-PMO at the desired treatment concentration diluted in RNase free water and 9% saline (to a final concentration of 0.9% saline).

1.4 In Vivo P-PMO Treatment Assessment 1.4.1 Systemic Administration of P-PMO

All animal experiments were conducted in the Biomedical Sciences Unit, University of Oxford, under Home Office Project Licence (UK) authorisation and in accordance with The Animals (Scientific Procedures) Act 1986 and institutional ethical review. Mice were housed in a specific pathogen free disease facility; the environment was temperature and humidity controlled with a 12-hour light-dark cycle. All animals received commercial rodent chow and water ad libitum.

Experiments were performed on female C57BL/6 mice aged 8-10 weeks old. Mice were administered a single bolus intravenous tail vein injection of 0.9% saline, 10 mg/kg, 30 mg/kg or 50 mg/kg of P-PMO. One-week post injection mice were sacrificed and tibialis anterior, diaphragm and heart muscles removed and snap frozen on dry-ice and stored at −80° C.

1.4.2 Toxicological Assessment of P-PMO

Following intravenous administration of P-PMO (See Section 1.4.1) urine was non-invasively collected under chilled conditions at day 2 and day 7 post-administration following 20 hours housing in metabolic cages. Blood was collected from jugular vein at day 7 during necropsy and the blood was fractionated and serum collected. Tibialis anterior, diaphragm and heart tissue was collected at day 7 during necropsy. Urinary levels of kidney injury molecule-1 (KIM-1) was quantified by ELISA following appropriate dilution of urine to fit standard curves. KIM-1 values were normalised to urinary creatinine levels that were quantified at MRC Harwell Institute, Mary Lyon Centre, Oxfordshire, UK.

1.4.3 qPCR Analysis of P-PMO Induced Exon Skipping

Quantification of P-PMO induced exon skipping was performed on tibialis anterior (TA), diaphragm and heart muscles 7 days post administration. Briefly, RNA was extracted from homogenised tissue using TRIzol-based extraction method and cDNA synthesised using random primers. Primer/probes were synthesised by Integrated DNA Technologies and designed to amplify a region spanning exon 23-24 representing unskipped product (mDMD23-24, see Table 14), or to amplify specifically transcripts lacking exon 23 using a probe spanning the boundary of exon 22 and 24 (mDMD22-24). Levels of respective transcripts were determined by skipped and unskipped transcripts and expressed as percentage of skipped versus total (skipped and unskipped) transcripts (see Table 15 for sequences).

mg/ml of proteinase K) for 45 min at 55° C. Total RNAs were isolated using TriReagent according to the manufacturer's protocol. One microgram of RNA was reverse transcribed using M-MLV first-strand synthesis system (Life Technologies) according to the manufacturer's instructions in a total of 20 pL. One microliter of cDNA preparation was subsequently used in a semi-quantitative PCR analysis according to standard protocol (ReddyMix, Thermo Scientific). PCR amplification was carried out for 25-35 cycles within the linear range of amplification for each gene. PCR products were resolved on 1.5-2% agarose gels, ethidium bromide-stained and quantified with ImageJ software. The ratios of exon inclusion were quantified as a percentage of inclusion relative to total intensity of isoform signals. To quantify the mRNA expression, real-time PCR was performed according to the manufacturer's instructions. PCR cycles were a 15-min denaturation step followed by 50 cycles with a 94° C. denaturation for 15 s, 58° C. annealing for 20 s and 72° C. extension for 20 s.

TABLE 15

Primer and probe sequences for quantification of mouse dystrophin (exon 23) exon skipping by qPCR methods.

| Transcript | Forward primer (5'-3') | SEQ ID NO: | Reverse primer (5'-3') | SEQ ID NO: | Probe | SEQ ID NO: |
|---|---|---|---|---|---|---|
| mDMD (exon 23-24) | CAGGCCATTCC TCTTTCAGG | 186 | GAAACTTTCCTC CCAGTTGGT | 187 | /5FAM/TCAACTTCA/ ZEN/GCCATCCATT TCTGTAAGGT/ 3IABkFQ/ | 188 |
| mDMD (exon 22-24) | CTGAATATGAAA TAATGGAGGAG G | 189 | CTTCAGCCATCC ATTTCTGTAAGG T | 190 | /5FAM/ATGTGATTC/ ZEN/TGTAATTTCC/ 3IABkFQ/ | 191 |

2. Further Examples

Synthesis of Peptide-PMO Conjugates. Peptides were synthesized and conjugated to PMO as described previously. The PMO sequence targeting CUG expanded repeats (5-CAGCAGCAGCAGCAGCAGCAG-3' (SEQ ID NO: 192) was purchased from Gene Tools LLC and used to make further conjugates.

Cell Culture and Peptide-PMO Treatment.

Immortalized myoblasts from healthy individual or DM1 patient with 2600 CTG repeats were cultivated in a growth medium consisting of a mix of M199: DMEM (1:4 ratio; Life technologies) supplemented with 20% FBS (Life technologies), 50 pg/ml gentamycin (Life technologies), 25 pg/ml fetuin, 0.5 ng/ml bFGF, 5 ng/ml EGF and 0.2 pg/ml dexamethasone (Sigma-Aldrich). Myogenic differentiation was induced by switching confluent cell cultures to DMEM medium supplemented with 5 pg/ml insulin (Sigma-Aldrich) for myoblasts. For treatment, WT or DM1 cells are differentiated for 4 days. Then, medium was changed with fresh differentiation medium with peptide-PMOs at a 1, 2, 5 10, 20 or 40 pM concentration. Cells were harvested for analysis 48 h after treatment. Cell viability was quantified in after 2 days of transfection of peptide-PMOs at 40 uM in human hepatocytes or at a 1, 2, 5 10, 20 or 40 pM concentration in human myoblasts using a fluorescent-based assay (Promega).

RNA Isolation, RT-PCR

For human cells: prior to RNA extraction, cells were lysed in a proteinase K buffer (500 mM NaCl, 10 mM Tris-HCl, pH 7.2, 1.5 mM MgCl2, 10 mM EDTA, 2% SDS and 0.5

TABLE 16 primers for PCR

| Primer Name | SEQ ID NO. | Species/Gene/ Exon | Sequence (5'-3') |
|---|---|---|---|
| Mbnl1.F | 177 | Mouse-Human/ mbnl1/exon5 | GCTGCCCAATACCAGGTCAAC |
| Mbnl1.R | 178 | Mouse-Human/ mbnl1/exon5 | TGGTGGGAGAAATGCTGTATGC |
| DMD.F | 179 | Human/DMD/ exon78 | TTAGAGGAGGTGATGGAGCA |
| DMD.R | 180 | Human/DMD/ exon78 | GATACTAAGGACTCCATCGC |

Animal experiments and ASO injections. Experiments were carried out in the University of Oxford according to UK legislation. The intravenous injections in HSA-LR C57BL/6 mice were performed by single or repeated administrations via the tail vein. Doses of 30, 12.5, 7.5 and 5 mg/kg of peptide-PMO-$CAG_7$ (SEQ ID NO: 192) were diluted in 0.9% saline and given at a volume of 5-6 pL/g of body weight. KIM-1 levels in C57BL6 female mice measured by ELISA (R&D cat #MKM100) with samples diluted to fit within standard curve. Values were normalised to urinary creatinine levels (Harwell) to account for urine protein concentration.

TABLE 17

Recovery times of C57BL6 mice after injections with DPEP based $[CAG]_7$ PMO (SEQ ID NO: 192) conjugates are shorter than after injection with conjugates formed with prior peptide carriers such as Pip6a.

| Summary of recovery times after injection with peptide-PMOCAG7 | Mouse | Age | Time AV ± SD |
|---|---|---|---|
| DPEP1.9 6X 5 mg/kg repeated injections | HSA-LR | 8-12 weeks | 0 min |
| DPEP3.8 6X 5 mg/kg repeated injections | HSA-LR | 8-12 weeks | 0 min |
| DPEP1.9 4X 7.5 mg/kg repeated injections | HSA-LR | 8-12 weeks | 0 min |
| DPEP3.8 4X 7.5 mg/kg repeated injections | HSA-LR | 8-12 weeks | 0 min |
| DPEP1.9 7.5 mg/kg | HSA-LR | 8-12 weeks | 0 min |
| DPEP3.8 7.5 mg/kg | HSA-LR | 8-12 weeks | 0 min |
| DPEP1.9 30 mg/kg | WT | 8-12 weeks | 17.5 min ± 2.5 |
| DPEP1.9b 30 mg/kg | WT | 8-12 weeks | 15 min |
| DPEP3.8 30 mg/kg | WT | 8-12 weeks | 7.5 min ± 2.5 |
| DPEP3.1a 30 mg/kg | WT | 8-12 weeks | 10 min |
| DPEP3.8 30 mg/kg | HSA-LR | 8-12 weeks | 60 min ± 10 |
| DPEP1.9 40 mg/kg | HSA-LR | 8-12 weeks | 57.5 min ± 26 |
| DPEP3.8 40 mg/kg | HSA-LR | 8-12 weeks | 60 min ± 15.5 |
| DPEP3.8 30 mg/kg | HSA-LR | 30 weeks | 60 min |
| DPEP1.9 30 mg/kg | HSA-LR | 30 weeks | >60 min |
| pip6a 12.5 mg/kg | HSA-LR | 8-12 weeks | >60 min |

Example 3

Any of the following conjugates may be prepared using techniques and methods described in Examples 1 and 2 above:

Ac-RBRRBRFQILYBRBR
|
(E)
|
5′-CAATGCCATCCTGGAGTTCCTG-3′,

RBRRBRFQILYBRBR-$NH_2$
|
(E)
|
5′-CAATGCCATCCTGGAGTTCCTG-3′
,

Ac-RBRRBRFQILYRBHBH
|
(E)
|
5′-CAATGCCATCCTGGAGTTCCTG-3′,

Ac-RBRRBRFQILYRBHBH
|
(B)
|
5′-CAATGCCATCCTGGAGTTCCTG-3′,

Ac-RBRRBRFQILYBRBR
|
(B)
|
5′-CAATGCCATCCTGGAGTTCCTG-3′,

Ac-RBRRBRFQILYRBHBH
|
(E)
|
5′-GCTGCCCAATGCCATCCTGGAGTTCCTGTAA-3′,

Ac-RBRRBRFQILYRBHBH
|
(B)
|
5′-GCTGCCCAATGCCATCCTGGAGTTCCTGTAA-3′,

Ac-RBRRBRFQILYBRBR
|
(B)
|
5′-GCTGCCCAATGCCATCCTGGAGTTCCTGTAA-3′,

RBRRBRFQILYBRBR-$NH_2$
|
(E)
|
5′-ACATCAAGGAAGATGGCATTTCTAGTTTGG-3′
,

Ac-RBRRBRFQILYBRBR
|
(B)
|
5′-ACATCAAGGAAGATGGCATTTCTAGTTTGG-3′,

Ac-RBRRBRFQILYRBHBH
|
(B)
|
5′-ACATCAAGGAAGATGGCATTTCTAGTTTGG-3′,

Ac-RBRRBRFQILYRBHBH
|
(E)
|
5′-ACATCAAGGAAGATGGCATTTCTAGTTTGG-3′,

Ac-RBRRBRFQILYBRBR
|
(E)
|
5′-CTCCAACATCAAGGAAGATGGCATTTCTAG-3′,

RBRRBRFQILYBRBR-$NH_2$
|
(E)
|
5′-CTCCAACATCAAGGAAGATGGCATTTCTAG-3′
,

Ac-RBRRBRFQILYRBHBH
|
(B)
|
5′-CTCCAACATCAAGGAAGATGGCATTTCTAG-3′,

Ac-RBRRBRFQILYRBHBH
|
(E)
|
5′-CTCCAACATCAAGGAAGATGGCATTTCTAG-3′,

Ac-RBRRBRFQILYBRBR
|
(B)
|
5′-CTCCAACATCAAGGAAGATGGCATTTCTAG-3′,

-continued

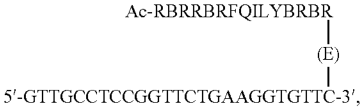, 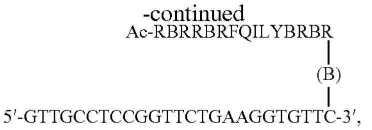, 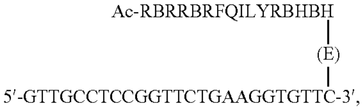, 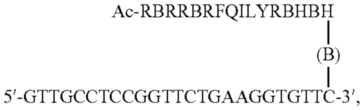, 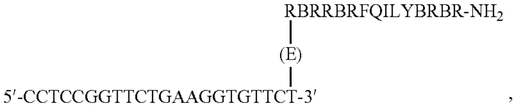, 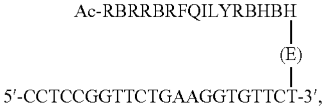, 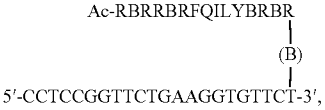, 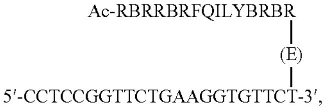, 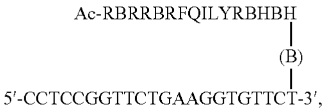, 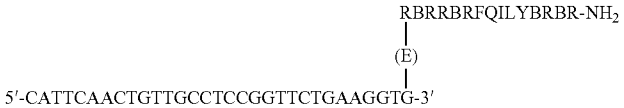, 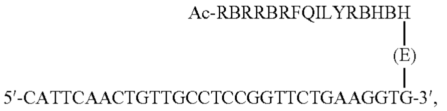, 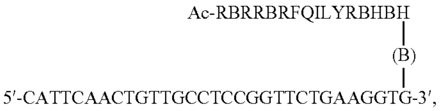, 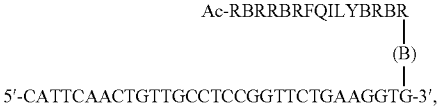, or 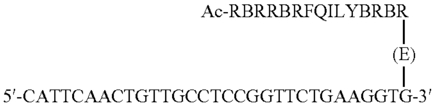

where (B) is a beta-alanine residue, (Ab) is a gamma-aminobutyric acid residue, and (E) is a glutamic acid residue, provided that —COOH, if present in the glutamic acid residue, is replaced with —$CONH_2$.

In the above conjugates, the oligonucleotides can be morpholinos with all morpholino internucleoside linkages being —$P(O)(NMe_2)O$— and with a group of the following structure at the 5' terminus:

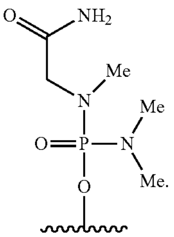

Example 4. Non-human Primate Study

Conjugate 1 shown below, comprising a morpholino oligonucleotide, was reconstituted to 25 mg/mL with 0.9% sterile saline.

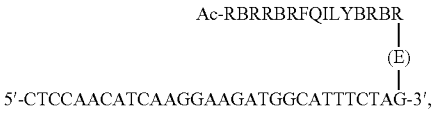, where 5' group is

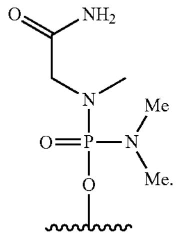 [SMILES: *OP(=O)(N(C)C)N(C)CC(N)=O]

and linker (E) is

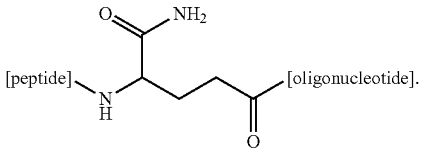

NHP Single Infusion Dose Response Study

The efficacy of exon skipping of Conjugate 1 was tested in non-human primates (NHP). Specifically, naïve cynomolgus monkeys aged 2-4 years were administered the conjugate by a single intravenous slow bolus injection (1-2 minutes) at 20 mg/kg, 40 mg/kg, or 60 mg/kg (n=1 male and n=1 female per group).

Animals were sacrificed one-week post administration. At scheduled necropsy section of tissue were collected for exon skipping analysis and tissue bioanalysis.

Tissue Bioanalysis

Figure 33:
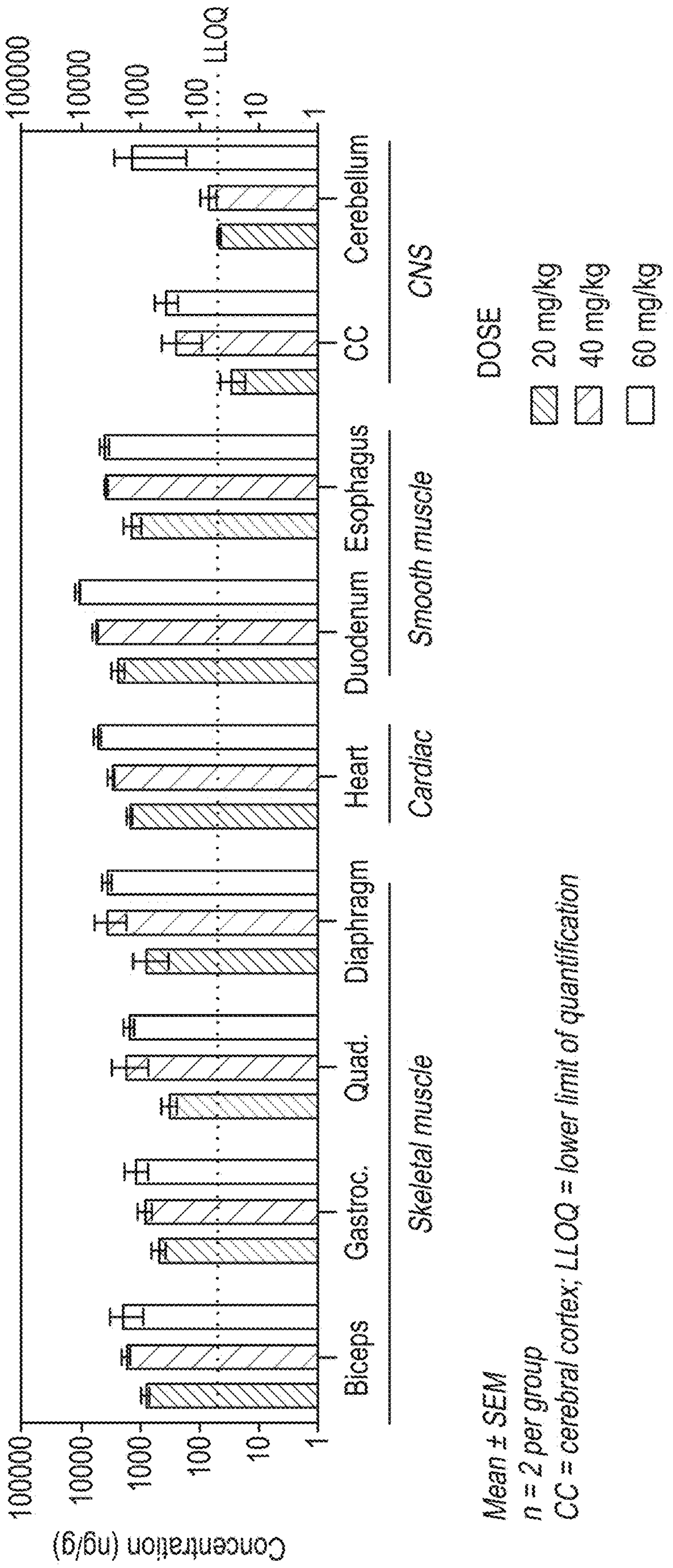
FIG. 33 is a plot demonstrating the biodistribution in key skeletal, cardiac, and smooth muscle and central nervous system tissues in conjugate-treated animals. The key muscle tissues include the hard-to-reach cardiac tissue. The plot also demonstrates the conjugate is delivered across the blood-brain barrier.

The biodistribution of Conjugate 1 was assessed by an AEX-HPLC analytical method with fluorescence detection that allowed the sensitive and specific detection of Conjugate 1 from NHP tissue samples. The assay is based on the specific hybridization of a 30-mer complementary RNA-probe conjugated at both termini with an Atto425 dye. The duplex of RNA and parent compound yielded a specific signal in the subsequent analysis by AEX-HPLC coupled to a fluorescence detector. Quantification was performed based on an external calibration curve generated from a standard dilution series in NHP tissues. Linear calibration curves (weighted 1/X) are calculated from 50 ng/g to 5,000.0 ng/g. The biodistribution results are shown in FIG. 33.

RT-PCR Analysis

The level of exon 51 skipping was determined by RT-PCR. Skeletal, cardiac, and smooth muscle tissue was homogenized using a bead-based homogenization method. RNA was extracted using a Maxwell RSC 48 instrument (Promega) and a simplyRNA Tissue Kit (Promega) according to the manufacturer's recommendations. Concentration and purity of the RNA was determined using a ClarioStar (BMG LabTech). Quantified RNA was reverse transcribed using a High-Capacity cDNA Reverse Transcription Kit (ThermoFisher Scientific, 4368813), under the thermal cycling conditions described in Table 18.

TABLE 18

Reverse transcription thermal cycling conditions.
Thermal Cycling Conditions

| Step | Temperature (° C.) | Time (min) |
|---|---|---|
| 1 | 25 | 10 |
| 2 | 37 | 120 |
| 3 | 85 | 5 |
| 4 | 4 | Hold |

A nested-PCR was performed as 2 consecutive PCR reactions. The first PCR was performed using the reverse transcribed cDNA template. The second PCR was performed using product from the first PCR. All primers used in for PCR reactions are identified in Table 19, and thermal cycling conditions are outlined in Table 20. Final PCR products were analyzed by agarose (2%) gel electrophoresis. Gels were prepared using Midori Green Advance Stain (Nippon Genetics). HyperLadder 50 bp (Bioline, BIO-33039) and PCR product were loaded on the agarose gel and run until an appropriate degree of band separation was achieved. Subsequently gel image acquisition was performed on resolved gels using a G:BOX (Syngene) gel imaging system. Unskipped/native and skipped/Δex51 bands from nested-PCR gels were subjected to densitometry analysis using ImageJ software (Fiji). Densitometry values from band quantification were used to determine nhpDMD exon 51 skipping, using the below formula: nhpDMD exon 51 skipping formula: ([peak area of skipped fragment]/[peak area of skipped fragment+peak area of unskipped fragment])×100.

TABLE 19

Primers and primer sequences.

| | PCR Primers | | |
|---|---|---|---|
| | Name | Exon target | Sequence (5'-3') |
| PCR-1 | nhpDMDex48 (F) | Ex48 | TGCTCCTGTGGCTGTCTCCT (SEQ ID NO: 227) |
| | nhpDMDex53 (R) | Ex53 | AGCTTGGCTCTGGCCTGTCCT (SEQ ID NO: 228) |
| PCR-2 | nhpDMDex49 (F) | Ex49 | ACCAGCCACTCAGCCAGTGA (SEQ ID NO: 229) |
| | nhpDMDex52 (R) | Ex52 | GATTGTTCTAGCCTCTTGATTGC (SEQ ID NO: 230) |

TABLE 20

Thermal cycling conditions.

| Step | Temperature (° C.) | Time | Cycles |
|---|---|---|---|
| Initial denaturing | 95 | 5 min | 1 |
| Denaturing | 95 | 25 s | 20 |
| Annealing | 62 | 35 s | |
| Extension | 72 | 65 s | |
| Final extension | 72 | 5 min | 1 |
| Hold | 4 | N/A | N/A |
| Initial denaturing | 95 | 5 min | 1 |
| Denaturing | 95 | 25 s | 32 |
| Annealing | 58 | 35 s | |
| Extension | 72 | 65 s | |
| Final extension | 72 | 5 min | 1 |
| Hold | 4 | N/A | N/A |

Figure 34:
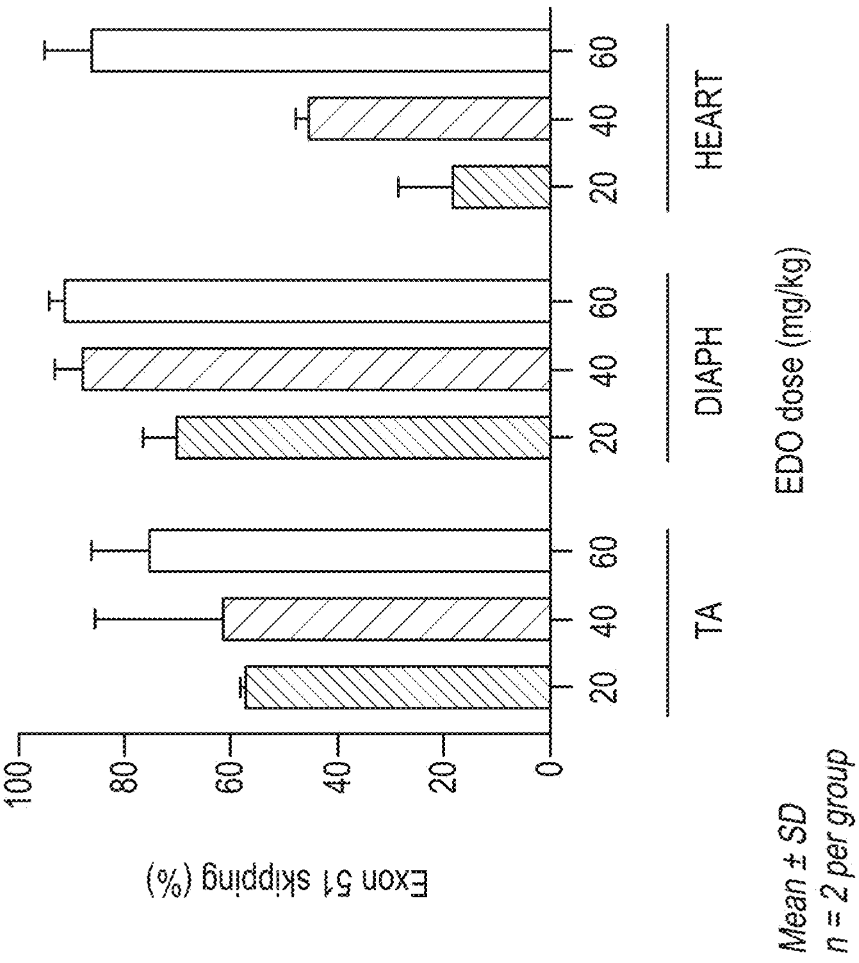
FIG. 34 is a plot demonstrating exon 51 skipping efficacy in skeletal and cardiac muscle tissues. TA is tibialis anterior, and DIAPH is diaphragm.

Exon 51 skipping efficiency in the non-human primates receiving Conjugate 1 is summarized in FIG. 34.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A conjugate, or a pharmaceutically acceptable salt thereof, is of the following structure having a glutamic acid residue:

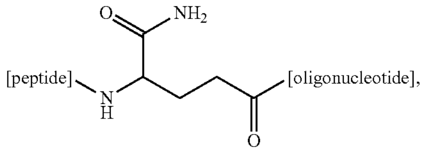

wherein the peptide consists of the sequence RBRRBRFQILYBRBR (SEQ ID NO: 35) and is covalently linked to the glutamic acid residue at the C-terminus of the peptide, wherein the peptide is acetylated at its N-terminus; and wherein the oligonucleotide is a PMO and consists of the sequence 5'-CTCCAACATCAAGGAAGATGGCATTTCTAG-3' (SEQ ID NO: 195), wherein the oligonucleotide is linked by its 3'-terminus to the glutamic acid residue and has the following group at its 5' terminus:

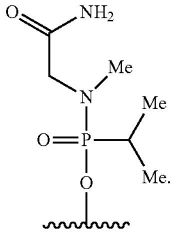 [SMILES: *OP(=O)(C(C)C)N(C)CC(N)=O]

2. A pharmaceutical composition comprising a conjugate, or a pharmaceutically acceptable salt thereof, is of the following structure having a glutamic acid residue:

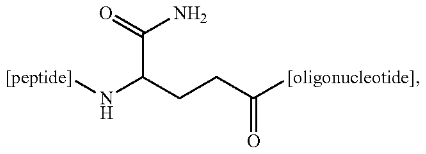

wherein the peptide consists of the sequence RBRRBRFQILYBRBR (SEQ ID NO: 35) and is covalently linked to the glutamic acid residue at the C-terminus of the peptide, wherein the peptide is acetylated at its N-terminus; and wherein the oligonucleotide is a PMO and consists of the sequence 5'-CTCCAACATCAAGGAAGATGGCATTTCTAG-3' (SEQ ID NO: 195), wherein the oligonucleotide is linked by its 3'-terminus to the glutamic acid residue and has the following group at its 5' terminus:

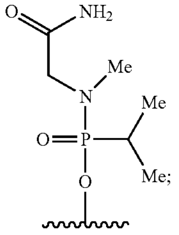 [SMILES: *OP(=O)(C(C)C)N(C)CC(N)=O]

and a pharmaceutically acceptable carrier.

3. A pharmaceutically acceptable salt of a conjugate of the following structure having a glutamic acid residue:

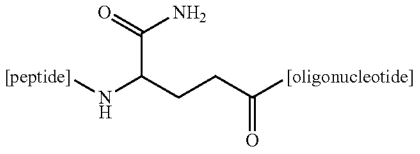

wherein the peptide consists of the sequence RBRRBRFQILYBRBR (SEQ ID NO: 35) and is covalently linked to the glutamic acid residue at the C-terminus of the peptide, wherein the peptide is acetylated at its N-terminus; and wherein the oligonucleotide is a PMO and consists of the sequence 5'-CTCCAACATCAAGGAAGATGGCATTTCTAG-3' (SEQ ID NO: 195), wherein the oligonucleotide is linked by its 3'-terminus to the glutamic acid residue and has the following group at its 5' terminus:

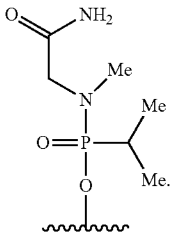 [SMILES: *OP(=O)(C(C)C)N(C)CC(N)=O]

4. A pharmaceutical composition comprising a pharmaceutically acceptable salt of a conjugate of the following structure having a glutamic acid residue:

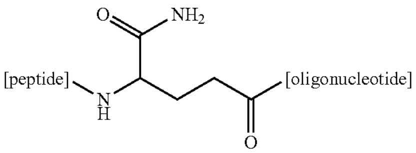

wherein the peptide consists of the sequence RBRRBRFQILYBRBR (SEQ ID NO: 35) and is covalently linked to the glutamic acid residue at the C-terminus of the peptide, wherein the peptide is acetylated at its N-terminus; and wherein the oligonucleotide is a PMO and consists of the sequence 5'-CTCCAACATCAAGGAAGATGGCATTTCTAG-3' (SEQ ID NO: 195), wherein the oligonucleotide is linked by its 3'-terminus to the glutamic acid residue and has the following group at its 5' terminus:

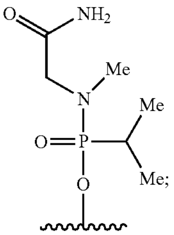 [SMILES: *OP(=O)(C(C)C)N(C)CC(N)=O]

and a pharmaceutically acceptable carrier.

* * * * *

SEQUENCE LISTING

```
Sequence total quantity: 230
SEQ ID NO: 1            moltype = AA  length = 7
FEATURE                 Location/Qualifiers
MOD_RES                 2
                        note = misc_feature - Xaa is bAla
MOD_RES                 5
                        note = misc_feature - Xaa is bAla
source                  1..7
                        mol_type = protein
                        organism = synthetic construct
SEQUENCE: 1
```

-continued

```
RXRRXRR                                                        7

SEQ ID NO: 2          moltype =   length =
SEQUENCE: 2
000

SEQ ID NO: 3          moltype =   length =
SEQUENCE: 3
000

SEQ ID NO: 4          moltype = AA  length = 6
FEATURE               Location/Qualifiers
MOD_RES               2
                      note = misc_feature - Xaa is bAla
MOD_RES               5
                      note = misc_feature - Xaa is bAla
source                1..6
                      mol_type = protein
                      organism = synthetic construct
SEQUENCE: 4
RXRRXR                                                         6

SEQ ID NO: 5          moltype = AA  length = 6
FEATURE               Location/Qualifiers
MOD_RES               3
                      note = misc_feature - Xaa is bAla
MOD_RES               5
                      note = misc_feature - Xaa is bAla
source                1..6
                      mol_type = protein
                      organism = synthetic construct
SEQUENCE: 5
RRXRXR                                                         6

SEQ ID NO: 6          moltype =   length =
SEQUENCE: 6
000

SEQ ID NO: 7          moltype =   length =
SEQUENCE: 7
000

SEQ ID NO: 8          moltype =   length =
SEQUENCE: 8
000

SEQ ID NO: 9          moltype =   length =
SEQUENCE: 9
000

SEQ ID NO: 10         moltype = AA  length = 7
FEATURE               Location/Qualifiers
MOD_RES               2
                      note = misc_feature - Xaa is bAla
MOD_RES               5
                      note = misc_feature - Xaa is bAla
source                1..7
                      mol_type = protein
                      organism = synthetic construct
SEQUENCE: 10
RXRHXHR                                                        7

SEQ ID NO: 11         moltype = AA  length = 7
FEATURE               Location/Qualifiers
MOD_RES               2
                      note = misc_feature - Xaa is bAla
MOD_RES               4..5
                      note = misc_feature - Xaa is bAla
source                1..7
                      mol_type = protein
                      organism = synthetic construct
SEQUENCE: 11
RXRXXHR                                                        7

SEQ ID NO: 12         moltype = AA  length = 6
FEATURE               Location/Qualifiers
MOD_RES               2
                      note = misc_feature - Xaa is bAla
MOD_RES               5
```

```
                        note = misc_feature - Xaa is bAla
source                  1..6
                        mol_type = protein
                        organism = synthetic construct
SEQUENCE: 12
RXRRXH                                                                      6

SEQ ID NO: 13           moltype = AA  length = 6
FEATURE                 Location/Qualifiers
MOD_RES                 2
                        note = misc_feature - Xaa is bAla
MOD_RES                 5
                        note = misc_feature - Xaa is bAla
source                  1..6
                        mol_type = protein
                        organism = synthetic construct
SEQUENCE: 13
HXRRXR                                                                      6

SEQ ID NO: 14           moltype =   length =
SEQUENCE: 14
000

SEQ ID NO: 15           moltype =   length =
SEQUENCE: 15
000

SEQ ID NO: 16           moltype =   length =
SEQUENCE: 16
000

SEQ ID NO: 17           moltype =   length =
SEQUENCE: 17
000

SEQ ID NO: 18           moltype =   length =
SEQUENCE: 18
000

SEQ ID NO: 19           moltype = AA  length = 6
FEATURE                 Location/Qualifiers
MOD_RES                 2
                        note = misc_feature - Xaa is hydroxyproline
MOD_RES                 5
                        note = misc_feature - Xaa is hydroxyproline
source                  1..6
                        mol_type = protein
                        organism = synthetic construct
SEQUENCE: 19
RXRRXR                                                                      6

SEQ ID NO: 20           moltype = AA  length = 5
FEATURE                 Location/Qualifiers
source                  1..5
                        mol_type = protein
                        organism = synthetic construct
SEQUENCE: 20
YQFLI                                                                       5

SEQ ID NO: 21           moltype = AA  length = 5
FEATURE                 Location/Qualifiers
source                  1..5
                        mol_type = protein
                        organism = synthetic construct
SEQUENCE: 21
FQILY                                                                       5

SEQ ID NO: 22           moltype = AA  length = 5
FEATURE                 Location/Qualifiers
source                  1..5
                        mol_type = protein
                        organism = synthetic construct
SEQUENCE: 22
ILFQY                                                                       5

SEQ ID NO: 23           moltype = AA  length = 4
FEATURE                 Location/Qualifiers
source                  1..4
                        mol_type = protein
```

```
                        organism = synthetic construct
SEQUENCE: 23
FQIY                                                                       4

SEQ ID NO: 24           moltype = AA  length = 5
FEATURE                 Location/Qualifiers
source                  1..5
                        mol_type = protein
                        organism = synthetic construct
SEQUENCE: 24
WWPWW                                                                      5

SEQ ID NO: 25           moltype = AA  length = 4
FEATURE                 Location/Qualifiers
source                  1..4
                        mol_type = protein
                        organism = synthetic construct
SEQUENCE: 25
WPWW                                                                       4

SEQ ID NO: 26           moltype = AA  length = 4
FEATURE                 Location/Qualifiers
source                  1..4
                        mol_type = protein
                        organism = synthetic construct
SEQUENCE: 26
WWPW                                                                       4

SEQ ID NO: 27           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 27
RXRRXRRFQI LYRXRXR                                                         17

SEQ ID NO: 28           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
source                  1..16
                        mol_type = protein
                        organism = synthetic construct
SEQUENCE: 28
RXRRXRRFQI LYRXRR                                                          16

SEQ ID NO: 29           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 29
RXRRXRFQIL YRRXRXR                                                         17

SEQ ID NO: 30           moltype = AA  length = 17
FEATURE                 Location/Qualifiers
MOD_RES                 2
                        note = misc_feature - Xaa is bAla
MOD_RES                 4
```

```
                        note = misc_feature - Xaa is bAla
MOD_RES                 12
                        note = misc_feature - Xaa is bAla
MOD_RES                 15
                        note = misc_feature - Xaa is bAla
source                  1..17
                        mol_type = protein
                        organism = synthetic construct
SEQUENCE: 30
RXRXRFQILY RXRRXRR                                                17

SEQ ID NO: 31           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 31
RXRRXRRYQF LIRXRXR                                                17

SEQ ID NO: 32           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 32
RXRRXRRILF QYRXRXR                                                17

SEQ ID NO: 33           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 33
RXRRXRFQIL YRXRXR                                                 16

SEQ ID NO: 34           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 15
                        note = misc_feature - Xaa is bAla
source                  1..16
                        mol_type = protein
                        organism = synthetic construct
SEQUENCE: 34
RXRRXFQILY RXRRXR                                                 16

SEQ ID NO: 35           moltype = AA  length = 15
FEATURE                 Location/Qualifiers
MOD_RES                 2
                        note = misc_feature - Xaa is bAla
```

-continued

```
MOD_RES                5
                       note = misc_feature - Xaa is bAla
MOD_RES                12
                       note = misc_feature - Xaa is bAla
MOD_RES                14
                       note = misc_feature - Xaa is bAla
source                 1..15
                       mol_type = protein
                       organism = synthetic construct
SEQUENCE: 35
RXRRXRFQIL YXRXR                                                   15

SEQ ID NO: 36          moltype = AA  length = 15
FEATURE                Location/Qualifiers
MOD_RES                2
                       note = misc_feature - Xaa is bAla
MOD_RES                5
                       note = misc_feature - Xaa is bAla
MOD_RES                12
                       note = misc_feature - Xaa is bAla
MOD_RES                14
                       note = misc_feature - Xaa is bAla
source                 1..15
                       mol_type = protein
                       organism = synthetic construct
SEQUENCE: 36
RXRRXFQILY RXRXR                                                   15

SEQ ID NO: 37          moltype = AA  length = 17
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
source                 1..17
                       mol_type = protein
                       organism = synthetic construct
SEQUENCE: 37
RXRRXRRFQI LYRXHXH                                                 17

SEQ ID NO: 38          moltype = AA  length = 17
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
source                 1..17
                       mol_type = protein
                       organism = synthetic construct
SEQUENCE: 38
RXRRXRRFQI LYHXHXR                                                 17

SEQ ID NO: 39          moltype = AA  length = 17
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
source                 1..17
                       mol_type = protein
                       organism = synthetic construct
SEQUENCE: 39
RXRRXRRFQI LYHXRXH                                                 17

SEQ ID NO: 40          moltype = AA  length = 17
FEATURE                Location/Qualifiers
MOD_RES                2
```

```
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 40
RXRRXRRYQF LIRXHXH                                                        17

SEQ ID NO: 41           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 41
RXRRXRRILF QYRXHXH                                                        17

SEQ ID NO: 42           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 42
RXRHXHRFQI LYRXRXR                                                        17

SEQ ID NO: 43           moltype = AA  length = 17
FEATURE                 Location/Qualifiers
MOD_RES                 2
                        note = misc_feature - Xaa is bAla
MOD_RES                 4
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 43
RXRXXHRFQI LYRXHXH                                                        17

SEQ ID NO: 44           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 44
RXRRXRFQIL YRXHXH                                                         16
```

```
SEQ ID NO: 45           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 45
RXRRXRFQIL YHXHXH                                                   16

SEQ ID NO: 46           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 46
RXRRXHFQIL YRXHXH                                                   16

SEQ ID NO: 47           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 47
HXRRXRFQIL YRXHXH                                                   16

SEQ ID NO: 48           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 48
RXRRXFQILY RXHXH                                                    15

SEQ ID NO: 49           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 49
RXRRXRFQIL YXHXH                                                    15
```

```
SEQ ID NO: 50          moltype = AA  length = 16
FEATURE                Location/Qualifiers
MOD_RES                2
                       note = misc_feature - Xaa is bAla
MOD_RES                5
                       note = misc_feature - Xaa is bAla
MOD_RES                13
                       note = misc_feature - Xaa is bAla
MOD_RES                15
                       note = misc_feature - Xaa is bAla
source                 1..16
                       mol_type = protein
                       organism = synthetic construct
SEQUENCE: 50
RXRRXRYQFL IHXHXH                                              16

SEQ ID NO: 51          moltype = AA  length = 16
FEATURE                Location/Qualifiers
MOD_RES                2
                       note = misc_feature - Xaa is bAla
MOD_RES                5
                       note = misc_feature - Xaa is bAla
MOD_RES                13
                       note = misc_feature - Xaa is bAla
MOD_RES                15
                       note = misc_feature - Xaa is bAla
source                 1..16
                       mol_type = protein
                       organism = synthetic construct
SEQUENCE: 51
RXRRXRILFQ YHXHXH                                              16

SEQ ID NO: 52          moltype = AA  length = 17
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
source                 1..17
                       mol_type = protein
                       organism = synthetic construct
SEQUENCE: 52
RXRRXRRFQI LYHXHXH                                             17

SEQ ID NO: 53          moltype = AA  length = 15
FEATURE                Location/Qualifiers
MOD_RES                2
                       note = misc_feature - Xaa is bAla
MOD_RES                5
                       note = misc_feature - Xaa is bAla
MOD_RES                12
                       note = misc_feature - Xaa is bAla
MOD_RES                14
                       note = misc_feature - Xaa is bAla
source                 1..15
                       mol_type = protein
                       organism = synthetic construct
SEQUENCE: 53
RXRRXRFQIL YXRXS                                               15

SEQ ID NO: 54          moltype = AA  length = 15
FEATURE                Location/Qualifiers
MOD_RES                2
                       note = misc_feature - Xaa is bAla
MOD_RES                5
                       note = misc_feature - Xaa is bAla
MOD_RES                12
                       note = misc_feature - Xaa is bAla
MOD_RES                14
                       note = misc_feature - Xaa is bAla
MOD_RES                15
                       note = misc_feature - Xaa is hydroxyproline
source                 1..15
                       mol_type = protein
```

```
                        organism = synthetic construct
SEQUENCE: 54
RXRRXRFQIL YXRXX                                                      15

SEQ ID NO: 55           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is hydroxyproline
source                  1..15
                        mol_type = protein
                        organism = synthetic construct
SEQUENCE: 55
RXRRXRFQIL YXRXR                                                      15

SEQ ID NO: 56           moltype = AA  length = 16
FEATURE                 Location/Qualifiers
MOD_RES                 3
                        note = misc_feature - Xaa is bAla
MOD_RES                 6
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 56
RRXRRXRFQI LYXRXR                                                     16

SEQ ID NO: 57           moltype = AA  length = 15
FEATURE                 Location/Qualifiers
MOD_RES                 1
                        note = misc_feature - Xaa is bAla
MOD_RES                 4
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 57
XRRXRRFQIL YXRXR                                                      15

SEQ ID NO: 58           moltype = AA  length = 13
FEATURE                 Location/Qualifiers
MOD_RES                 2
                        note = misc_feature - Xaa is bAla
MOD_RES                 5
                        note = misc_feature - Xaa is bAla
MOD_RES                 10
                        note = misc_feature - Xaa is bAla
MOD_RES                 12
                        note = misc_feature - Xaa is bAla
source                  1..13
                        mol_type = protein
                        organism = synthetic construct
SEQUENCE: 58
RXRRXRWWWX RXR                                                        13

SEQ ID NO: 59           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
```

```
                        mol_type = protein
                        organism = synthetic construct
SEQUENCE: 59
RXRRXRWWPW WXRXR                                                    15

SEQ ID NO: 60           moltype = AA  length = 14
FEATURE                 Location/Qualifiers
MOD_RES                 2
                        note = misc_feature - Xaa is bAla
MOD_RES                 5
                        note = misc_feature - Xaa is bAla
MOD_RES                 11
                        note = misc_feature - Xaa is bAla
MOD_RES                 13
                        note = misc_feature - Xaa is bAla
source                  1..14
                        mol_type = protein
                        organism = synthetic construct
SEQUENCE: 60
RXRRXRWPWW XRXR                                                     14

SEQ ID NO: 61           moltype = AA  length = 14
FEATURE                 Location/Qualifiers
MOD_RES                 2
                        note = misc_feature - Xaa is bAla
MOD_RES                 5
                        note = misc_feature - Xaa is bAla
MOD_RES                 11
                        note = misc_feature - Xaa is bAla
MOD_RES                 13
                        note = misc_feature - Xaa is bAla
source                  1..14
                        mol_type = protein
                        organism = synthetic construct
SEQUENCE: 61
RXRRXRWWPW XRXR                                                     14

SEQ ID NO: 62           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 62
RXRRXRRWWW RXRXR                                                    15

SEQ ID NO: 63           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 63
RXRRXRRWWP WWRXRXR                                                  17

SEQ ID NO: 64           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
```

```
source                  1..16
                        mol_type = protein
                        organism = synthetic construct
SEQUENCE: 64
RXRRXRRWPW WRXRXR                                                           16

SEQ ID NO: 65           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 65
RXRRXRRWWP WRXRXR                                                           16

SEQ ID NO: 66           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 66
RXRRXRRFQI LYXRXR                                                           16

SEQ ID NO: 67           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
source                  1..15
                        mol_type = protein
                        organism = synthetic construct
SEQUENCE: 67
RXRRXRRFQI LYRXR                                                            15

SEQ ID NO: 68           moltype = AA  length = 16
FEATURE                 Location/Qualifiers
MOD_RES                 1
                        note = misc_feature - Xaa is bAla
MOD_RES                 3
                        note = misc_feature - Xaa is bAla
MOD_RES                 5
                        note = misc_feature - Xaa is bAla
MOD_RES                 12
                        note = misc_feature - Xaa is bAla
MOD_RES                 15
                        note = misc_feature - Xaa is bAla
source                  1..16
                        mol_type = protein
                        organism = synthetic construct
SEQUENCE: 68
XRXRXWWPWW RXRRXR                                                           16

SEQ ID NO: 69           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
```

```
                        note = misc_feature - Xaa is bAla
source                  1..16
                        mol_type = protein
                        organism = synthetic construct
SEQUENCE: 69
RXRRXRRFQI LYXHXH                                                       16

SEQ ID NO: 70           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 70
RXRRXRRFQI YRXHXH                                                       16

SEQ ID NO: 71           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 71
RXRRXRFQIL YXRXH                                                        15

SEQ ID NO: 72           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is hydroxyproline
MOD_RES                 15
                        note = misc_feature - Xaa is hydroxyproline
source                  1..16
                        mol_type = protein
                        organism = synthetic construct
SEQUENCE: 72
RXRRXRFQIL YRXHXH                                                       16

SEQ ID NO: 73           moltype = AA  length = 16
FEATURE                 Location/Qualifiers
MOD_RES                 2
                        note = misc_feature - Xaa is hydroxyproline
MOD_RES                 5
                        note = misc_feature - Xaa is hydroxyproline
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 73
RXRRXRFQIL YRXHXH                                                       16

SEQ ID NO: 74           moltype = AA  length = 16
FEATURE                 Location/Qualifiers
MOD_RES                 2
                        note = misc_feature - Xaa is hydroxyproline
MOD_RES                 5
                        note = misc_feature - Xaa is hydroxyproline
MOD_RES                 13
                        note = misc_feature - Xaa is hydroxyproline
```

```
MOD_RES                 15
                        note = misc_feature - Xaa is hydroxyproline
source                  1..16
                        mol_type = protein
                        organism = synthetic construct
SEQUENCE: 74
RXRRXRFQIL YRXHXH                                                        16

SEQ ID NO: 75           moltype = AA  length = 14
FEATURE                 Location/Qualifiers
MOD_RES                 2
                        note = misc_feature - Xaa is bAla
MOD_RES                 5
                        note = misc_feature - Xaa is bAla
MOD_RES                 11
                        note = misc_feature - Xaa is bAla
MOD_RES                 13
                        note = misc_feature - Xaa is bAla
source                  1..14
                        mol_type = protein
                        organism = synthetic construct
SEQUENCE: 75
RXRRXRWWWR XHXH                                                          14

SEQ ID NO: 76           moltype = AA  length = 14
FEATURE                 Location/Qualifiers
MOD_RES                 2
                        note = misc_feature - Xaa is bAla
MOD_RES                 5
                        note = misc_feature - Xaa is bAla
MOD_RES                 11
                        note = misc_feature - Xaa is bAla
MOD_RES                 13
                        note = misc_feature - Xaa is bAla
source                  1..14
                        mol_type = protein
                        organism = synthetic construct
SEQUENCE: 76
RXRRXRWWPR XHXH                                                          14

SEQ ID NO: 77           moltype = AA  length = 14
FEATURE                 Location/Qualifiers
MOD_RES                 2
                        note = misc_feature - Xaa is bAla
MOD_RES                 5
                        note = misc_feature - Xaa is bAla
MOD_RES                 11
                        note = misc_feature - Xaa is bAla
MOD_RES                 13
                        note = misc_feature - Xaa is bAla
source                  1..14
                        mol_type = protein
                        organism = synthetic construct
SEQUENCE: 77
RXRRXRPWWR XHXH                                                          14

SEQ ID NO: 78           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 78
RXRRXRWWPW WRXHXH                                                        16

SEQ ID NO: 79           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
```

-continued

```
                        note = misc_feature - Xaa is bAla
MOD_RES                 14
                        note = misc_feature - Xaa is bAla
source                  1..15
                        mol_type = protein
                        organism = synthetic construct
SEQUENCE: 79
RXRRXRWWPW RXHXH                                                            15

SEQ ID NO: 80           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 80
RXRRXRWPWW RXHXH                                                            15

SEQ ID NO: 81           moltype = AA  length = 15
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
source                  1..15
                        mol_type = protein
                        organism = synthetic construct
SEQUENCE: 81
RXRRXRRWWW RXHXH                                                            15

SEQ ID NO: 82           moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 82
RXRRXRRWWP WWRXHXH                                                          17

SEQ ID NO: 83           moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 83
RXRRXRRWPW WRXHXH                                                           16

SEQ ID NO: 84           moltype = AA  length = 16
FEATURE                 Location/Qualifiers
MOD_RES                 2
                        note = misc_feature - Xaa is bAla
MOD_RES                 5
                        note = misc_feature - Xaa is bAla
```

```
MOD_RES                13
                       note = misc_feature - Xaa is bAla
MOD_RES                15
                       note = misc_feature - Xaa is bAla
source                 1..16
                       mol_type = protein
                       organism = synthetic construct
SEQUENCE: 84
RXRRXRRWWP WRXHXH                                                          16

SEQ ID NO: 85          moltype = AA  length = 17
FEATURE                Location/Qualifiers
MOD_RES                3
                       note = misc_feature - Xaa is bAla
MOD_RES                6
                       note = misc_feature - Xaa is bAla
MOD_RES                14
                       note = misc_feature - Xaa is bAla
MOD_RES                16
                       note = misc_feature - Xaa is bAla
source                 1..17
                       mol_type = protein
                       organism = synthetic construct
SEQUENCE: 85
RRXRRXRFQI LYRXHXH                                                         17

SEQ ID NO: 86          moltype = AA  length = 16
FEATURE                Location/Qualifiers
MOD_RES                1
                       note = misc_feature - Xaa is bAla
MOD_RES                4
                       note = misc_feature - Xaa is bAla
MOD_RES                13
                       note = misc_feature - Xaa is bAla
MOD_RES                15
                       note = misc_feature - Xaa is bAla
source                 1..16
                       mol_type = protein
                       organism = synthetic construct
SEQUENCE: 86
XRRXRRFQIL YRXHXH                                                          16

SEQ ID NO: 87          moltype = AA  length = 16
FEATURE                Location/Qualifiers
MOD_RES                3
                       note = misc_feature - Xaa is bAla
MOD_RES                6
                       note = misc_feature - Xaa is bAla
MOD_RES                13
                       note = misc_feature - Xaa is bAla
MOD_RES                15
                       note = misc_feature - Xaa is bAla
source                 1..16
                       mol_type = protein
                       organism = synthetic construct
SEQUENCE: 87
RRXRRXRFQI LYXHXH                                                          16

SEQ ID NO: 88          moltype = AA  length = 15
FEATURE                Location/Qualifiers
MOD_RES                1
                       note = misc_feature - Xaa is bAla
MOD_RES                4
                       note = misc_feature - Xaa is bAla
MOD_RES                12
                       note = misc_feature - Xaa is bAla
MOD_RES                14
                       note = misc_feature - Xaa is bAla
source                 1..15
                       mol_type = protein
                       organism = synthetic construct
SEQUENCE: 88
XRRXRRFQIL YXHXH                                                           15

SEQ ID NO: 89          moltype = AA  length = 17
FEATURE                Location/Qualifiers
MOD_RES                2
                       note = misc_feature - Xaa is bAla
MOD_RES                5
```

```
                        note = misc_feature - Xaa is bAla
MOD_RES                 14
                        note = misc_feature - Xaa is bAla
MOD_RES                 16
                        note = misc_feature - Xaa is bAla
source                  1..17
                        mol_type = protein
                        organism = synthetic construct
SEQUENCE: 89
RXRRXHRFQI LYRXHXH                                                17

SEQ ID NO: 90           moltype = DNA  length = 25
FEATURE                 Location/Qualifiers
source                  1..25
                        mol_type = other DNA
                        organism = synthetic construct
SEQUENCE: 90
ggccaaacct cggcttacct gaaat                                       25

SEQ ID NO: 91           moltype = DNA  length = 22
FEATURE                 Location/Qualifiers
source                  1..22
                        mol_type = other DNA
                        organism = synthetic construct
SEQUENCE: 91
cagaattctg ccaattgctg ag                                          22

SEQ ID NO: 92           moltype = DNA  length = 20
FEATURE                 Location/Qualifiers
source                  1..20
                        mol_type = other DNA
                        organism = synthetic construct
SEQUENCE: 92
ttcttcagct tgtgtcatcc                                             20

SEQ ID NO: 93           moltype = DNA  length = 24
FEATURE                 Location/Qualifiers
source                  1..24
                        mol_type = other DNA
                        organism = synthetic construct
SEQUENCE: 93
cccagtctac caccctatca gagc                                        24

SEQ ID NO: 94           moltype = DNA  length = 20
FEATURE                 Location/Qualifiers
source                  1..20
                        mol_type = other DNA
                        organism = synthetic construct
SEQUENCE: 94
cctgccttta aggcttcctt                                             20

SEQ ID NO: 95           moltype = DNA  length = 20
FEATURE                 Location/Qualifiers
source                  1..20
                        mol_type = other DNA
                        organism = synthetic construct
SEQUENCE: 95
caggccattc ctctttcagg                                             20

SEQ ID NO: 96           moltype = DNA  length = 21
FEATURE                 Location/Qualifiers
source                  1..21
                        mol_type = other DNA
                        organism = synthetic construct
SEQUENCE: 96
gaaactttcc tcccagttgg t                                           21

SEQ ID NO: 97           moltype = DNA  length = 29
FEATURE                 Location/Qualifiers
modified_base           1
                        mod_base = OTHER
                        note = misc_feature - Labelled with FAM
modified_base           9..10
                        mod_base = OTHER
                        note = misc_feature - Residues no. 9 and no. 10 are linked
                         through an internal quencher ZEN
modified_base           29
                        mod_base = OTHER
                        note = misc_feature - Labelled with IABkFQ
```

```
source                 1..29
                       mol_type = other DNA
                       organism = synthetic construct
SEQUENCE: 97
tcaacttcag ccatccattt ctgtaaggt                                    29

SEQ ID NO: 98          moltype = DNA  length = 30
FEATURE                Location/Qualifiers
source                 1..30
                       mol_type = other DNA
                       organism = synthetic construct
SEQUENCE: 98
ctgaatatga aataatggag gagagactcg                                   30

SEQ ID NO: 99          moltype = DNA  length = 25
FEATURE                Location/Qualifiers
source                 1..25
                       mol_type = other DNA
                       organism = synthetic construct
SEQUENCE: 99
cttcagccat ccatttctgt aaggt                                        25

SEQ ID NO: 100         moltype = DNA  length = 19
FEATURE                Location/Qualifiers
modified_base          1
                       mod_base = OTHER
                       note = misc_feature - Labelled with FAM
modified_base          9..10
                       mod_base = OTHER
                       note = misc_feature - residues no. 9 and no. 10 are linked
                        through an internal quencher ZEN
modified_base          19
                       mod_base = OTHER
                       note = misc_feature - Labelled with IABkFQ
source                 1..19
                       mol_type = other DNA
                       organism = synthetic construct
SEQUENCE: 100
atgtgattct gtaatttcc                                               19

SEQ ID NO: 101         moltype = AA  length = 15
FEATURE                Location/Qualifiers
MOD_RES                2
                       note = misc_feature - Xaa is bAla
MOD_RES                5
                       note = misc_feature - Xaa is bAla
MOD_RES                12
                       note = misc_feature - Xaa is hydroxyproline
MOD_RES                14
                       note = misc_feature - Xaa is hydroxyproline
source                 1..15
                       mol_type = protein
                       organism = synthetic construct
SEQUENCE: 101
RXRRXRFQIL YXRXR                                                   15

SEQ ID NO: 102         moltype = AA  length = 15
FEATURE                Location/Qualifiers
MOD_RES                2
                       note = misc_feature - Xaa is hydroxyproline
MOD_RES                5
                       note = misc_feature - Xaa is hydroxyproline
MOD_RES                12
                       note = misc_feature - Xaa is bAla
MOD_RES                14
                       note = misc_feature - Xaa is bAla
source                 1..15
                       mol_type = protein
                       organism = synthetic construct
SEQUENCE: 102
RXRRXRFQIL YXRXR                                                   15

SEQ ID NO: 103         moltype = AA  length = 15
FEATURE                Location/Qualifiers
MOD_RES                2
                       note = misc_feature - Xaa is hydroxyproline
MOD_RES                5
                       note = misc_feature - Xaa is hydroxyproline
MOD_RES                12
```

```
                     note = misc_feature - Xaa is hydroxyproline
MOD_RES              14
                     note = misc_feature - Xaa is hydroxyproline
source               1..15
                     mol_type = protein
                     organism = synthetic construct
SEQUENCE: 103
RXRRXRFQIL YXRXR                                             15

SEQ ID NO: 104       moltype = AA  length = 13
FEATURE              Location/Qualifiers
MOD_RES              2
                     note = misc_feature - Xaa is bAla
MOD_RES              5
                     note = misc_feature - Xaa is bAla
MOD_RES              10
                     note = misc_feature - Xaa is bAla
MOD_RES              12
                     note = misc_feature - Xaa is bAla
source               1..13
                     mol_type = protein
                     organism = synthetic construct
SEQUENCE: 104
RXRRXRWWWX RXR                                               13

SEQ ID NO: 105       moltype = AA  length = 15
FEATURE              Location/Qualifiers
MOD_RES              2
                     note = misc_feature - Xaa is bAla
MOD_RES              5
                     note = misc_feature - Xaa is bAla
MOD_RES              12
                     note = misc_feature - Xaa is bAla
MOD_RES              14
                     note = misc_feature - Xaa is bAla
source               1..15
                     mol_type = protein
                     organism = synthetic construct
SEQUENCE: 105
RXRRXRWWPW WXRXR                                             15

SEQ ID NO: 106       moltype = RNA  length = 30
FEATURE              Location/Qualifiers
source               1..30
                     mol_type = other RNA
                     organism = synthetic construct
SEQUENCE: 106
ccaatgccat cctggagttc ctgtaagata                             30

SEQ ID NO: 107       moltype = RNA  length = 30
FEATURE              Location/Qualifiers
source               1..30
                     mol_type = other RNA
                     organism = synthetic construct
SEQUENCE: 107
gctgcccaat gccatcctgg agttcctgta                             30

SEQ ID NO: 108       moltype = RNA  length = 27
FEATURE              Location/Qualifiers
source               1..27
                     mol_type = other RNA
                     organism = synthetic construct
SEQUENCE: 108
caatgccatc ctggagttcc tgtaaga                                27

SEQ ID NO: 109       moltype = RNA  length = 30
FEATURE              Location/Qualifiers
source               1..30
                     mol_type = other RNA
                     organism = synthetic construct
SEQUENCE: 109
gctgcccaat gccatcctgg agttcctgta                             30

SEQ ID NO: 110       moltype = RNA  length = 39
FEATURE              Location/Qualifiers
source               1..39
                     mol_type = other RNA
                     organism = synthetic construct
SEQUENCE: 110
```

```
gctgcccaat gccatcctgg agttcctgta agataccaa                          39

SEQ ID NO: 111          moltype = RNA  length = 30
FEATURE                 Location/Qualifiers
source                  1..30
                        mol_type = other RNA
                        organism = synthetic construct
SEQUENCE: 111
gcccaatgcc atcctggagt tcctgtaaga                                    30

SEQ ID NO: 112          moltype = RNA  length = 28
FEATURE                 Location/Qualifiers
source                  1..28
                        mol_type = other RNA
                        organism = synthetic construct
SEQUENCE: 112
tgccatcctg gagttcctgt aagatacc                                      28

SEQ ID NO: 113          moltype = RNA  length = 25
FEATURE                 Location/Qualifiers
source                  1..25
                        mol_type = other RNA
                        organism = synthetic construct
SEQUENCE: 113
gcccaatgcc atcctggagt tcctg                                         25

SEQ ID NO: 114          moltype = RNA  length = 28
FEATURE                 Location/Qualifiers
source                  1..28
                        mol_type = other RNA
                        organism = synthetic construct
SEQUENCE: 114
gctgcccaat gccatcctgg agttcctg                                      28

SEQ ID NO: 115          moltype = RNA  length = 25
FEATURE                 Location/Qualifiers
source                  1..25
                        mol_type = other RNA
                        organism = synthetic construct
SEQUENCE: 115
tgccatcctg gagttcctgt aagat                                         25

SEQ ID NO: 116          moltype = RNA  length = 28
FEATURE                 Location/Qualifiers
source                  1..28
                        mol_type = other RNA
                        organism = synthetic construct
SEQUENCE: 116
caatgccatc ctggagttcc tgtaagat                                      28

SEQ ID NO: 117          moltype = RNA  length = 31
FEATURE                 Location/Qualifiers
source                  1..31
                        mol_type = other RNA
                        organism = synthetic construct
SEQUENCE: 117
gcccaatgcc atcctggagt tcctgtaaga t                                  31

SEQ ID NO: 118          moltype = RNA  length = 30
FEATURE                 Location/Qualifiers
source                  1..30
                        mol_type = other RNA
                        organism = synthetic construct
SEQUENCE: 118
ttgccgctgc ccaatgccat cctggagttc                                    30

SEQ ID NO: 119          moltype = RNA  length = 30
FEATURE                 Location/Qualifiers
source                  1..30
                        mol_type = other RNA
                        organism = synthetic construct
SEQUENCE: 119
gctgcccaat gccatcctgg agttcctgta                                    30

SEQ ID NO: 120          moltype = RNA  length = 28
FEATURE                 Location/Qualifiers
source                  1..28
                        mol_type = other RNA
                        organism = synthetic construct
```

```
SEQUENCE: 120
gcccaatgcc atcctggagt tcctgtaa                                28

SEQ ID NO: 121          moltype = RNA  length = 30
FEATURE                 Location/Qualifiers
source                  1..30
                        mol_type = other RNA
                        organism = synthetic construct
SEQUENCE: 121
gccgctgccc aatgccatcc tggagttcct                              30

SEQ ID NO: 122          moltype = RNA  length = 22
FEATURE                 Location/Qualifiers
source                  1..22
                        mol_type = other RNA
                        organism = synthetic construct
SEQUENCE: 122
caatgccatc ctggagttcc tg                                      22

SEQ ID NO: 123          moltype = RNA  length = 31
FEATURE                 Location/Qualifiers
source                  1..31
                        mol_type = other RNA
                        organism = synthetic construct
SEQUENCE: 123
gctgcccaat gccatcctgg agttcctgta a                            31

SEQ ID NO: 124          moltype = RNA  length = 31
FEATURE                 Location/Qualifiers
source                  1..31
                        mol_type = other RNA
                        organism = synthetic construct
SEQUENCE: 124
caatgccatc ctggagttcc tgtaagatac c                            31

SEQ ID NO: 125          moltype = RNA  length = 26
FEATURE                 Location/Qualifiers
source                  1..26
                        mol_type = other RNA
                        organism = synthetic construct
SEQUENCE: 125
accagagtaa cagtctgagt aggagc                                  26

SEQ ID NO: 126          moltype = RNA  length = 23
FEATURE                 Location/Qualifiers
source                  1..23
                        mol_type = other RNA
                        organism = synthetic construct
SEQUENCE: 126
ctcatacctt ctgcttgatg atc                                     23

SEQ ID NO: 127          moltype = RNA  length = 24
FEATURE                 Location/Qualifiers
source                  1..24
                        mol_type = other RNA
                        organism = synthetic construct
SEQUENCE: 127
ttctgtccaa gcccggttga aatc                                    24

SEQ ID NO: 128          moltype = RNA  length = 30
FEATURE                 Location/Qualifiers
source                  1..30
                        mol_type = other RNA
                        organism = synthetic construct
SEQUENCE: 128
acatcaagga agatggcatt tctagtttgg                              30

SEQ ID NO: 129          moltype = RNA  length = 25
FEATURE                 Location/Qualifiers
source                  1..25
                        mol_type = other RNA
                        organism = synthetic construct
SEQUENCE: 129
acatcaagga agatggcatt tctag                                   25

SEQ ID NO: 130          moltype = RNA  length = 30
FEATURE                 Location/Qualifiers
source                  1..30
                        mol_type = other RNA
```

```
                        organism = synthetic construct
SEQUENCE: 130
ctccaacatc aaggaagatg gcatttctag                                        30

SEQ ID NO: 131          moltype = RNA  length = 27
FEATURE                 Location/Qualifiers
source                  1..27
                        mol_type = other RNA
                        organism = synthetic construct
SEQUENCE: 131
atcatttttt ctcatacctt ctgctag                                           27

SEQ ID NO: 132          moltype = RNA  length = 38
FEATURE                 Location/Qualifiers
source                  1..38
                        mol_type = other RNA
                        organism = synthetic construct
SEQUENCE: 132
atcatttttt ctcatacctt ctgctaggag ctaaaaag                               38

SEQ ID NO: 133          moltype = RNA  length = 21
FEATURE                 Location/Qualifiers
source                  1..21
                        mol_type = other RNA
                        organism = synthetic construct
SEQUENCE: 133
cacccaccat caccctctgt g                                                 21

SEQ ID NO: 134          moltype = RNA  length = 22
FEATURE                 Location/Qualifiers
source                  1..22
                        mol_type = other RNA
                        organism = synthetic construct
SEQUENCE: 134
atcatctcgt tgatatcctc aa                                                22

SEQ ID NO: 135          moltype = DNA  length = 23
FEATURE                 Location/Qualifiers
source                  1..23
                        mol_type = other DNA
                        organism = synthetic construct
SEQUENCE: 135
ccggttctga aggtgttctt gta                                               23

SEQ ID NO: 136          moltype = DNA  length = 24
FEATURE                 Location/Qualifiers
source                  1..24
                        mol_type = other DNA
                        organism = synthetic construct
SEQUENCE: 136
tccggttctg aaggtgttct tgta                                              24

SEQ ID NO: 137          moltype = DNA  length = 25
FEATURE                 Location/Qualifiers
source                  1..25
                        mol_type = other DNA
                        organism = synthetic construct
SEQUENCE: 137
ctccggttct gaaggtgttc ttgta                                             25

SEQ ID NO: 138          moltype = DNA  length = 26
FEATURE                 Location/Qualifiers
source                  1..26
                        mol_type = other DNA
                        organism = synthetic construct
SEQUENCE: 138
cctccggttc tgaaggtgtt cttgta                                            26

SEQ ID NO: 139          moltype = DNA  length = 27
FEATURE                 Location/Qualifiers
source                  1..27
                        mol_type = other DNA
                        organism = synthetic construct
SEQUENCE: 139
gcctccggtt ctgaaggtgt tcttgta                                           27

SEQ ID NO: 140          moltype = DNA  length = 28
FEATURE                 Location/Qualifiers
source                  1..28
```

```
                        mol_type = other DNA
                        organism = synthetic construct
SEQUENCE: 140
tgcctccggt tctgaaggtg ttcttgta                                        28

SEQ ID NO: 141          moltype = DNA  length = 22
FEATURE                 Location/Qualifiers
source                  1..22
                        mol_type = other DNA
                        organism = synthetic construct
SEQUENCE: 141
ccggttctga aggtgttctt gt                                              22

SEQ ID NO: 142          moltype = DNA  length = 23
FEATURE                 Location/Qualifiers
source                  1..23
                        mol_type = other DNA
                        organism = synthetic construct
SEQUENCE: 142
tccggttctg aaggtgttct tgt                                             23

SEQ ID NO: 143          moltype = DNA  length = 24
FEATURE                 Location/Qualifiers
source                  1..24
                        mol_type = other DNA
                        organism = synthetic construct
SEQUENCE: 143
ctccggttct gaaggtgttc ttgt                                            24

SEQ ID NO: 144          moltype = DNA  length = 25
FEATURE                 Location/Qualifiers
source                  1..25
                        mol_type = other DNA
                        organism = synthetic construct
SEQUENCE: 144
cctccggttc tgaaggtgtt cttgt                                           25

SEQ ID NO: 145          moltype = DNA  length = 26
FEATURE                 Location/Qualifiers
source                  1..26
                        mol_type = other DNA
                        organism = synthetic construct
SEQUENCE: 145
gcctccggtt ctgaaggtgt tcttgt                                          26

SEQ ID NO: 146          moltype = DNA  length = 27
FEATURE                 Location/Qualifiers
source                  1..27
                        mol_type = other DNA
                        organism = synthetic construct
SEQUENCE: 146
tgcctccggt tctgaaggtg ttcttgt                                         27

SEQ ID NO: 147          moltype = DNA  length = 21
FEATURE                 Location/Qualifiers
source                  1..21
                        mol_type = other DNA
                        organism = synthetic construct
SEQUENCE: 147
ccggttctga aggtgttctt g                                               21

SEQ ID NO: 148          moltype = DNA  length = 22
FEATURE                 Location/Qualifiers
source                  1..22
                        mol_type = other DNA
                        organism = synthetic construct
SEQUENCE: 148
tccggttctg aaggtgttct tg                                              22

SEQ ID NO: 149          moltype = DNA  length = 23
FEATURE                 Location/Qualifiers
source                  1..23
                        mol_type = other DNA
                        organism = synthetic construct
SEQUENCE: 149
ctccggttct gaaggtgttc ttg                                             23

SEQ ID NO: 150          moltype = DNA  length = 24
FEATURE                 Location/Qualifiers
```

```
source                  1..24
                        mol_type = other DNA
                        organism = synthetic construct
SEQUENCE: 150
cctccggttc tgaaggtgtt cttg                                              24

SEQ ID NO: 151          moltype = DNA  length = 25
FEATURE                 Location/Qualifiers
source                  1..25
                        mol_type = other DNA
                        organism = synthetic construct
SEQUENCE: 151
gcctccggtt ctgaaggtgt tcttg                                             25

SEQ ID NO: 152          moltype = DNA  length = 26
FEATURE                 Location/Qualifiers
source                  1..26
                        mol_type = other DNA
                        organism = synthetic construct
SEQUENCE: 152
tgcctccggt tctgaaggtg ttcttg                                            26

SEQ ID NO: 153          moltype = DNA  length = 20
FEATURE                 Location/Qualifiers
source                  1..20
                        mol_type = other DNA
                        organism = synthetic construct
SEQUENCE: 153
ccggttctga aggtgttctt                                                   20

SEQ ID NO: 154          moltype = DNA  length = 21
FEATURE                 Location/Qualifiers
source                  1..21
                        mol_type = other DNA
                        organism = synthetic construct
SEQUENCE: 154
tccggttctg aaggtgttct t                                                 21

SEQ ID NO: 155          moltype = DNA  length = 22
FEATURE                 Location/Qualifiers
source                  1..22
                        mol_type = other DNA
                        organism = synthetic construct
SEQUENCE: 155
ctccggttct gaaggtgttc tt                                                22

SEQ ID NO: 156          moltype = DNA  length = 23
FEATURE                 Location/Qualifiers
source                  1..23
                        mol_type = other DNA
                        organism = synthetic construct
SEQUENCE: 156
cctccggttc tgaaggtgtt ctt                                               23

SEQ ID NO: 157          moltype = DNA  length = 24
FEATURE                 Location/Qualifiers
source                  1..24
                        mol_type = other DNA
                        organism = synthetic construct
SEQUENCE: 157
gcctccggtt ctgaaggtgt tctt                                              24

SEQ ID NO: 158          moltype = DNA  length = 25
FEATURE                 Location/Qualifiers
source                  1..25
                        mol_type = other DNA
                        organism = synthetic construct
SEQUENCE: 158
tgcctccggt tctgaaggtg ttctt                                             25

SEQ ID NO: 159          moltype = DNA  length = 19
FEATURE                 Location/Qualifiers
source                  1..19
                        mol_type = other DNA
                        organism = synthetic construct
SEQUENCE: 159
ccggttctga aggtgttct                                                    19

SEQ ID NO: 160          moltype = DNA  length = 20
```

```
FEATURE                Location/Qualifiers
source                 1..20
                       mol_type = other DNA
                       organism = synthetic construct
SEQUENCE: 160
tccggttctg aaggtgttct                                              20

SEQ ID NO: 161         moltype = DNA  length = 21
FEATURE                Location/Qualifiers
source                 1..21
                       mol_type = other DNA
                       organism = synthetic construct
SEQUENCE: 161
ctccggttct gaaggtgttc t                                            21

SEQ ID NO: 162         moltype = DNA  length = 22
FEATURE                Location/Qualifiers
source                 1..22
                       mol_type = other DNA
                       organism = synthetic construct
SEQUENCE: 162
cctccggttc tgaaggtgtt ct                                           22

SEQ ID NO: 163         moltype = DNA  length = 23
FEATURE                Location/Qualifiers
source                 1..23
                       mol_type = other DNA
                       organism = synthetic construct
SEQUENCE: 163
gcctccggtt ctgaaggtgt tct                                          23

SEQ ID NO: 164         moltype = DNA  length = 24
FEATURE                Location/Qualifiers
source                 1..24
                       mol_type = other DNA
                       organism = synthetic construct
SEQUENCE: 164
tgcctccggt tctgaaggtg ttct                                         24

SEQ ID NO: 165         moltype = DNA  length = 18
FEATURE                Location/Qualifiers
source                 1..18
                       mol_type = other DNA
                       organism = synthetic construct
SEQUENCE: 165
ccggttctga aggtgttc                                                18

SEQ ID NO: 166         moltype = DNA  length = 19
FEATURE                Location/Qualifiers
source                 1..19
                       mol_type = other DNA
                       organism = synthetic construct
SEQUENCE: 166
tccggttctg aaggtgttc                                               19

SEQ ID NO: 167         moltype = DNA  length = 20
FEATURE                Location/Qualifiers
source                 1..20
                       mol_type = other DNA
                       organism = synthetic construct
SEQUENCE: 167
ctccggttct gaaggtgttc                                              20

SEQ ID NO: 168         moltype = DNA  length = 21
FEATURE                Location/Qualifiers
source                 1..21
                       mol_type = other DNA
                       organism = synthetic construct
SEQUENCE: 168
cctccggttc tgaaggtgtt c                                            21

SEQ ID NO: 169         moltype = DNA  length = 22
FEATURE                Location/Qualifiers
source                 1..22
                       mol_type = other DNA
                       organism = synthetic construct
SEQUENCE: 169
gcctccggtt ctgaaggtgt tc                                           22
```

```
SEQ ID NO: 170          moltype = DNA  length = 23
FEATURE                 Location/Qualifiers
source                  1..23
                        mol_type = other DNA
                        organism = synthetic construct
SEQUENCE: 170
tgcctccggt tctgaaggtg ttc                                          23

SEQ ID NO: 171          moltype = DNA  length = 25
FEATURE                 Location/Qualifiers
source                  1..25
                        mol_type = other DNA
                        organism = synthetic construct
SEQUENCE: 171
gttgcctccg gttctgaagg tgttc                                        25

SEQ ID NO: 172          moltype = RNA  length = 31
FEATURE                 Location/Qualifiers
source                  1..31
                        mol_type = other RNA
                        organism = synthetic construct
SEQUENCE: 172
cattcaactg ttgcctccgg ttctgaaggt g                                 31

SEQ ID NO: 173          moltype = AA  length = 12
FEATURE                 Location/Qualifiers
MOD_RES                 2
                        note = misc_feature - Xaa is bAla
MOD_RES                 4
                        note = misc_feature - Xaa is bAla
MOD_RES                 6
                        note = misc_feature - Xaa is glucosylated serine
MOD_RES                 8
                        note = misc_feature - Xaa is bAla
MOD_RES                 10
                        note = misc_feature - Xaa is bAla
MOD_RES                 12
                        note = misc_feature - Xaa is bAla
source                  1..12
                        mol_type = protein
                        organism = synthetic construct
SEQUENCE: 173
RXRXRXRXRX RX                                                      12

SEQ ID NO: 174          moltype = AA  length = 22
FEATURE                 Location/Qualifiers
MOD_RES                 2
                        note = misc_feature - Xaa is 6-aminohexanoic acid
MOD_RES                 5
                        note = misc_feature - Xaa is bAla
MOD_RES                 8
                        note = misc_feature - Xaa is 6-aminohexanoic acid
MOD_RES                 16
                        note = misc_feature - Xaa is 6-aminohexanoic acid
MOD_RES                 18
                        note = misc_feature - Xaa is bAla
MOD_RES                 20
                        note = misc_feature - Xaa is 6-aminohexanoic acid
MOD_RES                 22
                        note = misc_feature - Xaa is bAla
source                  1..22
                        mol_type = protein
                        organism = synthetic construct
SEQUENCE: 174
RXRRXRRXRY QFLIRXRXRX RX                                           22

SEQ ID NO: 175          moltype = AA  length = 18
FEATURE                 Location/Qualifiers
MOD_RES                 2
                        note = misc_feature - Xaa is 6-aminohexanoic acid
MOD_RES                 5
                        note = misc_feature - Xaa is bAla
MOD_RES                 14
                        note = misc_feature - Xaa is bAla
MOD_RES                 16
                        note = misc_feature - Xaa is 6-aminohexanoic acid
MOD_RES                 18
                        note = misc_feature - Xaa is bAla
source                  1..18
```

```
                        mol_type = protein
                        organism = synthetic construct
SEQUENCE: 175
RXRRXRRFQI LYRXRXRX                                               18

SEQ ID NO: 176          moltype = AA  length = 7
FEATURE                 Location/Qualifiers
source                  1..7
                        mol_type = protein
                        organism = synthetic construct
SEQUENCE: 176
RRRRRRG                                                           7

SEQ ID NO: 177          moltype = DNA  length = 21
FEATURE                 Location/Qualifiers
source                  1..21
                        mol_type = other DNA
                        organism = synthetic construct
SEQUENCE: 177
gctgcccaat accaggtcaa c                                           21

SEQ ID NO: 178          moltype = DNA  length = 22
FEATURE                 Location/Qualifiers
source                  1..22
                        mol_type = other DNA
                        organism = synthetic construct
SEQUENCE: 178
tggtgggaga aatgctgtat gc                                          22

SEQ ID NO: 179          moltype = DNA  length = 20
FEATURE                 Location/Qualifiers
source                  1..20
                        mol_type = other DNA
                        organism = synthetic construct
SEQUENCE: 179
ttagaggagg tgatggagca                                             20

SEQ ID NO: 180          moltype = DNA  length = 20
FEATURE                 Location/Qualifiers
source                  1..20
                        mol_type = other DNA
                        organism = synthetic construct
SEQUENCE: 180
gatactaagg actccatcgc                                             20

SEQ ID NO: 181          moltype = AA  length = 16
FEATURE                 Location/Qualifiers
MOD_RES                 3
                        note = misc_feature - Xaa is bAla
MOD_RES                 6
                        note = misc_feature - Xaa is bAla
MOD_RES                 13
                        note = misc_feature - Xaa is bAla
MOD_RES                 15
                        note = misc_feature - Xaa is bAla
source                  1..16
                        mol_type = protein
                        organism = synthetic construct
SEQUENCE: 181
ERXRRXRFQI LYXRXR                                                 16

SEQ ID NO: 182          moltype = AA  length = 18
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
MOD_RES                 18
                        note = misc_feature - Xaa is aminobutyric acid
source                  1..18
                        mol_type = protein
                        organism = synthetic construct
SEQUENCE: 182
RXRRXRRFQI LYRXHXHX                                               18
```

```
SEQ ID NO: 183          moltype = AA  length = 18
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
source                  1..18
                        mol_type = protein
                        organism = synthetic construct
SEQUENCE: 183
RXRRXRRFQI LYRXHXHE                                                18

SEQ ID NO: 184          moltype = AA  length = 18
FEATURE                 Location/Qualifiers
MOD_RES                 3
                        note = misc_feature - Xaa is bAla
MOD_RES                 6
                        note = misc_feature - Xaa is bAla
MOD_RES                 15
                        note = misc_feature - Xaa is bAla
MOD_RES                 17
                        note = misc_feature - Xaa is bAla
source                  1..18
                        mol_type = protein
                        organism = synthetic construct
SEQUENCE: 184
ERXRRXRRFQ ILYRXHXH                                                18

SEQ ID NO: 185          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
source                  1..17
                        mol_type = protein
                        organism = synthetic construct
SEQUENCE: 185
RXRRXRFQIL YRXHXHE                                                 17

SEQ ID NO: 186          moltype = DNA  length = 20
FEATURE                 Location/Qualifiers
source                  1..20
                        mol_type = other DNA
                        organism = synthetic construct
SEQUENCE: 186
caggccattc ctctttcagg                                              20

SEQ ID NO: 187          moltype = DNA  length = 21
FEATURE                 Location/Qualifiers
source                  1..21
                        mol_type = other DNA
                        organism = synthetic construct
SEQUENCE: 187
gaaactttcc tcccagttgg t                                            21

SEQ ID NO: 188          moltype = DNA  length = 29
FEATURE                 Location/Qualifiers
modified_base           1
                        mod_base = OTHER
                        note = misc_feature - Labelled with FAM
modified_base           9..10
                        mod_base = OTHER
                        note = misc_feature - Residues no. 9 and no. 10 are linked
                         through an internal quencher ZEN
modified_base           29
                        mod_base = OTHER
                        note = misc_feature - Labelled with IABkFQ
source                  1..29
                        mol_type = other DNA
                        organism = synthetic construct
```

```
SEQUENCE: 188
tcaacttcag ccatccattt ctgtaaggt                                29

SEQ ID NO: 189          moltype = DNA  length = 24
FEATURE                 Location/Qualifiers
source                  1..24
                        mol_type = other DNA
                        organism = synthetic construct
SEQUENCE: 189
ctgaatatga aataatggag gagg                                     24

SEQ ID NO: 190          moltype = DNA  length = 25
FEATURE                 Location/Qualifiers
source                  1..25
                        mol_type = other DNA
                        organism = synthetic construct
SEQUENCE: 190
cttcagccat ccatttctgt aaggt                                    25

SEQ ID NO: 191          moltype = DNA  length = 19
FEATURE                 Location/Qualifiers
modified_base           1
                        mod_base = OTHER
                        note = misc_feature - Labelled with FAM
modified_base           9..10
                        mod_base = OTHER
                        note = misc_feature - Residues no. 9 and no. 10 are linked
                         through an internal quencher ZEN
modified_base           19
                        mod_base = OTHER
                        note = misc_feature - Labelled with IABkFQ
source                  1..19
                        mol_type = other DNA
                        organism = synthetic construct
SEQUENCE: 191
atgtgattct gtaatttcc                                           19

SEQ ID NO: 192          moltype = DNA  length = 21
FEATURE                 Location/Qualifiers
source                  1..21
                        mol_type = other DNA
                        organism = synthetic construct
SEQUENCE: 192
cagcagcagc agcagcagca g                                        21

SEQ ID NO: 193          moltype = DNA  length = 31
FEATURE                 Location/Qualifiers
source                  1..31
                        mol_type = other DNA
                        organism = synthetic construct
SEQUENCE: 193
gctgcccaat gccatcctgg agttcctgta a                             31

SEQ ID NO: 194          moltype = DNA  length = 22
FEATURE                 Location/Qualifiers
source                  1..22
                        mol_type = other DNA
                        organism = synthetic construct
SEQUENCE: 194
caatgccatc ctggagttcc tg                                       22

SEQ ID NO: 195          moltype = DNA  length = 30
FEATURE                 Location/Qualifiers
source                  1..30
                        mol_type = other DNA
                        organism = synthetic construct
SEQUENCE: 195
ctccaacatc aaggaagatg gcatttctag                               30

SEQ ID NO: 196          moltype = DNA  length = 30
FEATURE                 Location/Qualifiers
source                  1..30
                        mol_type = other DNA
                        organism = synthetic construct
SEQUENCE: 196
acatcaagga agatggcatt tctagtttgg                               30

SEQ ID NO: 197          moltype = AA  length = 16
FEATURE                 Location/Qualifiers
```

```
MOD_RES                2
                       note = misc_feature - Xaa is bAla
MOD_RES                5
                       note = misc_feature - Xaa is bAla
MOD_RES                12
                       note = misc_feature - Xaa is bAla
MOD_RES                14
                       note = misc_feature - Xaa is bAla
source                 1..16
                       mol_type = protein
                       organism = synthetic construct
SEQUENCE: 197
RXRRXRFQIL YXRXRE                                                    16

SEQ ID NO: 198         moltype = DNA  length = 31
FEATURE                Location/Qualifiers
source                 1..31
                       mol_type = other DNA
                       organism = synthetic construct
SEQUENCE: 198
cattcaactg ttgcctccgg ttctgaaggt g                                   31

SEQ ID NO: 199         moltype = AA  length = 18
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
MOD_RES                18
                       note = misc_feature - Xaa is bAla
source                 1..18
                       mol_type = protein
                       organism = synthetic construct
SEQUENCE: 199
RXRRXRRFQI LYRXRXRX                                                  18

SEQ ID NO: 200         moltype = AA  length = 17
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                17
                       note = misc_feature - Xaa is bAla
source                 1..17
                       mol_type = protein
                       organism = synthetic construct
SEQUENCE: 200
RXRRXRRFQI LYRXRRX                                                   17

SEQ ID NO: 201         moltype = AA  length = 18
FEATURE                Location/Qualifiers
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
MOD_RES                18
                       note = misc_feature - Xaa is bAla
source                 1..18
                       mol_type = protein
                       organism = synthetic construct
SEQUENCE: 201
RXRRXRFQIL YRRXRXRX                                                  18

SEQ ID NO: 202         moltype = AA  length = 18
FEATURE                Location/Qualifiers
MOD_RES                2
                       note = misc_feature - Xaa is bAla
MOD_RES                4
```

```
                         note = misc_feature - Xaa is bAla
MOD_RES                  12
                         note = misc_feature - Xaa is bAla
MOD_RES                  15
                         note = misc_feature - Xaa is bAla
MOD_RES                  18
                         note = misc_feature - Xaa is bAla
source                   1..18
                         mol_type = protein
                         organism = synthetic construct
SEQUENCE: 202
RXRXRFQILY RXRRXRRX                                                 18

SEQ ID NO: 203           moltype = AA  length = 18
FEATURE                  Location/Qualifiers
MOD_RES                  2
                         note = misc_feature - Xaa is bAla
MOD_RES                  5
                         note = misc_feature - Xaa is bAla
MOD_RES                  14
                         note = misc_feature - Xaa is bAla
MOD_RES                  16
                         note = misc_feature - Xaa is bAla
MOD_RES                  18
                         note = misc_feature - Xaa is bAla
source                   1..18
                         mol_type = protein
                         organism = synthetic construct
SEQUENCE: 203
RXRRXRRYQF LIRXRXRX                                                 18

SEQ ID NO: 204           moltype = AA  length = 18
FEATURE                  Location/Qualifiers
MOD_RES                  2
                         note = misc_feature - Xaa is bAla
MOD_RES                  5
                         note = misc_feature - Xaa is bAla
MOD_RES                  14
                         note = misc_feature - Xaa is bAla
MOD_RES                  16
                         note = misc_feature - Xaa is bAla
MOD_RES                  18
                         note = misc_feature - Xaa is bAla
source                   1..18
                         mol_type = protein
                         organism = synthetic construct
SEQUENCE: 204
RXRRXRRILF QYRXRXRX                                                 18

SEQ ID NO: 205           moltype = AA  length = 17
FEATURE                  Location/Qualifiers
MOD_RES                  2
                         note = misc_feature - Xaa is bAla
MOD_RES                  5
                         note = misc_feature - Xaa is bAla
MOD_RES                  13
                         note = misc_feature - Xaa is bAla
MOD_RES                  15
                         note = misc_feature - Xaa is bAla
MOD_RES                  17
                         note = misc_feature - Xaa is bAla
source                   1..17
                         mol_type = protein
                         organism = synthetic construct
SEQUENCE: 205
RXRRXRFQIL YRXRXRX                                                  17

SEQ ID NO: 206           moltype = AA  length = 17
FEATURE                  Location/Qualifiers
MOD_RES                  2
                         note = misc_feature - Xaa is bAla
MOD_RES                  5
                         note = misc_feature - Xaa is bAla
MOD_RES                  12
                         note = misc_feature - Xaa is bAla
MOD_RES                  15
                         note = misc_feature - Xaa is bAla
MOD_RES                  17
                         note = misc_feature - Xaa is bAla
```

```
source                  1..17
                        mol_type = protein
                        organism = synthetic construct
SEQUENCE: 206
RXRRXFQILY RXRRXRX                                                   17

SEQ ID NO: 207          moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
MOD_RES                 16
                        note = misc_feature - Xaa is bAla
source                  1..16
                        mol_type = protein
                        organism = synthetic construct
SEQUENCE: 207
RXRRXRFQIL YXRXRX                                                    16

SEQ ID NO: 208          moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
MOD_RES                 16
                        note = misc_feature - Xaa is bAla
source                  1..16
                        mol_type = protein
                        organism = synthetic construct
SEQUENCE: 208
RXRRXFQILY RXRXRX                                                    16

SEQ ID NO: 209          moltype = AA  length = 18
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
MOD_RES                 18
                        note = misc_feature - Xaa is bAla
source                  1..18
                        mol_type = protein
                        organism = synthetic construct
SEQUENCE: 209
RXRRXRRFQI LYRXHXHX                                                  18

SEQ ID NO: 210          moltype = AA  length = 18
FEATURE                 Location/Qualifiers
MOD_RES                 2
                        note = misc_feature - Xaa is bAla
MOD_RES                 5
                        note = misc_feature - Xaa is bAla
MOD_RES                 14
                        note = misc_feature - Xaa is bAla
MOD_RES                 16
                        note = misc_feature - Xaa is bAla
MOD_RES                 18
                        note = misc_feature - Xaa is bAla
source                  1..18
                        mol_type = protein
                        organism = synthetic construct
SEQUENCE: 210
RXRRXRRFQI LYHXHXRX                                                  18

SEQ ID NO: 211          moltype = AA  length = 18
```

```
FEATURE              Location/Qualifiers
MOD_RES              2
                     note = misc_feature - Xaa is bAla
MOD_RES              5
                     note = misc_feature - Xaa is bAla
MOD_RES              14
                     note = misc_feature - Xaa is bAla
MOD_RES              16
                     note = misc_feature - Xaa is bAla
MOD_RES              18
                     note = misc_feature - Xaa is bAla
source               1..18
                     mol_type = protein
                     organism = synthetic construct
SEQUENCE: 211
RXRRXRRFQI LYHXRXHX                                            18

SEQ ID NO: 212       moltype = AA  length = 18
FEATURE              Location/Qualifiers
MOD_RES              2
                     note = misc_feature - Xaa is bAla
MOD_RES              5
                     note = misc_feature - Xaa is bAla
MOD_RES              14
                     note = misc_feature - Xaa is bAla
MOD_RES              16
                     note = misc_feature - Xaa is bAla
MOD_RES              18
                     note = misc_feature - Xaa is bAla
source               1..18
                     mol_type = protein
                     organism = synthetic construct
SEQUENCE: 212
RXRRXRRYQF LIRXHXHX                                            18

SEQ ID NO: 213       moltype = AA  length = 18
FEATURE              Location/Qualifiers
MOD_RES              2
                     note = misc_feature - Xaa is bAla
MOD_RES              5
                     note = misc_feature - Xaa is bAla
MOD_RES              14
                     note = misc_feature - Xaa is bAla
MOD_RES              16
                     note = misc_feature - Xaa is bAla
MOD_RES              18
                     note = misc_feature - Xaa is bAla
source               1..18
                     mol_type = protein
                     organism = synthetic construct
SEQUENCE: 213
RXRRXRRILF QYRXHXHX                                            18

SEQ ID NO: 214       moltype = AA  length = 18
FEATURE              Location/Qualifiers
MOD_RES              2
                     note = misc_feature - Xaa is bAla
MOD_RES              5
                     note = misc_feature - Xaa is bAla
MOD_RES              14
                     note = misc_feature - Xaa is bAla
MOD_RES              16
                     note = misc_feature - Xaa is bAla
MOD_RES              18
                     note = misc_feature - Xaa is bAla
source               1..18
                     mol_type = protein
                     organism = synthetic construct
SEQUENCE: 214
RXRHXHRFQI LYRXRXRX                                            18

SEQ ID NO: 215       moltype = AA  length = 18
FEATURE              Location/Qualifiers
MOD_RES              2
                     note = misc_feature - Xaa is bAla
MOD_RES              4
                     note = misc_feature - Xaa is bAla
MOD_RES              5
                     note = misc_feature - Xaa is bAla
```

```
MOD_RES                 14
                        note = misc_feature - Xaa is bAla
MOD_RES                 16
                        note = misc_feature - Xaa is bAla
MOD_RES                 18
                        note = misc_feature - Xaa is bAla
source                  1..18
                        mol_type = protein
                        organism = synthetic construct
SEQUENCE: 215
RXRXXHRFQI LYRXHXHX                                                    18

SEQ ID NO: 216          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
                        mol_type = protein
                        organism = synthetic construct
SEQUENCE: 216
RXRRXRFQIL YRXHXHX                                                     17

SEQ ID NO: 217          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
                        mol_type = protein
                        organism = synthetic construct
SEQUENCE: 217
RXRRXRFQIL YHXHXHX                                                     17

SEQ ID NO: 218          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
                        mol_type = protein
                        organism = synthetic construct
SEQUENCE: 218
RXRRXHFQIL YRXHXHX                                                     17

SEQ ID NO: 219          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
```

```
                        mol_type = protein
                        organism = synthetic construct
SEQUENCE: 219
HXRRXRFQIL YRXHXHX                                                  17

SEQ ID NO: 220          moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
MOD_RES                 16
                        note = misc_feature - Xaa is bAla
source                  1..16
                        mol_type = protein
                        organism = synthetic construct
SEQUENCE: 220
RXRRXFQILY RXHXHX                                                   16

SEQ ID NO: 221          moltype = AA  length = 16
FEATURE                 Location/Qualifiers
MOD_RES                 2
                        note = misc_feature - Xaa is bAla
MOD_RES                 5
                        note = misc_feature - Xaa is bAla
MOD_RES                 12
                        note = misc_feature - Xaa is bAla
MOD_RES                 14
                        note = misc_feature - Xaa is bAla
MOD_RES                 16
                        note = misc_feature - Xaa is bAla
source                  1..16
                        mol_type = protein
                        organism = synthetic construct
SEQUENCE: 221
RXRRXRFQIL YXHXHX                                                   16

SEQ ID NO: 222          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
                        mol_type = protein
                        organism = synthetic construct
SEQUENCE: 222
RXRRXRYQFL IHXHXHX                                                  17

SEQ ID NO: 223          moltype = AA  length = 17
FEATURE                 Location/Qualifiers
MOD_RES                 2
                        note = misc_feature - Xaa is bAla
MOD_RES                 5
                        note = misc_feature - Xaa is bAla
MOD_RES                 13
                        note = misc_feature - Xaa is bAla
MOD_RES                 15
                        note = misc_feature - Xaa is bAla
MOD_RES                 17
                        note = misc_feature - Xaa is bAla
source                  1..17
                        mol_type = protein
                        organism = synthetic construct
SEQUENCE: 223
RXRRXRILFQ YHXHXHX                                                  17

SEQ ID NO: 224          moltype = AA  length = 18
FEATURE                 Location/Qualifiers
```

```
MOD_RES                2
                       note = misc_feature - Xaa is bAla
MOD_RES                5
                       note = misc_feature - Xaa is bAla
MOD_RES                14
                       note = misc_feature - Xaa is bAla
MOD_RES                16
                       note = misc_feature - Xaa is bAla
MOD_RES                18
                       note = misc_feature - Xaa is bAla
source                 1..18
                       mol_type = protein
                       organism = synthetic construct
SEQUENCE: 224
RXRRXRRFQI LYHXHXHX                                          18

SEQ ID NO: 225         moltype = AA  length = 14
FEATURE                Location/Qualifiers
MOD_RES                2
                       note = misc_feature - Xaa is bAla
MOD_RES                5
                       note = misc_feature - Xaa is bAla
MOD_RES                10
                       note = misc_feature - Xaa is bAla
MOD_RES                12
                       note = misc_feature - Xaa is bAla
MOD_RES                14
                       note = misc_feature - Xaa is bAla
source                 1..14
                       mol_type = protein
                       organism = synthetic construct
SEQUENCE: 225
RXRRXRWWWX RXRX                                              14

SEQ ID NO: 226         moltype = AA  length = 16
FEATURE                Location/Qualifiers
MOD_RES                2
                       note = misc_feature - Xaa is bAla
MOD_RES                5
                       note = misc_feature - Xaa is bAla
MOD_RES                12
                       note = misc_feature - Xaa is bAla
MOD_RES                14
                       note = misc_feature - Xaa is bAla
MOD_RES                16
                       note = misc_feature - Xaa is bAla
source                 1..16
                       mol_type = protein
                       organism = synthetic construct
SEQUENCE: 226
RXRRXRWWPW WXRXRX                                            16

SEQ ID NO: 227         moltype = DNA  length = 20
FEATURE                Location/Qualifiers
source                 1..20
                       mol_type = other DNA
                       organism = synthetic construct
SEQUENCE: 227
tgctcctgtg gctgtctcct                                        20

SEQ ID NO: 228         moltype = DNA  length = 21
FEATURE                Location/Qualifiers
source                 1..21
                       mol_type = other DNA
                       organism = synthetic construct
SEQUENCE: 228
agcttggctc tggcctgtcc t                                      21

SEQ ID NO: 229         moltype = DNA  length = 20
FEATURE                Location/Qualifiers
source                 1..20
                       mol_type = other DNA
                       organism = synthetic construct
SEQUENCE: 229
accagccact cagccagtga                                        20

SEQ ID NO: 230         moltype = DNA  length = 23
FEATURE                Location/Qualifiers
source                 1..23
```

-continued

```
                    mol_type = other DNA
                    organism = synthetic construct
SEQUENCE: 230
gattgttcta gcctcttgat tgc                                23
```